United States Patent
Qian et al.

(10) Patent No.: US 10,954,253 B2
(45) Date of Patent: Mar. 23, 2021

(54) 1,2-DIHYDRO-3H-PYRAZOLO[3,4-D]PYRIMIDIN-3-ONE DERIVATIVE AS WEE1 INHIBITOR

(71) Applicant: SHIJIAZHUANG SAGACITY NEW DRUG DEVELOPMENT CO., LTD., Hebei (CN)

(72) Inventors: Wenyuan Qian, Shanghai (CN); Chundao Yang, Shanghai (CN); Zhengwei Li, Shanghai (CN); Jie Li, Shanghai (CN); Jian Li, Shanghai (CN); Shuhui Chen, Shanghai (CN)

(73) Assignee: SHIJIAZHUANG SAGACITY NEW DRUG DEVELOPMENT CO., LTD., Shijiazhuang (CN)

( * ) Notice: Subject to any disclaimer, the term of this patent is extended or adjusted under 35 U.S.C. 154(b) by 0 days.

(21) Appl. No.: 16/479,936

(22) PCT Filed: Jan. 19, 2018

(86) PCT No.: PCT/CN2018/073360
§ 371 (c)(1),
(2) Date: Sep. 19, 2019

(87) PCT Pub. No.: WO2018/133829
PCT Pub. Date: Jul. 26, 2018

(65) Prior Publication Data
US 2020/0017528 A1    Jan. 16, 2020

(30) Foreign Application Priority Data

Jan. 23, 2017   (CN) .......................... 201710058856.8
Dec. 19, 2017  (CN) .......................... 201711376769.3

(51) Int. Cl.
*C07D 519/00*   (2006.01)
*C07D 487/02*   (2006.01)
*A61K 31/519*   (2006.01)
*A61K 31/506*   (2006.01)

(52) U.S. Cl.
CPC ................ *C07D 519/00* (2013.01)

(58) Field of Classification Search
CPC .. C07D 519/00; C07D 487/02; A61K 31/519; A61K 31/506
USPC ..................................... 514/210.21
See application file for complete search history.

(56) References Cited

U.S. PATENT DOCUMENTS 9,345,705 B2 *   5/2016   Shumway .............. A61K 45/06
2017/0129909 A1   5/2017   Ding et al.

FOREIGN PATENT DOCUMENTS

| CA | 2650119 A1 | 11/2007 |
|---|---|---|
| CA | 2703489 A1 | 4/2009 |
| CN | 101432284 A | 5/2009 |
| CN | 103703005 A | 4/2014 |
| CN | 104130265 A | 11/2014 |
| CN | 105209463 A | 12/2015 |
| CN | 105829315 A | 8/2016 |
| EP | 2213673 A | 8/2010 |
| WO | 2007126122 A1 | 11/2007 |
| WO | 2007126128 A1 | 11/2007 |
| WO | 2009054332 A1 | 4/2009 |
| WO | 2012161812 A1 | 11/2012 |
| WO | 2016000581 A1 | 1/2016 |
| WO | 2017075629 A2 | 5/2017 |

OTHER PUBLICATIONS

Extended European Search Report issued in European application No. 18741681.3 dated Jul. 17, 2020.
1st Office Action of priority Chinese application CN201880008008A dated Oct. 15, 2020.

* cited by examiner

*Primary Examiner* — Niloofar Rahmani
(74) *Attorney, Agent, or Firm* — SZDC Law P.C.

(57) ABSTRACT

The present invention provides a 1,2-dihydro-3H-pyrazolo[3,4-d]pyrimidin-3-one compound having an inhibitory effect on Wee1, and includes an application of the compound in treating various types of tumors.

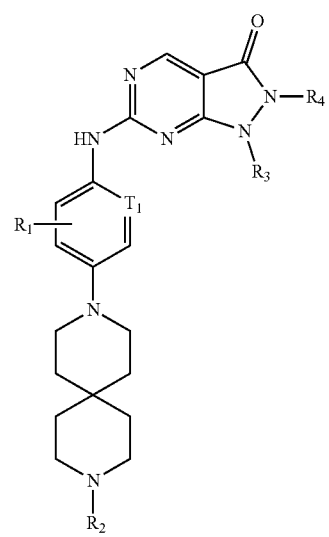

19 Claims, No Drawings

1,2-DIHYDRO-3H-PYRAZOLO[3,4-D]PYRIMIDIN-3-ONE DERIVATIVE AS WEE1 INHIBITOR

This application is the National Stage Application of PCT/CN2018/073360, filed on Jan. 19, 2018, which claims priority to Chinese Patent Application Nos.: 201710058856.8, filed on Jan. 23, 2017, and 201711376769.3, filed on Dec. 19, 2017, all of which are incorporated by reference for all purposes as if fully set forth herein.

REFERENCE TO RELATED APPLICATION

The present invention claims priority to the Chinese patent application No. 201710058856.8 filed to the State Intellectual Property Office of the People's Republic of China on Jan. 23, 2017, and the Chinese patent application No. 201711376769.3 to the State Intellectual Property Office of the People's Republic of China on Dec. 19, 2017, the contents of which are incorporated herein by reference in their entireties.

FIELD OF INVENTION

The present invention relates to a class of 1,2-dihydro-3H-pyrazolo[3,4-d]pyrimidin-3-one compounds having an inhibitory effect on Wee1, and includes the use of the compounds in treating various types of tumors.

PRIOR ARTS

The process of the cell cycle is a complex process controlled by a series of cell cycle regulatory systems, the core component of the cell cycle regulatory system is CDKs/Cyclins complex formed by the combination of cyclin-dependent kinases (CDKs) and cyclins, these complexes may promote cells entry into the proliferative cycle, wherein the CDK1 (also known as CDC2 for human homolog)/Cyclin B complex plays a key role in controlling cell entry into the M phase.

It is necessary for cells to complete the replication of DNA before entering M phase, due to interferences of various endogenous and exogenous factors, the DNA often undergoes mutation or damage, these abnormal DNA must be repaired, otherwise it will cause mitotic catastrophe and lead to cell death.

The main function of the cell cycle checkpoint is to pause the cell cycle and let the cells complete the DNA repair before entering M phase. The G1/S checkpoint at the end of G1 and the G2/M checkpoint at G2 are two major cell cycle checkpoints that share the identification and repair functions of DNA damage. Normal cells can use G1/S checkpoints to complete DNA repair in G1 phase, while nearly 50% of cancerous cells have defects in tumor suppressor gene p53, which also makes them lack G1/S checkpoint function, they are more relied on G2/M checkpoints to complete the DNA repair. G2/M checkpoints rarely mutate, and because of it, cancer cells may escape the treatment of DNA damaging agents and radiation.

Wee1 protein kinase is a cell cycle regulator that belongs to the nuclear serine and threonine protein kinase family and is a key kinase at the G2/M checkpoint. The human "Wee" protein kinase family mainly includes Wee1 and Myt1, both of which may phosphorylate the Tyr15 site on CDC2, inhibit the activation of CDC2/CyclinB complex, and block the cells from entering M phase until DNA repair is completed, Myt1 may also phosphorylates the Thr14 site on CDC2, which is also a negative regulation of CDC2 activity. In many cancerous cells, Wee1 kinase is highly expressed, by inhibiting Wee1 kinase, tumor cells can directly skip the G2 DNA repair and begin mitosis in advance, leading to tumor cell death and achieve the purpose of cancer treatment.

At present, AstraZeneca's Wee1 inhibitor AZD-1775 has entered clinical phase II, and more than 30 clinical trials are under development and have shown good therapeutic effects. AZD-1775 was first developed by Merck, hence also called MK-1775, Merck transferred the compound to AstraZeneca worldwide in September 2013, and the related patents mainly include US20070254892, WO2007126122, EP2213673, WO2008133866, WO2011034743 and the like. Abbott and Abbvie have also conducted research on Wee1 inhibitors, and the related patents mainly include US2012220572, WO2013126656, WO2013012681, WO2013059485, WO2013013031, WO2013126656 and the like. Almac's patents related to Wee1 inhibitors include WO2014167347, WO2015019037, and WO2015092431.

Content of the Present Invention

The present invention provides a compound represented by formula (I) or a pharmaceutically acceptable salt thereof,

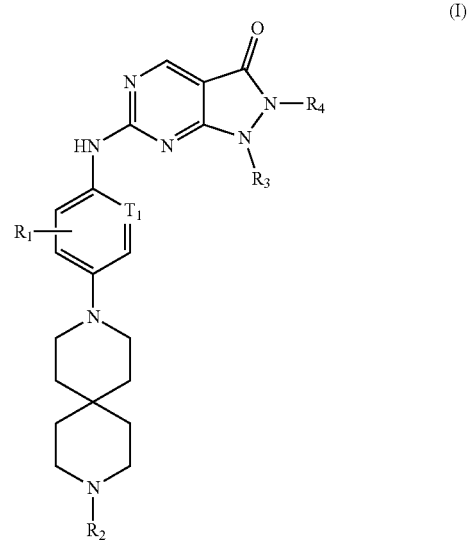

wherein, $T_1$ is N or CH;

$R_1$ is selected from H, halogen, OH, $NH_2$, or selected from the group consisting of $C_{1-3}$ alkyl, $C_{1-3}$ heteroalkyl, each of which is optionally substituted by 1, 2 or 3 R;

$R_2$ is H, or selected from the group consisting of $C_{1-3}$ alkyl, $C_{1-3}$ heteroalkyl and 3-6 membered heterocycloalkyl, each of which is optionally substituted by 1, 2 or 3 R;

$R_3$ is selected from the group consisting of $C_{3-5}$ alkenyl,

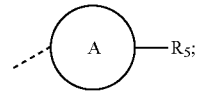

ring A is selected from the group consisting of phenyl, 5-6 membered heteroaryl, each of which is optionally substituted by 1, 2 or 3 R;

$R_5$ is selected from halogen, OH, $NH_2$, —C(=O)$NH_2$, or selected from the group consisting of $C_{1-6}$ alkyl, $C_{1-6}$ heteroalkyl, $C_{3-6}$ cycloalkyl, 3-6 membered heterocycloalkyl, $C_{3-6}$ cycloalkyl-O—, 3-6 membered heterocycloalkyl-O— and

each of which is optionally substituted by 1, 2 or 3 R;

$R_4$ is selected from the group consisting of $C_{1-6}$ alkyl, $C_{3-5}$ alkenyl, phenyl, —$C_{1-3}$ alkyl-phenyl, each of which is optionally substituted by 1, 2 or 3 R;

R is selected from the group consisting of F, Cl, Br, I, OH, $NH_2$, $NH(CH_3)$, $N(CH_3)_2$, Me, Et, $CH_2F$, $CHF_2$, $CF_3$,

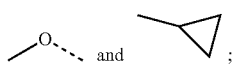

the "hetero" in $C_{1-3}$ heteroalkyl, $C_{1-6}$ heteroalkyl, 5-6 membered heteroaryl, 3-6 membered heterocycloalkyl is selected from the group consisting of —O—, —S—, —C(=O)—, —C(=O)NH—, —C(=O)O—, —NH— and N;

In any one of the cases above, the number of the heteroatoms or the heteroatom groups is independently selected from 1, 2 or 3.

In some embodiments of the present invention, said $R_1$ is selected from H, F, Cl, Br, I, OH and $NH_2$, or selected from the group consisting of $C_{1-3}$ alkyl, $C_{1-3}$ alkoxyl, each of which is optionally substituted by 1, 2 or 3 R.

In some embodiments of the present invention, said $R_1$ is selected from the group consisting of H, F, Cl, Br, I, OH, $NH_2$, Me and

In some embodiments of the present invention, said $R_2$ is H, or selected from the group consisting of $C_{1-3}$ alkyl, —C(=O)—$C_{1-3}$ alkyl, —C(=O)O—$C_{1-3}$ alkyl and oxetanyl, each of which is optionally substituted by 1, 2 or 3 R.

In some embodiments of the present invention, said $R_2$ is selected from the group consisting of H, Me,

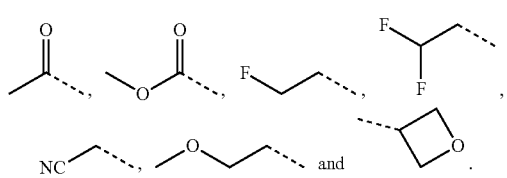

In some embodiments of the present invention, said ring A is selected from the group consisting of phenyl, pyridinyl, pyrimidyl, thienyl, thiazolyl, and isothiazolyl, each of which is optionally substituted by 1, 2 or 3 R.

In some embodiments of the present invention, said ring A is selected from the group consisting of

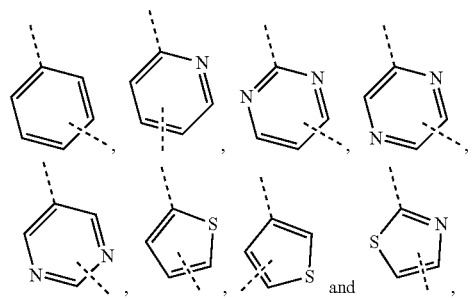

each of which is optionally substituted by 1, 2 or 3 R.

In some embodiments of the present invention, said ring A is selected from the group consisting of

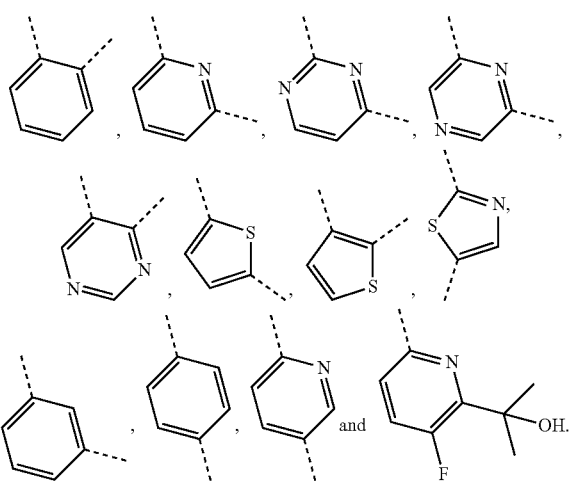

In some embodiments of the present invention, said $R_5$ is selected from F, Cl, Br, I, OH, $NH_2$, —C(=O)$NH_2$, or selected from the group consisting of $C_{1-3}$ alkyl, $C_{1-3}$ alkoxyl, —C(=O)NH—$C_{1-3}$ alkyl, $C_{3-6}$ cycloalkyl, oxetanyl, 2-pyrrolidinonyl, cyclopropyl-O—, cyclobutyl-O—, oxacyclobutyl-O—, oxacyclopentyl-O—, azocyclobutyl, 2-oxazolidinonyl, 2-imidazolidinonyl and

each of which is optionally substituted by 1, 2 or 3 R.

In some embodiments of the present invention, said $R_5$ is selected from F, Cl, Br, I, OH, $NH_2$, —C(=O)$NH_2$, or selected from the group consisting of Me, Et,

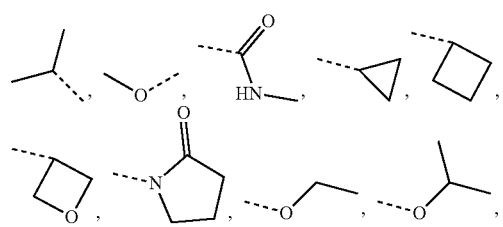

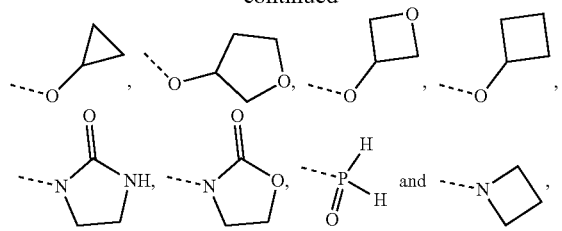
each of which is optionally substituted by 1, 2 or 3 R.
In some embodiments of the present invention, said R₅ is selected from the group consisting of F, Cl, Br, I, OH, NH₂, —C(=O)NH₂, Me, CF₃,
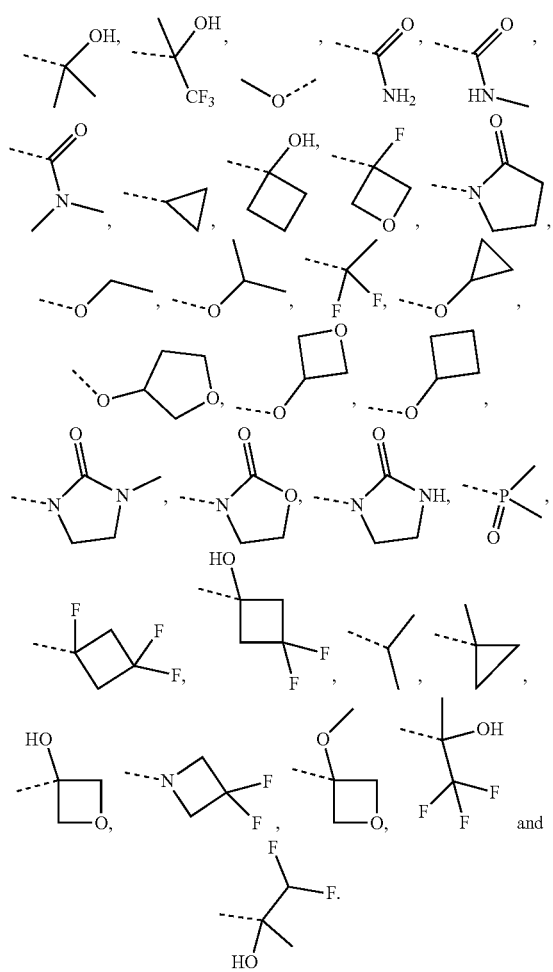
In some embodiments of the present invention, said
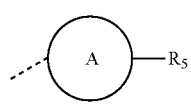
is selected from the group consisting of
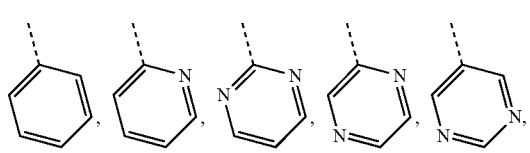
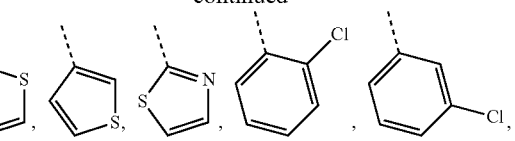
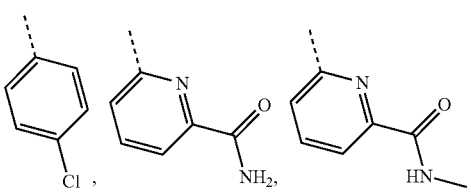
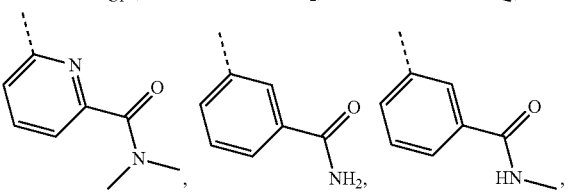
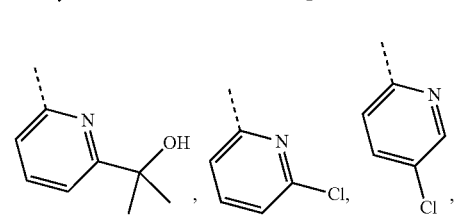
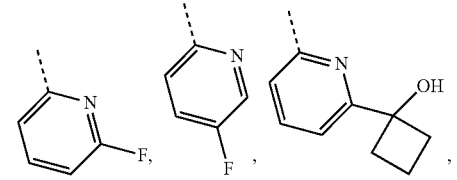
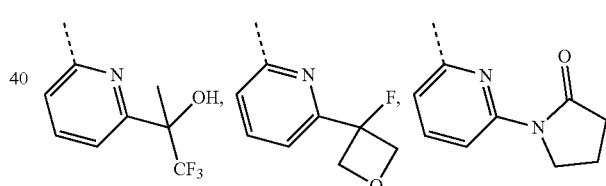
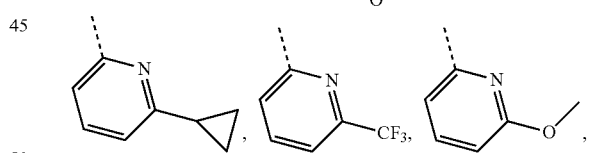
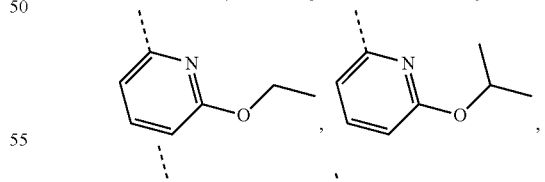
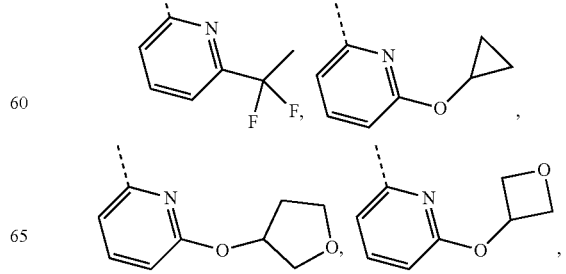

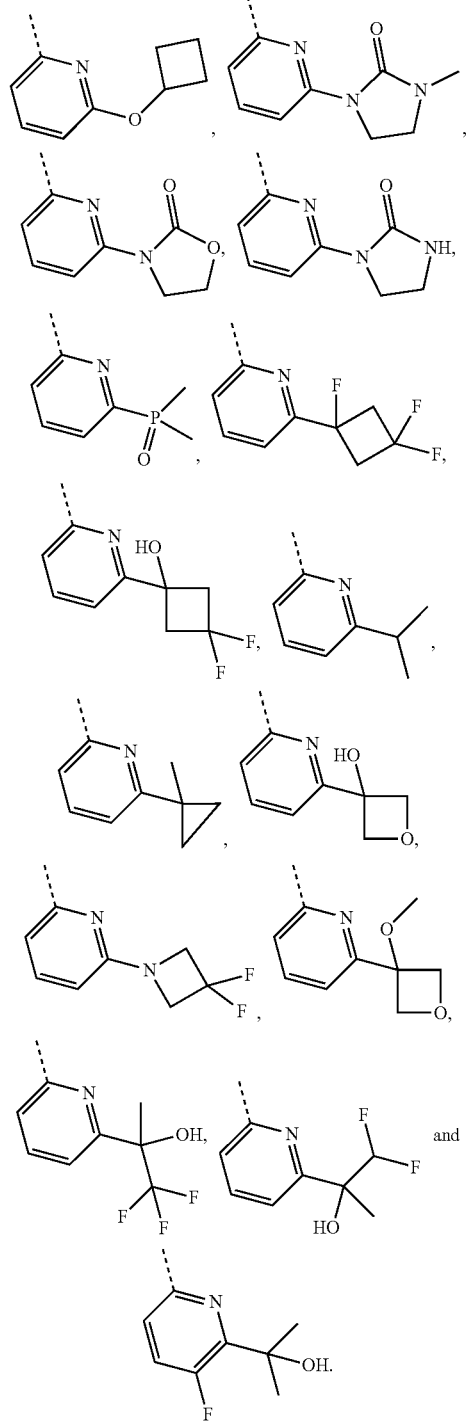
In some embodiments of the present invention, said $R_3$ is selected from the group consisting of
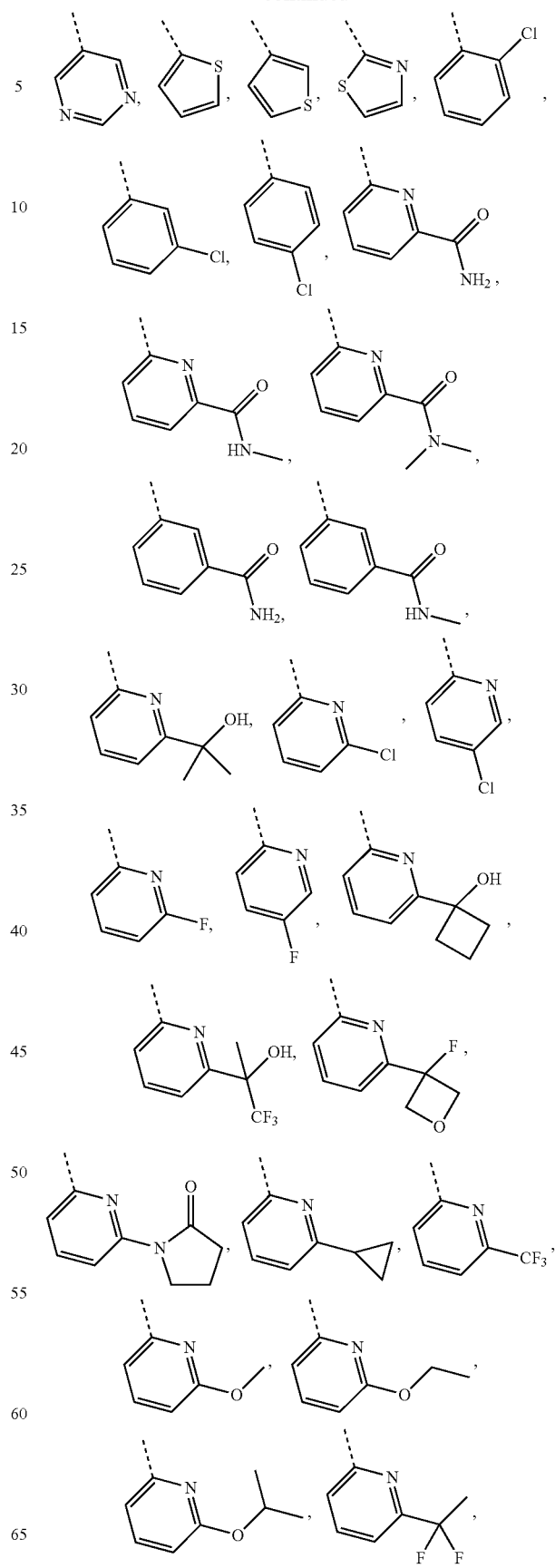

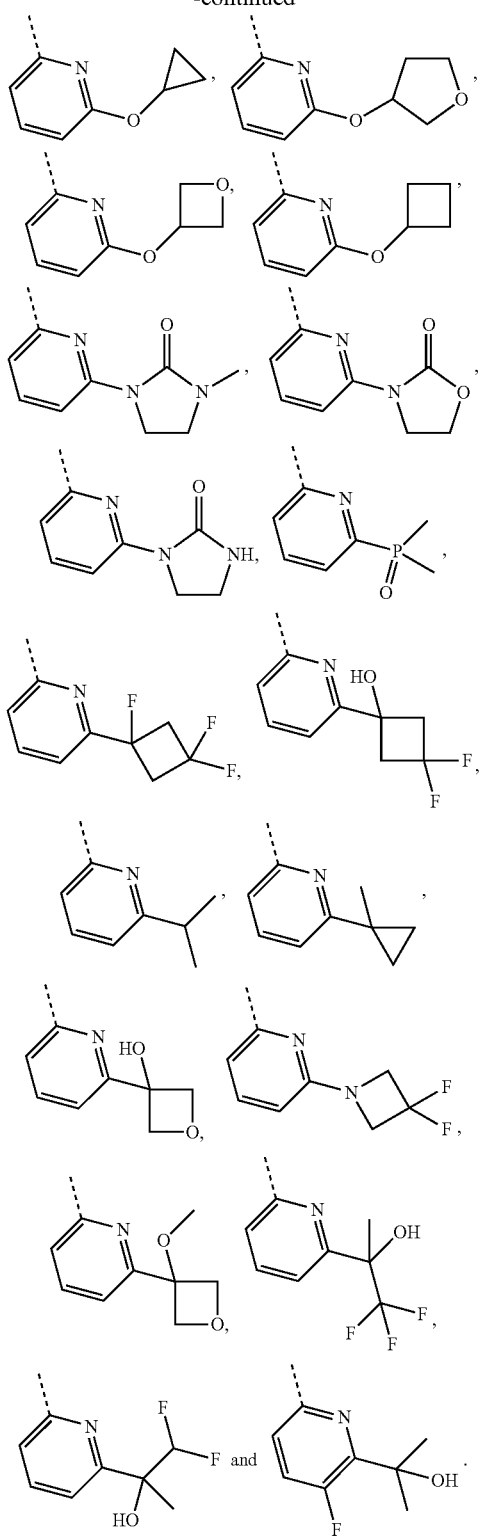

each of which is optionally substituted by 1, 2 or 3 R.

In some embodiments of the present invention, said R₄ is selected from the group consisting of Me, In some embodiments of the present invention, said moiety

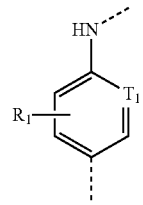

is selected from the group consisting of

In some embodiments of the present invention, said R₄ is selected from the group consisting of C₁₋₃ alkyl, C₃₋₅ alkenyl, phenyl, and benzyl, each of which is optionally substituted by 1, 2 or 3 R.

In some embodiments of the present invention, said R₄ is selected from the group consisting of Me, In some embodiments of the present invention, said moiety

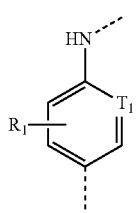

is selected from the group consisting of

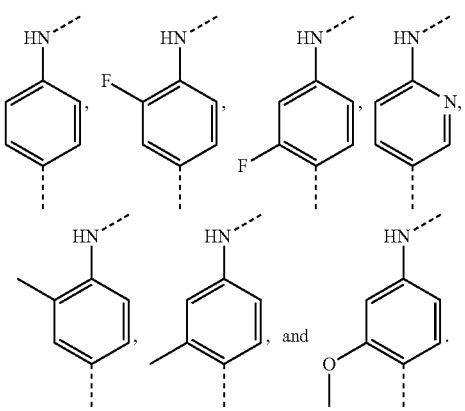

In some embodiments of the present invention, said $R_1$ is selected from H, F, Cl, Br, I, OH, $NH_2$, or selected from the group consisting of $C_{1-3}$ alkyl and $C_{1-3}$ alkoxyl, each of which is optionally substituted by 1, 2 or 3 R, the other variants are as defined above.

In some embodiments of the present invention, said $R_1$ is selected from the group consisting of H, F, Cl, Br, I, OH, $NH_2$, Me and

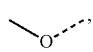

the other variants are as defined above.

In some embodiments of the present invention, said $R_2$ is selected from H, or selected from the group consisting of $C_{1-3}$ alkyl, —C(═O)—$C_{1-3}$ alkyl, —C(═O)O—$C_{1-3}$ alkyl and oxetanyl, the other variants are as defined above.

In some embodiments of the present invention, said $R_2$ is selected from the group consisting of H, Me,

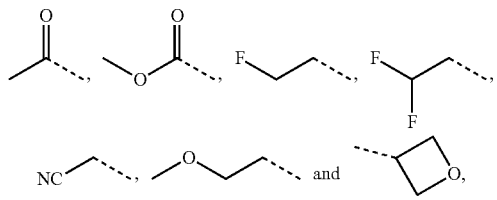

the other variants are as defined above.

In some embodiments of the present invention, said ring A is selected from the group consisting of phenyl, pyridinyl, pyrimidyl, thienyl, thiazolyl and isothiazolyl, each of which is optionally substituted by 1, 2 or 3 R, the other variants are as defined above.

In some embodiments of the present invention, said ring A is selected from the group consisting of

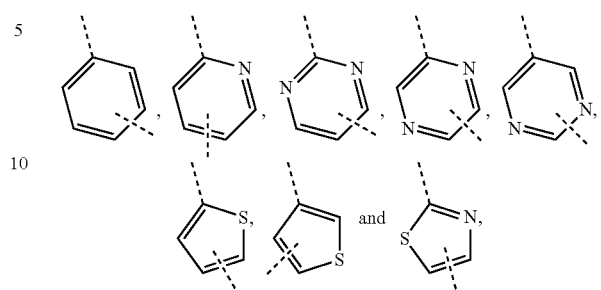

each of which is optionally substituted by 1, 2 or 3 R, the other variants are as defined above.

In some embodiments of the present invention, said ring A is selected from the group consisting of

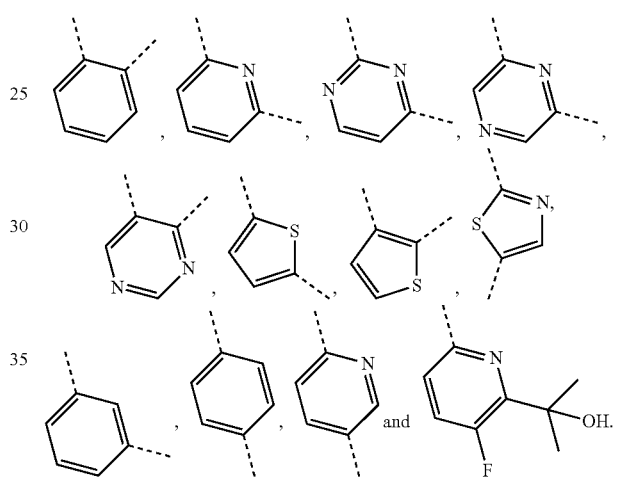

the other variants are as defined above.

In some embodiments of the present invention, said $R_5$ is selected from F, Cl, Br, I, OH, $NH_2$, —C(═O)$NH_2$, or selected from the group consisting of $C_{1-3}$ alkyl, $C_{1-3}$ alkoxyl, —C(═O)NH—$C_{1-3}$ alkyl, $C_{3-6}$ cycloalkyl, oxetanyl, 2-pyrrolidinonyl, cyclopropyl-O—, cyclobutyl-O—, oxacyclobutyl-O—, oxacyclopentyl-O—, azocyclobutyl, 2-oxazolidinonyl, 2-imidazolidinonyl and

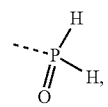

each of which is optionally substituted by 1, 2 or 3 R, the other variants are as defined above.

In some embodiments of the present invention, said $R_5$ is selected from F, Cl, Br, I, OH, $NH_2$, —C(═O)$NH_2$, or selected from the group consisting of Me, Et

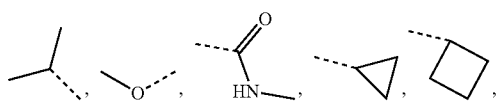

-continued
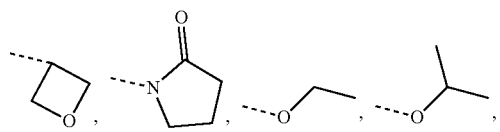
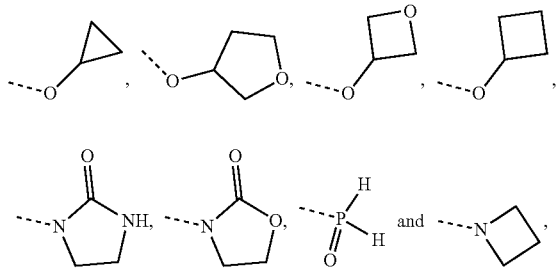
each of which is optionally substituted by 1, 2 or 3 R, the other variants are as defined above.
In some embodiments of the present invention, said R₅ is selected from the group consisting of F, Cl, Br, I, OH, NH₂, —C(=O)NH₂, Me, CF₃,
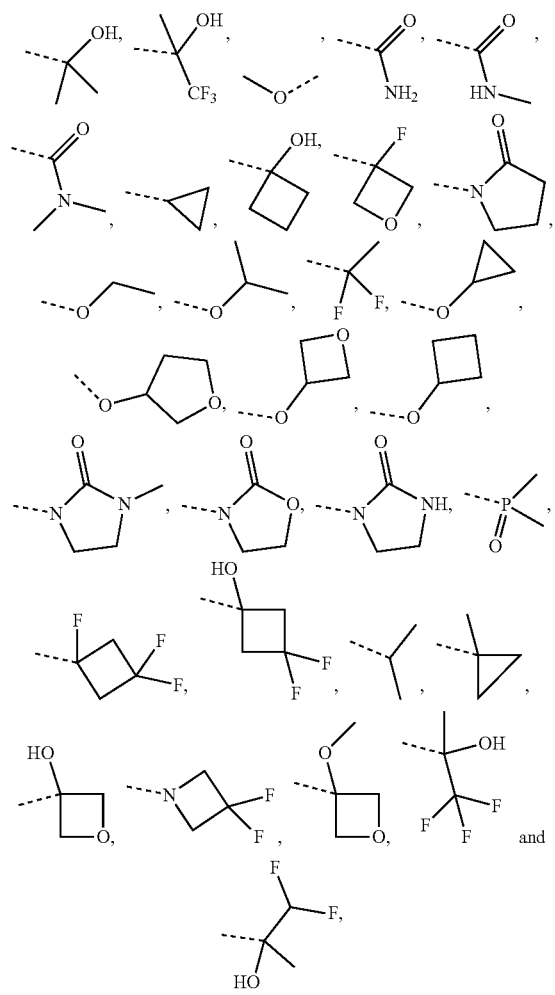
the other variants are as defined above.
In some embodiments of the present invention, said
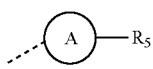
is selected from the group consisting of -continued
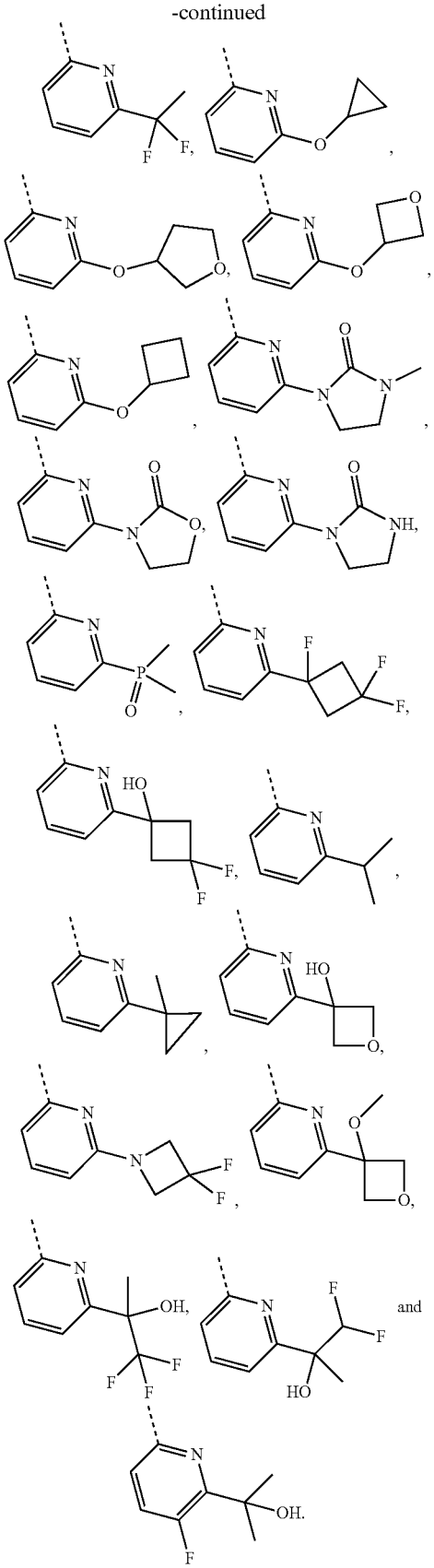
the other variants are as defined above.
In some embodiments of the present invention, said $R_3$ is selected from the group consisting of
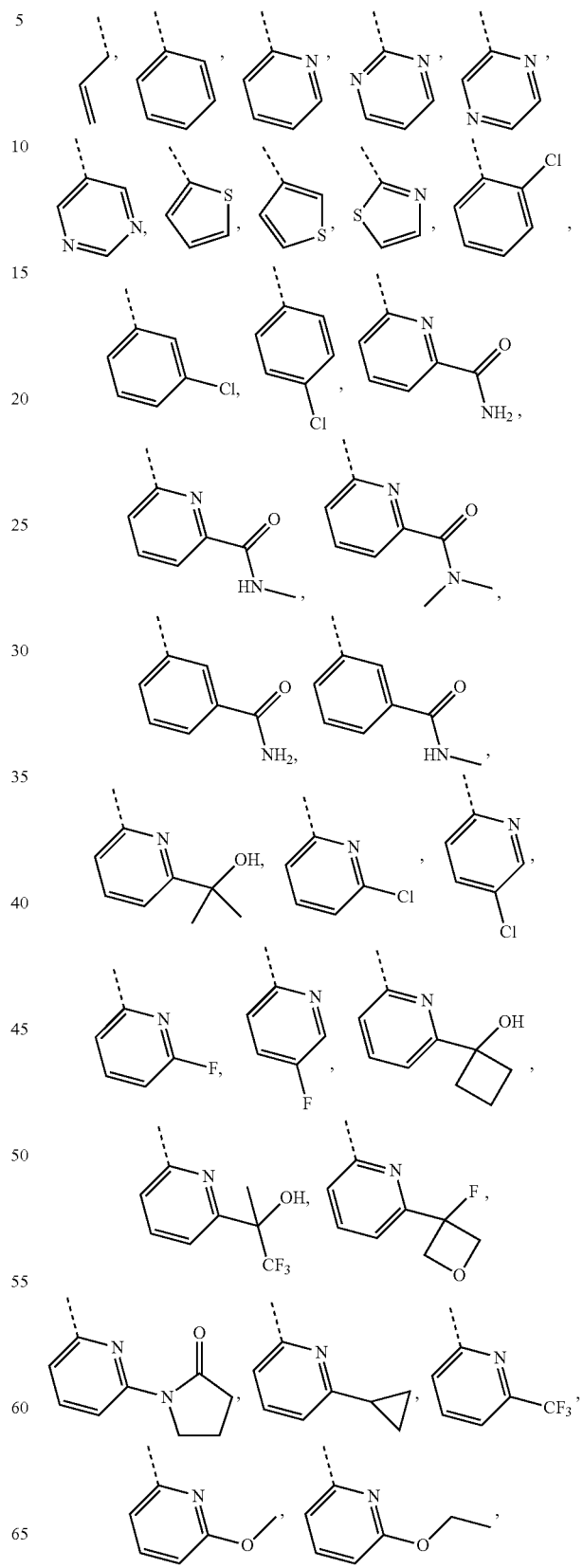

-continued

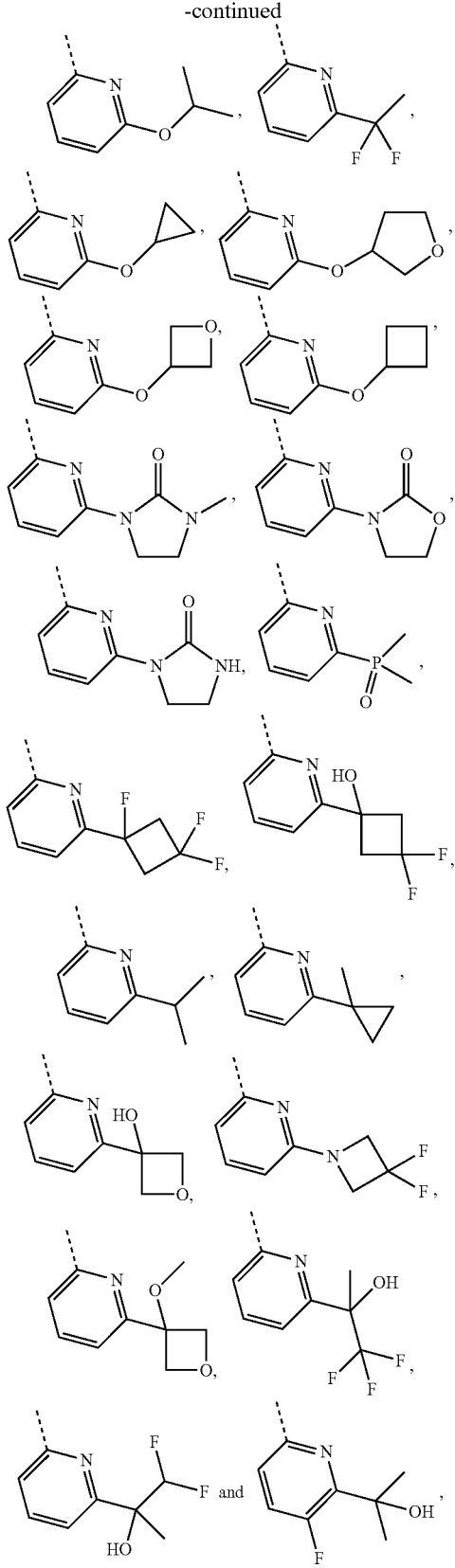

the other variants are as defined above.

In some embodiments of the present invention, said $R_4$ is selected from the group consisting of $C_{1-3}$ alkyl, $C_{3-5}$ alkenyl, phenyl, and benzyl, each of which is optionally substituted by 1, 2 or 3 R, the other variants are as defined above.

In some embodiments of the present invention, said $R_4$ is selected from the group consisting of

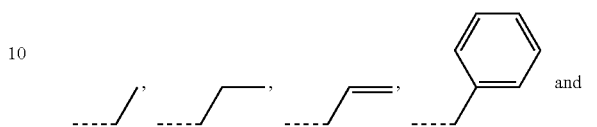

each of which is optionally substituted by optionally substituted by 1, 2 or 3 R, the other variants are as defined above.

In some embodiments of the present invention, said $R_4$ is selected from the group consisting of

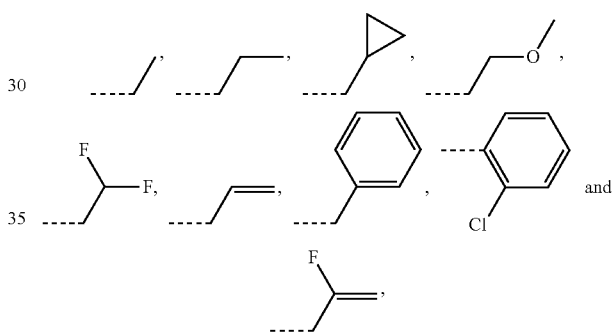

the other variants are as defined above.

In some embodiments of the present invention, said moiety

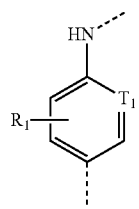

is selected from the group consisting of

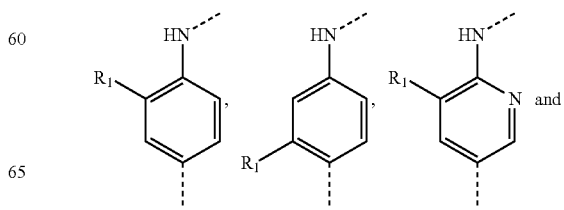

-continued

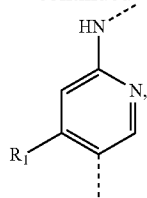

the other variants are as defined above.

In some embodiments of the present invention, said moiety

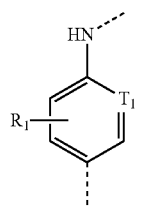

is selected from the group consisting of

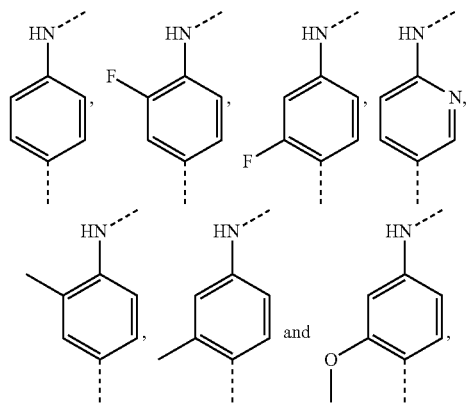

the other variants are as defined above.

In some embodiments of the present invention, the compound or the pharmaceutically acceptable salt thereof is selected from:

(I-1)

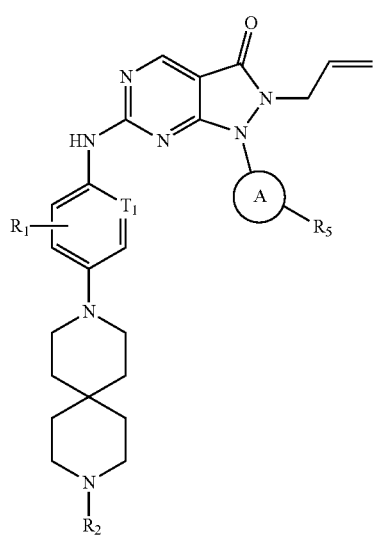

wherein,
$R_1$, $R_2$, $R_5$, $T_1$ and ring A are as defined above.

In some embodiments of the present invention, the compound or the pharmaceutically acceptable salt thereof is selected from the group consisting of (2-1)

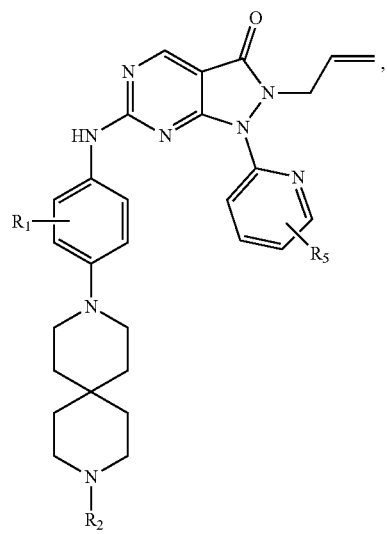

(2-2)

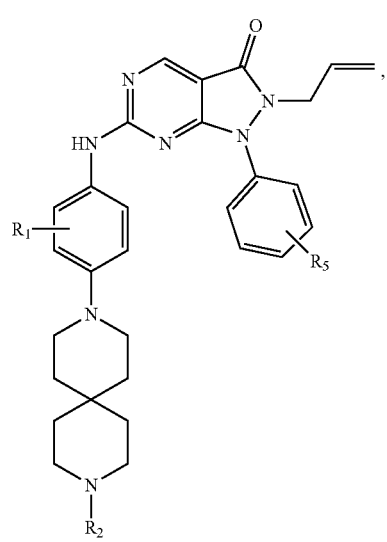

(2-3)

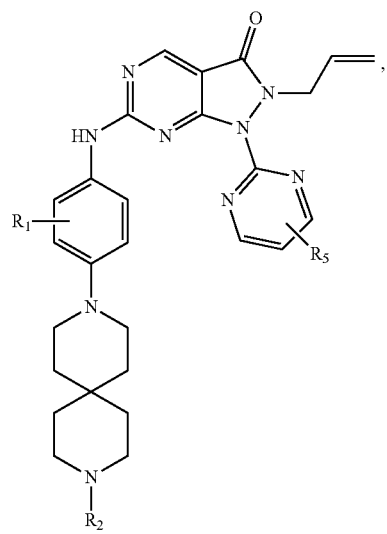

(2-4)
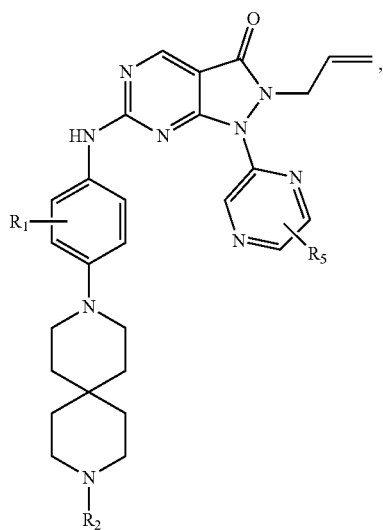
(2-5)
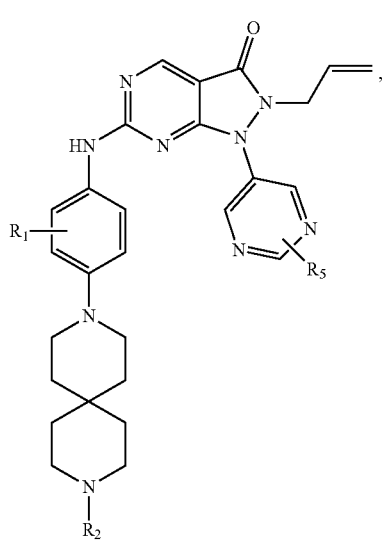
(2-6)
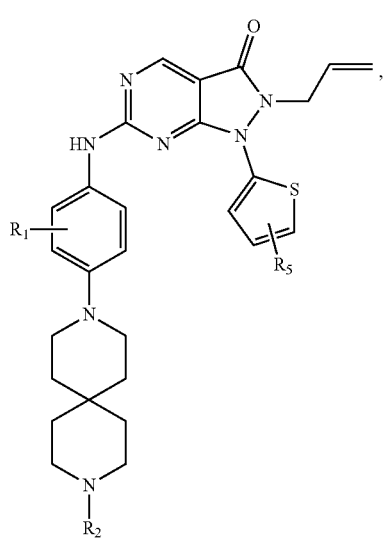
(2-7)
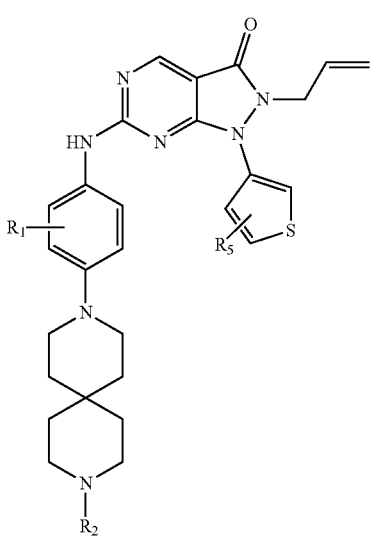
and
(2-8)
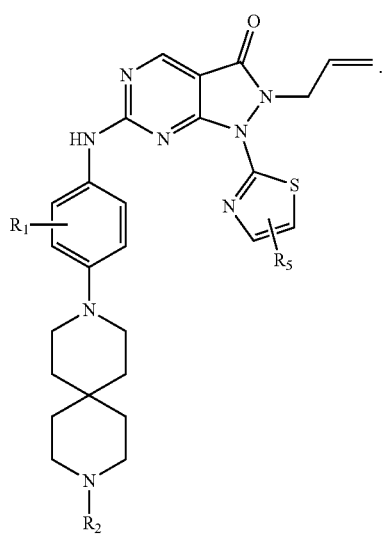
wherein, $R_1$, $R_2$ and $R_5$ are as defined above.

The present invention also provides the compound or the pharmaceutically acceptable salt thereof, which is selected from the group consisting of

| Number | formula | Chemical name |
|---|---|---|
| 1 | | 2-allyl-6-((4-(9-methyl-3,9-diazaspiro[5.5]undecan-3-yl)phenyl)amino)-1-phenyl-1H-pyrazolo[3,4-d]pyrimidin-3(2H)-one |
| 2 | | 6-((4-(3,9-diazaspiro[5.5]undecan-3-yl)phenyl)amino)-2-allyl-1-phenyl-1H-pyrazolo[3,4-d]pyrimidin-3(2H)-one |
| 3 | | 2-allyl-6-((4-(9-methyl-3,9-diazaspiro[5.5]undecan-3-yl)phenyl)amino)-1-(pyridin-2-yl)-1H-pyrazolo[3,4-d]pyrimidin-3(2H)-one |
| 4 | | 2-allyl-6-((4-(9-methyl-3,9-diazaspiro[5.5]undecan-3-yl)phenyl)amino)-1-(pyrimidin-2-yl)-1H-pyrazolo[3,4-d]pyrimidine-3(2H)-one |

-continued

| Number | formula | Chemical name |
|---|---|---|
| 5 | 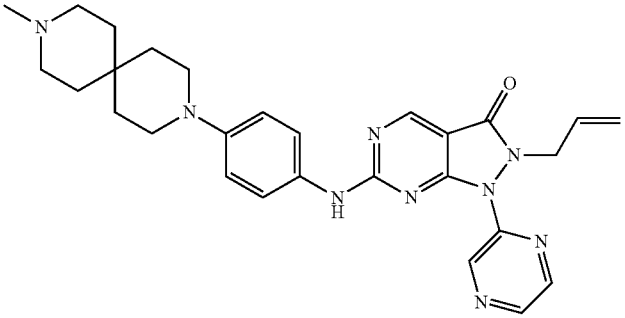 [SMILES: C=CCn1c(=O)c2cnc(Nc3ccc(N4CCC5(CCN(C)CC5)CC4)cc3)nc2n1-c1cnccn1] | 2-allyl-6-((4-(9-methyl-3,9-diazaspiro[5.5]undecan-3-yl)phenyl)amino)-1-(pyridazin-2-yl)-1H-pyrazolo[3,4-d]pyrimidin-3(2H)-one |
| 6 | 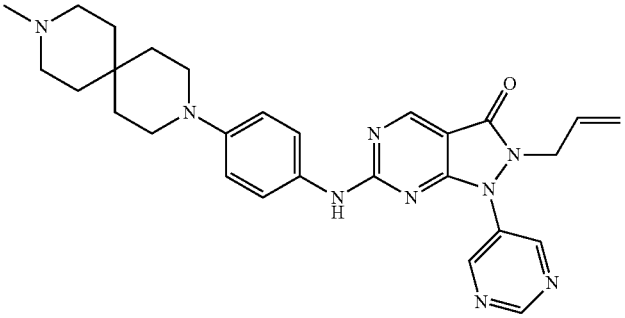 [SMILES: C=CCn1c(=O)c2cnc(Nc3ccc(N4CCC5(CCN(C)CC5)CC4)cc3)nc2n1-c1cncnc1] | 2-allyl-6-((4-(9-methyl-3,9-diazaspiro[5.5]undecan-3-yl)phenyl)amino)-1-(pyrimidin-5-yl)-1H-pyrazolo[3,4-d]pyrimidin-3(2H)-one |
| 7 | 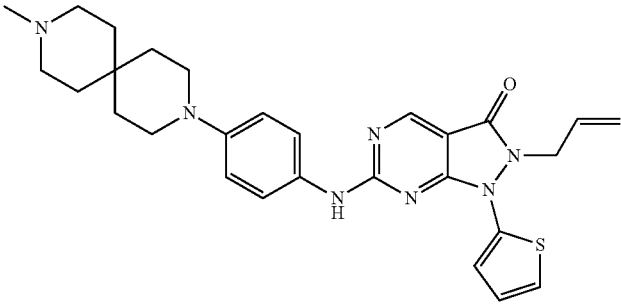 [SMILES: C=CCn1c(=O)c2cnc(Nc3ccc(N4CCC5(CCN(C)CC5)CC4)cc3)nc2n1-c1cccs1] | 2-allyl-6-((4-(9-methyl-3,9-diazaspiro[5.5]undecan-3-yl)phenyl)amino)-1-(thiophen-2-yl)-1H-pyrazolo[3,4-d]pyrimidin-3(2H)-one |
| 8 | 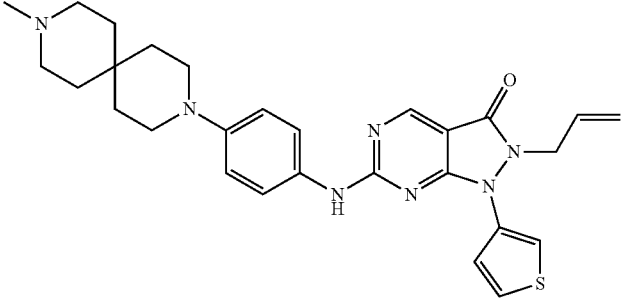 [SMILES: C=CCn1c(=O)c2cnc(Nc3ccc(N4CCC5(CCN(C)CC5)CC4)cc3)nc2n1-c1ccsc1] | 2-allyl-6-((4-(9-methyl-3,9-diazaspiro[5.5]undecan-3-yl)phenyl)amino)-1-(thiophen-3-yl)-1H-pyrazolo[3,4-d]pyrimidin-3(2H)-one |

| Number | formula | Chemical name |
|---|---|---|
| 9 | 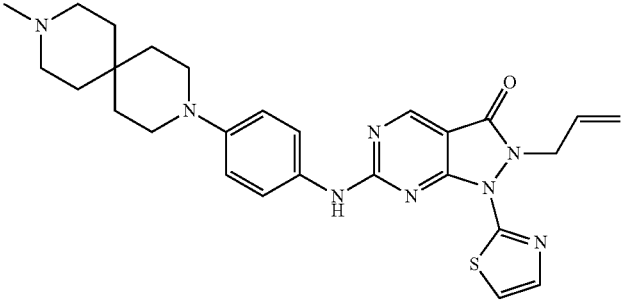 [SMILES: C=CCn1c(=O)c2cnc(Nc3ccc(N4CCC5(CCN(C)CC5)CC4)cc3)nc2n1-c1nccs1] | 2-allyl-6-((4-(9-methyl-3,9-diazaspiro[5.5]undecan-3-yl)phenyl)amino)-1-(thiazol-2-yl)-1H-pyrazolo[3,4-d]pyrimidin-3(2H)-one |
| 10 | 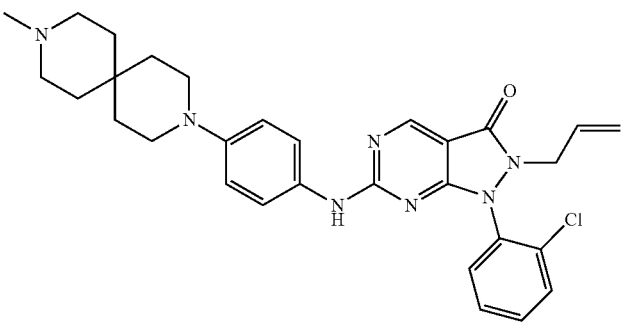 [SMILES: C=CCn1c(=O)c2cnc(Nc3ccc(N4CCC5(CCN(C)CC5)CC4)cc3)nc2n1-c1ccccc1Cl] | 2-allyl-1-(2-chlorophenyl)-6-((4-(9-methyl-3,9-diazaspiro[5.5]undecan-3-yl)phenyl)amino)-1H-pyrazolo[3,4-d]pyrimidin-3(2H)-one |
| 11 | 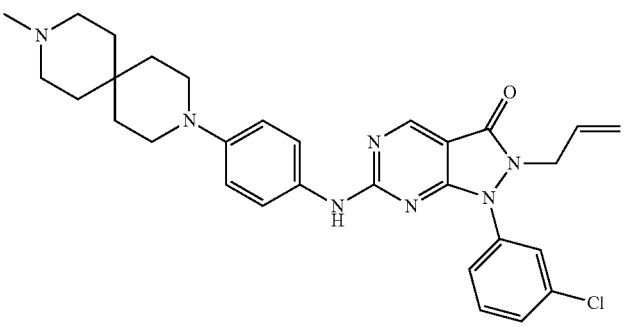 [SMILES: C=CCn1c(=O)c2cnc(Nc3ccc(N4CCC5(CCN(C)CC5)CC4)cc3)nc2n1-c1cccc(Cl)c1] | 2-allyl-1-(3-chlorophenyl)-6-((4-(9-methyl-3,9-diazaspiro[5.5]undecan-3-yl)phenyl)amino)-1H-pyrazolo[3,4-d]pyrimidin-3(2H)-one |
| 12 | 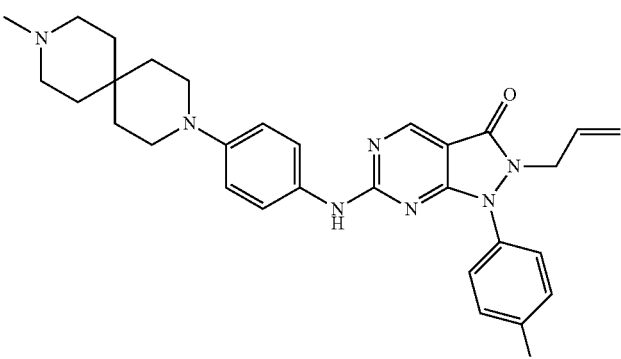 | 2-allyl-1-(4-chlorophenyl)-6-((4-(9-methyl-3,9-diazaspiro[5.5]undecan-3-yl)phenyl)amino)-1H-pyrazolo[3,4-d]pyrimidin-3(2H)-one |

-continued

| Number | formula | Chemical name |
|---|---|---|
| 13 | | 6-(2-allyl-6-((4-(9-methyl-3,9-diazaspiro[5.5]undecan-3-yl)phenyl)amino)-3-oxo-2,3-dihydro-1H-pyrazolo[3,4-d]pyrimidin-1-yl)picolinamide |
| 14 | | 6-(2-allyl-6-((4-(9-methyl-3,9-diazaspiro[5.5]undecan-3-yl)phenyl)amino)-3-oxo-2,3-dihydro-1H-pyrazolo[3,4-d]pyrimidin-1-yl)-N-methylpicolinamide |
| 15 | | 6-(2-allyl-6-((4-(9-methyl-3,9-diazaspiro[5.5]undecan-3-yl)phenyl)amino)-3-oxo-2,3-dihydro-1H-pyrazolo[3,4-d]pyrimidin-1-yl)-N,N-dimethylpicolinamide |
| 16 | | 3-(2-allyl-6-((4-(9-methyl-3,9-diazaspiro[5.5]undecan-3-yl)phenyl)amino)-3-oxo-2,3-dihydro-1H-pyrazolo[3,4-d]pyrimidin-1-yl)benzamide |

-continued

| Number | formula | Chemical name |
|---|---|---|
| 17 | 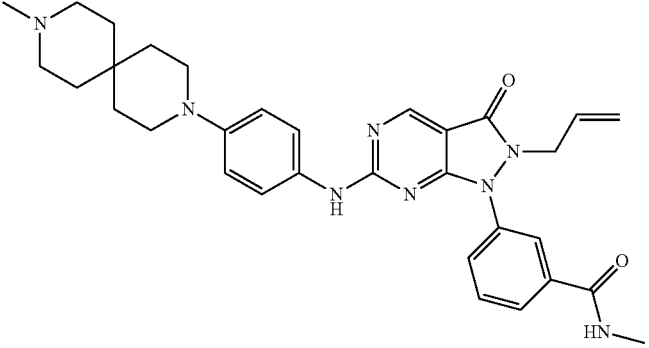 | 3-(2-allyl-6-((4-(9-methyl-3,9-diazaspiro[5.5]undecan-3-yl)phenyl)amino)-3-oxo-2,3-dihydro-1H-pyrazolo[3,4-d]pyrimidin-1-yl)-N-methylbenzamide |
| 18 | 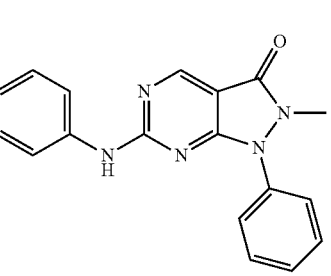 | 2-methyl-6-((4-(9-methyl-3,9-diazaspiro[5.5]undecane-3-yl)phenyl)amino)-1-phenyl-1H-pyrazolo[3,4-d](2H)-one |
| 19 | 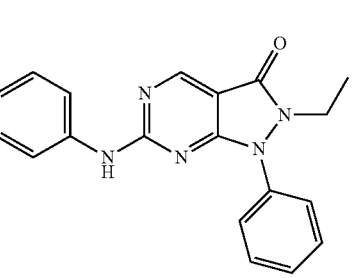 | 2-ethyl-6-((4-(9-methyl-3,9-diazaspiro[5.5]undecan-3-yl)phenyl)amino)-1-phenyl-1H-pyrazolo[3,4-d](2H)-one |
| 20 | 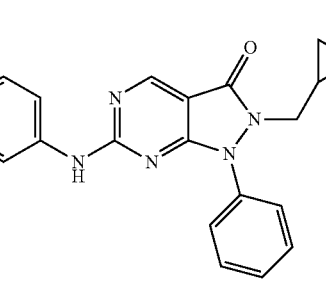 | 2-(cyclopropylmethyl)-6-((4-(9-methyl-3,9-diazaspiro[5.5]undecan-3-yl)phenyl)amino)-1-phenyl-1H-pyrazolo[3,4-d](2H)-one |

| Number | formula | Chemical name |
|---|---|---|
| 21 | 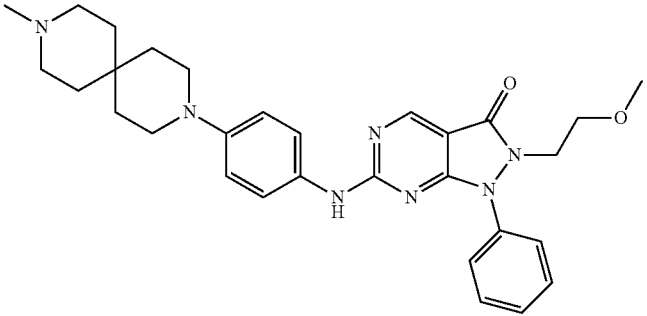 | 2-(2-methoxylethyl)-6-((4-(9-methyl-3,9-diazaspiro[5.5]undecan-3-yl)phenyl)amino)-1-phenyl-1H-pyrazolo[3,4-d](2H)-one |
| 22 | 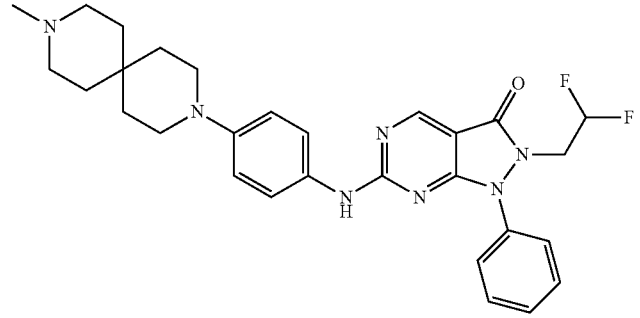 [SMILES: CN1CCC2(CC1)CCN(c1ccc(Nc3ncc4c(=O)n(CC(F)F)n(-c5ccccc5)c4n3)cc1)CC2] | 2-(2,2-difluroethyl)-6-((4-(9-methyl-3,9-diazaspiro[5.5]undecan-3-yl)phenyl)amino)-1-phenyl-1H-pyrazolo[3,4-d](2H)-one |
| 23 | 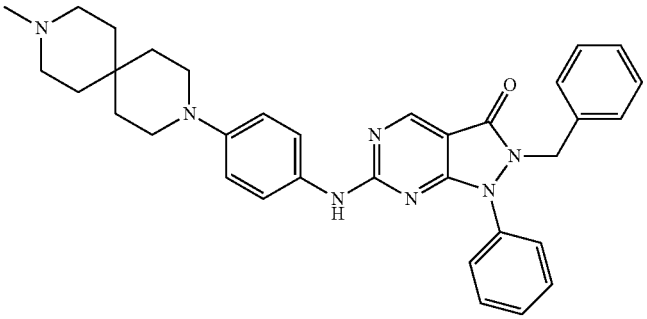 [SMILES: CN1CCC2(CC1)CCN(c1ccc(Nc3ncc4c(=O)n(Cc5ccccc5)n(-c5ccccc5)c4n3)cc1)CC2] | 2-benzyl-6-((4-(9-methyl-3,9-diazaspiro[5.5]undecane-3-yl)phenyl)amino)-1-phenyl-1H-pyrazolo[3,4-d](2H)-one |
| 24 | 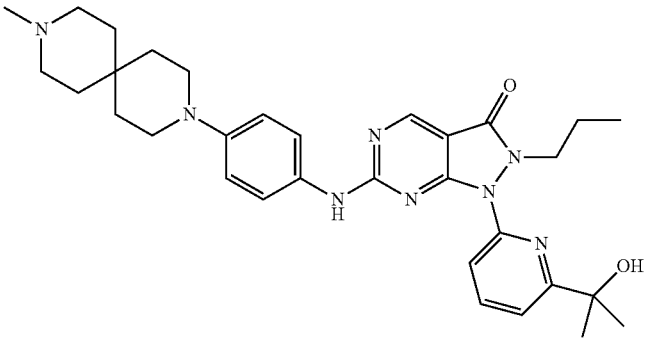 [SMILES: CCCn1c(=O)c2cnc(Nc3ccc(N4CCC5(CCN(C)CC5)CC4)cc3)nc2n1-c1cccc(C(C)(C)O)n1] | 1-(6-(2-hydroxypropan-2-yl)pyridin-2-yl)-6-((4-(9-methyl-3,9-diazaspiro[5.5]undecan-3-yl)phenyl)amino)-2-propyl-1H-pyrazolo[3,4-d]pyrimidin-3(2H)-one |

| Number | formula | Chemical name |
|---|---|---|
| 25 | 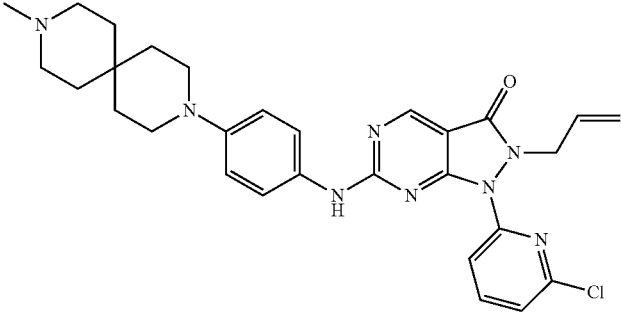 | 2-allyl-1-(6-chloropyridin-2-yl)-6-((4-(9-methyl-3,9-diazaspiro[5.5]undecan-3-yl)phenyl)amino)-1H-pyrazolo[3,4-d]pyrimidin-3(2H)-one |
| 26 | 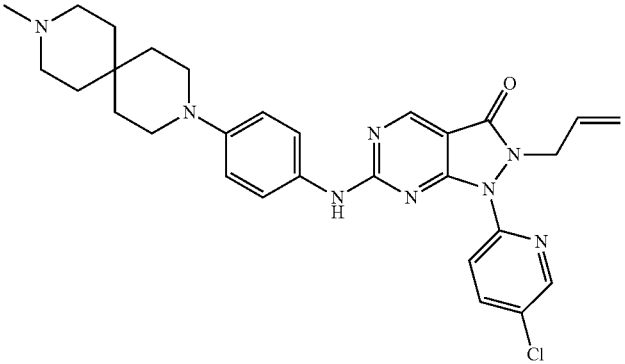 | 2-allyl-1-(5-chloropyridin-2-yl)-6-((4-(9-methyl-3,9-diazaspiro[5.5]undecan-3-yl)phenyl)amino)-1H-pyrazolo[3,4-d]pyrimidin-3(2H)-one |
| 27 | 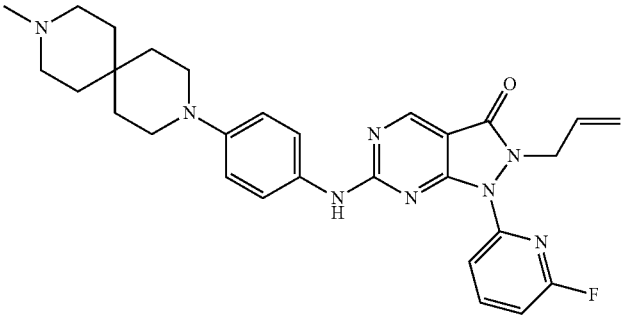 [SMILES: C=CCn1c(=O)c2cnc(Nc3ccc(N4CCC5(CCN(C)CC5)CC4)cc3)nc2n1-c1cccc(F)n1] | 2-allyl-1-(6-fluoropyridin-2-yl)-6-((4-(9-methyl-3,9-diazaspiro[5.5]undecane-3-yl)phenyl)amino)-1H-pyrazolo[3,4-d]pyrimidin-3(2H)-one |
| 28 | 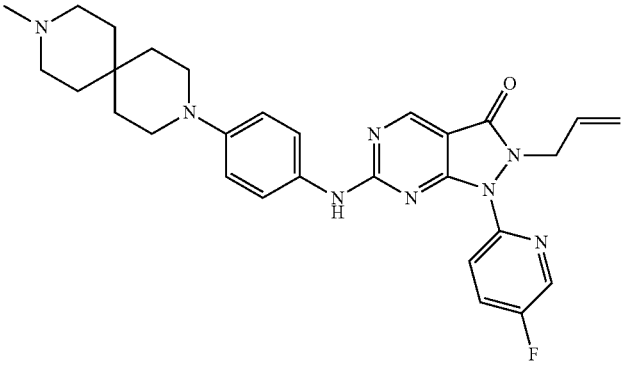 [SMILES: C=CCn1c(=O)c2cnc(Nc3ccc(N4CCC5(CCN(C)CC5)CC4)cc3)nc2n1-c1ccc(F)cn1] | 2-allyl-1-(5-fluoropyridin-2-yl)-6-((4-(9-methyl-3,9-diazaspiro[5.5]undecan-3-yl)phenyl)amino)-1H-pyrazolo[3,4-d]pyrimidin-3(2H)-one |

-continued

| Number | formula | Chemical name |
|---|---|---|
| 29 | 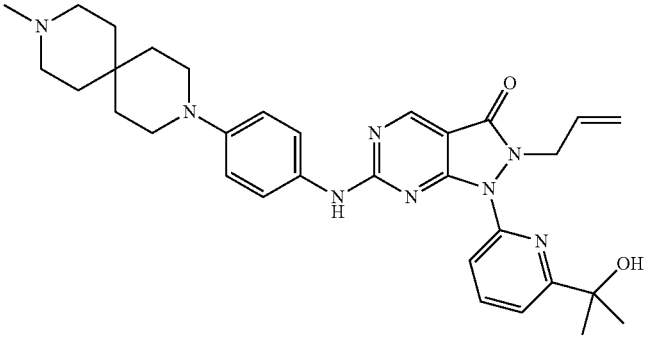 [SMILES: C=CCn1c(=O)c2cnc(Nc3ccc(N4CCC5(CCN(C)CC5)CC4)cc3)nc2n1-c1cccc(C(C)(C)O)n1] | 2-allyl-1-(6-(2-hydroxypropan-2-yl)pyridin-2-yl)-6-((4-(9-methyl-3,9-diazaspiro[5.5]undecan-3-yl)phenyl)amino)-1H-pyrazolo[3,4-d]pyrimidin-3(2H)-one |
| 30 | 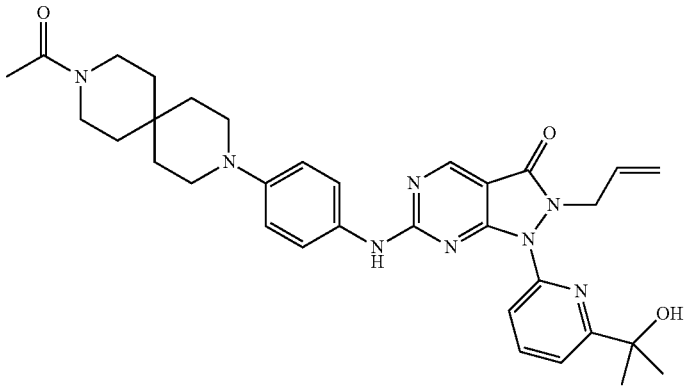 [SMILES: C=CCn1c(=O)c2cnc(Nc3ccc(N4CCC5(CCN(C(C)=O)CC5)CC4)cc3)nc2n1-c1cccc(C(C)(C)O)n1] | 6-((4-(9-acetyl-3,9-diazaspiro[5.5]undecan-3-yl)phenyl)amino)-2-allyl-1-(6-(2-hydroxypropan-2-yl)pyridin-2-yl)-1H-pyrazolo[3,4-d]pyrimidin-3(2H)-one |
| 31 | 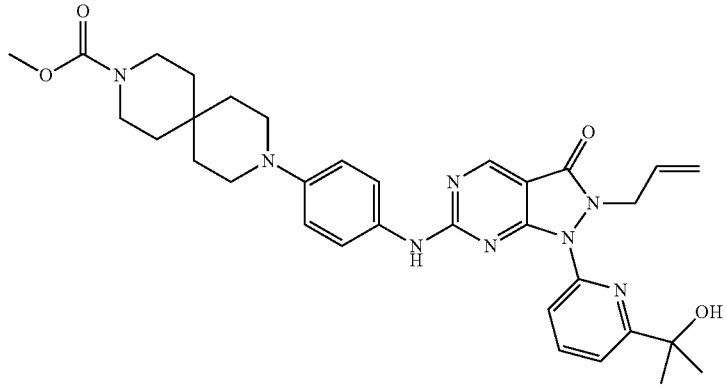 [SMILES: C=CCn1c(=O)c2cnc(Nc3ccc(N4CCC5(CCN(C(=O)OC)CC5)CC4)cc3)nc2n1-c1cccc(C(C)(C)O)n1] | methyl-9-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)-3,9-diazaspiro[5.5]undecan-3-ethyl carboxylate |
| 32 | 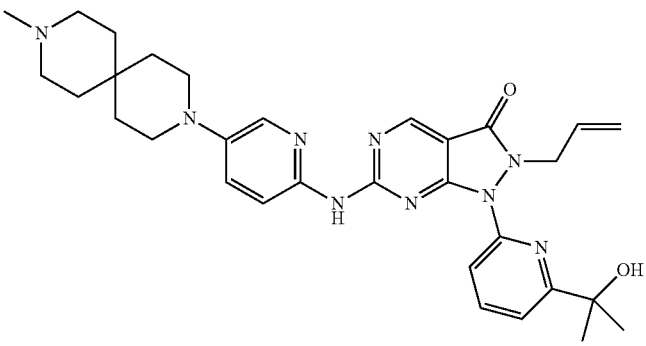 [SMILES: C=CCn1c(=O)c2cnc(Nc3ccc(N4CCC5(CCN(C)CC5)CC4)cn3)nc2n1-c1cccc(C(C)(C)O)n1] | 2-allyl-1-(6-(2-hydroxypropan-2-yl)pyridin-2-yl)-6-((4-(9-methyl-3,9-diazaspiro[5.5]undecan-3-yl)pyridin-2-yl)amino)-1H-pyrazolo[3,4-d]pyrimidin-3(2H)-one |

-continued

| Number | formula | Chemical name |
|---|---|---|
| 33 | 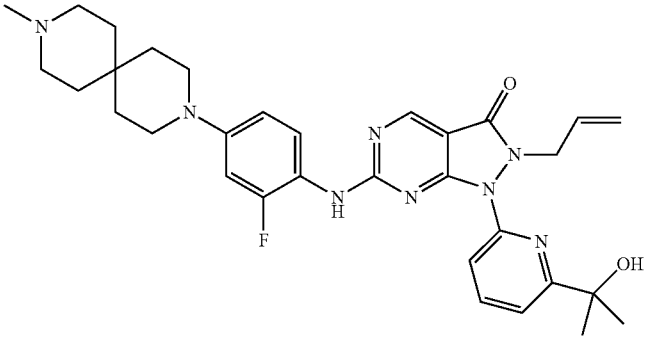 | 2-allyl-6-((2-fluoro-4-(9-methyl-3,9-diazaspiro[5.5]undecan-3-yl)phenyl)amino)-1-(6-(2-hydroxypropan-2-yl)pyridin-2-yl)-1H-pyrazolo[3,4-d]pyrimidin-3(2H)-one |
| 34 | 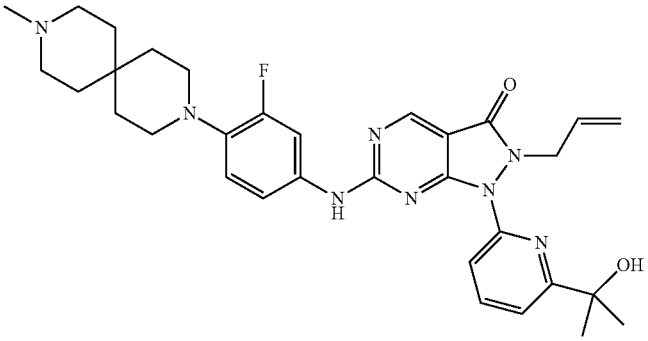 [SMILES: C=CCn1c(=O)c2cnc(Nc3ccc(N4CCC5(CCN(C)CC5)CC4)c(F)c3)nc2n1-c1cccc(C(C)(C)O)n1] | 2-allyl-6-((3-fluoro-4-(9-methyl-3,9-diazaspiro[5.5]undecan-3-yl)phenyl)amino)-1-(6-(2-hydroxypropan-2-yl)pyridin-2-yl)-1H-pyrazolo[3,4-d]pyrimidin-3(2H)-one |
| 35 | 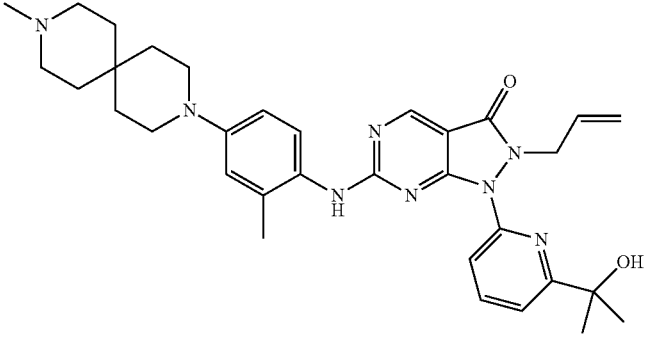 [SMILES: C=CCn1c(=O)c2cnc(Nc3ccc(N4CCC5(CCN(C)CC5)CC4)cc3C)nc2n1-c1cccc(C(C)(C)O)n1] | 2-allyl-1-(6-(2-hydroxypropan-2-yl)pyridin-2-yl)-6-((2-methyl-4-(9-methyl-3,9-diazaspiro[5.5]undecan-3-yl)phenyl)amino)-1H-pyrazolo[3,4-d]pyrimidine-3(2H)-one |
| 36 | 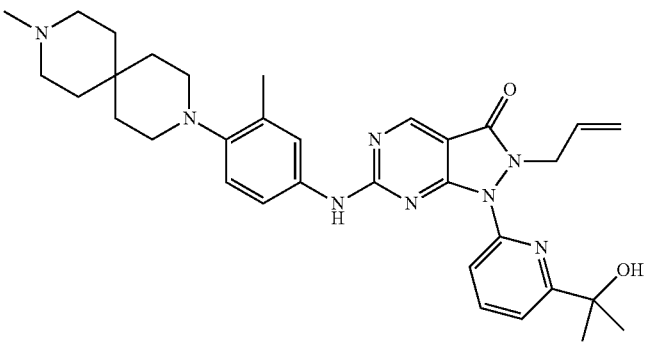 [SMILES: C=CCn1c(=O)c2cnc(Nc3ccc(N4CCC5(CCN(C)CC5)CC4)c(C)c3)nc2n1-c1cccc(C(C)(C)O)n1] | 2-allyl-1-(6-(2-hydroxypropan-2-yl)pyridin-2-yl)-6-((3-methyl-4-(9-methyl-3,9-diazaspiro[5.5]undecan-3-yl)phenyl)amino)-1H-pyrazolo[3,4-d]pyrimidine-3(2H)-one |

| Number | formula | Chemical name |
|---|---|---|
| 37 | 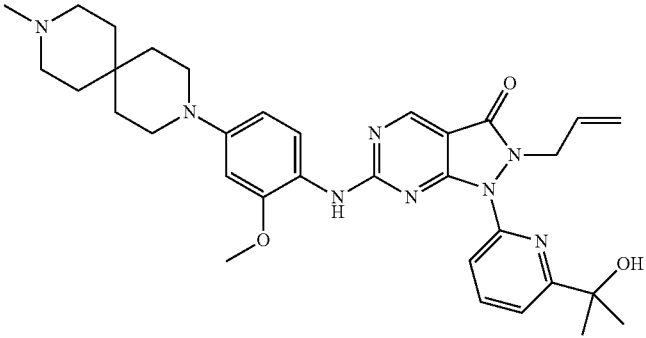 [SMILES: C=CCn1c(=O)c2cnc(Nc3ccc(N4CCC5(CCN(C)CC5)CC4)cc3OC)nc2n1-c1cccc(C(C)(C)O)n1] | 2-allyl-1-(6-(2-hydroxypropan-2-yl)pyridin-2-yl)-6((2-methoxy-4-(9-methyl-3,9-diazaspiro[5.5]undecan-3-yl)phenyl)amino)-1H-pyrazolo[3,4-d]pyrimidin-3(2H)-one |
| 38 | 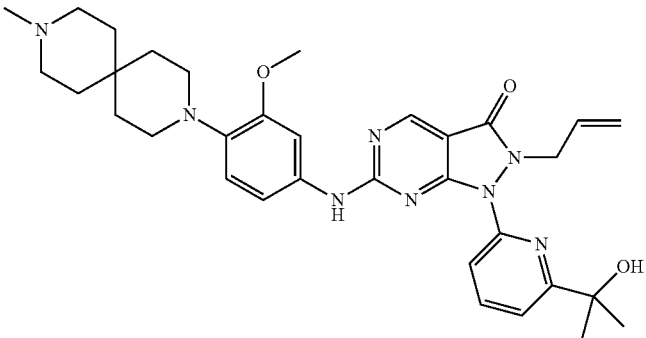 [SMILES: C=CCn1c(=O)c2cnc(Nc3ccc(N4CCC5(CCN(C)CC5)CC4)c(OC)c3)nc2n1-c1cccc(C(C)(C)O)n1] | 2-allyl-1-(6-(2-hdyroxypropan-2-yl)pyridin-2-yl)-6((3-methoxy-4-(9-methyl-3,9-diazaspiro[5.5]undecan-3-yl)phenyl)amino)-1H-pyrazolo[3,4-d]pyrimidine-3(2H)-one |
| 39 | 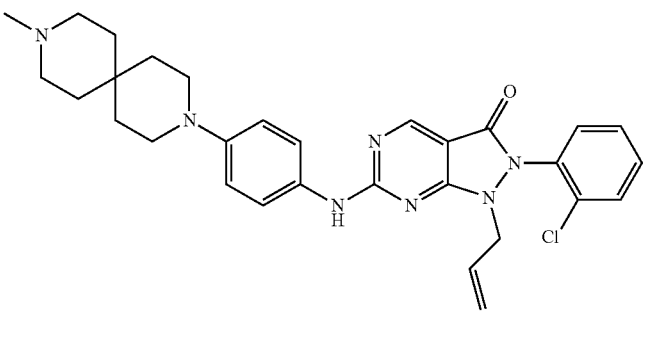 [SMILES: C=CCn1c2nc(Nc3ccc(N4CCC5(CCN(C)CC5)CC4)cc3)ncc2c(=O)n1-c1ccccc1Cl] | 1-allyl-2-(2-fluorophenyl)-6-((4-(9-methyl-3,9-diazaspiro[5.5]undecan-3-yl)phenyl)amino)-1H-pyrazolo[3,4-d]pyrimidin-3(2H)-one |
| 40 | 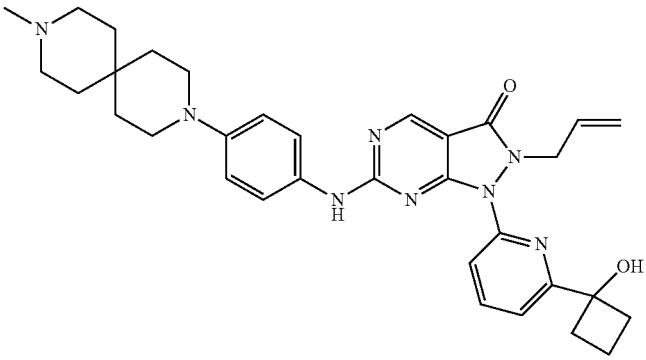 [SMILES: C=CCn1c(=O)c2cnc(Nc3ccc(N4CCC5(CCN(C)CC5)CC4)cc3)nc2n1-c1cccc(C2(O)CCC2)n1] | 2-allyl-1-(6-(1-hydroxycyclobutyl)pyridin-2-yl)-6-((4-(9-methyl-3,9-diazaspiro[5.5]undecan-3-yl)phenyl)amino)-1H-pyrazolo[3,4-d]pyrimidin-3(2H)-one |

-continued

| Number | formula | Chemical name |
|---|---|---|
| 41 | 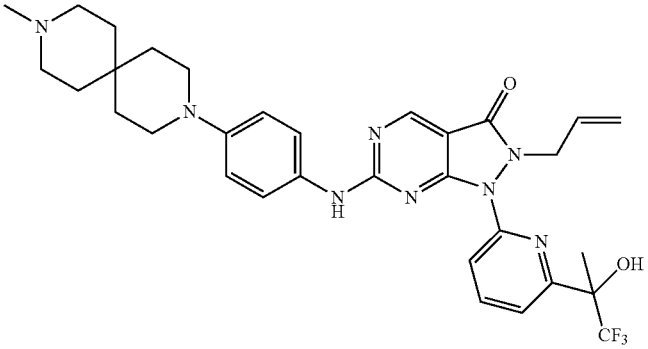 [SMILES: C=CCn1c(=O)c2cnc(Nc3ccc(N4CCC5(CCN(C)CC5)CC4)cc3)nc2n1-c1cccc(C(C)(O)C(F)(F)F)n1] | 2-allyl-6-((4-(9-methyl-3,9-diazaspiro[5.5]undecan-3-yl)phenyl)amino)-1-(6-(1,1,1-trifluoro-2-hydroxypropan-2-yl)pyridin-2-yl)-1H-pyrazolo[3,4-d]pyrimidin-3(2H)-one |
| 42 | 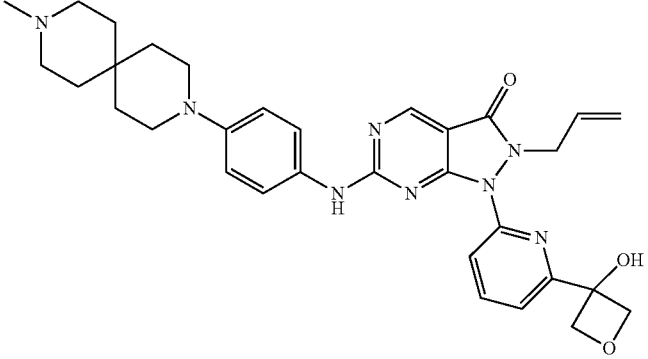 [SMILES: C=CCn1c(=O)c2cnc(Nc3ccc(N4CCC5(CCN(C)CC5)CC4)cc3)nc2n1-c1cccc(C2(O)COC2)n1] | 2-allyl-1-(6-(3-hydroxyoxetan-3-yl)pyridin-2-yl)-6-((4-(9-methyl-3,9-diazaspiro[5.5]undecan-3-yl)phenyl)amino)-1H-pyrazolo[3,4-d]pyrimidin-3(2H)-one |
| 43 | 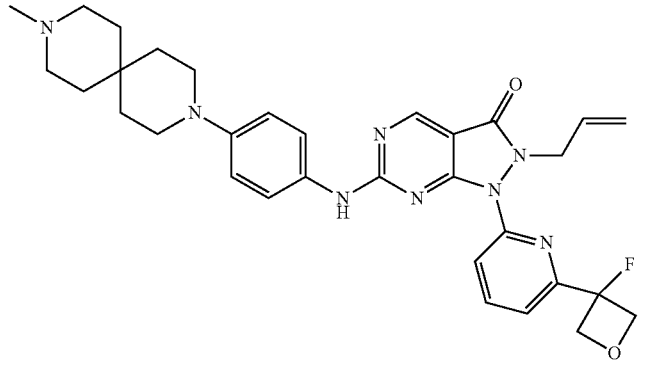 [SMILES: C=CCn1c(=O)c2cnc(Nc3ccc(N4CCC5(CCN(C)CC5)CC4)cc3)nc2n1-c1cccc(C2(F)COC2)n1] | 2-allyl-1-(6-(3-fluorooxetan-3-yl)pyridin-2-yl)-6-((4-(9-methyl-3,9-diazaspiro[5.5]undecan-3-yl)phenyl)amino)-1H-pyrazolo[3,4-d]pyrimidin-3(2H)-one |
| 44 | 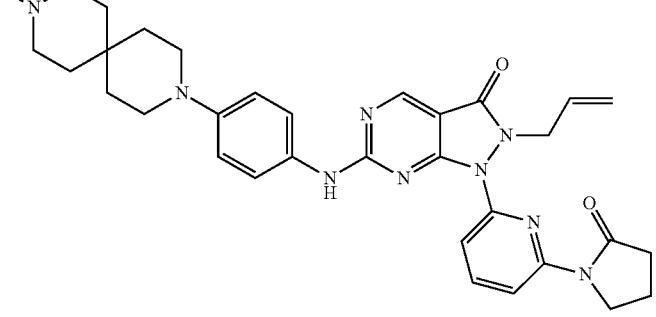 | 2-allyl-6-((4-(9-methyl-3,9-diazaspiro[5.5]undecan-3-yl)phenyl)amino)-1-(6-(2-pyrrolidin-1-yl)pyridin-2-yl)-1H-pyrazolo[3,4-d]pyrimidin-3(2H)-one |

| Number | formula | Chemical name |
|---|---|---|
| 45 | 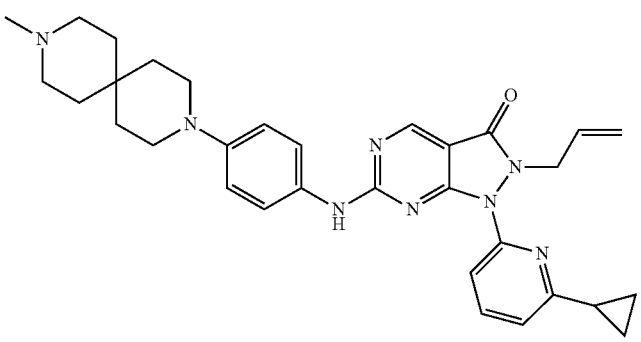 [SMILES: C=CCn1c(=O)c2cnc(Nc3ccc(N4CCC5(CCN(C)CC5)CC4)cc3)nc2n1-c1cccc(C2CC2)n1] | 2-allyl-1-(6-cyclopropylpyridin-2-yl)-6-((4-(9-methyl-3,9-diazaspiro[5.5]undecan-3-yl)phenyl)amino)-1H-pyrazolo[3,4-d]pyrimidin-3(2H)-one |
| 46 | 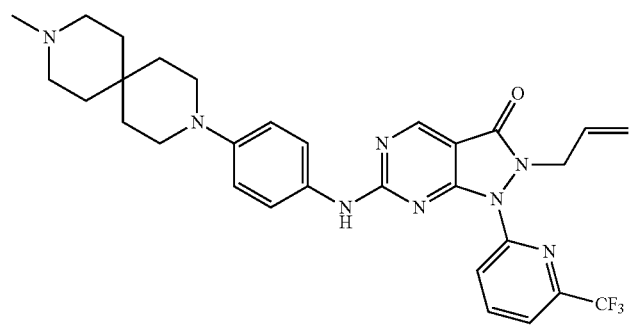 | 2-allyl-6-((4-(9-methyl-3,9-diazaspiro[5.5]undecane-3-yl)phenyl)amino)-1-(6-(trifluoromethyl)pyridin-2-yl)-1H-pyrazolo[3,4-d]pyrimidine-3(2H)-one |
| 47 | 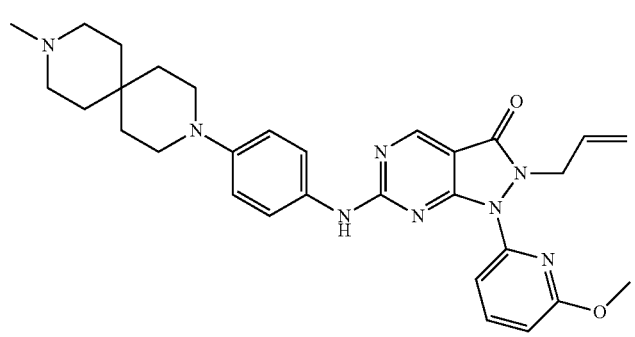 | 2-allyl-1-(6-methoxypyridin-2-yl)-6-((4-(9-methyl-3,9-diazaspiro[5.5]undecan-3-yl)phenyl)amino)-1H-pyrazolo[3,4-d]pyrimidin-3(2H)-one |
| 48 | 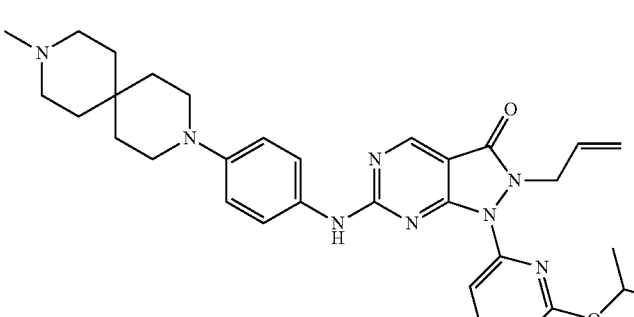 | 2-allyl-1-(6-isopropoxypyridin-2-yl)-6-((4-(9-methyl-3,9-diazaspiro[5.5]undecan-3-yl)phenyl)amino)-1H-pyrazolo[3,4-d]pyrimidin-3(2H)-one |

-continued

| Number | formula | Chemical name |
|---|---|---|
| 49 | 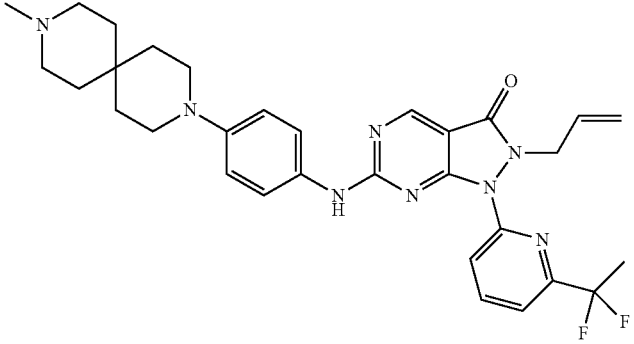 [SMILES: C=CCn1c(=O)c2cnc(Nc3ccc(N4CCC5(CCN(C)CC5)CC4)cc3)nc2n1-c1cccc(C(C)(F)F)n1] | 2-allyl-1-(6-(1,1-difluoroethyl)pyridin-2-yl)-6-((4-(9-methyl-3,9-diazaspiro[5.5]undecan-3-yl)phenyl)amino)-1H-pyrazolo[3,4-d]pyrimidin-3(2H)-one |
| 50 | 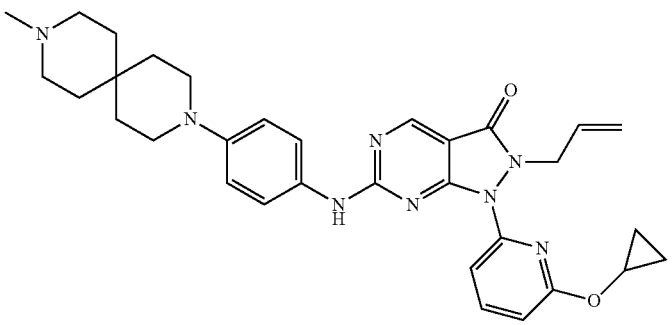 [SMILES: C=CCn1c(=O)c2cnc(Nc3ccc(N4CCC5(CCN(C)CC5)CC4)cc3)nc2n1-c1cccc(OC2CC2)n1] | 2-allyl-1-(6-cyclopropoxypyridin-2-yl)-6-((4-(9-methyl-3,9-diazaspiro[5.5]undecan-3-yl)phenyl)amino)-1H-pyrazolo[3,4-d]pyrimidin-3(2H)-one |
| 51 | 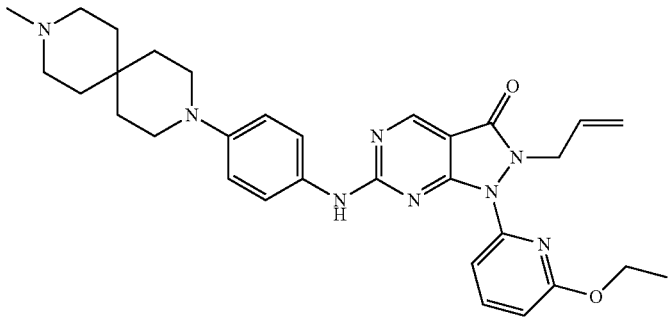 [SMILES: C=CCn1c(=O)c2cnc(Nc3ccc(N4CCC5(CCN(C)CC5)CC4)cc3)nc2n1-c1cccc(OCC)n1] | 2-allyl-1-(6-ethoxypyridin-2-yl)-6-((4-(9-methyl-3,9-diazaspiro[5.5]undecan-3-yl)phenyl)amino)-1H-pyrazolo[3,4-d]pyrimidin-3(2H)-one |
| 52 | 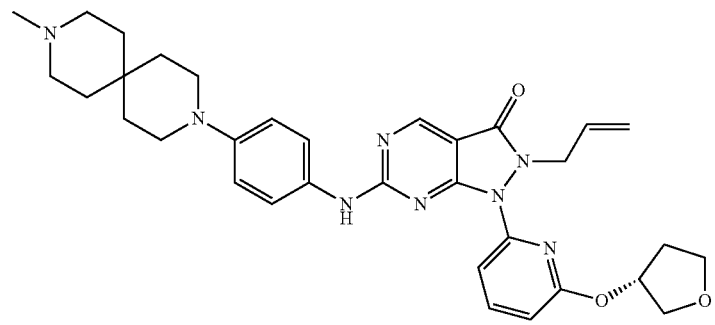 [SMILES: C=CCn1c(=O)c2cnc(Nc3ccc(N4CCC5(CCN(C)CC5)CC4)cc3)nc2n1-c1cccc(O[C@@H]2CCOC2)n1] | (R)-2-allyl-6-((4(9-methyl-3,9-diazaspiro[5.5]undecan-3-yl)phenyl)amino)-1-(6-(((tetrahydrofuran-3-yl)oxy)pyridin-2-yl)-1H-pyrazolo[3,4-d]pyrimidin-3(2H)-one |

| Number | formula | Chemical name |
|---|---|---|
| 53 | 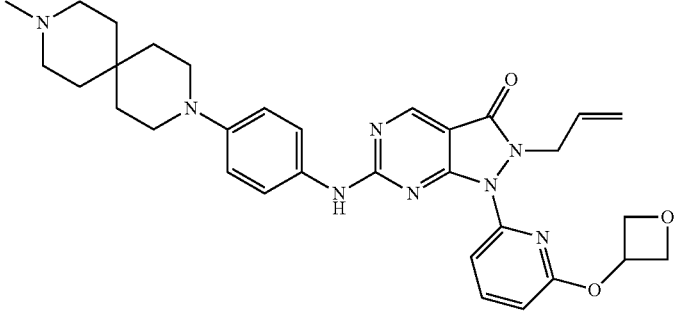 [SMILES: C=CCn1c(=O)c2cnc(Nc3ccc(N4CCC5(CCN(C)CC5)CC4)cc3)nc2n1-c1cccc(OC2COC2)n1] | 2-allyl-6-((4(9-methyl-3,9-diazaspiro[5.5]undecan-3-yl)phenyl)amino)-1-(6-(oxetan-3-yloxy)pyridin-2-yl)-1H-pyrazolo[3,4-d]pyrimidin-3(2H)-one |
| 54 | 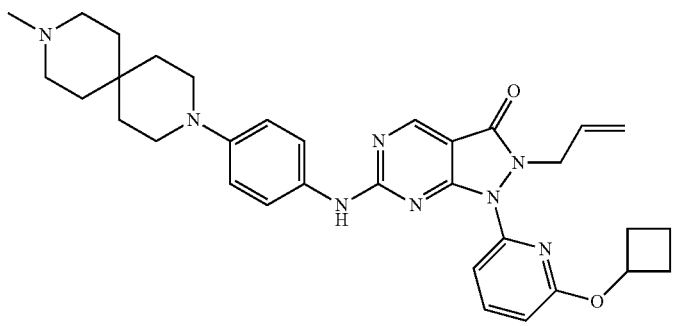 [SMILES: C=CCn1c(=O)c2cnc(Nc3ccc(N4CCC5(CCN(C)CC5)CC4)cc3)nc2n1-c1cccc(OC2CCC2)n1] | 2-allyl-1-(6-cyclobutoxypyridin-2-yl)-6-((4-(9-methyl-3,9-diazaspiro[5.5]undecan-3-yl)phenyl)amino)-1H-pyrazolo[3,4-d]pyrimidin-3(2H)-one |
| 55 | 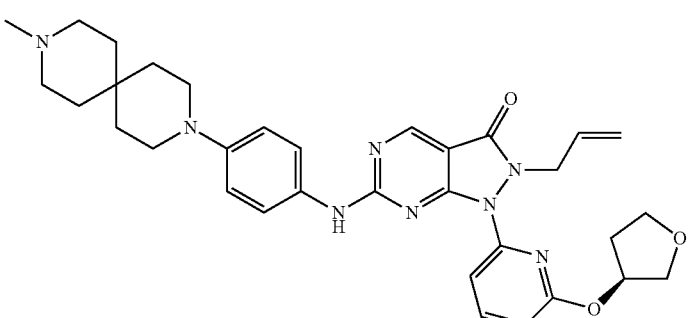 | (S)-2-allyl-6-((4(9-methyl-3,9-diazaspiro[5.5]undecan-3-yl)phenyl)amino)-1-(6-((tetrahydrofuran-3-yl)oxy)pyridin-2-yl)-1H-pyrazolo[3,4-d]pyrimidin-3(2H)-one |
| 56 | 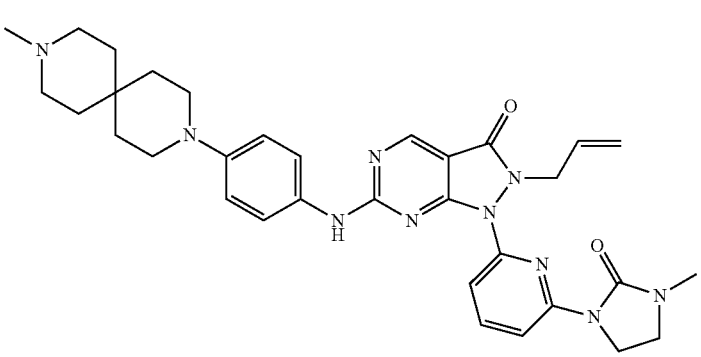 | 2-allyl-1-(6-(3-methyl-2-oxo-1-imidazolidinyl)pyridin-2-yl)-(6-((4(9-methyl-3,9-diazaspiro[5.5]undecane-3-yl)phenyl)amino)-1-hydro-pyrazolo[3,4-d]pyrimidine-3(2H)-one |

| Number | formula | Chemical name |
|---|---|---|
| 57 | 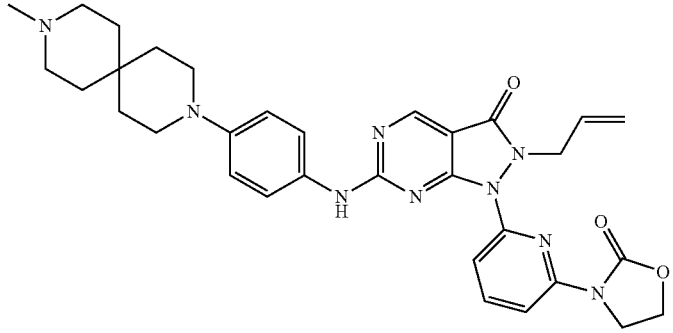 [SMILES: C=CCn1c(=O)c2cnc(Nc3ccc(N4CCC5(CCN(C)CC5)CC4)cc3)nc2n1-c1cccc(N2CCOC2=O)n1] | 3-(6-(2-allyl-6((4-(9-methyl-3,9-diazaspiro[5.5]undecan-3-yl)phenyl)amino)-3-oxo-2,3-dihydro-1H-pyrazolo[3,4-d]pyrimidin-1-yl)pyridin-2-yl)oxazolidin-2one |
| 58 | 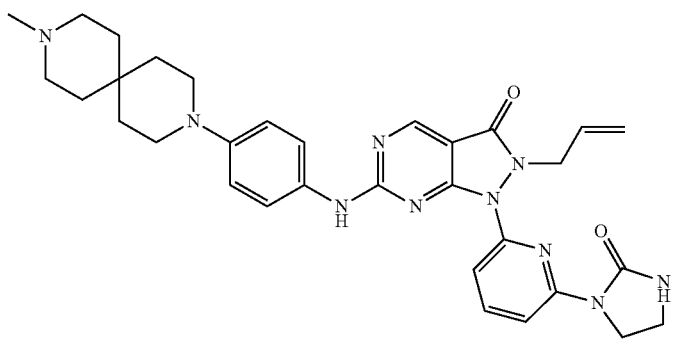 [SMILES: C=CCn1c(=O)c2cnc(Nc3ccc(N4CCC5(CCN(C)CC5)CC4)cc3)nc2n1-c1cccc(N2CCNC2=O)n1] | 2-allyl-6-((4(9-methyl-3,9-diazaspiro[5.5]undecan-3-yl)phenyl)amino)-1-(6-(2-oxo-1-imidazolidinyl)pyridin-2-yl)-1H-pyrazolo[3,4-d]pyrimidin-3(2H)-one |
| 59 | 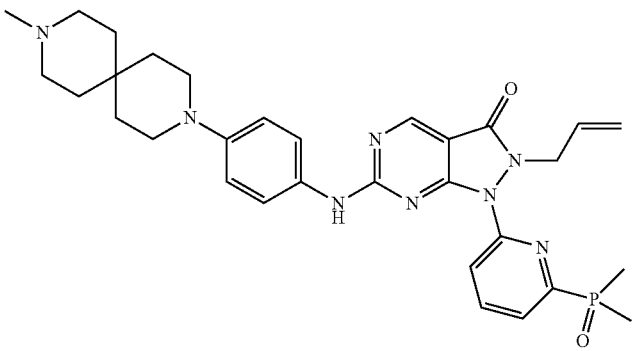 | 2-allyl-1-(6-(dimethylphosphory)pyridin-2-yl)-6-((4-(9-methyl-3,9-diazaspiro[5.5]undecan-3-yl)phenyl)amino)-1H-pyrazolo[3,4-d]pyrimidin-3(2H)-one |
| 60 | 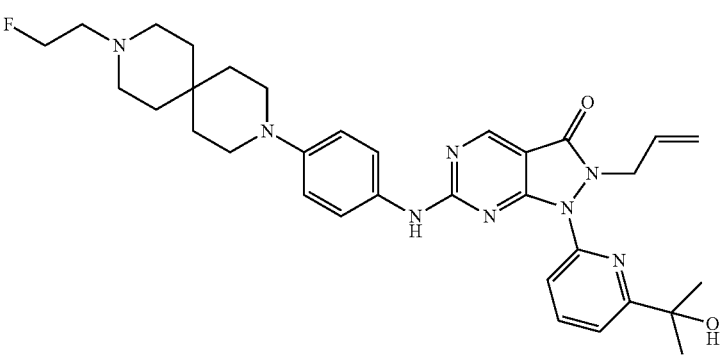 [SMILES: C=CCn1c(=O)c2cnc(Nc3ccc(N4CCC5(CCN(CCF)CC5)CC4)cc3)nc2n1-c1cccc(C(C)(C)O)n1] | 2-allyl-6-((4-(2-fluoroethyl)-3,9-diazaspiro[5.5]undecan-3-yl)phenyl)amino)-1-(6-(2-hydroxypropan-2-yl)pyridin-2-yl)-1H-pyrazolo[3,4-d]pyrimidin-3(2H)-one |

| Number | formula | Chemical name |
|---|---|---|
| 61 | 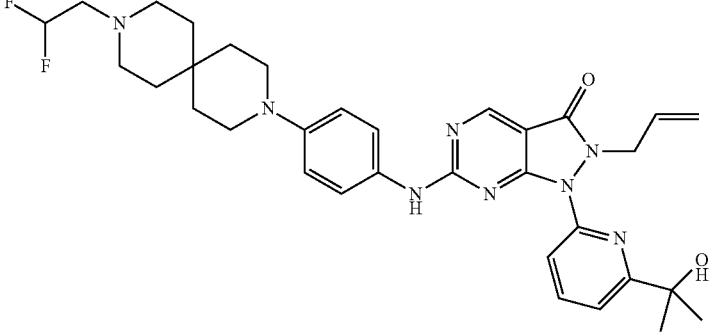 | 2-allyl-6-((4-(9-(2,2-difluoroethyl-3,9-diazaspiro[5.5]undecan-3-yl)phenyl)amino)-1-(6-(2-hydroxypropan-2-yl)pyridin-2-yl)-1H-pyrazolo[3,4-d]pyrimidin-3(2H)-one |
| 62 | 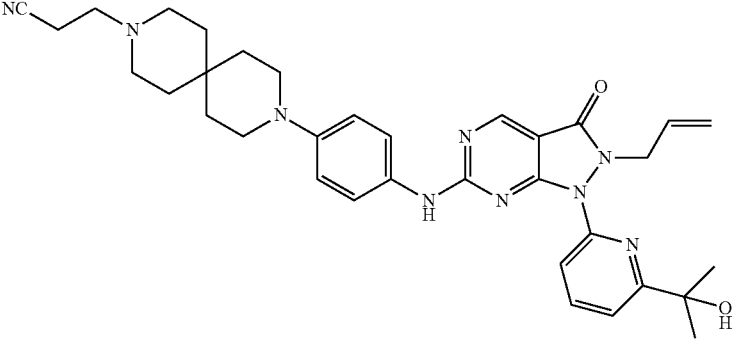 [SMILES: C=CCn1c(=O)c2cnc(Nc3ccc(N4CCC5(CCN(CCC#N)CC5)CC4)cc3)nc2n1-c1cccc(C(C)(C)O)n1] | 3-(9-(4((2-allyl-1(6-(2-hydroxypropan-2-yl)pyridin-2-yl)-3-oxo-2,3-dihydro-1H-pyrazolo[3,4-d]pyrimidin-6-yl)amino)phenyl)-3,9-diazaspiro[5.5]undecan-3-yl)propionitrile |
| 63 | 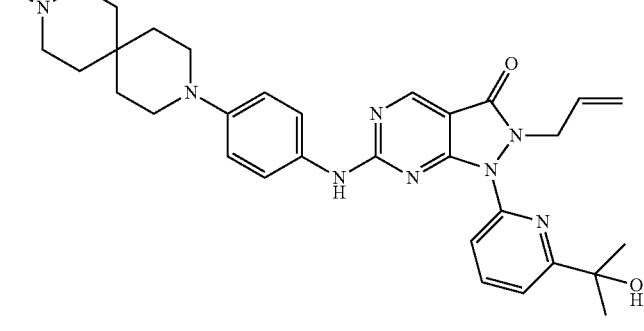 | 2-(9-(4((2-allyl-1(6-(2-hydroxypropan-2-yl)pyridin-2-yl)-3-oxo-2,3-dihydro-1H-pyrazolo[3,4-d]pyrimidin-6-yl)amino)phenyl)-3,9-diazaspiro[5.5]undecan-3-yl)acetonitrile |
| 64 | 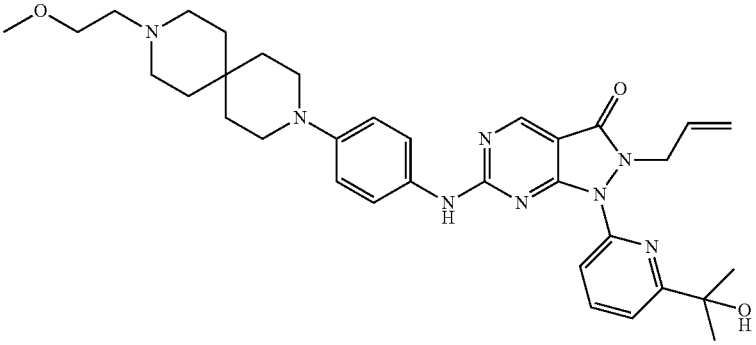 [SMILES: C=CCn1c(=O)c2cnc(Nc3ccc(N4CCC5(CCN(CCOC)CC5)CC4)cc3)nc2n1-c1cccc(C(C)(C)O)n1] | 2-allyl-1-(6-(2-hydroxypropan-2-yl)pyridin-2-yl)-6-((4-(9-(2-methoxylethyl)-3,9-diazaspiro[5.5]undecan-3-yl)phenyl)amino)-1H-pyrazolo[3,4-d]pyrimidin-3(2H)-one |

| Number | formula | Chemical name |
|---|---|---|
| 65 | 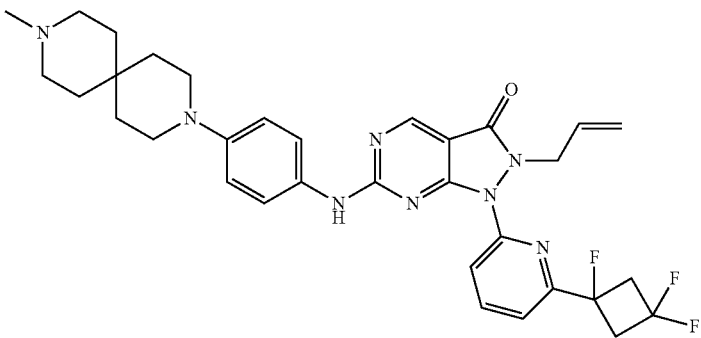 [SMILES: C=CCn1c(=O)c2cnc(Nc3ccc(N4CCC5(CCN(C)CC5)CC4)cc3)nc2n1-c1cccc(C2(F)CC(F)(F)C2)n1] | 2-allyl-6-((4-(9-methyl-3,9-diazaspiro[5.5]undecan-3-yl)phenyl)amino)-1-(6-(1,3,3-trifluorocyclobutyl)pyridin-2-yl)-1H-pyrazolo[3,4-d]pyrimidin-3(2H)-one |
| 66 | 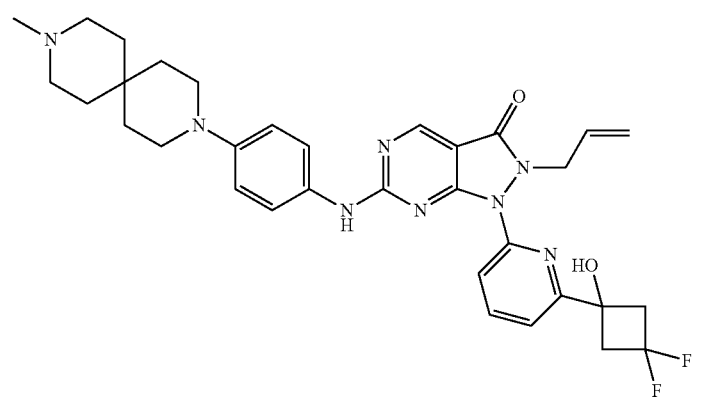 [SMILES: C=CCn1c(=O)c2cnc(Nc3ccc(N4CCC5(CCN(C)CC5)CC4)cc3)nc2n1-c1cccc(C2(O)CC(F)(F)C2)n1] | 2-allyl-1-(6-(3,3-difluoro-1-hydroxycyclobutyl)pyridin-2-yl)-6-((4-(9-methyl-3,9-diazaspiro[5.5]undecan-3-yl)phenyl)amino)-1H-pyrazolo[3,4-d]pyrimidin-3(2H)-one |
| 67 | 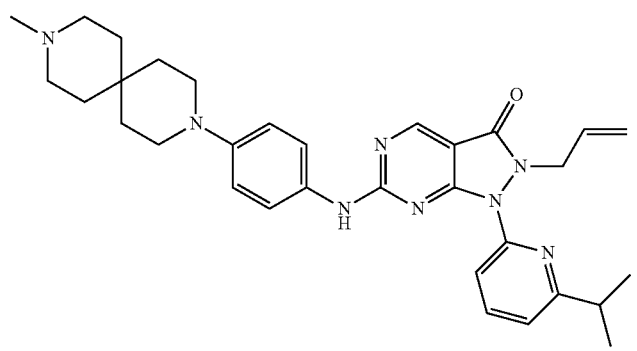 [SMILES: C=CCn1c(=O)c2cnc(Nc3ccc(N4CCC5(CCN(C)CC5)CC4)cc3)nc2n1-c1cccc(C(C)C)n1] | 2-allyl-1-(6-(isopropylpyridin-2-yl)-6-((4-(9-methyl-3,9-diazaspiro[5.5]undecan-3-yl)phenyl)amino)-1H-pyrazolo[3,4-d]pyrimidin-3(2H)-one |
| 68 | 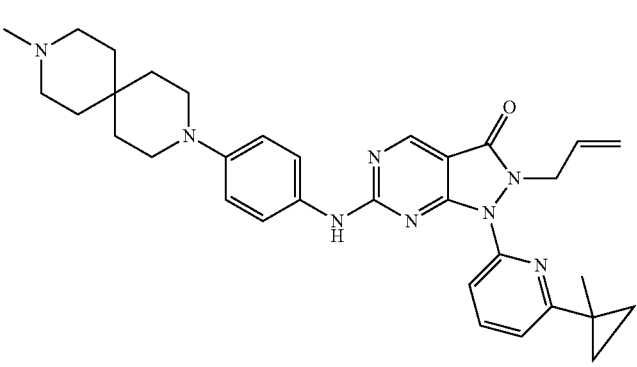 [SMILES: C=CCn1c(=O)c2cnc(Nc3ccc(N4CCC5(CCN(C)CC5)CC4)cc3)nc2n1-c1cccc(C2(C)CC2)n1] | 2-allyl-6-((4-(9-methyl-3,9-diazaspiro[5.5]undecan-3-yl)phenyl)amino)-1-(6-(1-methylcyclopropyl)pyridin-2-yl)-1H-pyrazolo[3,4-d]pyrimidin-3(2H)-one |

-continued

| Number | formula | Chemical name |
|---|---|---|
| 69 | | 2-allyl-1-(6-(2-hydroxypropan-2-yl)pyridin-2-yl)-6-((4-(9-(3-oxetanyl)-3,9-diazaspiro[5.5]undecan-3-yl)phenyl)amino)-1-(6-(2-hydroxypropan-2-yl)pyridin-2-yl)-1H-pyrazolo[3,4-d]pyrimidin-3(2H)-one |
| 70 | | methyl-9-(4-((2-allyl-1-(6-(dimethylaminoformyl)pyridin-2-yl)-3-oxo-2,3-dihydro-1H-pyrazolo[3,4-d]pyrimidin-6-yl)amino)phenyl)-3,9-diazaspiro[5.5]undecan-3-carboxylate |
| 71 | | methyl-9-(4-((2-allyl-1-(6-(3-hydroxyoxetan-3-yl)pyridin-2-yl)-3-oxo-2,3-dihydro-1H-pyrazolo[3,4-d]pyrimidin-6-yl)amino)phenyl)-3,9-diazaspiro[5.5]undecan-3-carboxylate |
| 72 | | 2-allyl-1-(6-(3,3-difluoroazetidin-1-yl)pyridin-2-yl)-6-(((4-(9-methyl-3,9-diazaspiro[5.5]undecan-3-yl)phenyl)amino)-1H-pyrazolo[4,3-c]]pyrimidin-3(2H)-one |

-continued

| Number | formula | Chemical name |
|---|---|---|
| 73 | | 2-allyl-1-(6-(3-methoxyoxetan-3-yl)pyridin-2-yl)-6-((4-(9-methyl-3,9-diazaspiro[5.5]undecan-3-yl)phenyl)amino)-1H-pyrazolo[3,4-d]pyrimidin-3(2H)-one |
| 74 | | (R)-2-allyl-6-((4-(9-methyl-3,9-diazaspiro[5.5]undecan-3-yl)phenyl)amino)-1-(6-(1,1,1-trifluoro-2-hydroxypropan-2-yl)pyridin-2-yl)-1H-pyrazolo[3,4-d]pyrimidin-3(2H)-one |
| 75 | | (S)-2-allyl-6-((4-(9-methyl-3,9-diazaspiro[5.5]undecan-3-yl)phenyl)amino)-1-(6-(1,1,1-trifluoro-2-hydroxypropan-2-yl)pyridin-2-yl)-1H-pyrazolo[3,4-d]pyrimidin-3(2H)-one |
| 76 | | 6-((4-(-3,9-diazaspiro[5.5]undecan-3-yl)phenyl)amino)-2-allyl-1-(6-(2-hydroxypropan-2-yl)pyridin-2-yl)-1H-pyrazolo[3,4-d]pyrimidin-3(2H)-one |

-continued

| Number | formula | Chemical name |
|---|---|---|
| 77 | 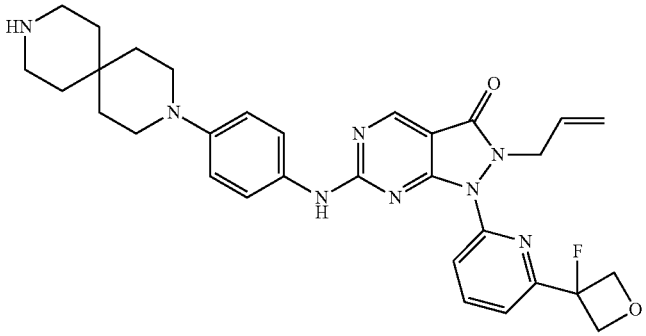 [SMILES: C=CCn1c(=O)c2cnc(Nc3ccc(N4CCC5(CCNCC5)CC4)cc3)nc2n1-c1cccc(C2(F)COC2)n1] | 6-((4-(-3,9-diazaspiro[5.5]undecan-3-yl)phenyl)amino)-2-allyl-1-(6-(3-fluoro-oxetan-3-yl)pyridin-2-yl)-1H-pyrazolo[3,4-d]pyrimidin-3(2H)-one |
| 78 | 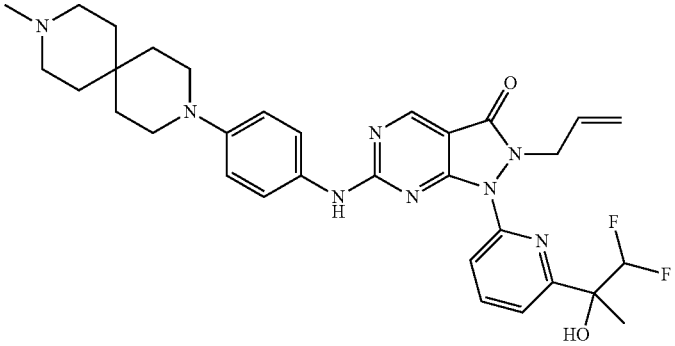 [SMILES: C=CCn1c(=O)c2cnc(Nc3ccc(N4CCC5(CCN(C)CC5)CC4)cc3)nc2n1-c1cccc(C(C)(O)C(F)F)n1] | 2-allyl-1-(6-(1,1-difluoro-2-hydroxypropan-2-yl)pyridin-2-yl)-6-((4-(9-methyl-3,9-diazaspiro[5.5]undecan-3-yl)phenyl)amino)-1H-pyrazolo[3,4-d]pyrimidin-3(2H)-one |
| 79 | 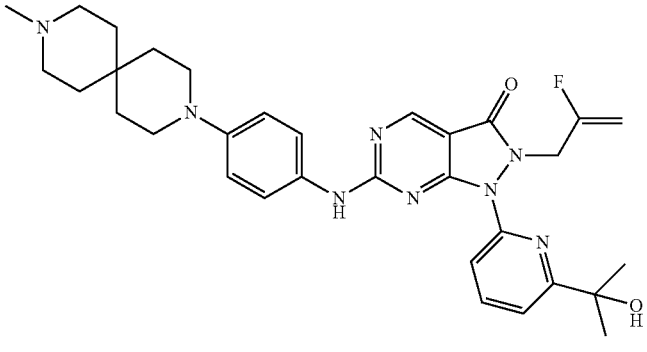 [SMILES: C=C(F)Cn1c(=O)c2cnc(Nc3ccc(N4CCC5(CCN(C)CC5)CC4)cc3)nc2n1-c1cccc(C(C)(C)O)n1] | 2-(2-fluoroallyl)-1-(6-(2-hydroxypropan-2-yl)pyridin-2-yl)-6-((4-(9-methyl-3,9-diazaspiro[5.5]undecan-3-yl)phenyl)amino)-1H-pyrazolo[3,4-d]pyrimidin-3(2H)-one |
| 80 | 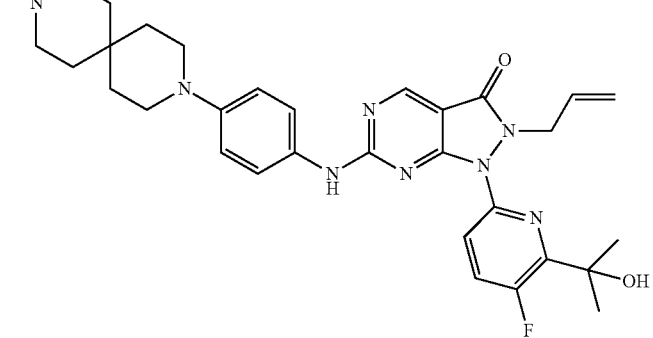 | 2-allyl-1-(5-fluoro-6-(2-hydroxypropan-2-yl)pyridin-2-yl)-6-((4-(9-methyl-3,9-diazaspiro[5.5]undecan-3-yl)phenyl)amino)-1H-pyrazolo[3,4-d]pyrimidin-3(2H)-one |

Some embodiments of the present invention are arbitrary combination of the variants defined above.

The present invention also provides the use of the compound or the pharmaceutically acceptable salt thereof in manufacturing a medicament for treating Wee1 related diseases.

Technical Effect:

As a novel Wee1 inhibitor, the compound of the present invention has a good inhibitory effect on Wee1 kinase; in terms of pharmacokinetics, a number of pharmacokinetics indexes are significantly improved, wherein the clearance rate in vivo, half-life period, and integral of concentration in vivo are all have significant advantages; the distribution in vivo is also significantly improved; the solubility of the compound is greatly improved; the activity of hERG is decreased, and the safety is higher.

Definitions and Descriptions

Unless otherwise indicated, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., "*Pharmaceutical Salts*", *Journal of Pharmaceutical Science* 66: 1-19 (1977)). Certain specific compounds of the present invention contain both basic and acidic functional groups and can be converted to any base or acid addition salt.

Preferably, through bringing the salt into contact with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound of the present invention, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the present invention can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided by the present invention also exists in prodrug form. The prodrug of the compound described herein is the compound that readily undergoes chemical change under physiological condition to be converted into the compound of the present invention. Additionally, the prodrug can be converted to the compound of the present invention by a chemical or biochemical method in vivo environment.

Certain compounds of the present invention can exist in an unsolvated form or a solvated form, including a hydrated form. Generally, the solvated form is equivalent to the unsolvated form, and both are encompassed within the scope of the present invention.

Certain compounds of the present invention can have an asymmetric carbon atom (optical center) or a double bond. The racemate, diastereomer, geometric isomer and individual isomer are all encompassed within the scope of the present invention.

Unless otherwise specified, a wedged bond and a dashed bond ( ◢ ╲╲╲ ) are used to indicate the absolute configuration of a stereogenic center, ◢ and ╲╲╲ are used to indicate the relative configuration of a stereogenic center. When the compound described herein contains an olefinic double bond or other geometric asymmetric centers, E and Z geometric isomers are included unless otherwise specified. Likewise, all tautomeric forms are encompassed within the scope of the present invention.

The compound of the present invention may present in a specific geometric or stereoisomeric form. The present invention contemplates all such compounds, including cis and trans isomer, (−)- and (+)-enantiomer, R- and (S)-enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Optically active (R)- and (S)-isomer, or D and L isomer can be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (for example, carbamate generated from amine).

The compound of the present invention may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). All isotopic variations of the compound of the present invention, whether radioactive or not, are encompassed within the scope of the present invention.

The term "pharmaceutically acceptable carrier" refers to any agent or carrier medium which is capable of delivering an effective amount of the active substance of the present invention, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field. The additional information about the carrier can be referred to Remington: The Science and Practice of Pharmacy, 21st Ed, Lippincott, Williams & Wilkins (2005), the disclosure of which is incorporated herein by reference.

The term "excipient" generally refers to a carrier, a diluent and/or a medium required for formulating an effective pharmaceutical composition.

For a medicament or a pharmacologically active agent, the term "effective amount" or "therapeutically effective amount" refers to a nontoxic but sufficient amount to achieve a desired effect of the medicament or the agent. For the oral dosage form of the present invention, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled in the art based on routine experiment.

The term "active ingredient", "therapeutic agent", "active substance" or "active agent" refers to a chemical entity which can effectively treat the target disorder, disease or condition.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted by a substituent, including deuterium and hydrogen variants, as long as the valence of the specific atom is normal and the substituted compound is stable. When the substituent is a keto group (i.e. =O), it means two hydrogen atoms are substituted. Positions on an aromatic ring cannot be substituted by a keto group. The term "optionally substituted" means an atom can be substituted by a substituent or not, unless otherwise specified, the species and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variable is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a bond of a substituent can be cross-linked to two atoms on a ring, such substituent can be bonded to any atom on the ring. When an enumerative substituent does not indicate by which atom it is attached to a compound included in the general chemical formula but not specifically mentioned, such substituent can be bonded by any of its atoms. For example, the structural unit

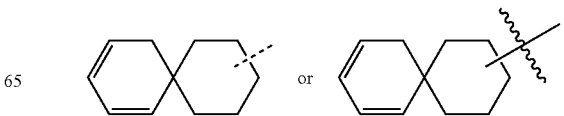

means that it can be substituted at any position on cyclohexyl or cyclohexadiene. When the listed substituents are not indicated through which atom it is attached to the substituted group, such a substituent may be bonded through any atom thereof, for example, a pyridyl group as a substituent may be attached to the substituted group through any one of carbon atoms on the pyridine rings. When there's no indication of the connecting direction for the listed linking group, its connecting direction is arbitrary, for example, the linking group L in

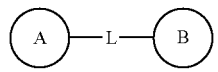

is -M-W-, in this case, -M-W may connect the ring A and ring B in the same direction as the reading order from left to right forming

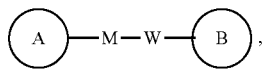, it may also connect the ring A and ring B in the opposite direction as the reading order from left to right forming

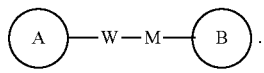.

Combinations of the linking groups, substituents and/or variants thereof are permissible only if such combinations formed a stable compounds.

Unless otherwise specified, the term "hetero" represents a heteroatom or a heteroatom group (e.g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a ring assembly, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclyl" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)p, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)p, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thienyl, thieno-oxazolyl, thieno-thiazolyl, thieno-imidazolyl, thienyl, triazinyl, 1,2,3-triazolyl, 1,2,4-triazolyl, 1,2,5-triazolyl, 1,3,4-triazolyl and xanthenyl. Fused-ring compounds and spiro compounds are also included.

Unless otherwise specified, the term "hydrocarbyl" or its hyponyms (e.g. alkyl, alkenyl, alkynyl, and aryl, etc.), by itself or as part of another substituent, refers to a linear, branched chain or cyclic hydrocarbon radical or any combination thereof. They can be fully saturated (e.g. alkyl), mono- or polyunsaturated (e.g. alkenyl, alkynyl, and aryl), can be mono-, di- or poly-substituted, can be monovalent (e.g. methyl), divalent (e.g. methylene) or multivalent (e.g. methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$ and —CH=CH—N(CH$_3$)—CH$_3$. Up to two consecutive heteroatoms can be present, such as, —CH$_2$—NH—OCH$_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g. heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbonyl, can be mono-substituted (e.g. —CH$_2$F) or poly-substituted (e.g. —CF$_3$), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, hexynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon single bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when combined with other terms (such as aryloxy, arylthio, arylalkyl), the aryl includes the aryl and heteroaryl ring as defined above. Thus, the term "aralkyl" is meant to include the group (e.g. benzyl, phenethyl, pyridylmethyl, etc.) where an aryl is attached to an alkyl, including an alkyl where the carbon atom (e.g. methylene) has been replaced by an atom such as oxygen, for example, phenoxymethyl, 2-pyridyloxy, 3-(1-naphthyloxy) propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present invention can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present invention.

All of the solvents used in the present invention are commercially available. The present invention employs the following abbreviations: aq represents water; HATU represents O-(7-azabenzotriazol-1-yl)-N,N,N',N'-tetramethyluronium hexafluorophosphate; EDC represents N-(3-dimethylaminopropyl)-N-ethylcarbodiimide hydrochloride; m-CPBA represents 3-chloroperoxybenzoic acid; eq represents equivalent or equivalence; CDI represents carbonyl diimidazole; DCM represents dichloromethane; PE represents petroleum ether; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amino protecting group; BOC represents tert-butylcarbonyl, which is an amino protecting group; HOAc represents acetic acid; $NaCNBH_3$ represents sodium cyanoborohydride; r.t. represents room temperature; O/N represents overnight; THF represents tetrahydrofuran; $Boc_2O$ represents di-tert-butyldicarbonate; TFA represents trifluoroacetic acid; DIPEA represents diisopropylethylamine; $SOCl_2$ represents thionyl chloride; $CS_2$ represents carbon disulfide; TsOH represents p-toluenesulfonic acid; NFSI represents N-fluorobenzenesulfonamide; NCS represents N-chlorosuccinimide; n-$Bu_4NF$ represents tetrabutylammonium fluoride; iPrOH represents 2-propanol; mp represents melting point; LDA represents lithium diisopropylamide; CAN represents acetonitrile; FA represents for formic acid; $Pd(dppf)Cl_2$ represents for [1,1'-bis(diphenylphosphino)ferrocene]palladium dichloride; $Pd(PPh_3)_4$ represents for tetrakis(triphenylphosphine)palladium; DIPEA represents for N,N-diisopropylethylamine.

Compounds are named manually or by ChemDraw® software, the commercially available compounds use their vendor directory names.

DETAILED DESCRIPTION OF THE PREFERRED EMBODIMENT

The present invention was described in detail herein by the embodiments, but it's not intended to limit the invention. The present invention has been described in detail herein, also disclosed are the specific embodiments thereof, it's apparent for those skilled in the art that modifications and improvements could be done to the specific embodiments of the present invention without departing form the spirit and scope of the present invention.

Intermediate 1

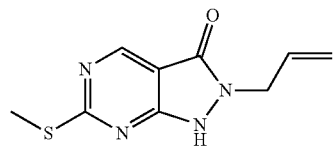

I1

Prepared according to the synthetic method in patent WO2007126122.

Intermediate 2

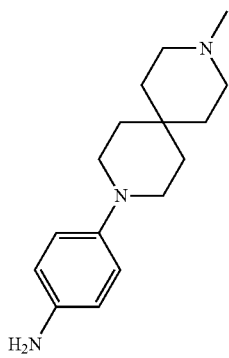

Synthetic Route:

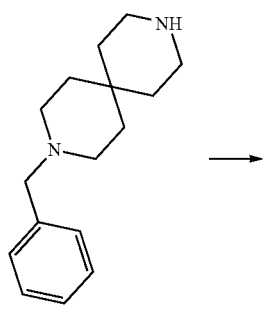

I2-A

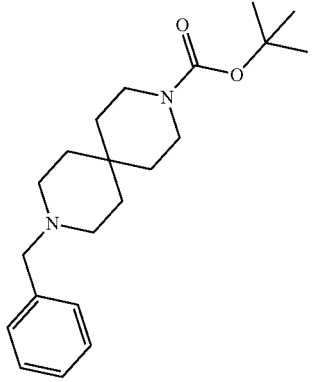

I2-B

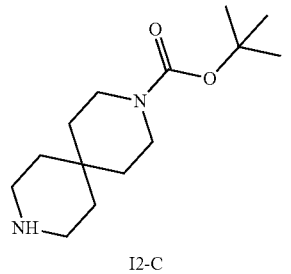

I2-C

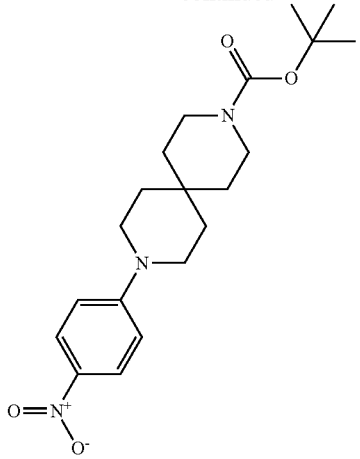

I2-D

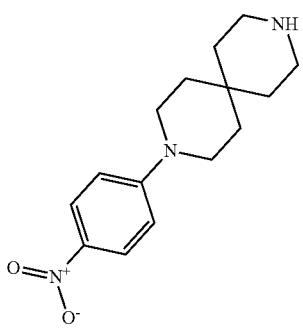

I2-E

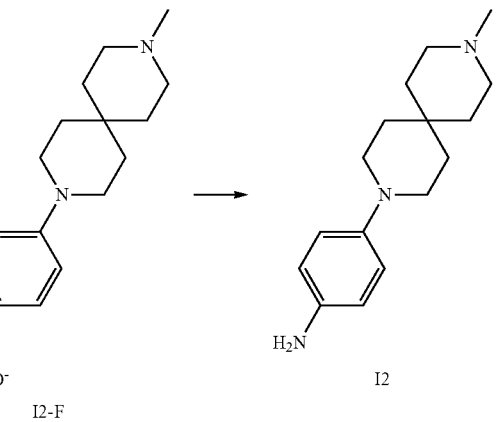

I2-F          I2

Step 1: Synthesis of Compound I2-B

Triethylamine (5.80 g, 57.29 mmol, 7.94 mL) and 4-dimethylaninopyridine (174.97 mg, 1.43 mmol) were slowly added into compound I2-A (3.50 g, 14.32 mmol) and Boc-anhydride (4.69 g, 21.48 mmol, 4.94 mL) in THF solution (40.00 mL) at r.t., the reaction mixture was stirred at 40° C. for 12 hours, then heated to 55° C. and stirred for 18 hours. The crude compound was concentrated up to dryness, purified by silica gel column (PE/EtOAc=6:1, 4:1) to give the compound I2-B. MS m z: 345.5 [M+H]+

Step 2: Synthesis of Compound I2-C

Under argon atmosphere, wet Pd/C (188.05 mg, 159.50 µmol, purity 10%) was added into the compound I2-B in THF solution (1.10 g, 3.19 mmol), after replacing the gas in the flask 3 times with hydrogen, the reaction was stirred at 40° C. for 40 hours under 45 Psi. After completion of the reaction, the solution was filtered through diatomite, the filtrate was concentrated to give the crude compound 12-C. MS m/z: 255.1[M+H]+

Step 3: Synthesis of Compound I2-D

Potassium carbonate (626.92 mg, 4.54 mmol) was added into compound I2C (825.00 mg, 3.24 mmol) and p-fluoronitrobenzene (457.16 mg, 3.24 mmol, 343.73 µL) in dimethyl sulfoxide solution (10.00 mL) at r.t. The reaction mixture was stirred at 120° C. for 2 hours. The reaction mixture was cooled down to r.t. and slowly added dropwise into water (50 mL) while stirring, solid precipitation appeared, then filtered to give the crude compound I2-D. MS m/z: 376.5 [M+H]+

Step 4: Synthesis of Compound I2-E

Trifluoroacetic acid (7.70 g, 67.53 mmol, 5.00 mL) was added into the compound I2-D (1.25 g, 3.33 mmol) in dichloromethane solution at r.t., the reaction mixture was stirred at 20-25° C. for 40 min. The reaction mixture was concentrated up to dryness, and diluted by 40 mL water, then pH was adjusted to 11-12 with 10% sodium hydroxide solution, the aqueous phase was extracted by 70 mL dichloromethane 3 times, the organic phase was washed by 100 mL saturated brine, dried over anhydrous sodium sulfate, filtered and the filtrate was concentrated up to dryness to give the crude compound I2-E. MS m/z: 276.0[M+H]+

Step 5: Synthesis of Compound I2-F

Formaldehyde (1.00 g, 33.41 mmol, 920.52 µL), sodium triacetoxyborohydride (1.42 g, 6.68 mmol, 2.00 eq) and acetic acid (1.05 g, 17.49 mmol, 1.00 mL) were added into the compound I2-E (920.00 mg, 3.34 mmol) in methanol (30.00 mL), and was stirred at 20-25° C. for 30 min. The reaction mixture was concentrated, add 5% sodium hydroxide 30 mL and extracted with 50 mL dichloromethane for 3 times, the organic phase was washed by 100 mL saturated brine, dried over anhydrous sodium sulfate, then filtered and concentrated to give the crude compound I2-F. MS m/z: 290.1[M+H]+

Step 6: Synthesis of Compound I2

Under argon atmosphere, wet Pd/C (97.62 mg, 82.80 µmol, 10% purity) was added into compound I2-F (800.00 mg, 2.76 mmol) in ethanol (20.00 mL) solution. The gas in the reactor was replaced by hydrogen for 3 times, the mixture was stirred at 20-25° C. and under hydrogen pressure (15 psi) for 32 hours. After the reaction was completed, the reaction mixture was passed through diatomite then filtered and concentrated to give the crude compound 12. MS m/z: 260.1 [M+H]+

Intermediate 3

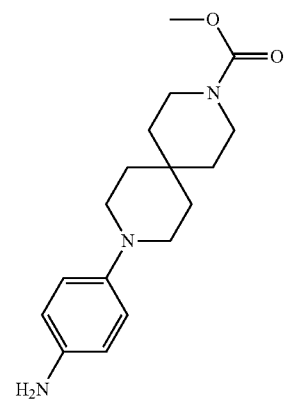 [SMILES: COC(=O)N1CCC2(CC1)CCN(c1ccc(N)cc1)CC2]

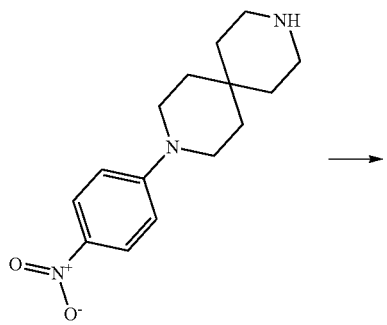

I2-E

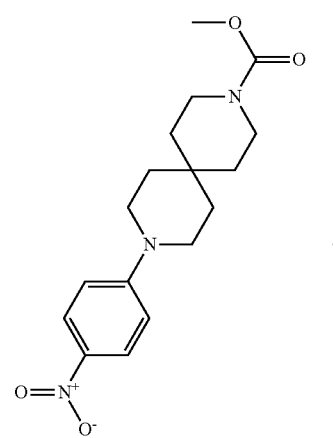

I3-A

-continued

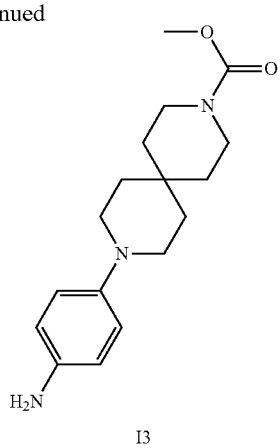

I3

Step 1: Synthesis of Compound I3-A

Oxalyl chloride (2.30 g, 24.34 mmol, 1.89 mL) was slowly added dropwise into the compound I2-E (500.00 mg, 1.82 mmol), triethylamine (920.83 mg, 9.10 mmol, 1.26 mL) in DCM (12.00 mL) solution at 0° C., the reaction mixture was stirred for 0.5 hours at 30° C. Water (20 mL) was added into the reaction system, the aqueous phase was extracted by 20 mL DCM for 3 times, the organic phase was washed by 20 mL saturated brine, dried over anhydrous sodium sulfate, filtered and the filtrate was concentrated up to dryness to give the crude compound I3-A. MS m/z: 334.1 [M+H]$^+$

Step 2: Synthesis of Compound I3

Ammonium chloride solution (834.33 mg, 15.60 mmol, 545.31 µL) and zinc powder (815.95 mg, 12.48 mmol) were added into the compound I3-A (520.00 mg, 1.56 mmol) in water (5.00 mL) and ethanol (50.00 mL) solution, the reaction mixture was stirred at 70° C. for 1 hour. The reaction mixture was filtered and concentrated to give I3. MS m/z: 304.1[M+H]$^+$

Embodiment 1: Compound 1

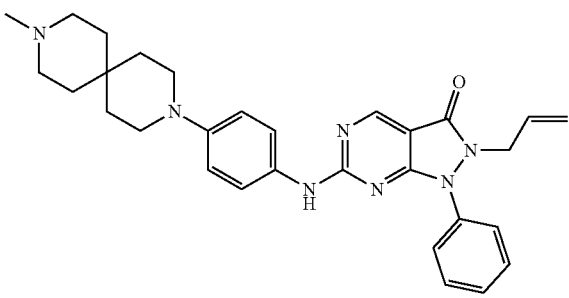 [SMILES: C=CCn1c(=O)c2cnc(Nc3ccc(N4CCC5(CCN(C)CC5)CC4)cc3)nc2n1-c1ccccc1]

Synthetic Route:

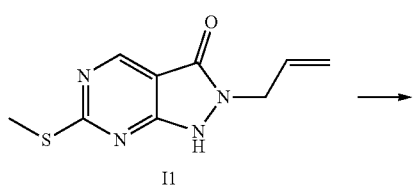

-continued

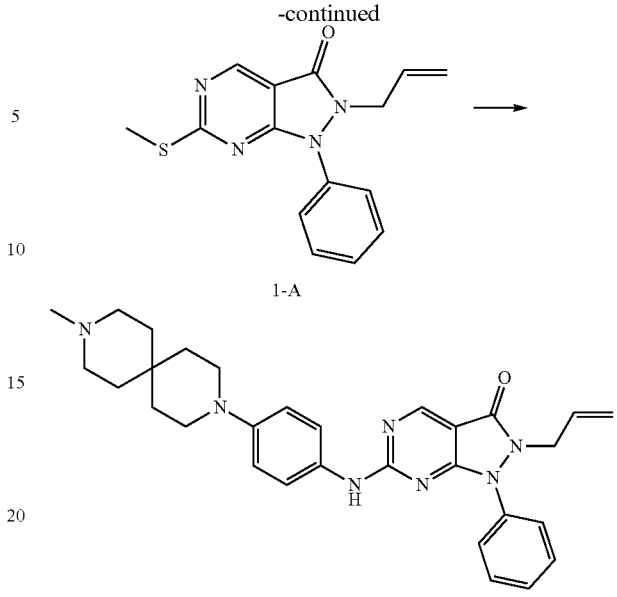

Step 1: Synthesis of Compound 1-A

The compound I1 (2.00 g, 9.00 mmol), phenylboronic acid (2.19 g, 18.00 mmol), pyridine (1.42 g, 18.00 mmol) and copper acetate (1.63 g, 9.00 mmol) in N,N-dimethylformamide (40.00 mL) was stirred at 20° C. for 2.0 hours, then stirred at 70° C. for 12 hours. The reaction system was diluted by 100 mL water, then extracted by EtOAc (100 mL×2). The organic phases were combined, washed by water (100 mL×3), and then washed by saturated brine (100 mL), dried over anhydrous sodium sulfate. The desiccant was filtered off, the solvent was eliminated under reduced pressure to give the crude product. The crude product was purified by column chromatography (PE/EtOAc=5/1) to give the compound 1-A. MS m/z: 298.9[M+H]$^+$

Step 2: Synthesis of Compound 1 m-Chloroperoxybenzoic acid (52.40 mg, 258.08 µmol, 85% purity) was added into the compound 1-A (70.00 mg, 234.62 µmol) in toluene (5.00 mL) solution. The reaction was stirred at 20° C. for 2 hours. Intermediate 12 (60.86 mg, 234.62 µmol) and N,N-diisopropylethylamine (90.97 mg, 703.86 µmol) were added into the reaction system. The reaction mixture was stirred at 20° C. for 14 hours. The reaction system was added into sodium thiosulfate (20 mL) while stirring, the aqueous phase was extracted by EtOAc (30 mL×3). The organic phases were combined, and washed by saturated brine (30 mL), dried over anhydrous sodium sulfate, filtered and concentrated in vacuum. The crude product was separated by preparative HPLC to give the compound 1. $^1$H NMR (400 MHz, DMSO-d$_6$) δ 8.80 (s, 1H), 7.75-7.31 (m, 7H), 6.85 (d, J=8.8 Hz, 2H), 5.78-5.53 (m, 1H), 5.08 (dd, J=1.2, 10.4 Hz, 1H), 4.92 (dd, J=1.2, 17.2 Hz, 1H), 4.28 (br s, 2H), 3.12-2.92 (m, 4H), 2.35-2.23 (m, 4H), 2.16 (s, 3H), 1.63-1.37 (m, 8H)

MS m/z: 496.1 [M+H]$^+$

Embodiment 2: Compound 2

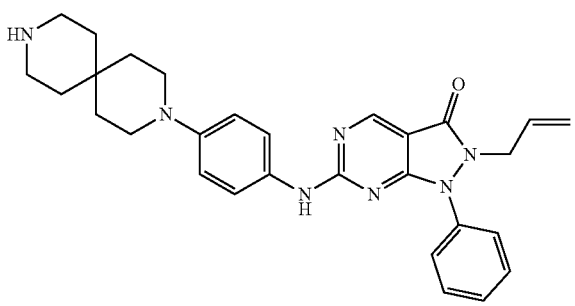 [SMILES: C=CCn1c(=O)c2cnc(Nc3ccc(N4CCC5(CCNCC5)CC4)cc3)nc2n1-c1ccccc1]

Synthetic Route:

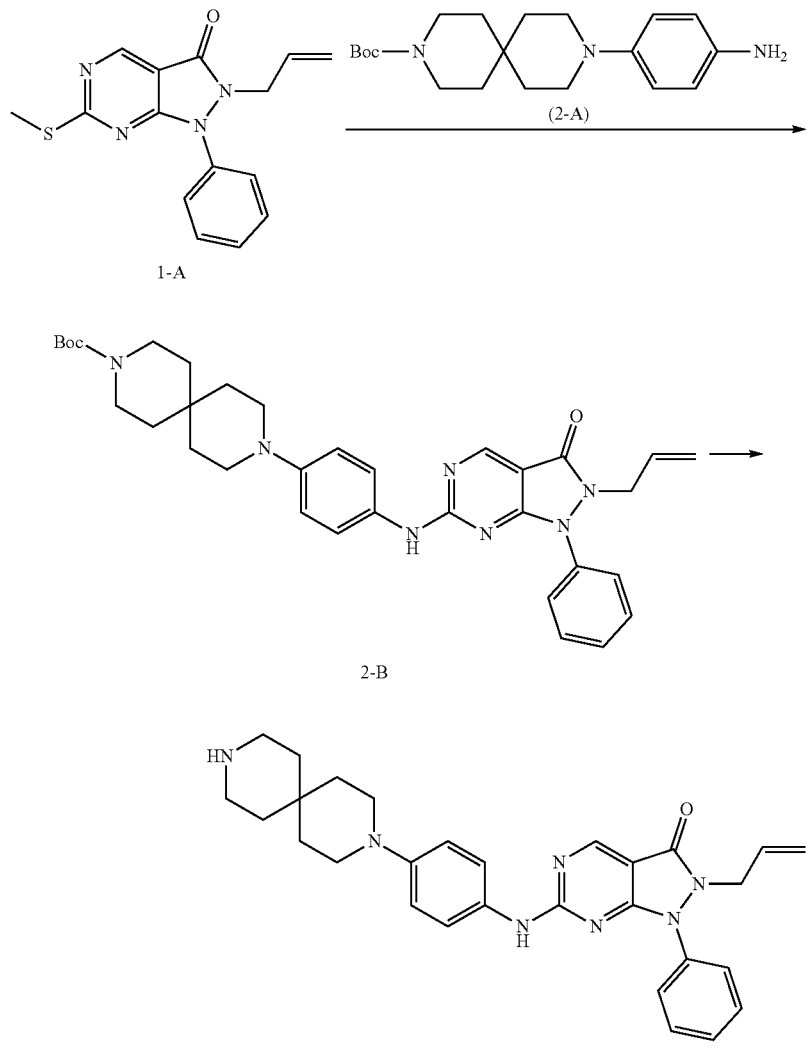

Step 1: Synthesis of Compound 2-B m-Chloroperoxybenzoic acid (82.34 mg, 405.55 μmol, 85% purity) was added into the compound 1-A (110.00 mg, 368.682 mmol) in toluene (10.00 mL) solution. The reaction was stirred at 20° C. for 2 hours. Compound 2-A (127.37 mg, 268.68 μmol, produced by hydrogenation reduction of I2-D) and N,N-diisopropylethylamine (142.94 mg, 1.11 mmol) were added into the reaction system. The reaction mixture was stirred at 20° C. for 12 hours. The aqueous phase was diluted by sodium hydroxide (30 mL, 0.5 N) and extracted by EtOAc (30 mL×2). The organic phases were combined, washed by saturated brine (30 mL) and dried over anhydrous sodium sulfate, filtered and concentrated in vacuum to give the crude product. The crude product was purified by thin phase chromatography (dichloromethane/methanol=10/1) to give the compound 2-B. MS m/z: 596.2 [M+H]$^+$

Step 2: Synthesis of Compound 2

Compound 2-B (170.00 mg, 285.36 μmol) was dissolved in dichloromethane (3.00 mL), trifluoroacetic acid (1.54 g, 13.51 mmol) was added into the reaction system, then was stirred at 20° C. for 10 min. The crude product was concentrated and separated by preparative HPLC to give the compound 2. $^1$H NMR (400 MHz, DMSO-d$_6$) δ=8.79 (s, 1H), 7.61-7.32 (m, 7H), 6.85-6.82 (d, J=9.2 Hz, 2H), 5.78-

5.54 (m, 1H), 5.06 (d, J=9.2 Hz, 1H), 4.95-4.77 (m, 1H), 3.13-2.99 (m, 4H), 2.79-2.65 (m, 4H), 1.61-1.46 (m, 4H), 1.46-1.29 (m, 4H).

MS m/z: 496.1[M+H]$^+$

Embodiment 3: Compound 3

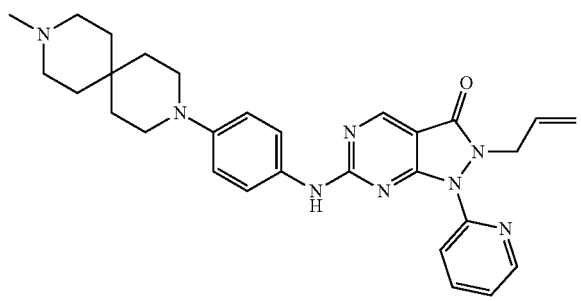 [SMILES: C=CCn1c(=O)c2cnc(Nc3ccc(N4CCC5(CCN(C)CC5)CC4)cc3)nc2n1-c1ccccn1]

Synthetic Route:

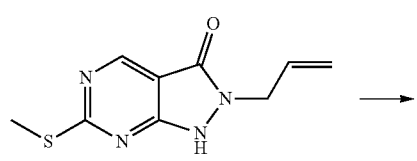

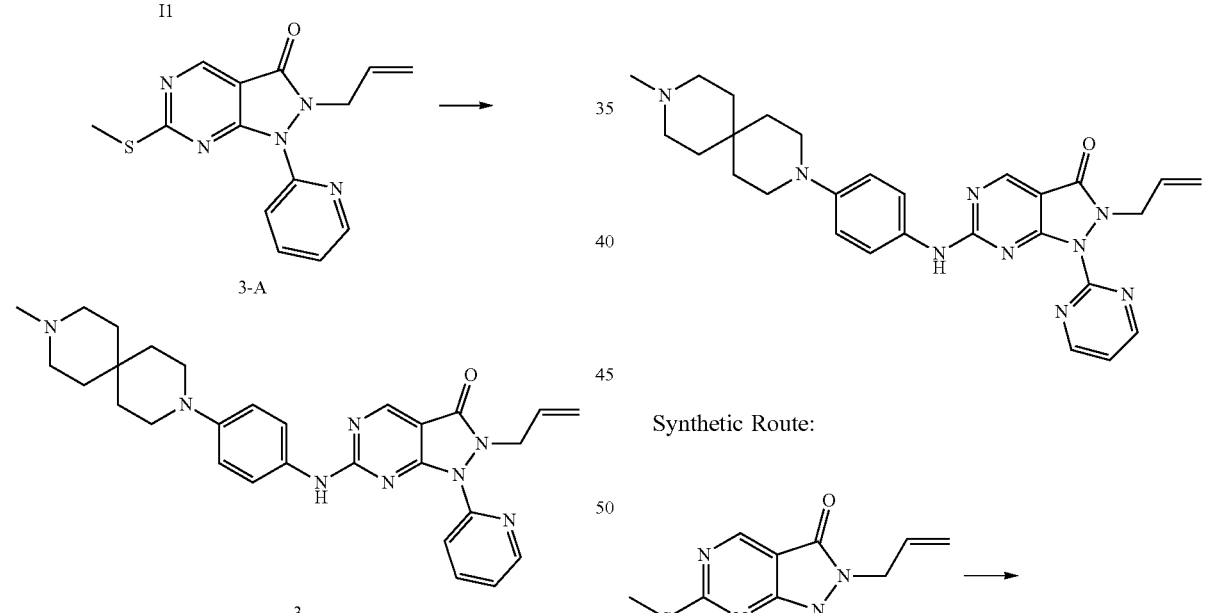

Step 1: Synthesis of Compound 3-A

Cuprous iodide (599.92 mg, 3.15 mmol), N,N-dimethylethylenediamine (310.99 mg, 3.53 mmol, 379.26 μL) and potassium carbonate (600.80 mg, 4.35 mmol) were added separately into compound I1 (700.00 mg, 3.15 mmol) and 2-bromopyridine (497.59 mg, 3.15 mmol, 299.75 μL) in dioxane solution. Under nitrogen atmosphere, the reaction mixture was stirred at 95° C. for 48 hours and then added 40 mL ammonia after concentration, then extracted by EtOAc 350 mL (70 mL×5), and washed by saturated brine 150 mL, dried over anhydrous sodium sulfate, then filtered to give the crude compound 3-A. MS m/z: 300.0[M+H]$^+$ Step 2: Synthesis of Compound 3 m-Chloroperoxybenzoic acid (88.17 mg, 434.28 μmol, 85% purity) was added into compound 3-A (100.00 mg, 334.06 μmol) in dichloromethane (10.00 mL) solution, the mixture was stirred at 20-25° C. for 2 hours, then added compound 12 (86.65 mg, 334.06 μmol) and N,N-diisopropylethylamine (129.52 mg, 1.00 mmol, 175.03 μL), then stirred for 14 hours. The reaction mixture was diluted by dichloromethane 80 mL, then washed separately by saturated sodium bicarbonate and sodium thiosulfate 60 mL (30 mL×2), dried over sodium sulfate, then filtered and concentrated to give the crude compound, the crude compound was purified by preparative HPLC (alkaline condition) to give the compound 3. $^1$H NMR (CHLOROFORM-d, 400 MHz): δ=8.75 (s, 1H), 8.45 (d, J=5.0 Hz, 1H), 7.74-7.83 (m, 2H), 7.37 (br d, J=9.0 Hz, 2H), 7.11-7.18 (m, 1H), 6.86 (d, J=9.0 Hz, 2H), 5.61 (ddt, J=16.9, 10.4, 6.1 Hz, 1H), 4.95 (d, J=10.0 Hz, 1H), 4.79-4.91 (m, 1H), 4.71 (br d, J=6.0 Hz, 2H), 3.02-3.12 (m, 4H), 2.35 (br s, 4H), 2.25 (s, 3H), 1.51-1.61 (m, 8H)

MS m/z: 511.1[M+H]$^+$

Embodiment 4: Synthesis of Compound 4

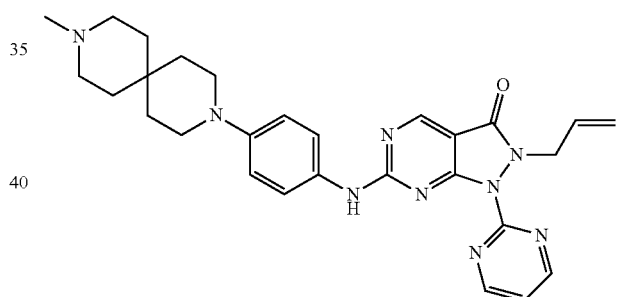

Synthetic Route:

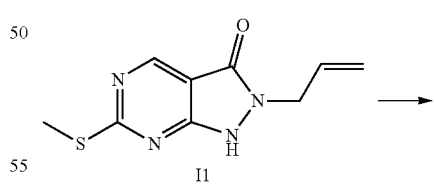

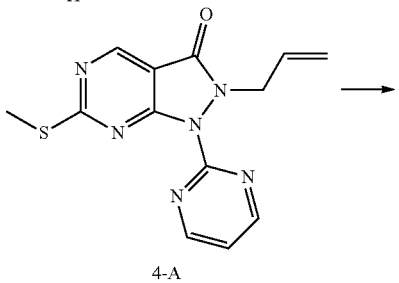

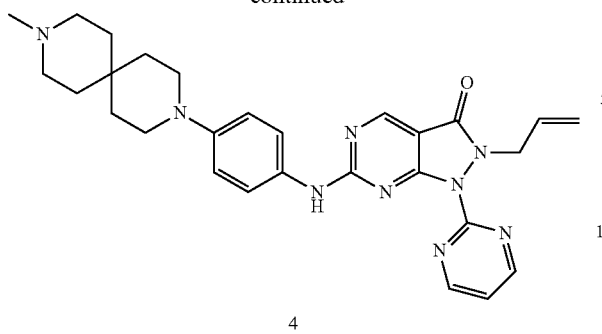

4

Step 1: Synthesis of Compound 4-A

According to the method for preparing the compound 3-A and the 2-bromopyridine was replaced by 2-bromopyrimidine, compound 4-A crude product was obtained, the crude compound was purified by silica gel column (PE/EtOAc=6/1, 1/1) to deliver the compound 4-A. MS m/z: 300.9 [M+H]+

Step 2: Synthesis of Compound 4

According to the method for preparing the compound 3 and started with the compound 4-A, the crude product of compound 4 was obtained. The crude compound was purified by preparative separation (neutral condition) to give the compound 4. $^1$H NMR (CDCl$_3$, 400 MHz): δ=8.84 (d, J=5.0 Hz, 3H), 7.52 (br s, 1H), 7.26-7.26 (m, 1H), 7.23-7.26 (m, 1H), 6.91-6.96 (m, 2H), 5.69 (ddt, J=16.9, 10.3, 6.3 Hz, 1H), 5.03 (dd, J=10.2, 0.9 Hz, 1H), 4.96 (dd, J=17.1, 1.3 Hz, 1H), 4.82 (br d, J=6.3 Hz, 1H), 4.79-4.86 (m, 1H), 3.10-3.17 (m, 4H), 2.42 (br s, 4H), 2.31 (s, 3H), 1.63-1.67 (m, 4H), 1.59 (br t, J=5.5 Hz, 4H)

MS m/z: 512.2[M+H]+

Embodiment 5: Compound 5

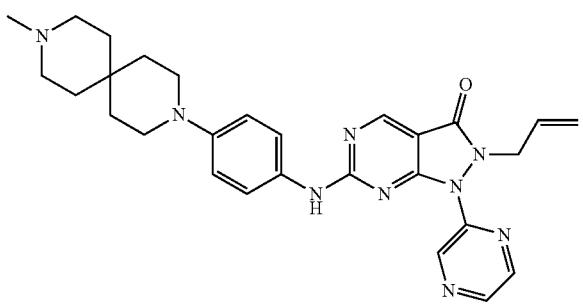 [SMILES: C=CCn1c(=O)c2cnc(Nc3ccc(N4CCC5(CCN(C)CC5)CC4)cc3)nc2n1-c1cnccn1]

Synthetic Route:

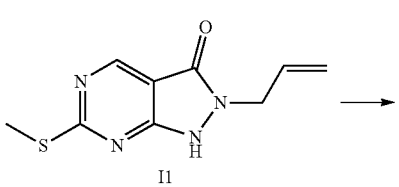

I1

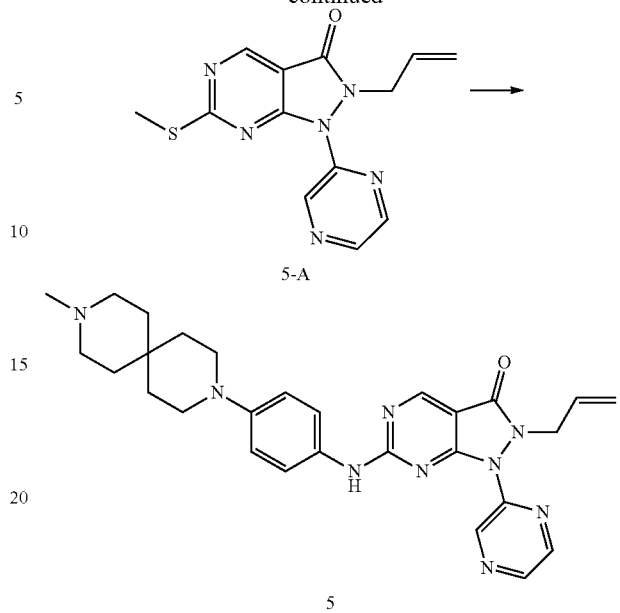

5-A

5

Step 1: Synthesis of Compound 5-A

According to the method for preparing the compound 3-A, and the 2-bromopyridine was replaced by 2-bromoyrazine, the compound 5-A was obtained. MS m/z: 301.0 [M+H]+

Step 2: Synthesis of Compound 5 m-Chloroperoxybenzoic acid (146.01 mg, 719.18 μmol, 85% purity) was added into the compound 5-A (135.00 mg, 449.49 μmol) in toluene (10.00 mL) solution, the mixture was stirred at 20-25° C. for 2 hours and then added the compound 12 (86.65 mg, 334.06 μmol) and N,N-diisopropylethylamine (174.28 mg, 1.35 mmol, 235.51 μL), followed by stirring for 13 hours. The reaction mixture was diluted by dichloromethane 80 mL, and washed by saturated sodium bicarbonate 60 mL (30 mL×2), dried over anhydrous sodium sulfate, then filtered and concentrated to give the crude compound, the crude compound was purified by preparative HPLC (neutral condition) to give the compound 5. $^1$H NMR (CHLOROFORM-d, 400 MHz): δ=9.26 (d, J=1.5 Hz, 1H), 8.77 (s, 1H), 8.37-8.41 (m, 2H), 7.37 (br d, J=8.5 Hz, 2H), 6.90 (d, J=9.0 Hz, 2H), 5.54-5.65 (m, 1H), 4.97 (d, J=9.5 Hz, 1H), 4.87 (d, J=18.1 Hz, 1H), 4.70 (d, J=6.5 Hz, 2H), 3.05-3.12 (m, 4H), 2.41 (br s, 4H), 2.28 (s, 3H), 1.60 (br s, 8H)

MS m/z: 512.1[M+H]+

Embodiment 6: Compound 6

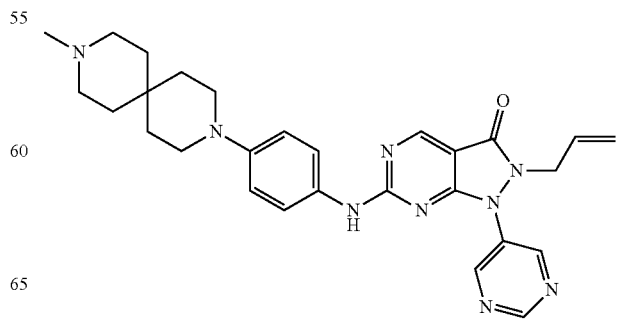

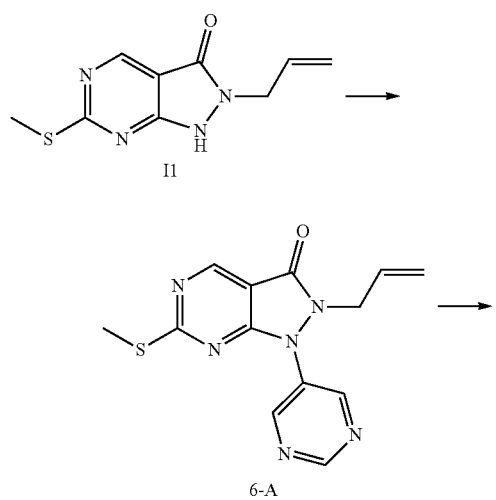

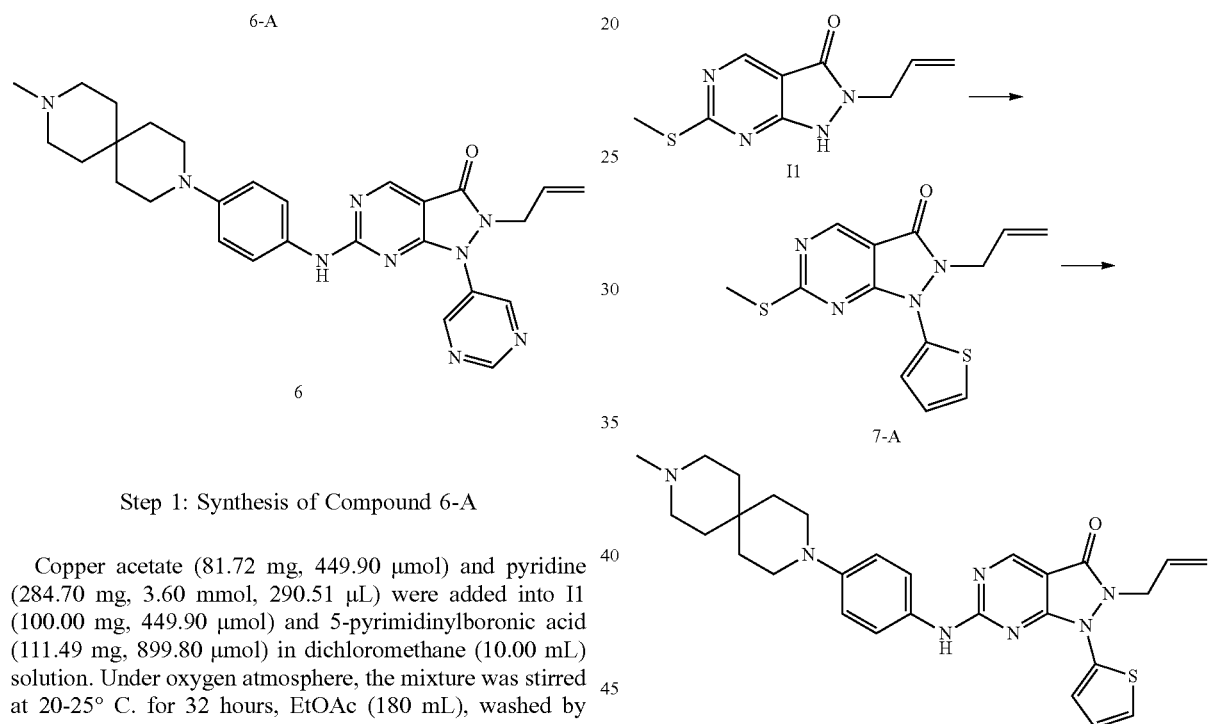

Step 1: Synthesis of Compound 6-A

Copper acetate (81.72 mg, 449.90 μmol) and pyridine (284.70 mg, 3.60 mmol, 290.51 μL) were added into I1 (100.00 mg, 449.90 μmol) and 5-pyrimidinylboronic acid (111.49 mg, 899.80 μmol) in dichloromethane (10.00 mL) solution. Under oxygen atmosphere, the mixture was stirred at 20-25° C. for 32 hours, EtOAc (180 mL), washed by water 240 mL (120 mL×2) and saturated brine 120 mL, dried over anhydrous sodium sulfate, then filtered and concentrated to give the crude compound 6-A, which was purified by thin phase chromatography (PE/EtOAc=2/1) to give compound 6-A.

MS m/z: 300.9[M+H]$^+$

Step 2: Synthesis of Compound 6

According to the method for preparing the compound 3 and started with compound 6-A, the crude product of compound 6 was prepared. The crude compound was purified by preparative separation (neutral condition) to give the compound 6. $^1$H NMR (CDCl$_3$, 400 MHz): δ=9.20 (s, 1H), 8.94 (s, 2H), 8.84 (br s, 1H), 7.41 (d, J=9.0 Hz, 2H), 6.96 (d, J=9.0 Hz, 2H), 5.65-5.77 (m, 1H), 5.17 (d, J=10.5 Hz, 1H), 5.05 (d, J=18.1 Hz, 1H), 4.42 (d, J=6.0 Hz, 2H), 3.14-3.20 (m, 4H), 2.49 (br s, 1H), 2.37 (s, 3H), 1.66-1.69 (m, 8H)

MS m/z: 512.1[M+H]$^+$

Embodiment 7: Compound 7

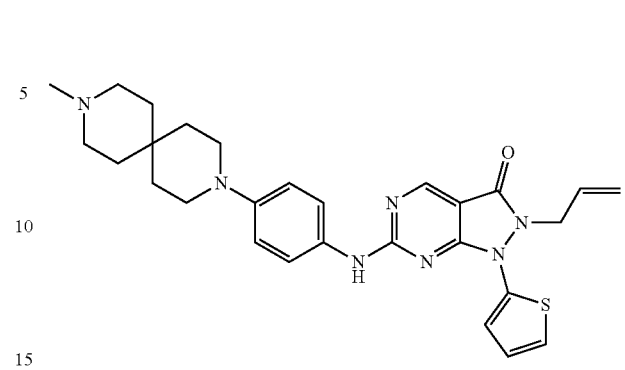

Synthetic Route:

Step 1: Synthesis of Compound 7-A

According to the method for preparing the compound 6-A, 5-pyrimidinylboronic acid was replaced by 2-thiophenylboronic acid to give the compound 7-A crude product, the crude compound was purified by silica gel column (PE: EtOAc=4:1) to give the compound 7-A. MS m/z: 304.9[M+H]$^+$

Step 2: Synthesis of Compound 7

According to the method for preparing the compound 3 and started with the compound 7-A, the crude product of compound 7 was obtained. The crude compound was purified by preparative HPLC (neutral condition) to give the compound 7. $^1$H NMR (CDCl$_3$, 400 MHz): δ=8.81 (s, 1H), 7.34-7.44 (m, 3H), 7.18 (d, J=2.8 Hz, 1H), 7.06 (dd, J=5.5, 3.8 Hz, 1H), 6.88 (br d, J=8.8 Hz, 2H), 5.74 (ddt, J=16.8, 10.5, 5.9 Hz, 1H), 4.97-5.22 (m, 2H), 4.34-4.45 (m, 2H), 3.05-3.17 (m, 4H), 2.41 (br s, 4H), 2.31 (s, 3H), 1.61 (dt, J=19.1, 5.6 Hz, 8H)

MS m/z: 516.0 [M+H]+

Embodiment 8: Compound 8

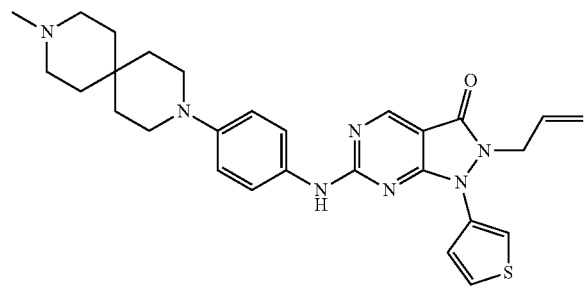 [SMILES: C=CCn1c(=O)c2cnc(Nc3ccc(N4CCC5(CCN(C)CC5)CC4)cc3)nc2n1-c1ccsc1]

Synthetic Route:

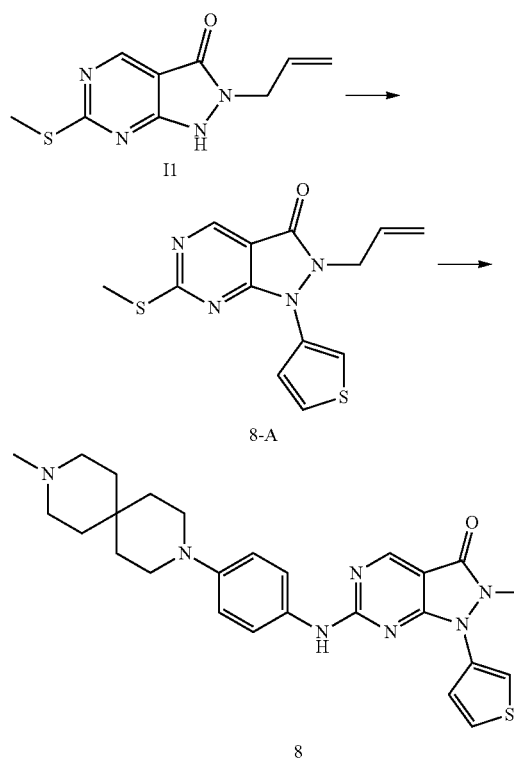

Step 1: Synthesis of Compound 7-A

According to the method for preparing the compound 3-A and 2-bromopyridine was replaced by 3-bromothiophene, the crude product of compound 8-A was obtained, the crude compound was purified by silica gel column (PE/EtOAc=10/1, 3/1) to give the compound 8-A. MS m/z: 304.9 [M+H]+

Step 2: Synthesis of Compound 8

According to the method for preparing the compound 3 and started with the compound 8-A, the crude product of compound 8 was obtained. The crude compound was purified by preparative HPLC (neutral condition) to give 8. ¹H NMR (CDCl₃, 400 MHz): δ=8.80 (s, 1H), 7.38-7.45 (m, 3H), 7.29-7.33 (m, 1H), 7.20 (br d, J=5.8 Hz, 1H), 6.90 (d, J=9.0 Hz, 2H), 5.71 (dd, J=17.1, 10.3 Hz, 1H), 5.10-5.15 (m, 1H), 4.98-5.10 (m, 1H), 4.41 (br d, J=5.5 Hz, 2H), 3.07-3.17 (m, 4H), 2.38-2.49 (m, 4H), 2.33 (s, 3H), 1.59-1.62 (m, 8H)

MS m/z: 516.0[M+H]+

Embodiment 9: Compound 9

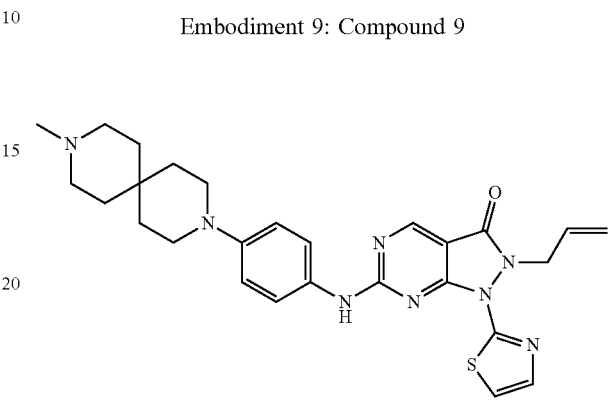

Synthetic Route:

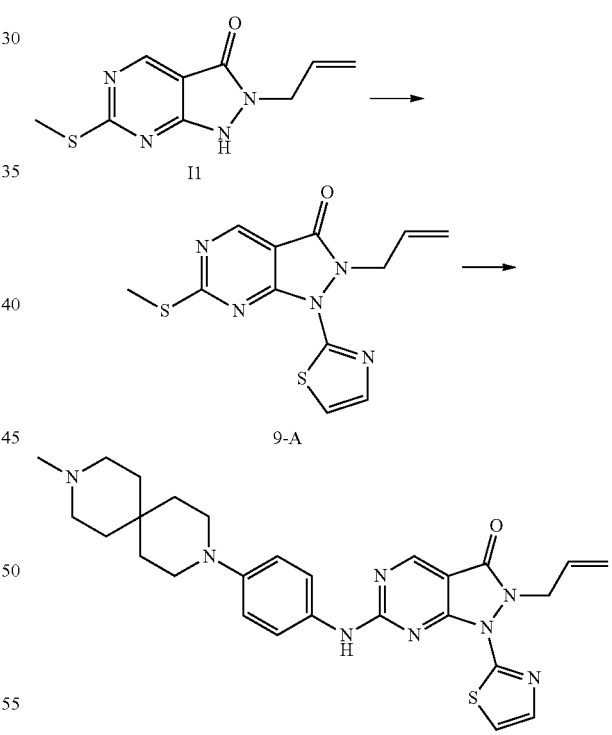

Step 1: Synthesis of Compound 9-A

According to the method for preparing the compound 3-A and 2-bromopyridine was replaced by 2-bromothiazole, crude product of the compound 9-A was obtained, the crude compound was purified by silica gel column (PE/EtOAc=6/1, 3/1) to give the compound 9-A. MS m/z: 305.9[M+H]+

Step 2: Synthesis of Compound 9

According to the method for preparing the compound 3 and started with the compound 9-A, crude product of compound 9 was obtained, the crude compound was purified by silica gel plate (dichloromethane/methanol=6/1) to give the compound 9. $^1$H NMR (CDCl$_3$, 400 MHz): δ=8.75 (s, 1H), 7.49 (br d, J=3.5 Hz, 2H), 7.09 (d, J=3.5 Hz, 1H), 6.91 (br d, J=9.0 Hz, 2H), 5.57-5.70 (m, 1H), 4.98-5.06 (m, 2H), 4.94 (br s, 2H), 3.07-3.13 (m, 4H), 2.38 (br s, 4H), 2.26 (s, 3H), 1.57-1.57 (m, 1H), 1.54-1.54 (m, 1H), 1.54-1.57 (m, 6H)

MS m/z: 517.0[M+H]$^+$

Embodiment 10: Compound 10

Synthetic Route:

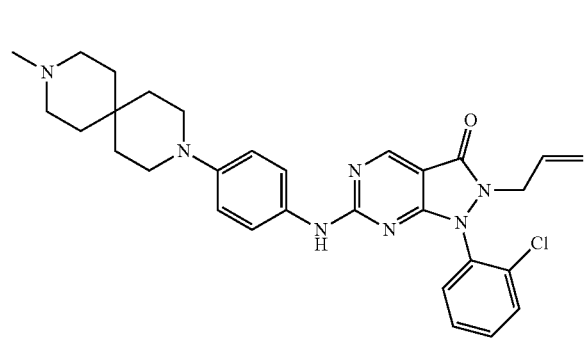 [SMILES: C=CCn1c(=O)c2cnc(Nc3ccc(N4CCC5(CCN(C)CC5)CC4)cc3)nc2n1-c1ccccc1Cl]

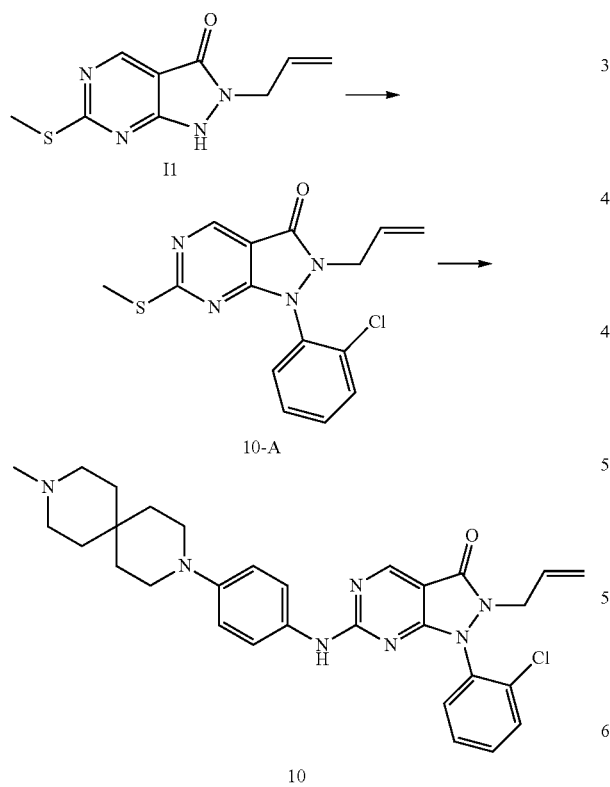

Step 1: Synthesis of Compound 10-A

According to the method for preparing the compound 11-A, and 3-chloro-phenylboronic acid was replaced by 2-chloro-phenylboronic acid, the compound 10-A was obtained. MS m/z: 333.0[M+H]$^+$

Step 2: Synthesis of Compound 10

According to the method for preparing the compound 3, and started with the compound 10-A, crude product of the compound 10 was obtained. The crude compound was separated by preparative HPLC to give the compound 10. $^1$H NMR (CDCl$_3$, 400 MHz): δ=8.76 (s, 1H), 7.48-7.52 (m, 1H), 7.28-7.39 (m, 5H), 6.77 (br d, J=9.0 Hz, 2H), 5.59-5.71 (m, 1H), 5.05 (d, J=11.0 Hz, 1H), 4.92 (d, J=18.1 Hz, 1H), 4.11-4.31 (m, 2H), 2.99-3.06 (m, 4H), 2.44 (br s, 4H), 2.29 (s, 3H), 1.56-1.61 (m, 4H), 1.56 (br s, 4H)

MS m/z: 544.0[M+H]$^+$

Embodiment 11: Compound 11

Synthetic Route:

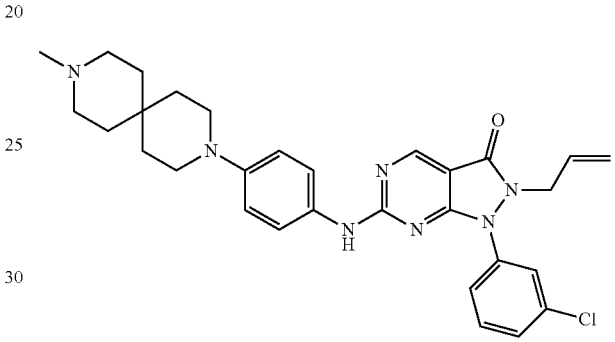

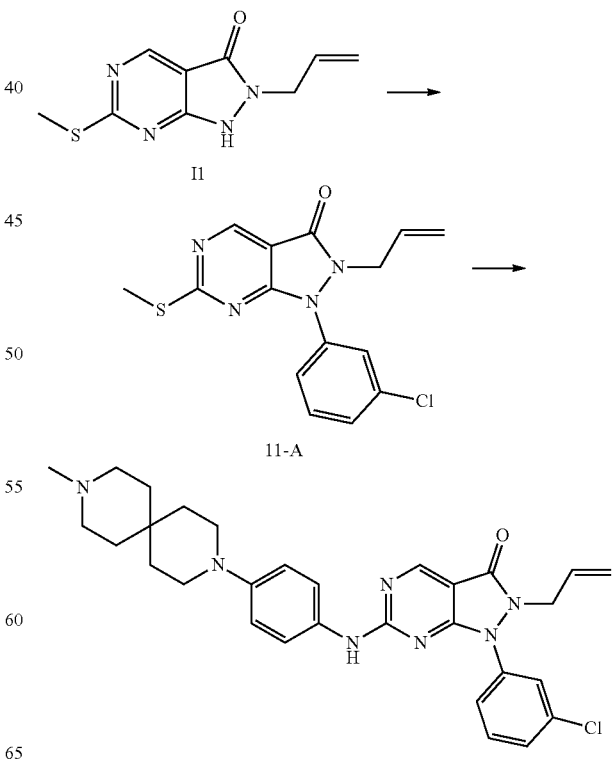

Step 1: Synthesis of Compound 11-A

At r.t., copper acetate (572.15 mg, 3.15 mmol) and pyridine (498.33 mg, 6.30 mmol, 508.50 μL) were added into 11 (700.00 mg, 3.15 mmol) and 3-chloro-phenylboronic acid (738.85 mg, 4.72 mmol) in N,N-dimethylformamide (20.00 mL) solution, and was stirred for 48 hours under oxygen atmosphere, EtOAc (180 mL), washed by water (120 mL×2) and saturated brine (120 mL), dried over anhydrous sodium sulfate, then filtered and concentrated to give the crude compound 11-A. MS m/z: 332.9 [M+H]$^+$

Step 2: Synthesis of Compound 11

According to the method for preparing the compound 3, and started with the compound 11-A, crude product of the compound 11 was obtained. The crude compound was purified by preparative HPLC to give the compound 11. $^1$H NMR (CDCl$_3$, 400 MHz): δ=8.72 (s, 1H), 7.41-7.52 (m, 4H), 7.29-7.36 (m, 2H), 6.92-6.94 (br d, J=9.0 Hz, 2H), 5.56-5.72 (m, 1H), 5.10 (d, J=11.0 Hz, 1H), 5.00 (d, J=18.1 Hz, 1H), 4.39-4.40 (m, 2H), 3.12-3.15 (m, 4H), 2.48 (br s, 4H), 2.35 (s, 3H), 1.50-1.61 (m, 8H)

MS m/z: 544.0[M+H]$^+$

Embodiment 12: Compound 12

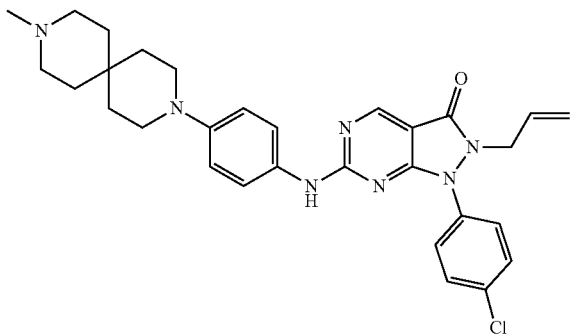 [SMILES: C=CCn1c(=O)c2cnc(Nc3ccc(N4CCC5(CCN(C)CC5)CC4)cc3)nc2n1-c1ccc(Cl)cc1]

Synthetic Route:

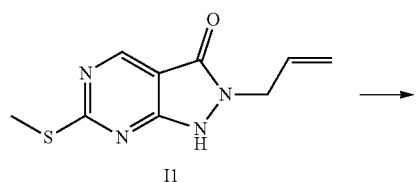

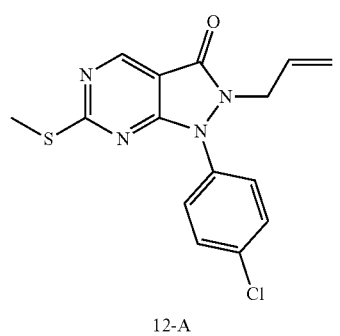

12-A

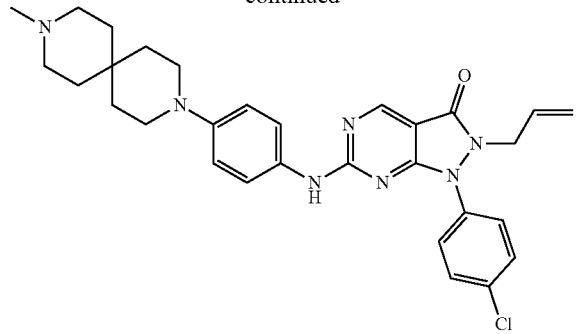

12

Step 1: Synthesis of Compound 12-A

According to the method for preparing the compound 11-A, and 3-chloro-phenylboronic acid was replaced by 4-chloro-phenylboronic acid, crude product of the compound 10-A was obtained, the crude compound was purified by silica gel (PE:EtOAc=10:1-5:1) to give the 12-A. MS m/z: 332.9[M+H]$^+$

Step 2: Synthesis of Compound 12

According to the method for preparing the compound 3, and started with the compound 12-A, crude product of the compound 12 was obtained, the crude compound was purified by preparative HPLC (neutral condition) to give the compound 12.

$^1$H NMR (CDCl$_3$, 400 MHz): δ=8.82 (s, 1H), 7.47-7.52 (m, 2H), 7.37-7.46 (m, 4H), 6.92 (d, J=9.0 Hz, 2H), 5.65-5.75 (m, 1H), 5.13 (d, J=10.0 Hz, 1H), 5.01 (dd, J=17.1, 1.0 Hz, 1H), 4.38 (br d, J=5.5 Hz, 2H), 3.08-3.23 (m, 4H), 2.44 (br s, 4H), 2.33 (s, 3H), 1.62 (br t, J=5.8 Hz, 8H)

MS m/z: 544.1[M+H]$^+$

Embodiment 13: Compound 13

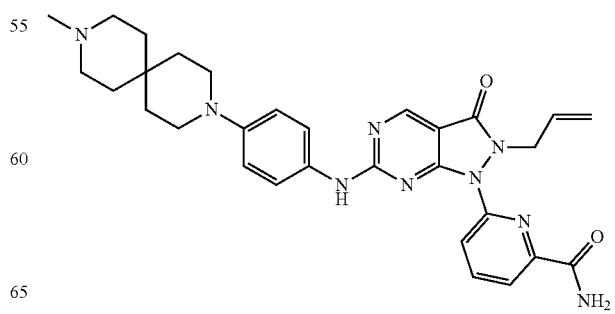

Synthetic Route:

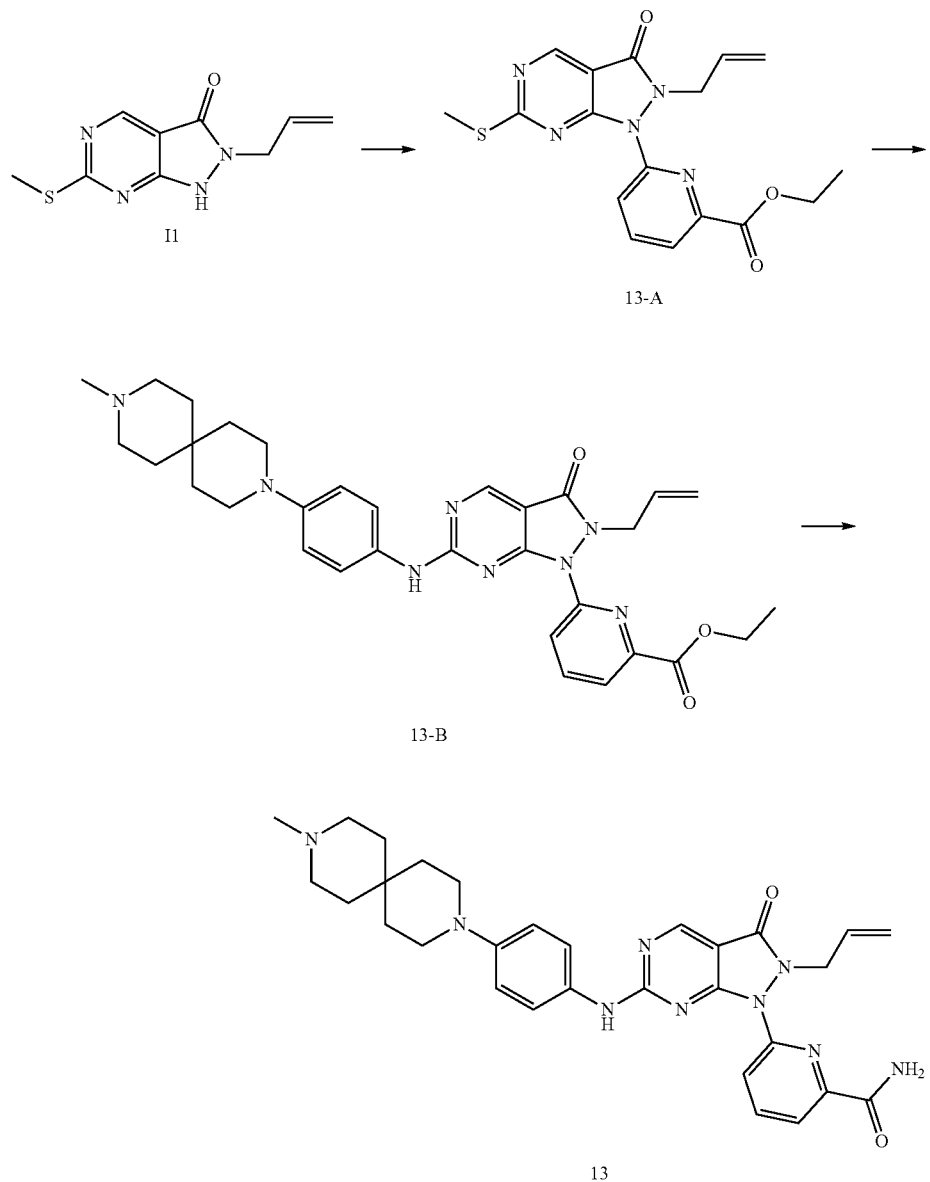

Step 1: Synthesis of Compound I3-A

According to the method for preparing the compound 3-A and 2-bromopyridine was replaced by 6-bromo-2-ethylpicolinate, crude product of the compound 13-A was obtained, the crude compound was purified by silica gel column (PE/EtOAc=5/1) to give the compound 13-A. MS m/z: 372.0 [M+H]$^+$

Step 2: Synthesis of Compound 13-B

According to the method for preparing the compound 5, and started with the compound 13-A, crude product of the compound 13-B (yellow solid, 100 mg) was obtained. MS m/z: 583 [M+1]$^+$

Step 3: Synthesis of Compound 13

According to the method for preparing the compound 14, methylamine solution was replaced by ammonia, crude product of the compound 13 was obtained, the crude compound was purified by preparative HPLC (neutral condition) to give the compound 13. $^1$H NMR (CDCl$_3$, 400 MHz): δ=8.83 (s, 1H), 8.11-8.16 (m, 1H), 8.00 (d, J=3.8 Hz, 2H), 7.79 (br d, J=5.0 Hz, 1H), 7.41-7.42 (m, 1H), 7.41-7.42 (m, 1H), 6.92 (d, J=9.0 Hz, 2H), 5.72 (ddt, J=16.9, 10.4, 6.1 Hz, 1H), 5.08 (dd, J=10.3, 1.0 Hz, 1H), 4.97 (dd, J=17.1, 1.3 Hz, 1H), 4.65 (d, J=6.3 Hz, 2H), 3.11-3.20 (m, 4H), 3.03-3.06 (m, 3H), 2.41 (br s, 4H), 2.30 (s, 3H), 1.51-1.71 (m, 8H)

MS m/z: 568.1 [M+H]$^+$

Embodiment 14: Compound 14

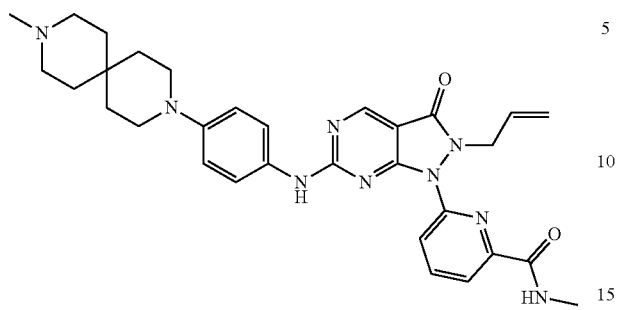

Synthetic Route:

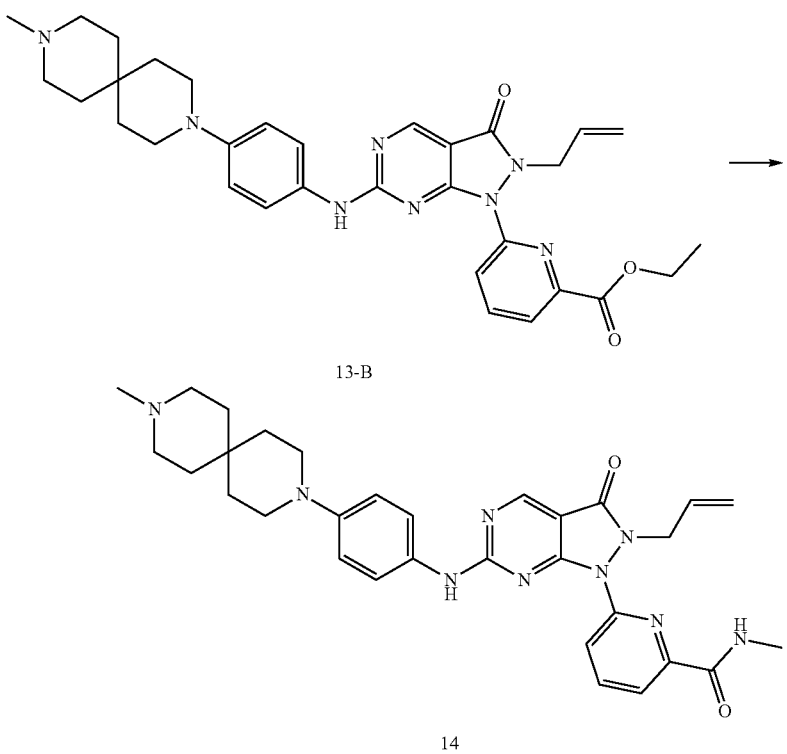

Step 1: Synthesis of Compound 14

Methylamine solution (5.00 mL, 27.5% purity) was added into the compound 13-B (50.00 mg, 85.81 μmol) in methanol (3 mL) solution, the mixture was stirred at 20-25° C. for 4.5 hours and concentrated under reduced pressure to give the crude compound, the product was purified by preparative HPLC (neutral condition) to give the compound 14. $^1$H NMR (CDCl$_3$, 400 MHz): δ=8.83 (s, 1H), 8.11-8.16 (m, 1H), 8.00 (d, J=3.8 Hz, 2H), 7.79 (br d, J=5.0 Hz, 1H), 7.41-7.42 (m, 1H), 7.41-7.42 (m, 1H), 6.92 (d, J=9.0 Hz, 2H), 5.72 (ddt, J=16.9, 10.4, 6.1 Hz, 1H), 5.08 (dd, J=10.3, 1.0 Hz, 1H), 4.97 (dd, J=17.1, 1.3 Hz, 1H), 4.65 (d, J=6.3 Hz, 2H), 3.11-3.20 (m, 4H), 3.03-3.06 (m, 3H), 2.41 (br s, 4H), 2.30 (s, 3H), 1.51-1.71 (m, 8H)

MS m/z: 568.1[M+1]$^+$

Embodiment 15: Compound 15

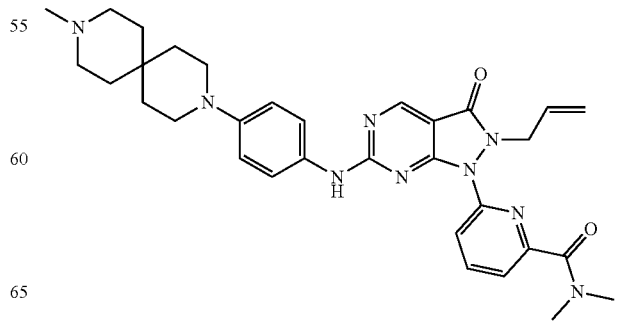

Synthetic Route:

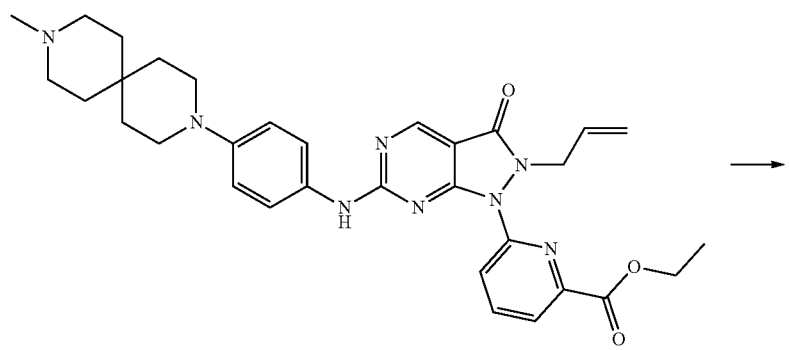

13-B

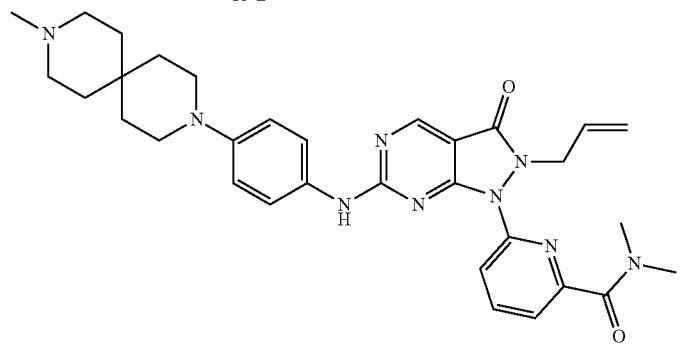

15

Step 1: Synthesis of Compound 15

According to the method for preparing the compound 14, and the methylamine solution was replaced by dimethylamine solution, crude product of the compound 15 was obtained, and the crude compound was purified by preparative HPLC (neutral condition) to give the compound 15. $^1$H NMR (CDCl$_3$, 400 MHz): δ=8.82 (s, 1H), 7.90-8.00 (m, 2H), 7.53-7.56 (m, 1H), 7.43 (br d, J=8.8 Hz, 2H), 6.93 (d, J=9.0 Hz, 2H), 5.67 (dd, J=17.1, 10.3 Hz, 2H), 5.03 (d, J=10.3 Hz, 1H), 4.95 (dd, J=17.1, 1.3 Hz, 1H), 4.76 (br d, J=5.8 Hz, 2H), 3.14-3.17 (m, 6H), 2.44 (br s, 4H), 2.32 (s, 3H), 1.58-1.65 (m, 8H)

MS m/z: 582.1[M+H]$^+$

Embodiment 16: Compound 16

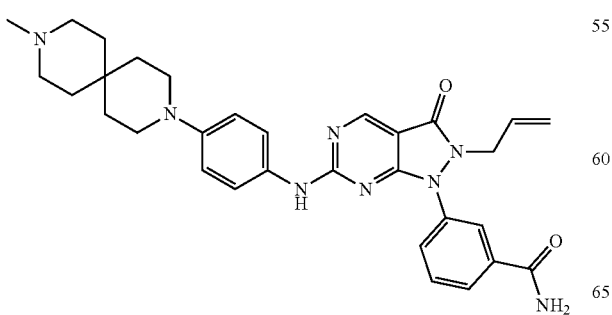

Synthetic Route:

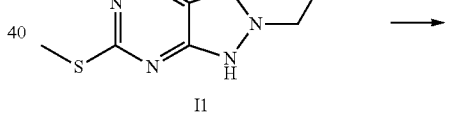

I1

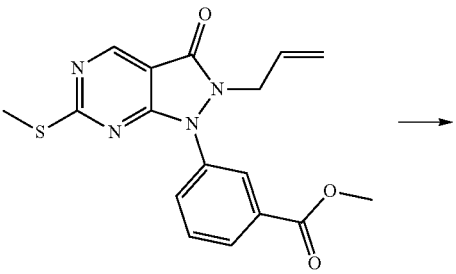

16-A

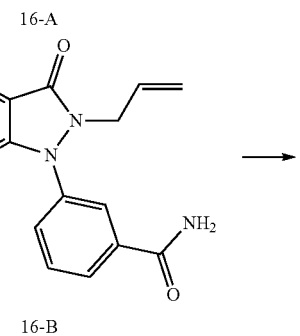

16-B

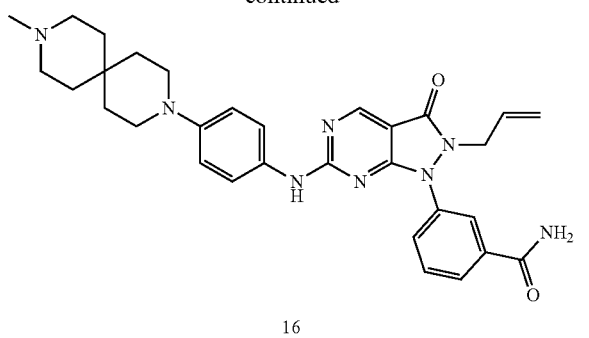

16

Step 1: Synthesis of Compound 16-A

According to the method for preparing the compound 6-A, and the 5-pyrimidinylboronic acid was replaced by 3-methoxycarbonylphenylboronic acid, compound 16-A was obtained. MS m/z: 357.2 [M+H]$^+$

Step 2: Synthesis of Compound 16-B

The compound 16-A (150.00 mg, 420.88 μmol) was added into ammonia 5 mL, and was stirred at 20-25° C. for 14 hours, then concentrated to give the crude compound, the product was purified by thin phase chromatography (PE/EtOAc=8/5) to give the compound 16-B. MS m/z: 342.0 [M+H]$^+$

Step 3: Synthesis of Compound 16

According to the method for preparing the compound 3, and started with the compound 16-B, crude product of the compound 16 was obtained, the crude compound was purified by HPLC (neutral condition) to give the compound 16. $^1$H NMR (CDCl$_3$, 400 MHz): δ=8.81 (s, 1H), 7.95 (s, 1H), 7.81 (d, J=7.0 Hz, 1H), 7.50-7.64 (m, 3H), 7.40 (br d, J=8.8 Hz, 2H), 6.90 (d, J=8.8 Hz, 2H), 5.65-5.65 (m, 1H), 5.65-5.71 (m, 1H), 5.11 (d, J=11.3 Hz, 1H), 4.99 (d, J=17.3 Hz, 1H), 4.41 (br d, J=5.5 Hz, 2H), 3.10-3.15 (m, 4H), 2.44 (br s, 4H), 2.33 (s, 3H), 1.65 (br d, J=6.0 Hz, 8H)

MS m/z: 553.1[M+H]$^+$

Embodiment 17: Compound 17

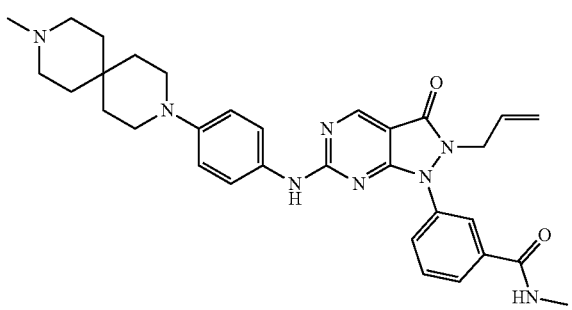

Synthetic Route:

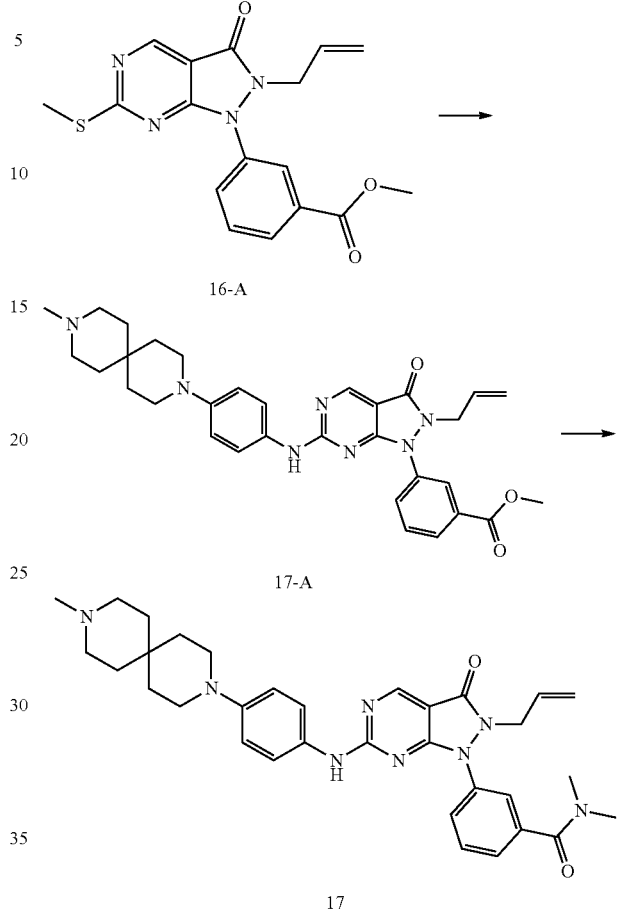

Step 1: Synthesis of Compound 17-A

According to the method for preparing the compound 3-A and the 2-bromopyridine was replaced by methyl 3-bromobenzoate, the compound 17-A was obtained. MS m/z: 357.2[M+H]$^+$

Step 2: Synthesis of Compound 17

Dimethylamine solution (4.45 g, 32.57 mmol, 5.00 mL, 33% purity) was added into the compound 17-A (165.00 mg, 290.66 μmol) in methanol (5.00 mL) solution. After stirring at 20-25° C. for 32 hours, the reaction mixture was concentrated, diluted by water 25 mL, extracted by dichloromethane 90 mL (30 mL×3), the organic phase was washed by saturated brine 40 mL, dried over anhydrous sodium sulfate, filtered and concentrated to give the crude compound, the crude compound was purified by preparative HPLC (alkaline condition) to give the compound 17. $^1$H NMR (CDCl$_3$, 400 MHz): δ=8.73 (s, 1H), 7.44-7.49 (m, 2H), 7.38-7.42 (m, 1H), 7.34 (br dd, J=8.3, 4.3 Hz, 2H), 7.31-7.37 (m, 1H), 6.82 (d, J=9.0 Hz, 2H), 5.56-5.68 (m, 1H), 5.03 (d, J=10.0 Hz, 1H), 4.93 (d, J=17.1 Hz, 1H), 4.67 (br s, 4H), 4.32 (br d, J=6.0 Hz, 2H), 3.06 (br t, J=5.5 Hz, 6H), 2.46 (br s, 4H), 2.31 (s, 3H), 1.59 (br t, J=5.3 Hz, 8H)

MS m/z: 581.1[M+H]$^+$

Embodiment 18: Compound 18

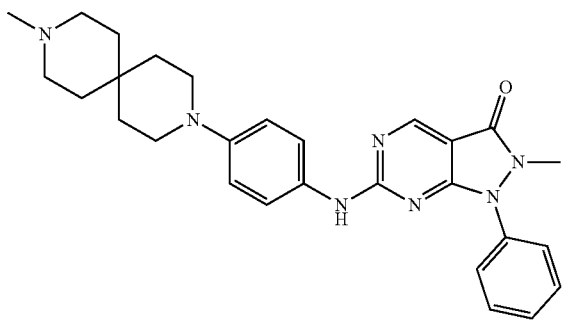 [SMILES: CN1CCC2(CC1)CCN(c1ccc(Nc3ncc4c(=O)n(C)n(-c5ccccc5)c4n3)cc1)CC2]

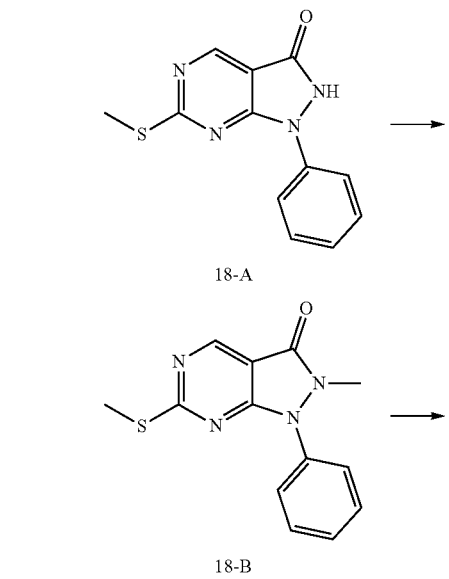

18

Step 1: Synthesis of Compound 18-A

Ammonium formate (8.45 g, 134.10 mmol), (1,1'-bis(diphenylphosphino)ferrocene) palladium dichloride*dichloromethane (1.64 g, 2.01 mmol) were added into the compound 1-A (4.00 g, 13.41 mmol) in THF (80.00 mL) solution. Under nitrogen atmosphere, the reaction mixture was stirred at 80° C. for 12 hours. The reaction was cooled down to 20° C., then filtered, the residue was washed by THF (30 mL) once to give crude product. Water (100 mL) was added into the crude product while stirring, the suspension was filtered and the residue was washed by water (50 mL) to give a pale yellow solid 18-A. MS m/z: 258.9 [M+H]$^+$ Step 2: Synthesis of Compound 18-B Potassium hydroxide (81.46 mg, 1.45 mmol) and methyl iodide (1.00 g, 7.05 mmol, 438.60 μL) were added into the compound 18-A (250.00 mg, 967.87 μmol, 1) in ethanol (20.00 mL) solution. The reaction mixture was stirred at 80° C. for 23 hours. The reaction mixture directly evaporated to give the crude product. The crude compound was purified by silica gel column (PE/EtOAc=3/1) to give 18-B. $^1$H NMR (400 MHz, CDCl$_3$) δ2.50 (s, 3H) 3.36 (s, 3H) 7.26 (s, 1H) 7.39-7.45 (m, 3H) 7.50-7.57 (m, 2H) 8.91 (s, 1H)
MS m/z: 272.9 [M+H]$^+$ Step 3: Synthesis of Compound 18 m-Chloroperoxybenzoic acid (67.10 mg, 330.48 μmol, 85% purity) was added into the compound 18-B (60.00 mg, 220.32 μmol) in toluene (8.00 mL) solution. The reaction was stirred at 25° C. for 2 hours. Intermediate 12 (74.29 mg, 286.42 μmol) and N,N-diisopropylethylamine (85.42 mg, 660.96 μmol) were added into the reaction system. The reaction mixture was stirred at 25° C. for 12 hours. Sodium thiosulfate solution (30 mL) was added into the reaction system to quench the extra m-chloroperoxybenzoic acid, then extracted with EtOAc (30 mL×3). The organic phases were combined and washed by saturated brine (50 mL), dried over anhydrous sodium sulfate. The desiccant was filtered off, the solvent was eliminated under reduced pressure to give the crude product. The crude product was purified by preparative HPLC (neutral) to give the compound 18. $^1$H NMR (400 MHz, CDCl$_3$) δ1.62 (dt, J=18.76, 5.55 Hz, 8H) 2.32 (s, 3H) 2.44 (br s, 4H) 3.09-3.14 (m, 4H) 3.31 (s, 3H) 6.89 (d, J=9.03 Hz, 2H) 7.38-7.46 (m, 5H) 7.50-7.55 (m, 2H) 8.80 (s, 1H)
MS m/z: 484.1 [M+H]$^+$ Embodiment 19: Compound 19

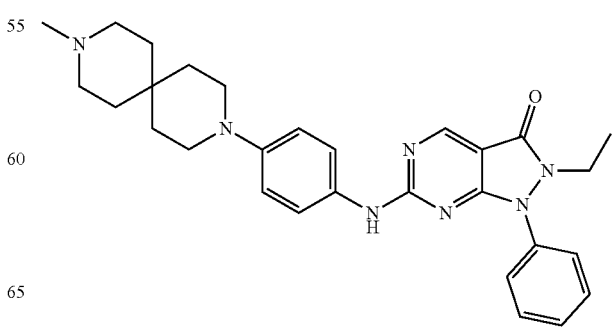

Synthetic Route:

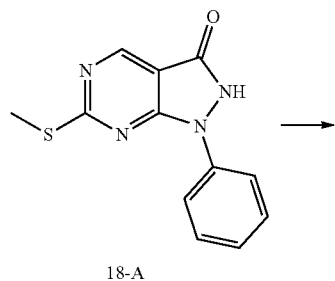

18-A

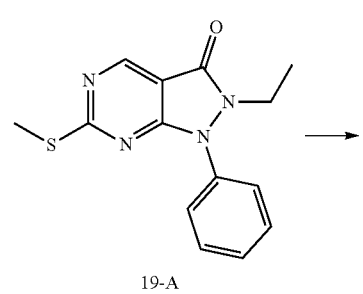

19-A

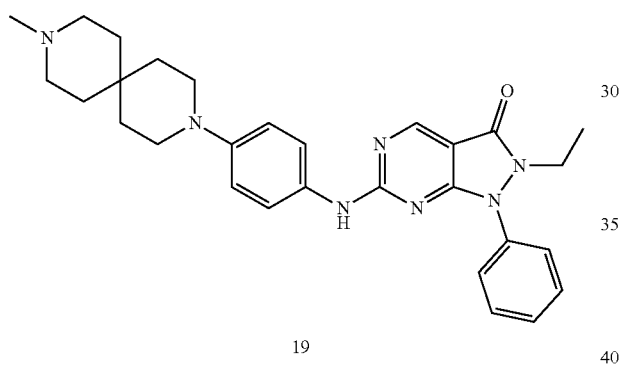

19

Step 1: Synthesis of Compound 19-A

According to the method for preparing the compound 18-B, and methyl iodide was replaced by bromoethane, crude product of the compound 19-A was obtained. The crude compound 19-A was purified by preparative TLC (PE/EtOAc=3/1) to give 19-A. $^1$H NMR (400 MHz, CDCl$_3$) δ1.09 (t, J=7.15 Hz, 3H) 2.50 (s, 3H) 3.91 (q, J=7.03 Hz, 2H) 7.39-7.45 (m, 3H) 7.50-7.56 (m, 2H) 8.90 (s, 1H)

MS m/z: 286.9 [M+H]$^+$

Step 2: Synthesis of Compound 19

According to the method for preparing the compound 18, and started with the compound 19-A, compound 19 was obtained. $^1$H NMR (400 MHz, CDCl$_3$) δ1.00 (t, J=6.78 Hz, 3H) 1.50-1.60 (m, 8H) 2.24 (s, 3H) 2.35 (br s, 4H) 3.03-3.07 (m, 4H) 3.80 (q, J=6.69 Hz, 2H) 6.82 (d, J=9.03 Hz, 2H) 7.31-7.41 (m, 5H) 7.43-7.48 (m, 2H) 8.72 (s, 1H)

MS m/z: 498.1 [M+H]$^+$

Embodiment 20: Compound 20

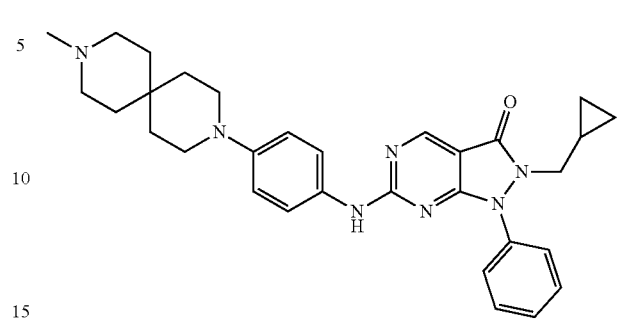

Synthetic Route:

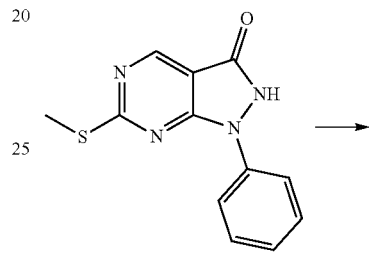

18-A

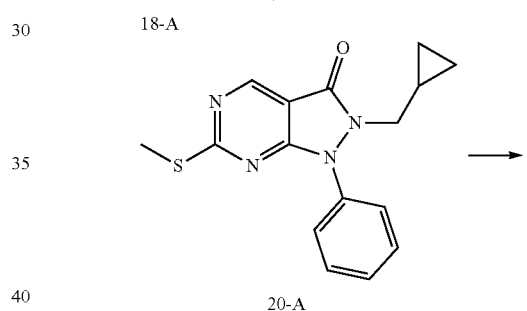

20-A

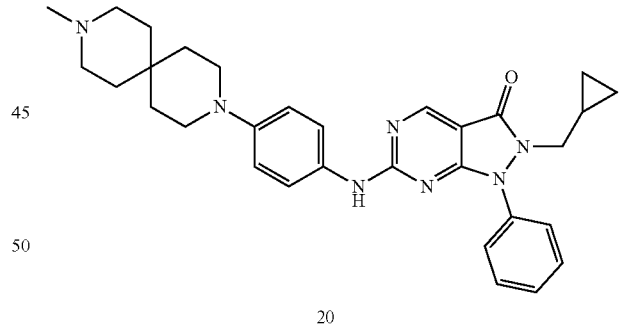

20

Step 1: Synthesis of Compound 20-A

According to the method for preparing the compound 18-B, and methyl iodide was replaced by bromomethylcyclopropane, compound 20-A was obtained. MS m/z: 313.0 [M+H]$^+$

Step 2: Synthesis of Compound 20

According to the method for preparing the compound 18, and started with the compound 20-A, compound 20 was obtained. $^1$H NMR (400 MHz, CDCl$_3$) δ 0.11-0.13 (m, 2H)

0.36-0.41 (m, 2H) 0.86-0.90 (m, 1H) 1.69 (br s, 8H) 2.43 (s, 3H) 2.60 (br s, 4H) 3.10-3.14 (m, 4H) 3.70 (br d, J=6.78 Hz, 2H) 4.41 (br s, 1H) 6.89 (br d, J=9.28 Hz, 2H) 7.38 (br d, J=7.04 Hz, 1H) 7.43-7.48 (m, 1H) 7.46 (br d, J=7.54 Hz, 3H) 7.51 (br d, J=7.54 Hz, 2H) 8.81 (s, 1H)

MS m/z: 524.1 [M+H]⁺

Embodiment 21: Compound 21

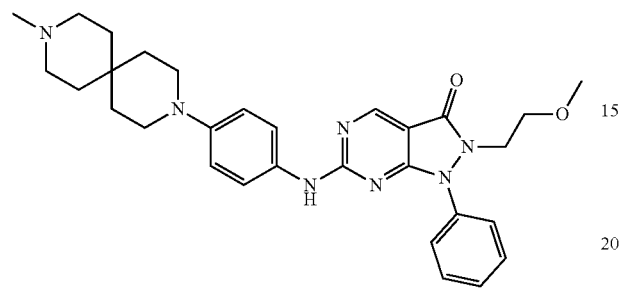

Synthetic Route:

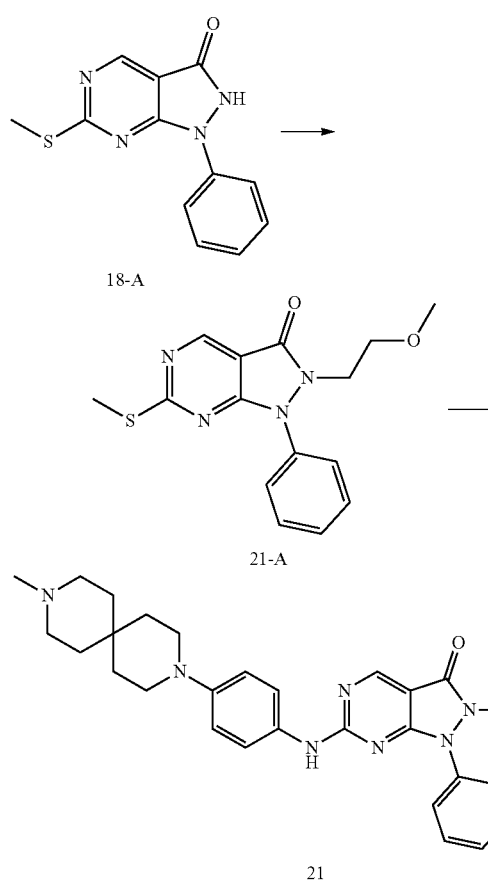

Step 1: Synthesis of Compound 21-A

According to the method for preparing the compound 18-B, and methyl iodide was replaced by 1-bromo-2-methoxyethane, compound 21-A was obtained. MS m/z: 317.0 [M+H]⁺

Step 2: Synthesis of Compound 21

According to the method for preparing the compound 18, and started with compound 21-A, compound 21 was obtained. ¹H NMR (400 MHz, CDCl₃) δ1.59-1.65 (m, 8H) 2.31 (s, 3H) 2.43 (br s, 4H) 3.10-3.14 (m, 4H) 3.23 (s, 3H) 3.46 (t, J=5.66 Hz, 2H) 4.01 (br t, J=5.40 Hz, 2H) 6.89 (d, J=8.78 Hz, 2H) 7.41-7.53 (m, 7H) 8.80 (s, 1H)

MS m/z: 528.1 [M+H]⁺

Embodiment 22: Compound 22

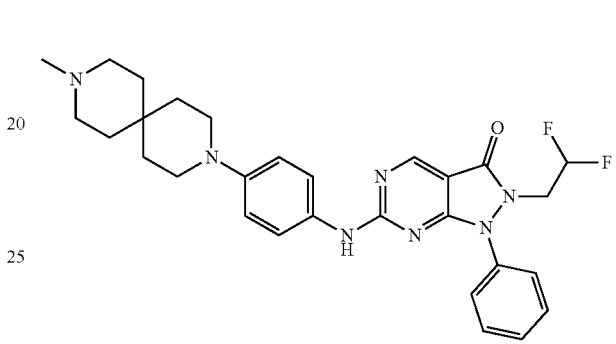

Synthetic Route:

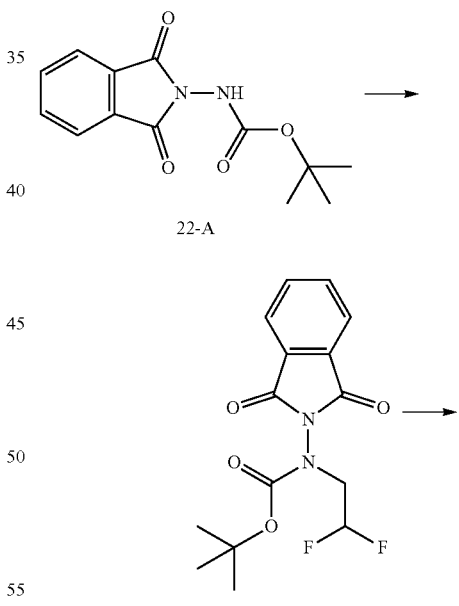

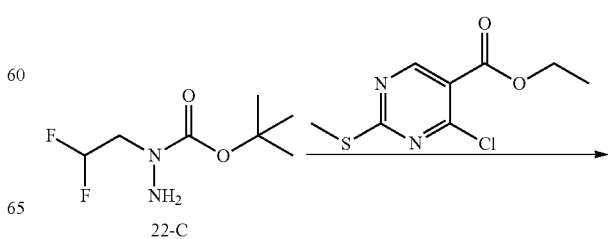

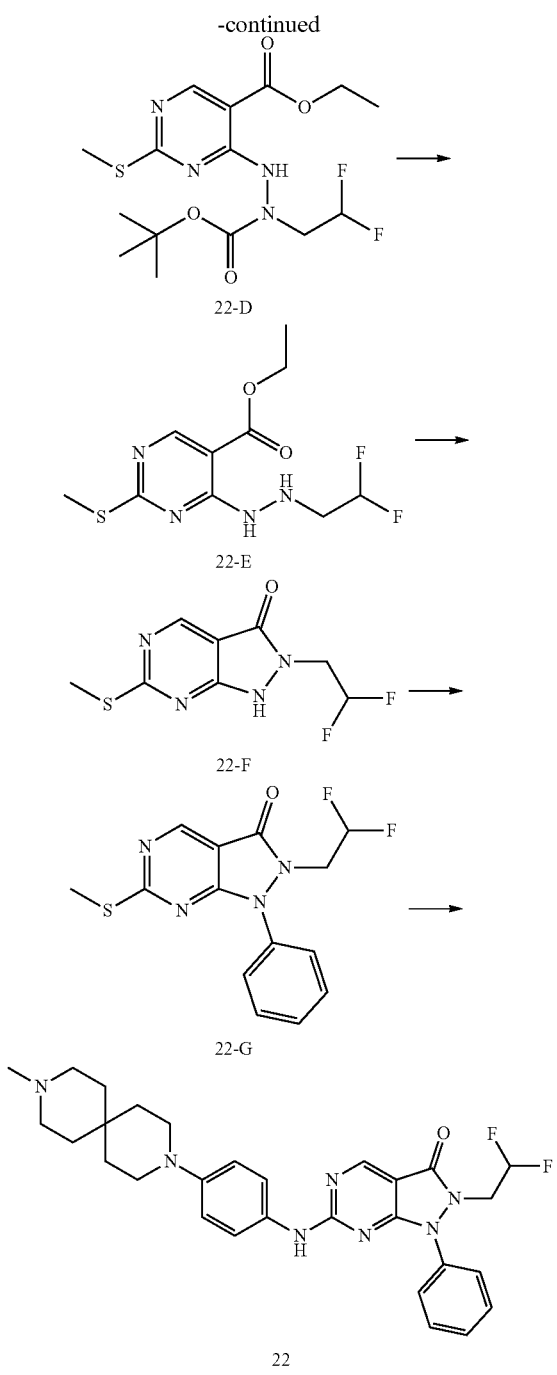

Step 1: Synthesis of Compound 22-B

Compound benzyl triethyl ammonium chloride (117.25 mg, 514.76 μmol), potassium carbonate (1.58 g, 11.44 mmol) and compound 1-bromo-2,2-difluoroethane (1.20 g, 8.29 mmol) were added into the compound 22-A (1.50 g, 5.72 mmol, obtained when preparing the Intermediate I1) in acetonitrile (15.00 mL) solution. The reaction mixture was stirred at 50° C. for 12 hours. The reaction mixture was evaporated to give the crude product, water (20 mL) was added into the crude product and extracted by EtOAc (30 mL×3). The organic phases were combined and washed by saturated brine (50 mL), dried over anhydrous sodium sulfate. The desiccant was filtered off, the solvent was eliminated under reduced pressure to give the crude product. The crude compound was purified by silica gel column (PE/EtOAc=5/1) to give the compound 22-B. $^1$H NMR (400 MHz, CDCl$_3$) δ1.36 (s, 6H) 1.56 (s, 3H) 3.95-4.08 (m, 2H) 5.90-6.24 (m, 1H) 7.79-7.87 (m, 2H) 7.94 (td, J=6.08, 3.14 Hz, 2H)

Step 2: Synthesis of Compound 22-C

Methyl hydrazine (316.73 mg, 2.75 mmol, 359.92 μL, 40% purity) was added into the compound 22-B (360.00 mg, 1.10 mmol) in THF (8.00 mL) solution at 0-5° C. The reaction mixture was stirred at 40° C. for 12 hours. The reaction mixture was cooled down to 25° C., then filtered, the filtrate was evaporated to give the crude product, hexane/EtOAc=3/1 (24 mL) was added into the crude product and stirred for 5 min, then filtered, the filtrate was concentrated and evaporated to dry to give the compound 22-C. $^1$H NMR (400 MHz, CDCl$_3$) δ1.48 (s, 9H) 3.68-3.78 (m, 2H) 5.75-6.11 (m, 1H)

Step 3: Synthesis of Compound 22-D

Compound 4-chloro-2-(methylthio)pyrimidin-5-ethyl formate (265.00 mg, 1.14 mmol) and N,N-diisopropylethylamine (442.00 mg, 3.42 mmol, 597.30 μL) were added into the compound 22-C (223.66 mg, 1.14 mmol) in THF (25.00 mL) solution. The reaction mixture was stirred at 80° C. for 12 hours. The crude product was diluted by EtOAc (30 mL) while stirring for 5 min, then filtered, the filtrate was evaporated to dry to give the compound 22-D. MS m/z: 393.1 [M+H]$^+$ Step 4: Synthesis of Compound 22-E Trifluoroacetic acid (10.00 mL) was slowly added dropwise into the compound 22-D (205.00 mg, 522.40 μmol) at 0-5° C., the reaction mixture was stirred at 25° C. for 4 hours. The reaction mixture was evaporated to dry to give the compound 22-E.
MS m/z: 292.9 [M+H]$^+$ Step 5: Synthesis of Compound 22-F At 0-5° C., sodium hydroxide solution (4 M, 2.00 mL) was added into the compound 22-E (700.00 mg, 2.39 mmol) in ethanol (8.00 mL) solution. The reaction mixture was stirred at 25° C. for 30 min. The reaction mixture was adjusted to pH=1 by diluted hydrochloric acid, then extracted by dichloromethane (50 mL×6), the organic phases were combined and washed by saturated brine (50 mL), dried over anhydrous sodium sulfate. The desiccant was filtered off, the solvent was eliminated under reduced pressure to give the compound 22-F. MS m/z: 247.0 [M+H]$^+$ Step 6: Synthesis of Compound 22-G According to the method for preparing the compound 3-A and 2-bromopyridine was replaced by bromobenzene, crude product of the compound 22-G was obtained. The crude product was purified by column chromatography (PE/EtOAc=5/1, 3/1) to give the compound 22-G. MS m/z: 323.0 [M+H]$^+$ Step 7: Synthesis of Compound 22 m-Chloroperoxybenzoic acid (54.67 mg, 269.29 μmol, 85% purity) was added into the compound 22-G (62.00 mg, 192.35 μmol) in toluene (5.00 mL) solution. The reaction was stirred at 30° C. for 1 hour. Intermediate 12 (74.84 mg, 288.52 μmol) and N,N-diisopropylethylamine (74.58 mg, 577.05 μmol) were added into the reaction system. The reaction mixture was stirred at 30° C. for 12 hours. Water (20 mL) was added into the reaction system, then extracted by EtOAc (20 mL×3). The organic phases were combined, the organic phase was quenched by saturated sodium bicarbonate (30 mL) for the extra m-chloroperoxybenzoic acid and then washed by saturated brine (30 mL), dried over anhydrous sodium sulfate. The desiccant was filtered off, the solvent was eliminated under reduced pressure to give the crude product, which was purified by preparative HPLC (neutral) to give to give the compound 22. $^1$H NMR (400 MHz, CDCl$_3$) δ1.64 (dt, J=19.02, 5.55 Hz, 8H) 2.34 (s, 3H) 2.44 (br s, 4H) 3.09-3.20 (m, 4H) 4.06-4.19 (m, 2H) 5.83-6.16 (m, 1H) 6.90 (br d, J=8.78 Hz, 2H) 7.45 (br d, J=7.78 Hz, 4H) 7.50-7.63 (m, 3H) 8.84 (s, 1H)

MS m/z: 534.0 [M+H]$^+$

Embodiment 23: Compound 23

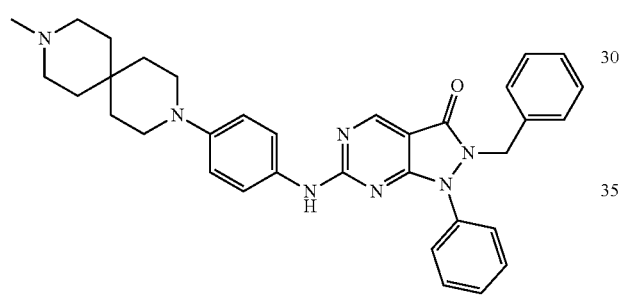

Synthetic Route:

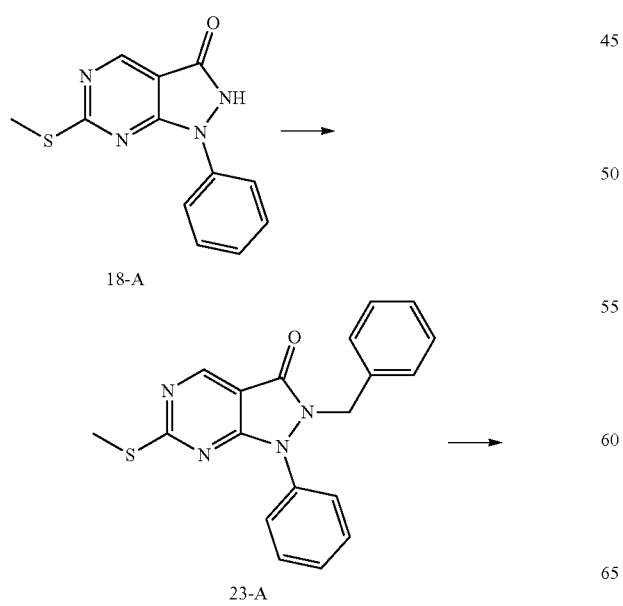

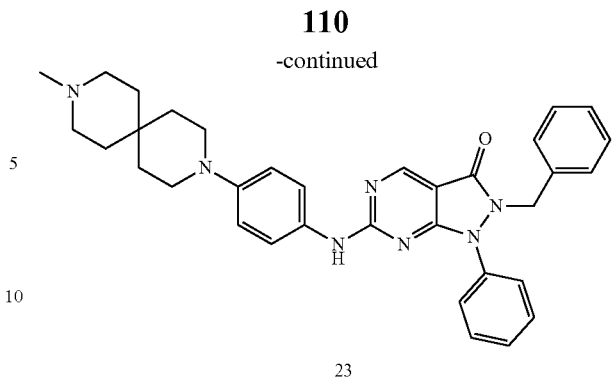

23

Step 1: Synthesis of Compound 23-A

According to the method for preparing the compound 18-B and methyl iodide was replaced by benzyl bromide, the compound 23-A was obtained. $^1$H NMR (400 MHz, CDCl$_3$) δ2.45 (s, 3H) 5.01 (s, 2H) 6.98 (dd, J=7.78, 1.76 Hz, 2H) 7.17-7.24 (m, 3H) 7.27-7.31 (m, 2H) 7.39-7.44 (m, 1H) 7.47-7.52 (m, 2H) 8.91 (s, 1H)

MS m/z: 348.9 [M+H]$^+$

Step 2: Synthesis of Compound 23

According to the method for preparing the compound 18, and started with the compound 23-A, the compound 23 was obtained. $^1$H NMR (400 MHz, CDCl$_3$) δ1.61 (dt, J=19.64, 5.36 Hz, 8H) 2.31 (s, 3H) 2.41 (br s, 4H) 3.06-3.14 (m, 4H) 4.94-4.98 (m, 1H) 4.96 (s, 2H) 6.85 (br d, J=8.54 Hz, 2H) 6.98-7.06 (m, 2H) 7.16-7.24 (m, 3H) 7.32-7.41 (m, 5H) 7.47-7.52 (m, 2H) 8.80 (s, 1H)

MS m/z: 560.1 [M+H]$^+$

Embodiment 24: Compound 24

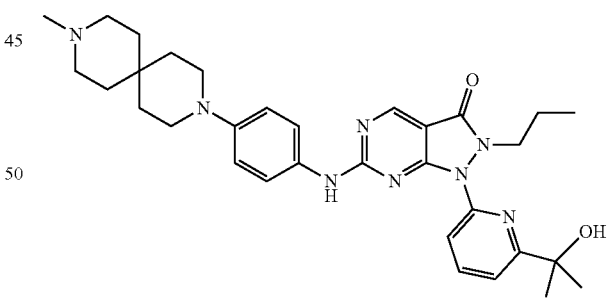

Synthetic Route:

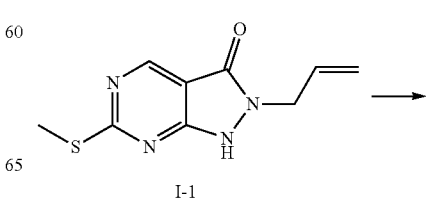

I-1

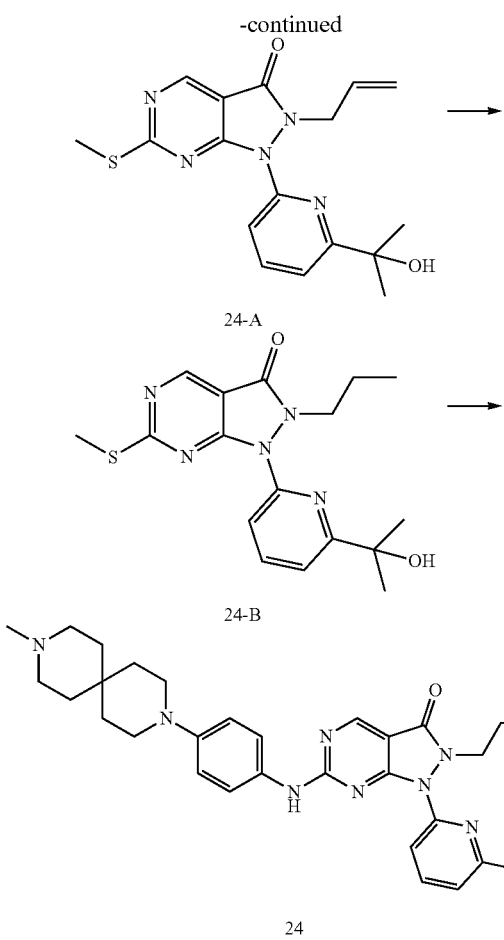

24-A

24-B

24

Step 1: Synthesis of Compound 24-A

According to the method for preparing the compound 3-A and 2-bromopyridine was replaced by 2-(6-bromopyridin-2-yl)isopropanol, the compound 24-A was obtained. $^1$H NMR (400 MHz, CDCl$_3$) δ1.59 (s, 6H) 2.58 (s, 3H) 3.71 (s, 1H) 4.81 (br d, J=6.02 Hz, 2H) 4.90-4.96 (m, 1H) 5.06 (br d, J=10.29 Hz, 1H) 5.69 (ddt, J=16.81, 10.42, 6.21, 6.21 Hz, 1H) 7.40 (d, J=7.78 Hz, 1H) 7.76 (d, J=7.78 Hz, 1H) 7.88-7.94 (m, 1H) 8.94 (s, 1H)

MS m/z: 358.0 [M+H]$^+$

Step 2: Synthesis of Compound 24-B

Pd(OH)$_2$/C (100.00 mg, 131.66 μmol, 20% purity) was added into the compound 24-A (100.00 mg, 279.78 μmol) in ethanol (8.00 mL) solution. The reaction mixture was stirred under hydrogen (15 Psi) at 25° C. for 12 hours. The reaction mixture was filtered, the filtrate was concentrated under reduced pressure to remove the solvent so as to give the compound 24-B.

MS m/z: 360.2 [M+H]$^+$

Step 3: Synthesis of Compound 24

According to the method for preparing the compound 18, and started with compound 24-B, the compound 24 was obtained. $^1$H NMR (400 MHz, CDCl$_3$) δ0.66 (t, J=7.28 Hz, 3H) 1.34-1.40 (m, 2H) 1.45 (s, 6H) 1.48-1.54 (m, 8H) 2.19 (s, 3H) 2.31 (br s, 4H) 3.00-3.04 (m, 4H) 3.99 (t, J=7.04 Hz, 2H) 6.81 (d, J=9.04 Hz, 2H) 7.24 (d, J=7.54 Hz, 1H) 7.33 (br d, J=9.04 Hz, 2H) 7.63 (d, J=8.04 Hz, 1H) 7.73-7.79 (m, 1H) 8.70 (s, 1H)

MS m/z: 571.1 [M+H]$^+$

Embodiment 25: Compound 25

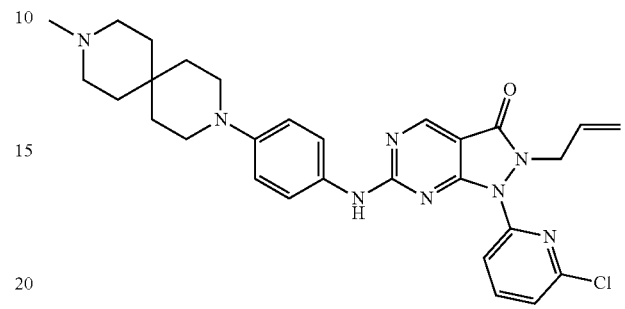

Synthetic Route:

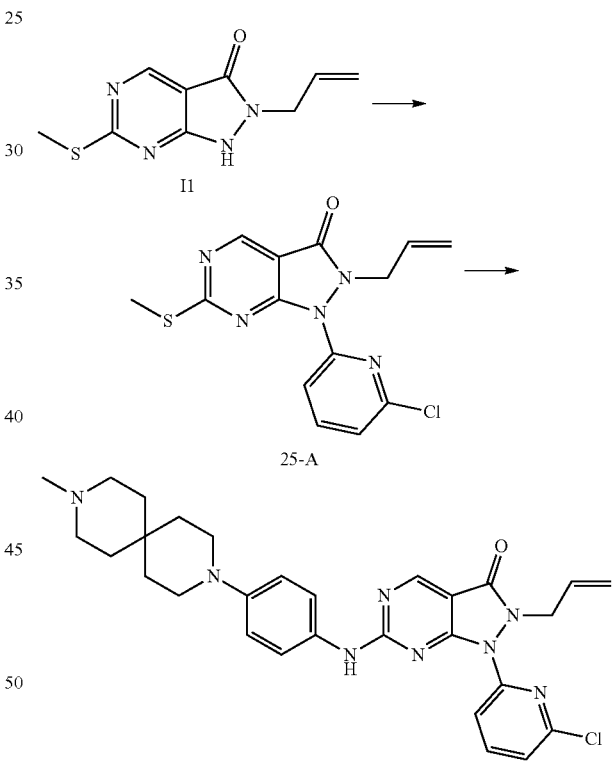

I1

25-A

25

Step 1: Synthesis of Compound 25-A

According to the method for preparing the compound 27-A in embodiment 27 except for the corresponding starting material 2-bromo-6-chloropyridine, compound 25-A was obtained. MS m/z: 334.0 [M+H]$^+$

Step 2: Synthesis of Compound 25

According to the method for preparing the compound 22, and started with the compound 25-A, the compound 25 was obtained. $^1$H NMR (400 MHz, CDCl$_3$) δ1.61-1.71 (m, 8H) 2.35 (s, 3H) 2.45-2.56 (m, 4H) 3.11-3.19 (m, 4H) 4.80 (br d, J=6.28 Hz, 2H) 4.97-5.06 (m, 2H) 5.69 (ddt, J=16.86, 10.32, 6.24, 6.24 Hz, 1H) 6.88-6.95 (m, 2H) 7.20-7.25 (m, 1H) 7.42-7.48 (m, 2H) 7.75-7.80 (m, 1H) 7.82-7.86 (m, 1H) 8.82 (s, 1H)

MS m/z: 545.0 [M+H]$^+$

Embodiment 26: Compound 26

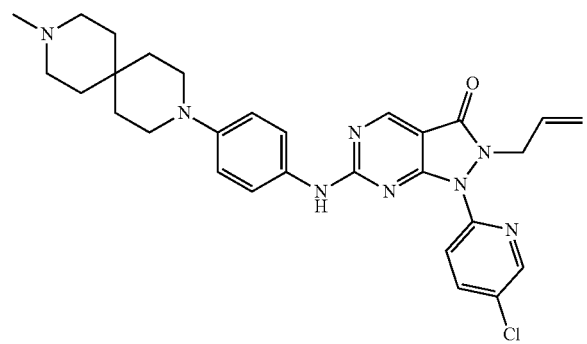 [SMILES: C=CCn1c(=O)c2cnc(Nc3ccc(N4CCC5(CCN(C)CC5)CC4)cc3)nc2n1-c1ccc(F)cn1]

Synthetic Route:

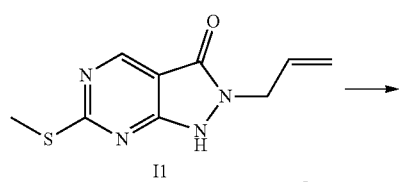

I1

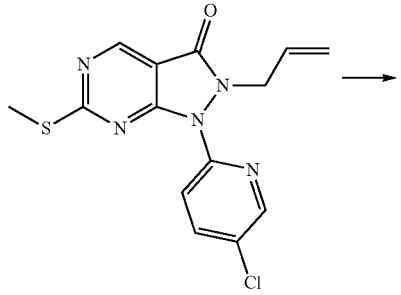

26-A

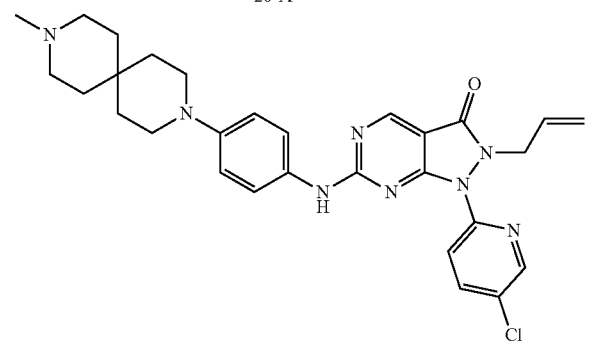

26

Step 1: Synthesis of Compound 26-A

According to the method for preparing the compound 27-A, 2-bromo-6-fluoropyridine was replaced by 2-bromo-5-chloropyridine, crude product of the compound 26-A was obtained, the crude product was purified by column chromatography (PE/EtOAc=5/1, 3/1) to give the compound 26-A. MS m/z: 333.9 [M+H]$^+$ Step 2: Synthesis of Compound 26

According to the method for preparing the compound 22, and started with the compound 26-A, the compound 26 was obtained. $^1$H NMR (400 MHz, CDCl$_3$) δ1.51-1.62 (m, 8H) 2.23 (s, 3H) 2.34 (br s, 4H) 3.07-3.11 (m, 4H) 4.69 (br d, J=6.02 Hz, 2H) 4.87 (d, J=17.08 Hz, 1H) 4.96 (d, J=9.54 Hz, 1H) 5.59 (ddt, J=16.88, 10.35, 6.46, 6.46 Hz, 1H) 6.87 (d, J=9.04 Hz, 2H) 7.35 (br d, J=9.04 Hz, 2H) 7.69-7.75 (m, 1H) 7.76-7.90 (m, 1H) 8.38 (d, J=2.52 Hz, 1H) 8.75 (s, 1H)

MS m/z: 545.0 [M+H]$^+$

Embodiment 27: Compound 27

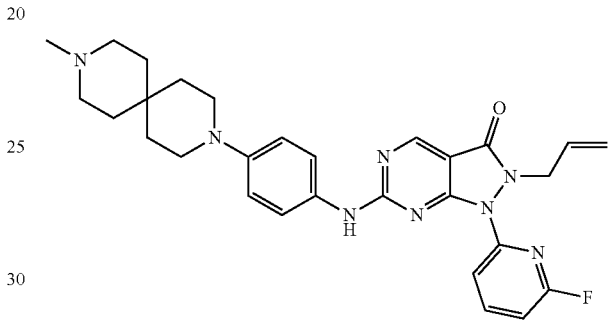

Synthetic Route:

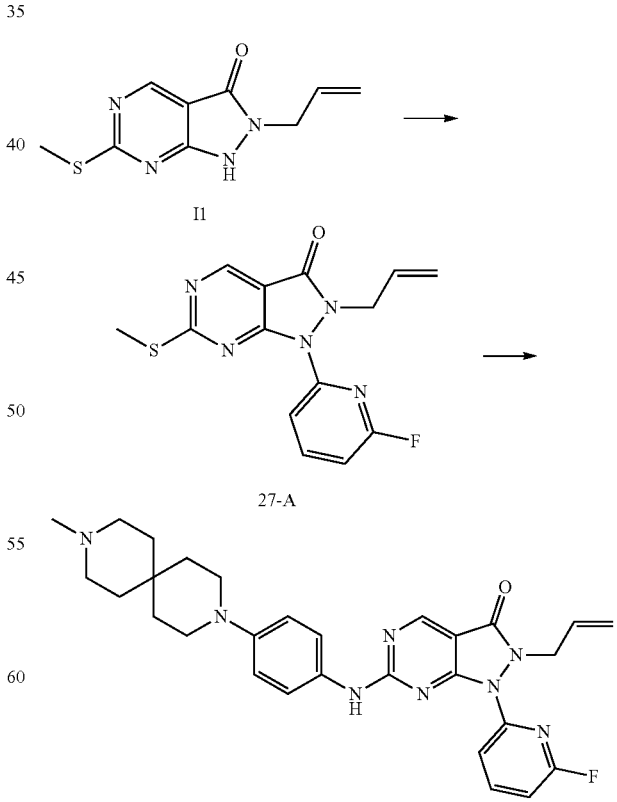

27

Step 1: Synthesis of Compound 27-A

Potassium carbonate (213.62 mg, 1.55 mmol), CuI (213.30 mg, 1.12 mmol, 1.00 eq) and N,N-dimethylethylenediamine (110.58 mg, 1.25 mmol, 134.85 μL) were added into compound I1 (250.00 mg, 1.12 mmol) and 2-bromo-6-fluoropyridine (203.02 mg, 1.15 mmol) in dioxane (8.00 mL) solution. The reaction mixture was stirred under nitrogen atmosphere at 95° C. for 1 hour. The reaction mixture was cooled down and then ammonia (30 mL) was added, extracted by EtOAc (50 mL×3), the organic phases were combined, the organic phase was washed by saturated brine (50 mL) once, dried over anhydrous sodium sulfate, then filtered, the filtrate was evaporated to give the compound 27-A. MS m/z: 318.0 [M+H]$^+$

Step 2: Synthesis of Compound 27

According to the method for preparing the compound 22, and started with the compound 27-A, the compound 27 was obtained. $^1$H NMR (400 MHz, CDCl$_3$) δ1.62 (br t, J=5.52 Hz, 8H) 2.33 (s, 3H) 2.43 (br s, 4H) 3.15-3.20 (m, 4H) 4.82 (d, J=6.54 Hz, 2H) 4.98-5.08 (m, 2H) 5.71 (ddt, J=16.94, 10.42, 6.16, 6.16 Hz, 1H) 6.85 (dd, J=8.04, 2.52 Hz, 1H) 6.96 (d, J=9.04 Hz, 2H) 7.47 (br d, J=8.54 Hz, 2H) 7.83 (d, J=8.04 Hz, 1H) 7.94 (q, J=7.70 Hz, 1H) 8.84 (s, 1H)
MS m/z: 529.1 [M+H]$^+$

Embodiment 28: Compound 28

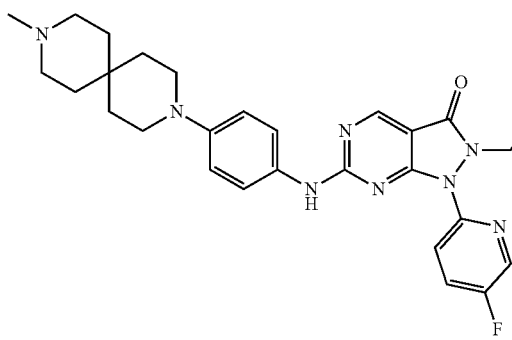

Synthetic Route:

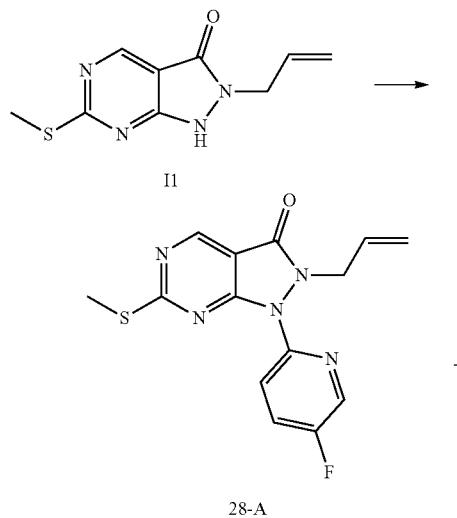

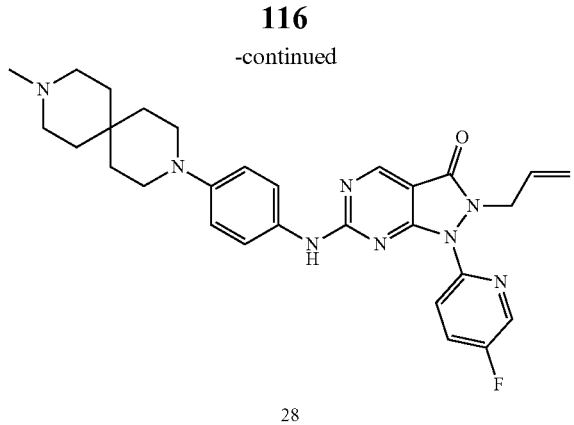

28

Step 1: Synthesis of Compound 28-A

According to the method for preparing the compound 27-A, the 2-bromo-6-fluoropyridine was replaced by 2-bromo-5-fluoropyridine, crude product of the compound 28-A was obtained, the crude product was purified by column chromatography (PE/EtOAc=5/1, 3/1) to give a yellow compound 28-A. MS m/z: 318.0 [M+H]$^+$

Step 2: Synthesis of Compound 28

According to the method for preparing the compound 22, and started with the compound 28-A, the compound 28 was obtained. $^1$H NMR (400 MHz, CDCl$_3$) δ1.60-1.70 (m, 8H) 2.32 (s, 3H) 2.42 (br s, 4H) 3.13-3.21 (m, 4H) 4.75 (br d, J=6.54 Hz, 2H) 4.95 (dd, J=17.08, 1.00 Hz, 1H) 5.04 (d, J=10.04 Hz, 1H) 5.69 (ddt, J=16.88, 10.36, 6.46, 6.46 Hz, 1H) 6.94 (d, J=8.54 Hz, 2H) 7.43 (d, J=9.04 Hz, 2H) 7.60 (td, J=8.16, 2.76 Hz, 1H) 7.89 (br dd, J=8.78, 3.76 Hz, 1H) 8.38 (d, J=2.52 Hz, 1H) 8.84 (s, 1H)
MS m/z: 529.0 [M+H]$^+$

Embodiment 29: Compound 29

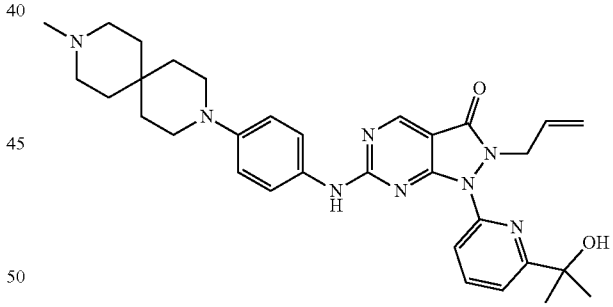

Synthetic Route:

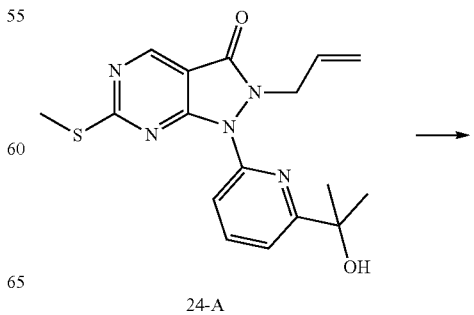

24-A

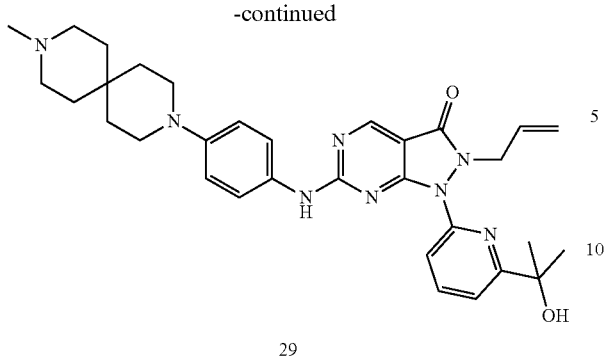

29

Step 1: Synthesis of Compound 29 m-Chloroperoxybenzoic acid (117.40 mg, 578.28 μmol, purity: 85%) was added into the 24-A (206.69 mg, 578.28 μmol) in toluene (15.00 mL) solution, the mixture was stirred at 20-25° C. for 1 hour and then added I2 (86.65 mg, 334.06 μmol) and N,N-diisopropylethylamine (224.21 mg, 1.73 mmol, 302.99 μL). After further stirring for 14 hours, the product was concentrated to give the crude compound, the crude compound was purified by preparative HPLC (neutral condition) to give the compound 29. $^1$H NMR (400 MHz, DMSO-d) δ1.47 (s, 6H) 1.47-1.50 (m, 4H) 1.54 (br s, 4H) 2.17 (s, 3H) 2.30 (br s, 4H) 3.09 (br s, 4H) 4.69 (br d, J=5.02 Hz, 2H) 4.83 (br d, J=17.07 Hz, 1H) 5.00 (br d, J=10.04 Hz, 1H) 5.34 (s, 1H) 5.60-5.79 (m, 1H) 6.92 (br d, J=8.53 Hz, 2H) 7.50-7.67 (m, 3H) 7.76 (br d, J=7.53 Hz, 1H) 8.06 (br s, 1H) 8.83 (s, 1H)

MS m/z: 569.3[M+H]$^+$

Embodiment 30: Compound 30

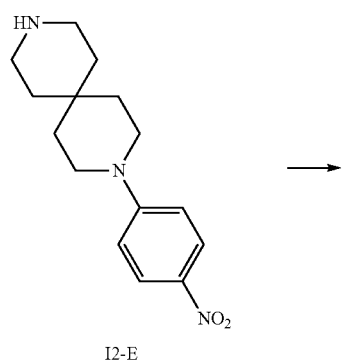

Synthetic Route:

I2-E

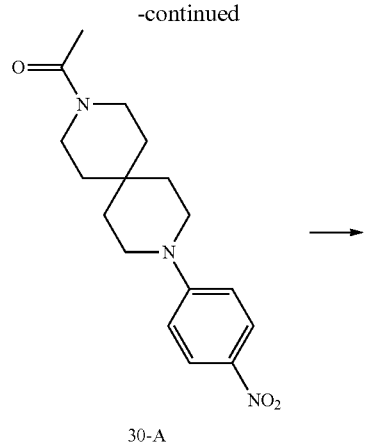

30-A

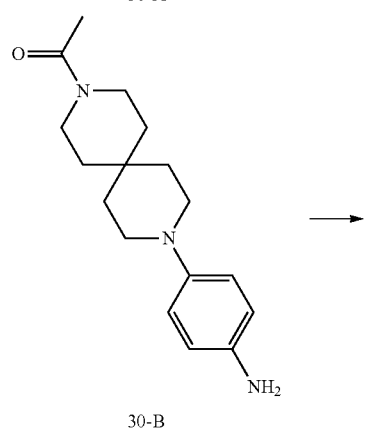

30-B

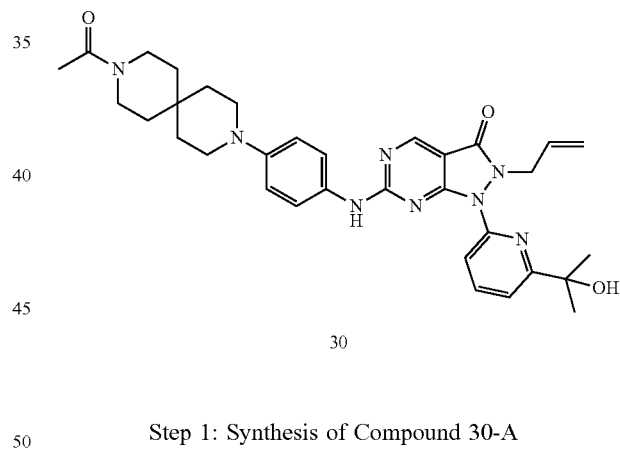

30

Step 1: Synthesis of Compound 30-A

Compound triethylamine (147.00 mg, 1.45 mmol, 201.37 μL) was added into the compound I2-E (80.00 mg, 290.54 μmol) in dichloromethane (2.00 mL) solution at 0° C., and then slowly added dropwise acetylchloride (45.61 mg, 581.08 μmol, 41.46 μL). The reaction mixture was stirred at 30° C. for 0.5 hours. Water (10 mL) was added into the reaction mixture, then extracted with dichloromethane (10 mL×3) and washed by saturated brine (20 mL), dried over anhydrous sodium sulfate, then filtered, the filtrate was evaporated to give the crude product. The crude product was purified by column chromatography (PE/EtOAc=1/1-0/1) to give the compound 30-A. $^1$H NMR (400 MHz, CDCl$_3$) δ1.55 (q, J=5.68 Hz, 4H) 1.65-1.71 (m, 4H) 2.10 (s, 3H) 3.41-3.47 (m, 6H) 3.56-3.65 (m, 2H) 6.80 (d, J=8.46 Hz, 2H) 8.12 (d, J=9.54 Hz, 2H)

MS m/z: 318.1 [M+H]$^+$

Step 2: Synthesis of Compound 30-B

According to the method for preparing the compound 37-B, and started with the compound 30-A, the compound 30-B was obtained.

MS m/z: 288.1 [M+H]+

Step 3: Synthesis of Compound 30

According to the method for preparing the compound 22, and started with the compound 30-B, the compound 30 was obtained. ¹H NMR (400 MHz, CDCl₃) δ1.52 (s, 6H) 1.64 (br d, J=5.52 Hz, 8H) 2.04 (s, 3H) 3.10 (t, J=5.52 Hz, 4H) 3.35-3.40 (m, 2H) 3.51-3.56 (m, 2H) 4.67 (d, J=6.02 Hz, 2H) 4.87 (dd, J=17.08, 1.00 Hz, 1H) 4.94-5.06 (m, 1H) 5.63 (ddt, J=16.82, 10.28, 6.28, 6.28 Hz, 1H) 6.87 (d, J=9.04 Hz, 2H) 7.27 (d, J=7.54 Hz, 1H) 7.40 (br d, J=8.54 Hz, 2H) 7.69 (d, J=8.04 Hz, 1H) 7.79 (t, J=8.04 Hz, 1H) 8.76 (s, 1H)

MS m/z: 597.1 [M+H]+

Embodiment 31: Compound 31

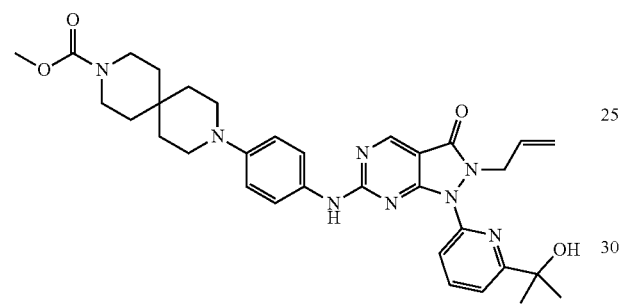

Synthetic Route:

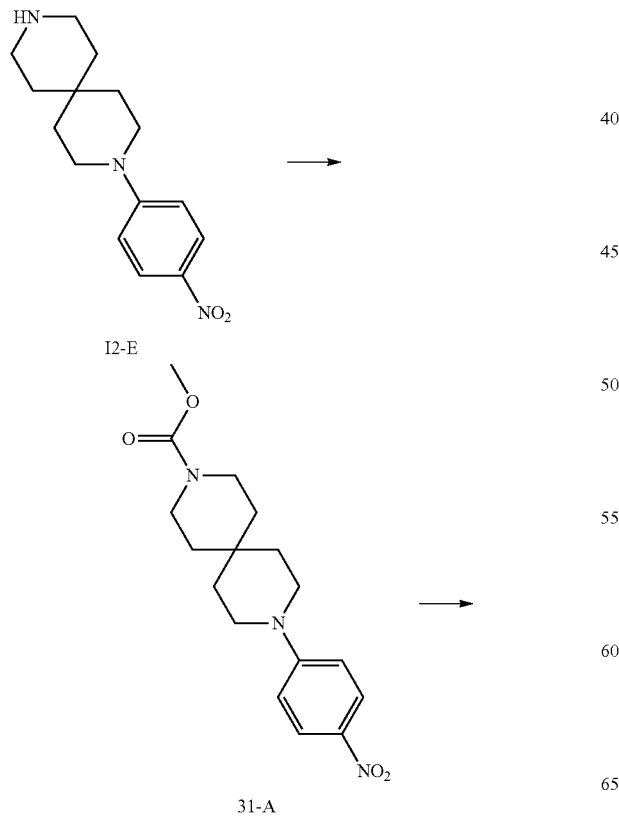

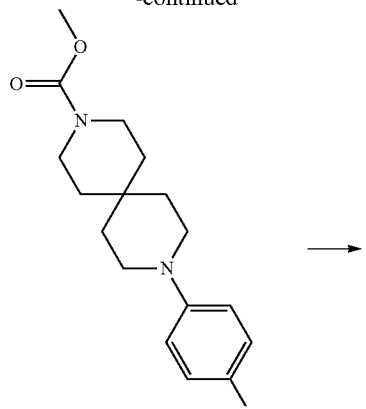

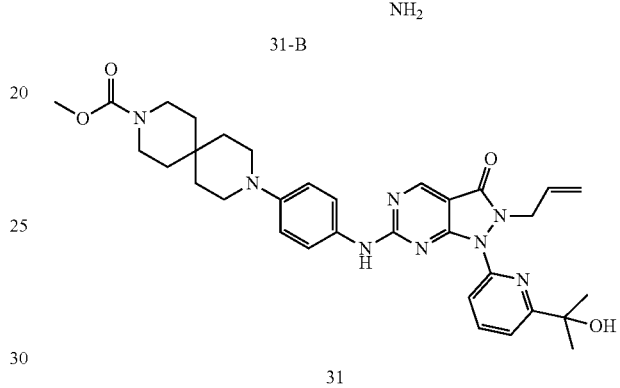

Step 1: Synthesis of Compound 31-A

According to the method for preparing the compound 30-A, and acetylchloride was replaced by methyl chloroformate, the compound 31-A was obtained. ¹H NMR (400 MHz, CDCl₃) δ1.47-1.56 (m, 4H) 1.61-1.69 (m, 4H) 3.40-3.52 (m, 8H) 3.64-3.75 (m, 3H) 6.80 (d, J=8.50 Hz, 2H) 8.09-8.14 (m, 2H)

MS m/z: 334.1 [M+H]+

Step 2: Synthesis of Compound 31-B

According to the method for preparing the compound 37-B, and started with the compound 31-A, the compound 31-B was obtained.

MS m/z: 304.1 [M+H]+

Step 3: Synthesis of Compound 31

According to the method for preparing the compound 22, and started with the compound 31-B, the compound 31 was obtained. ¹H NMR (400 MHz, CDCl₃) δ1.52 (s, 6H) 1.57-1.66 (m, 8H) 3.07-3.12 (m, 4H) 3.40 (br s, 4H) 3.63 (s, 3H) 3.90 (br s, 1H) 4.61-4.70 (m, 2H) 4.87 (dd, J=17.08, 1.00 Hz, 1H) 4.95-5.00 (m, 1H) 5.63 (ddt, J=17.00, 10.48, 6.08, 6.08 Hz, 1H) 6.86 (d, J=9.04 Hz, 2H) 7.27 (d, J=7.54 Hz, 1H) 7.39 (br d, J=8.54 Hz, 2H) 7.69 (d, J=8.04 Hz, 1H) 7.79 (t, J=7.78 Hz, 1H) 8.75 (s, 1H)

MS m/z: 613.0 [M+H]+

Embodiment 32: Compound 32

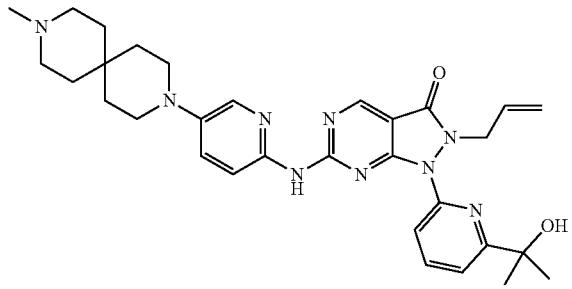 [SMILES: C=CCn1c(=O)c2cnc(Nc3ccc(N4CCC5(CCN(C)CC5)CC4)cn3)nc2n1-c1cccc(C(C)(C)O)n1]

Synthetic Route:

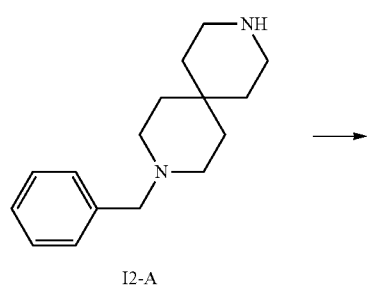

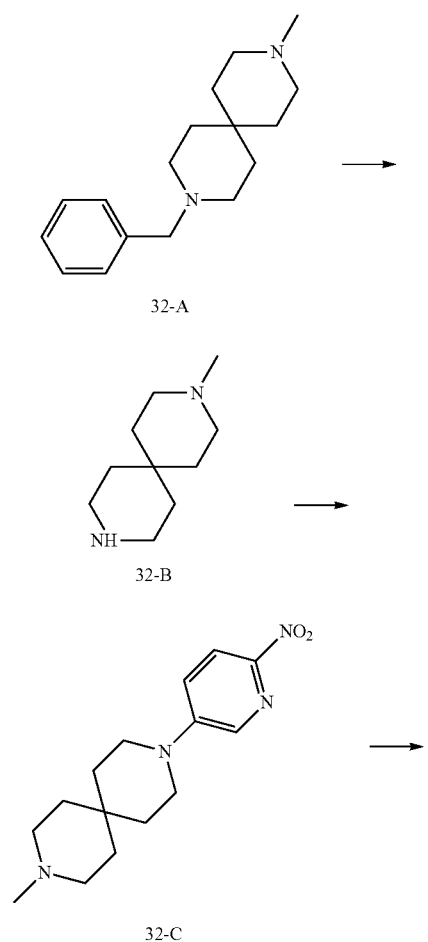

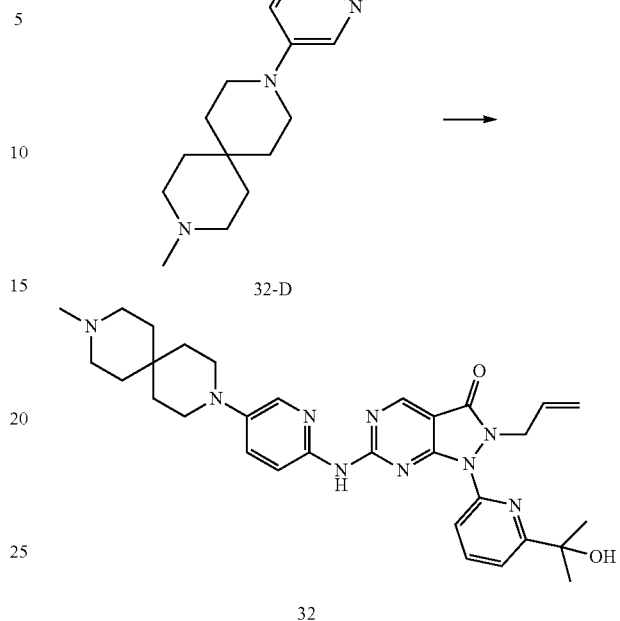

Step 1: Synthesis of Compound 32-A

Formaldehyde solution (27.25 g, 335.75 mmol, 25.00 mL, 37% purity), Sodium triacetoxyborohydride (17.52 g, 82.66 mmol) and glacial acetic acid (7.45 g, 123.99 mmol, 7.10 mL) were added separately into the compound I2-A (10.10 g, 41.33 mmol) in methanol (150.00 mL) solution, and was stirred at 20-25° C. for 2 hours, the solvent was concentrated, 10% NaOH solution was used to adjust the pH to around 8, then extracted by dichloromethane 800 mL (150 mL×6), the organic phase was washed by saturated brine 300 mL, dried over anhydrous sodium sulfate, then filtered and concentrated to give the compound 32-A. MS m/z: 259.1 [M+H]$^+$

Step 2: Synthesis of Compound 32-B

Under argon atmosphere, acetic acid (7.88 g, 131.19 mmol, 7.50 mL) and wet palladium hydroxide/carbon (600.00 mg, 20% purity) were added into the compound 32-A (7.50 g, 29.02 mmol) in ethanol (100.00 mL) solution, after replacing with hydrogen for 3 times, the mixture was stirred at 50° C. and hydrogen (50 psi) for 18 hours, the product was purified by diatomite and then filtered and concentrated to give the crude product compound 32-B. MS m/z: 169.0 [M+H]$^+$

Step 3: Synthesis of Compound 32-C

Triethylamine (361.25 mg, 3.57 mmol, 494.86 μL) was added into the compound 32-B (200.00 mg, 1.19 mmol) and 5-chloro-2-nitro-pyridine (188.66 mg, 1.19 mmol) in 5 mL dimethyl sulfoxide solution, and was stirred at 90° C. for 12 hours, diluted by 10 mL 10% hydrochloric acid solution, by EtOAc 60 mL (20 mL×3), the aqueous phase was adjusted by 10% sodium hydroxide to pH around 10, EtOAc 120 mL (40 mL×3) was added. The organic phase washed by saturated brine 70 mL, dried over anhydrous sodium sulfate, then filtered and concentrated to give the compound 32-C. MS m/z: 291.1 [M+H]$^+$

123

Step 4: Synthesis of Compound 32-D

Under argon atmosphere, 10% wet palladium carbon (25 mg) was added into the compound 32-C (200.00 mg, 688.80 mmol) in ethanol (20 mL) solution, after replacing with hydrogen 3 times, the mixture was stirred at 20-25° C. under hydrogen pressure (15 psi) for 16 hours, then filtered with diatomite, evaporated to give the crude product compound 32-D (brown oil, 180 mg). MS m/z: 261.3 [M+H]$^+$

Step 5: Synthesis of Compound 32

According to the method for preparing the compound 5, and started with the compound 32-D, crude product of the compound 32 was obtained, the product was purified by preparative HPLC (neutral condition) to give the compound 32. $^1$H NMR (CDCl$_3$, 400 MHz): δ=8.85 (s, 1H), 8.11 (d, J=9.0 Hz, 1H), 7.96 (d, J=2.5 Hz, 1H), 7.81-7.87 (m, 1H), 7.65 (d, J=8.0 Hz, 1H), 7.31 (d, J=7.5 Hz, 1H), 7.23 (dd, J=9.3, 2.8 Hz, 1H), 5.58-5.70 (m, 1H), 4.99 (d, J=10.0 Hz, 1H), 4.87 (d, J=17.1 Hz, 1H), 4.66 (d, J=6.0 Hz, 2H), 3.89 (br s, 1H), 3.03-3.12 (m, 4H), 2.44 (br s, 4H), 2.30 (s, 3H), 1.62 (br s, 8H), 1.53 (s, 6H)
MS m/z: 570.2[M+1]$^+$

Embodiment 33: Compound 33

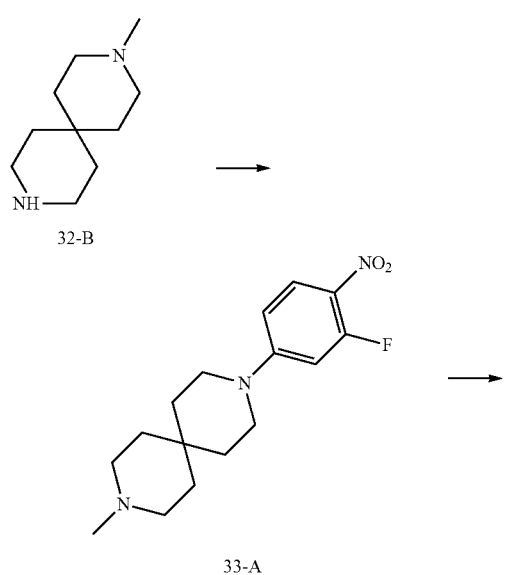

Synthetic Route:

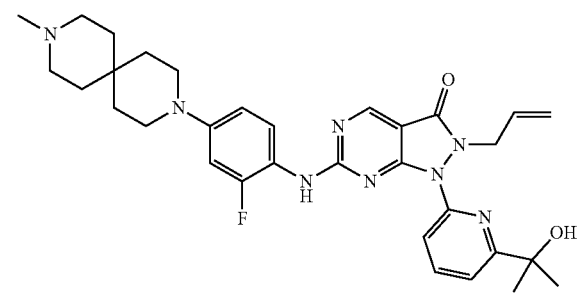 [SMILES: C=CCn1c(=O)c2cnc(Nc3ccc(N4CCC5(CCN(C)CC5)CC4)cc3F)nc2n1-c1cccc(C(C)(C)O)n1]

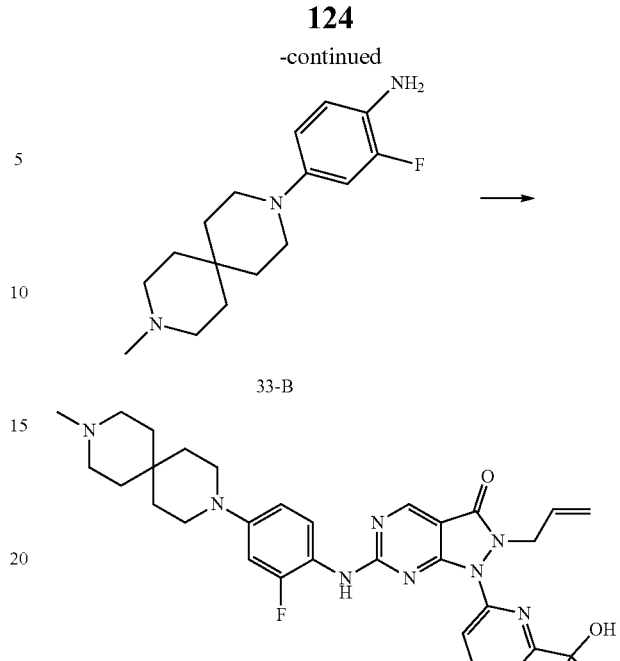

Step 1: Synthesis of Compound 33-A

Potassium carbonate (246.39 mg, 1.78 mmol) was added into the compound 32-B (100 mg, 594.25 μmol) and 2,4-difluoro-nitrobenzene (435 mg, 2.73 mmol) in 3 mL dimethyl sulfoxide solution, and stirred at 90° C. for 12 hours, then diluted with 10 mL 10% hydrochloric acid solution, and washed by EtOAc 60 mL (20 mL×3), the aqueous phase was adjusted by 10% sodium hydroxide to pH around 10, then extracted with EtOAc 120 mL (40 mL×3). The organic phase was washed by saturated brine 60 mL, dried over anhydrous sodium sulfate, then filtered and concentrated to give the crude product compound 33-A. MS m/z: 308.1 [M+H]$^+$

Step 2: Synthesis of Compound 33-B

According to the method for preparing the compound 32-D, and started with the compound 33-A, crude product of the compound 33-B was obtained. MS m/z: 277.9 [M+H]$^+$

Step 3: Synthesis of Compound 33

According to the method for preparing compound 5, and started with the compound 33-B, crude product of the compound 33 was obtained, the product was purified by preparative HPLC (neutral condition) to give the compound 33. $^1$H NMR (CDCl$_3$, 400 MHz): δ=8.78 (s, 1H), 8.04 (s, 1H), 7.77-7.82 (m, 1H), 7.66 (d, J=8.0 Hz, 1H), 7.28 (d, J=7.5 Hz, 1H), 6.60-6.65 (m, 2H), 5.59-5.67 (m, 1H), 4.98 (d, J=9.5 Hz, 1H), 4.87 (d, J=17.1 Hz, 1H), 4.83-4.84 (m, 1H), 4.67 (d, J=6.0 Hz, 2H), 3.06-3.10 (m, 4H), 2.47 (br s, 4H), 2.32 (s, 3H), 1.58 (br s, 8H), 1.52 (s, 6H)
MS m/z: 587.1[M+1]$^+$

Embodiment 34: Compound 34

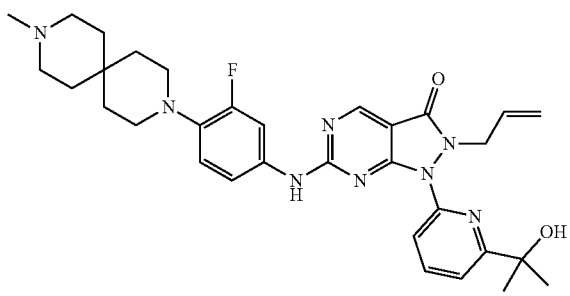 [SMILES: C=CCn1c(=O)c2cnc(Nc3ccc(N4CCC5(CCN(C)CC5)CC4)c(F)c3)nc2n1-c1cccc(C(C)(C)O)n1]

Synthetic Route:

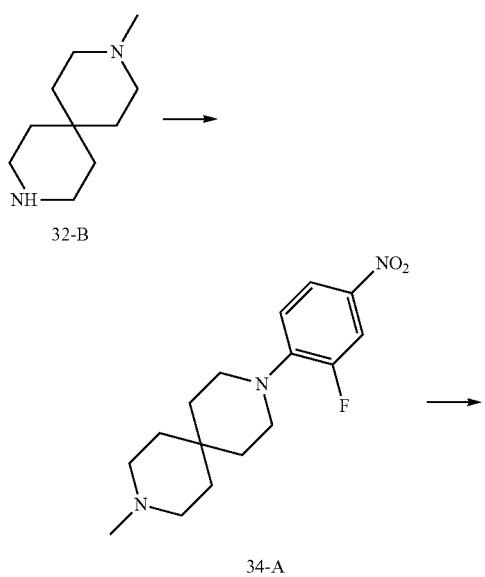

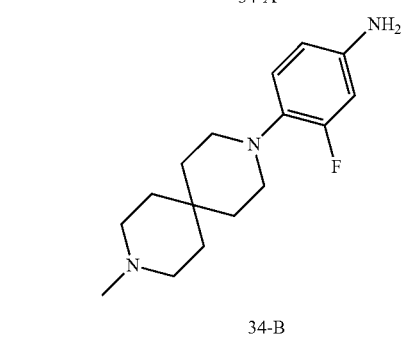

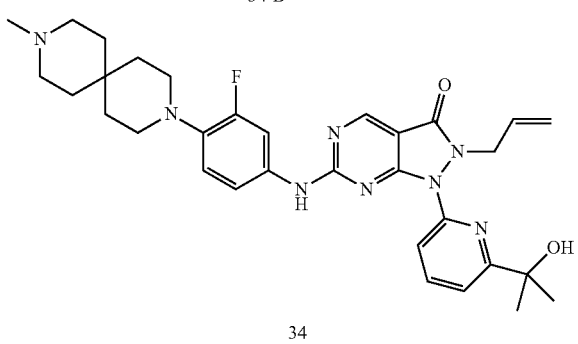

Step 1: Synthesis of Compound 34-A

Triethylamine (361.25 mg, 3.57 mmol, 494.86 μL) was added into the compound 32-B (200.00 mg, 1.19 mmol) and 1,2-difluoro-4-nitrobenzene (350 mg, 2.20 mmol) in 10 mL methanol solution, and was stirred at 20-25° C. for 13 hours, diluted by 10 mL 10% hydrochloric acid solution, EtOAc 60 mL (20 mL×3) was added, the aqueous phase was adjusted by 10% sodium hydroxide to pH around 10, EtOAc 120 mL (40 mL×3) was used. The organic phase was washed by saturated brine 70 mL, dried over anhydrous sodium sulfate, then filtered and concentrated to give the crude product compound 34-A. MS m/z: 308.1 [M+H]$^+$

Step 2: Synthesis of Compound 34-B

According to the method for preparing the compound 32-D, and started with the compound 34-A, crude product of the compound 34-B was obtained. MS m/z: 277.9 [M+H]$^+$

Step 3: Synthesis of Compound 34

According to the method for preparing the compound 5, and started with the compound 34-B, crude product of the compound 34 was obtained, the product was purified by preparative HPLC (neutral condition) to give the compound 34. $^1$H NMR (CDCl$_3$, 400 MHz): δ=8.78 (s, 1H), 7.84-7.90 (m, 1H), 7.72 (d, J=8.0 Hz, 1H), 7.39-7.52 (m, 1H), 7.45 (br s, 1H), 7.31 (d, J=7.5 Hz, 1H), 6.90-6.95 (m, 1H), 6.83-6.89 (m, 1H), 5.59-5.69 (m, 1H), 4.96-5.01 (m, 1H), 4.87 (dd, J=17.1, 1.0 Hz, 1H), 4.69 (d, J=6.0 Hz, 2H), 2.92-2.97 (m, 4H), 2.46 (br s, 4H), 2.31 (s, 3H), 1.61 (br d, J=6.0 Hz, 8H), 1.52 (s, 6H)

MS m/z: 587.1 [M/2+1]$^+$

Embodiment 35: Compound 35

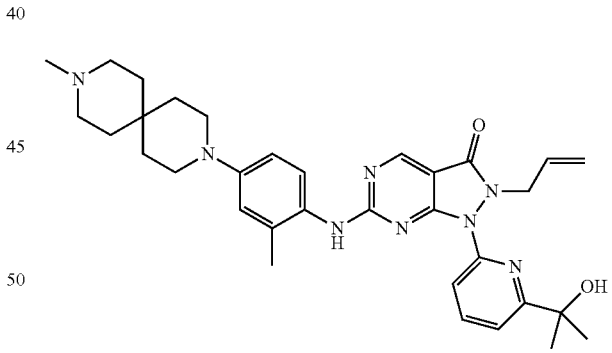

Synthetic Route:

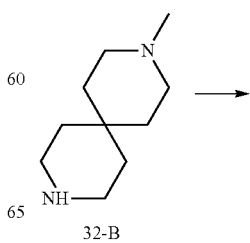

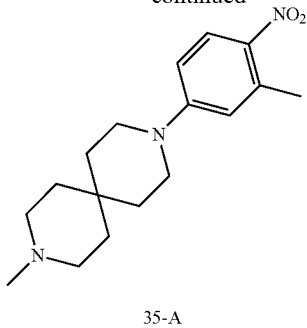

35-A

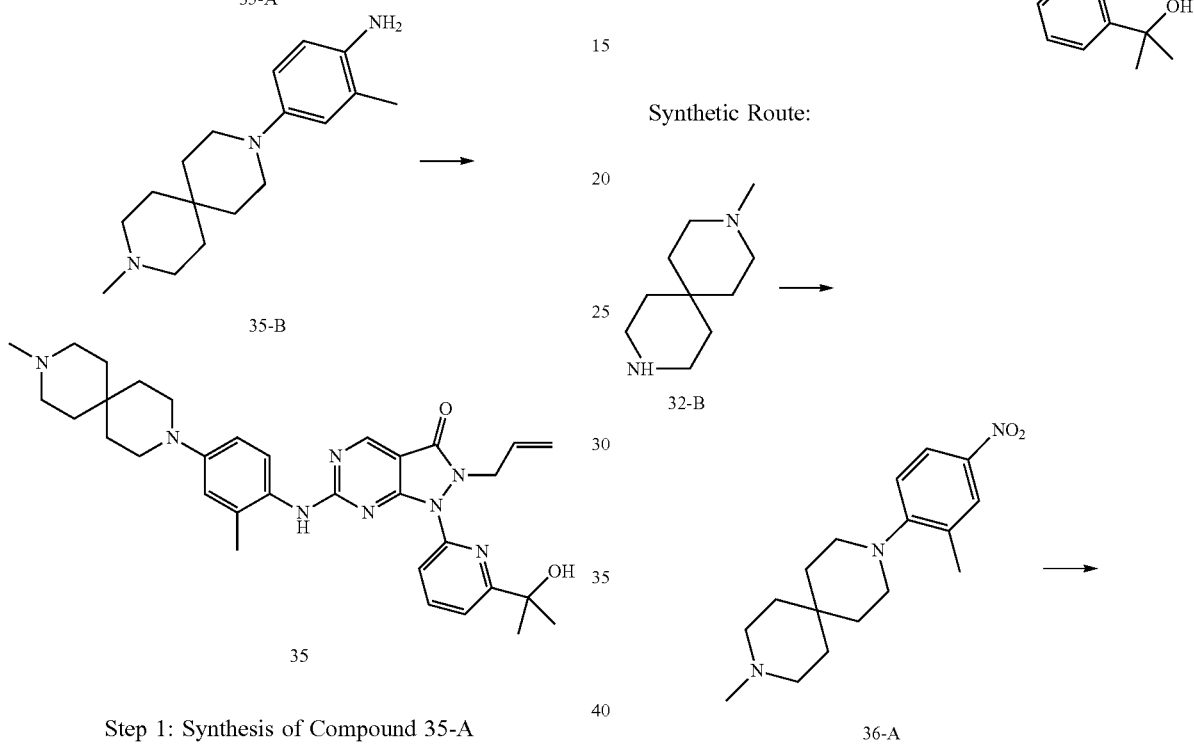

35-B

35

Step 1: Synthesis of Compound 35-A

According to the method for preparing the compound 33-A, 2,4-difluoro-nitrobenzene was replaced by 4-fluoro-2-methyl-nitrobenzene, the compound 35-A was obtained. MS m/z: 304.1 [M+H]+

Step 2: Synthesis of Compound 35-B

According to the method for preparing the compound 32-D, and started with the compound 35-A, the compound 35-B was obtained. MS m/z: 274.1 [M+H]+

Step 3: Synthesis of Compound 35

According to the method for preparing the compound 5, and started with the compound 35-B, crude product of the compound 35 was obtained, the product was purified by preparative HPLC (neutral condition) to give the compound 35. $^1$H NMR (CDCl$_3$, 400 MHz): δ=8.75 (s, 1H), 7.72 (br s, 1H), 7.63 (br d, J=8.0 Hz, 1H), 7.24 (d, J=7.5 Hz, 1H), 7.02 (br s, 1H), 6.70-6.75 (m, 2H), 5.57-5.67 (m, 1H), 4.97 (d, J=10.3 Hz, 1H), 4.87 (d, J=17.1 Hz, 1H), 4.67 (br d, J=6.0 Hz, 2H), 3.86 (br s, 1H), 3.07-3.13 (m, 4H), 2.87 (br s, 4H), 2.59 (s, 3H), 2.18 (s, 3H), 1.81 (br s, 3H), 1.72-1.78 (m, 3H), 1.63-1.69 (m, 6H)
MS m/z: 583.1[M+1]+

Embodiment 36: Compound 36

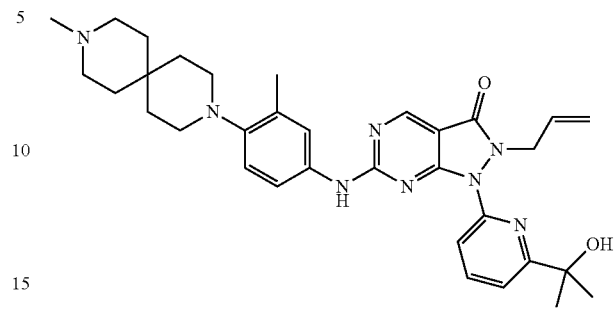

Synthetic Route:

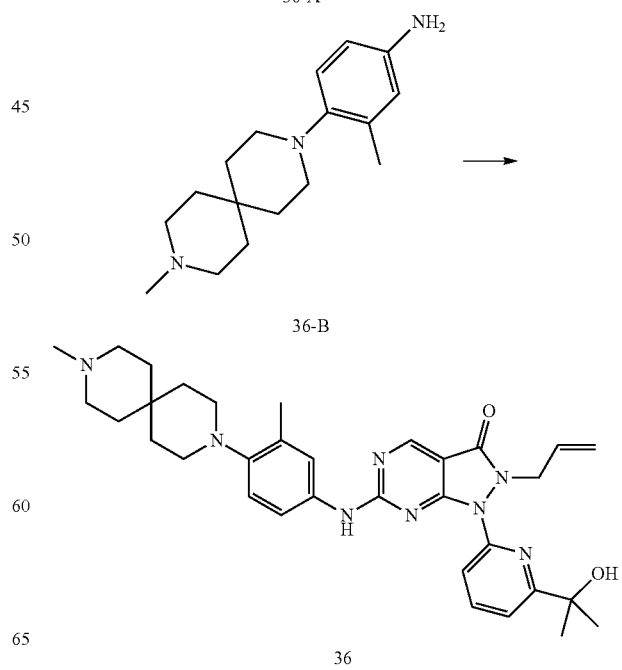

36

Step 1: Synthesis of Compound 36-A

According to the method for preparing the compound 33-A, 2,4-difluoro-nitrobenzene was replaced by 1-fluoro-2-methyl-4-nitrobenzene, the compound 36-A was obtained. MS m/z: 304.2 [M+H]⁺.

Step 2: Synthesis of Compound 36-B

According to the method for preparing the compound 32-D, and started with the compound 36-A, the compound 36-B was obtained. MS m/z: 274.3 [M+H]⁺.

Step 3: Synthesis of Compound 36

According to the method for preparing the compound 22, and started with the compound 36-B, the compound 36 was obtained. ¹H NMR (400 MHz, CDCl₃) δ1.52 (s, 6H) 1.61-1.65 (m, 4H) 1.78 (br t, J=5.28 Hz, 4H) 2.24 (s, 3H) 2.51 (s, 3H) 2.74-2.82 (m, 8H) 4.68 (br d, J=6.54 Hz, 2H) 4.86 (d, J=18.08 Hz, 1H) 4.97 (d, J=10.54 Hz, 1H) 5.63 (ddt, J=16.82, 10.42, 6.22, 6.22 Hz, 1H) 6.93 (d, J=8.54 Hz, 1H) 7.24 (dd, J=8.54, 2.51 Hz, 1H) 7.29 (d, J=7.54 Hz, 1H) 7.43 (br s, 1H) 7.70-7.75 (m, 1H) 7.76-7.86 (m, 1H) 8.77 (s, 1H) MS m/z: 583.1 [M+H]⁺

Embodiment 37: Compound 37

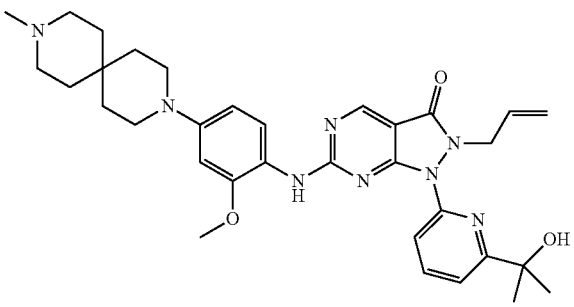

Synthetic Route:

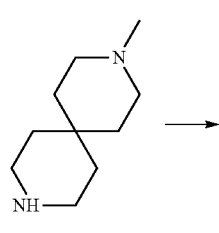

32-B

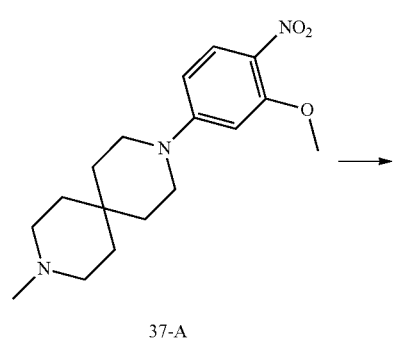

37-A

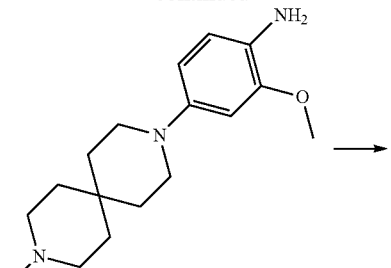

37-B

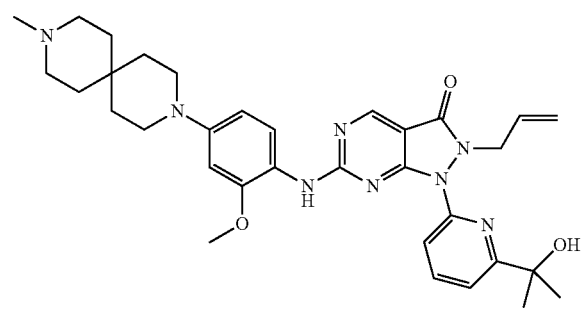 [SMILES: C=CCn1c(=O)c2cnc(Nc3ccc(N4CCC5(CCN(C)CC5)CC4)cc3OC)nc2n1-c1cccc(C(C)(C)O)n1]

37

Step 1: Synthesis of Compound 37-A

Potassium carbonate (323.41 mg, 2.34 mmol) and compound 32-B (334.71 mg, 1.99 mmol) were added into the compound 5-fluoro-2-nitroanisole (200.00 mg, 1.17 mmol) in dimethyl sulfoxide (7.00 mL) solution. The reaction mixture was stirred at 100° C. for 16 hours. The reaction mixture was concentrated under reduced pressure to remove the solvent and give the crude product. The crude compound preparative HPLC (neutral) to give the compound 37-A. MS m/z: 320.1 [M+H]⁺

Step 2: Synthesis of Compound 37-B

Pd/C (39.50 mg, 33.50 μmol, 10% purity) was added into the compound 37-A (107.00 mg, 335.00 μmol) in THF (10.00 mL) solution. The reaction mixture was stirred at 30° C. for 12 hours under hydrogen pressure (15 Psi). The reaction mixture was filtered, the filtrate was concentrated and evaporated to give the compound 37-B. MS m/z: 290.3 [M+H]⁺

Step 3: Synthesis of Compound 37

According to the method for preparing the compound 22, and started with the compound 37-B, the compound 37 was obtained. ¹H NMR (400 MHz, CDCl₃) δ1.52 (s, 6H) 1.57-1.63 (m, 8H) 2.24 (s, 3H) 2.34 (br s, 4H) 3.05-3.09 (m, 4H) 3.81 (s, 3H) 3.92 (br s, 1H) 4.67 (d, J=6.02 Hz, 2H) 4.87 (d, J=17.08 Hz, 1H) 4.97 (d, J=10.04 Hz, 1H) 5.64 (ddt, J=16.82, 10.42, 6.21, 6.21 Hz, 1H) 6.45-6.49 (m, 2H) 7.28 (d, J=7.54 Hz, 1H) 7.73 (d, J=8.04 Hz, 1H) 7.80-7.86 (m, 1H) 8.10 (br d, J=7.54 Hz, 1H) 8.77 (s, 1H) MS m/z: 599.1 [M+H]⁺

Embodiment 38: Compound 38

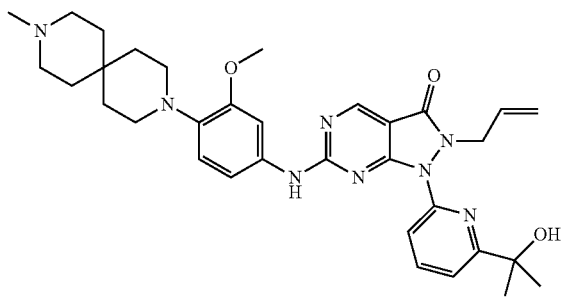 [SMILES: C=CCn1c(=O)c2cnc(Nc3ccc(N4CCC5(CCN(C)CC5)CC4)c(OC)c3)nc2n1-c1cccc(C(C)(C)O)n1]

Synthetic Route:

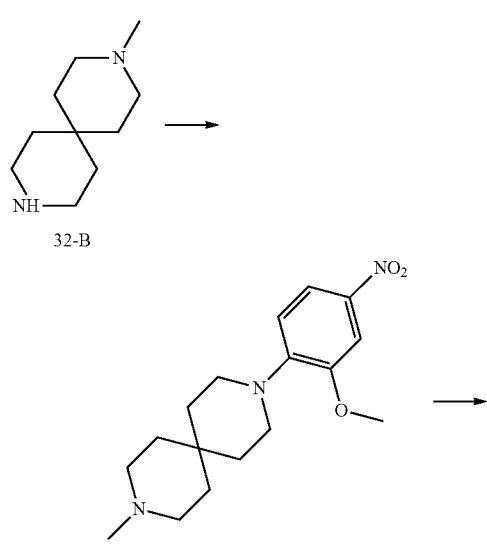

Step 1: Synthesis of Compound 38-A

Triethylamine (266.09 mg, 2.63 mmol, 364.51 μL) was added into the compound 32-B (221.25 mg, 1.31 mmol) and 1-fluoro-methoxyl-nitro-benzene (150 mg, 876.53 μmol) in 10 mL methanol solution, and was stirred at 60° C. for 32 hours, the mixture was then poured into 20 mL water, and was stirred for 30 min, then filtered, the filtrate was adjusted by 2 mol/L hydrochloric acid to pH=1-2, after washing by EtOAc (30 mL×2), 4 mol/L sodium hydroxide was used to adjust the pH=10-11, then extracted by EtOAc (40 mL×3), dried over anhydrous sodium sulfate, then filtered and concentrated to give the crude product compound 38-A. MS m/z: 319.9 [M+H]$^+$

Step 2: Synthesis of Compound 38-B

According to the method for preparing the compound 32-D, and started with the compound 38-A, the compound 38-B was obtained. MS m/z: 290.2 [M+H]$^+$

Step 3: Synthesis of Compound 38

According to the method for preparing the compound 22, and started with the compound 38-B, the compound 38 was obtained. $^1$H NMR (400 MHz, CDCl$_3$) δ1.60 (s, 6H) 1.64-1.72 (m, 8H) 2.31-2.36 (m, 3H) 2.46 (br s, 4H) 2.94-3.03 (m, 4H) 3.82 (s, 3H) 4.75 (d, J=6.02 Hz, 2H) 4.95 (d, J=16.06 Hz, 1H) 5.06 (d, J=10.04 Hz, 1H) 5.66-5.78 (m, 1H) 6.94 (d, J=8.54 Hz, 1H) 7.11 (br s, 2H) 7.35-7.46 (m, 1H) 7.76 (d, J=8.04 Hz, 1H) 7.86 (t, J=7.78 Hz, 1H) 8.87 (s, 1H)

MS m/z: 599.1 [M+H]$^+$

Embodiment 39: Compound 39

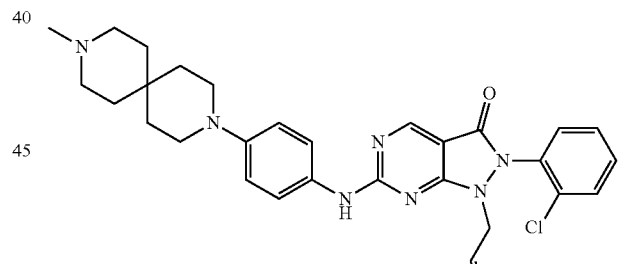

Synthetic Route:

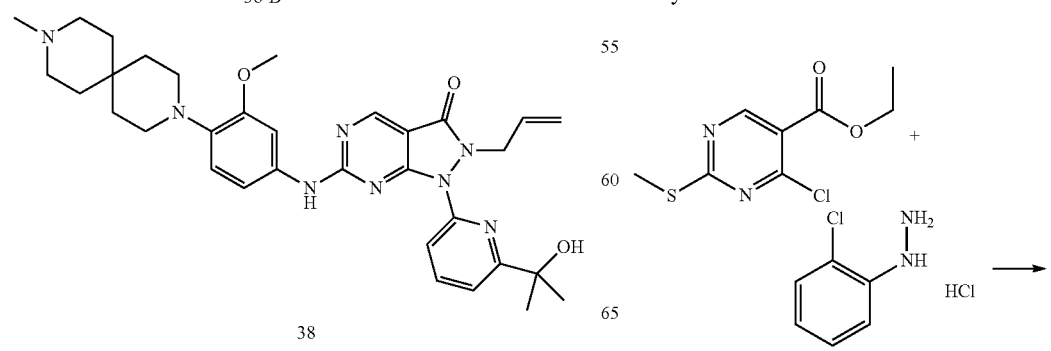

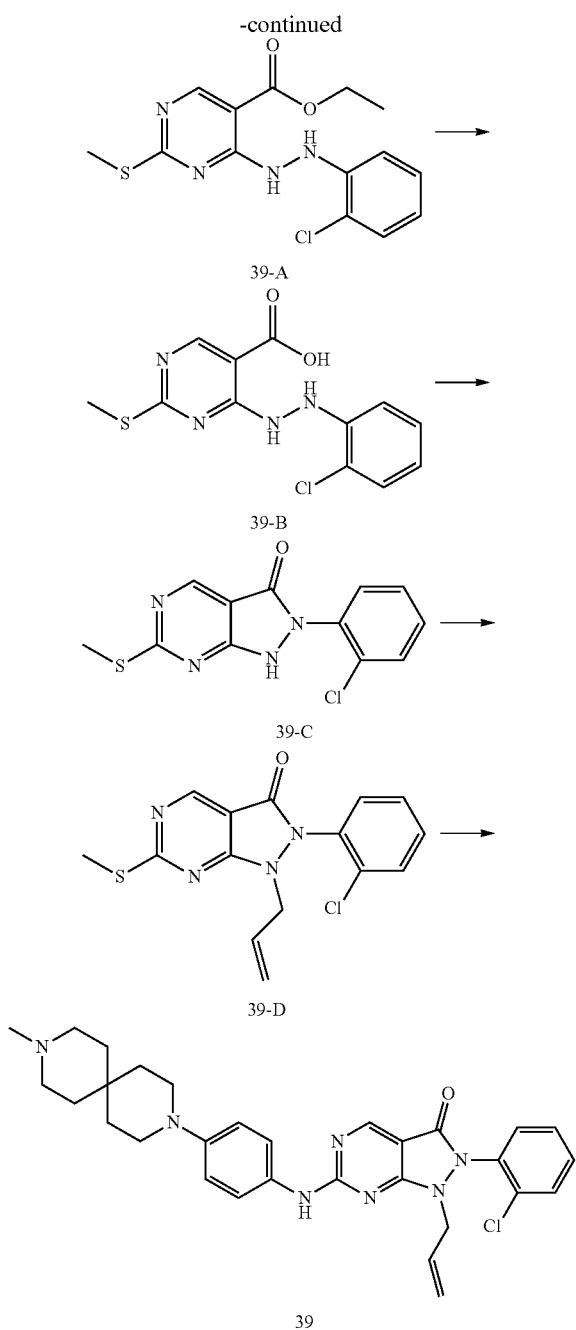

Step 1: Synthesis of Compound 39-A

Diisopropylethylamine (3.58 g, 27.67 mmol) was added into 4-chloro-2-methylthiopyrimidin-5-ethyl carboxylate (2.80 g, 12.03 mmol) and 2-chloro phenyl hydrazine (2.48 g, 13.83 mmol) in 90 mL THF solution, then heated to 80° C. and stirred for 16 hours. The reaction was monitored to be complete by LCMS. After concentrated under reduced pressure to remove the solvent, water 50 mL was added, and extracted by 20 mL EtOAc for 3 times, the combined EtOAc phase were washed by brine 20 mL, dried over anhydrous sodium sulfate, concentrated under reduced pressure to give the compound 39-A. $^1$H NMR (400 MHz, CDCl$_3$) δ=9.65 (br d, J=3.8 Hz, 1H), 8.71-8.65 (m, 1H), 7.30 (dd, J=1.2, 8.0 Hz, 1H), 7.15-7.08 (m, 1H), 6.92 (dd, J=1.6, 8.0 Hz, 1H), 6.84 (dt, J=1.6, 8.0 Hz, 1H), 6.78 (d, J=4.0 Hz, 1H), 4.40 (q, J=7.2 Hz, 2H), 2.25 (s, 3H), 1.42 (t, J=7.0 Hz, 3H)

Step 2: Synthesis of Compound 39-B

Sodium hydroxide (5 M, 15 mL) was added into compound 39-A (4.00 g, 11.81 mmol) in methanol (30 mL) and THF (30 mL) solution, then stirred at 20-25° C. for 3 hours. The reaction was monitored to be complete by LCMS. The reaction mixture was concentrated under reduced pressure, then added 150 mL water, 6 N hydrochloric acid was used to adjust pH=3, then filtered to give a solid. The solid was washed by water 100 mL×3, dried to give the compound 39-B. $^1$H NMR (400 MHz, DMSO-d$_6$) δ=9.79 (s, 1H), 8.60 (s, 1H), 7.80 (s, 1H), 7.33 (dd, J=1.2, 7.8 Hz, 1H), 7.16-7.09 (m, 1H), 6.85-6.72 (m, 2H), 2.17 (s, 3H)

Step 3: Synthesis of Compound 39-C

Toluene 25 mL and dichlorosulfoxide (8.20 g, 68.94 mmol) were added into compound 39-B (1.00 g, 3.22 mmol), the mixture was heated to 110° C. and stirred for 1 hour. The reaction was monitored to be complete by LCMS. After cooled down to r.t., the mixture was poured into the mixture of 200 mL ice and saturated sodium bicarbonate while stirring, then extracted by EtOAc (50 mL×3), the combined organic phases was washed by brine 50 mL, dried over anhydrous sodium sulfate, concentrated under reduced pressure to give the compound 39-C. $^1$H NMR (400 MHz, DMSO-d$_6$) δ=8.81-8.65 (m, 1H), 7.72-7.66 (m, 1H), 7.62-7.50 (m, 4H), 2.63 (s, 3H)

Step 4: Synthesis of Compound 39-D

Sodium carbonate (220.13 mg, 2.08 mmol) and 3-bromopropene (413.27 mg, 3.42 mmol) were added into compound 39-C (200.00 mg, 683.20 μmol) in 5 mL acetonitrile solution, then the mixture was heated to 85° C. and stirred for 1.5 hours. The reaction was monitored to be complete by LCMS. Water 20 mL was added into the mixture, then extracted by EtOAc (6 mL×3), the combined organic phases were washed by brine 6 mL, dried over anhydrous sodium sulfate, concentrated under reduced pressure to give a residue. The residue was purified by column chromatography (PE/EtOAc=4/1-0/1) to give the compound 39-D. $^1$H NMR (400 MHz, DMSO-d$_6$) δ=8.97 (s, 1H), 7.71-7.67 (m, 1H), 7.60-7.50 (m, 3H), 5.64 (m, 1H), 5.09 (dd, J=1.6, 10.4 Hz, 1H), 4.98 (dd, J=1.6, 17.2 Hz, 1H), 4.37 (t, J=6.0 Hz, 2H), 2.58 (s, 3H)

Step 5: Synthesis of Compound 39 m-Chloroperoxybenzoic acid (51.33 mg, 297.46 μmol) was added into compound 39-D (90.00 mg, 270.42 μmol) in 2 mL dichloromethane solution. The mixture was stirred at 25° C. for 60 min. Diisopropylethylamine (209.70 mg, 1.62 mmol) and 12 (73.65 mg, 283.94 μmol) were then added, the mixture was stirred at 25° C. for 16 hours. The reaction was monitored to be complete by LCMS. The reaction mixture was diluted by 20 mL dichloromethane, and washed by saturated sodium sulfite solution 10 mL and saturated sodium bicarbonate 10 mL, dried over anhydrous sodium sulfate, concentrated under reduced pressure to give residue. The residue was separated by preparative HPLC to give the compound 39. $^1$H NMR (400 MHz, CDCl$_3$) δ=8.81 (s, 1H), 7.58-7.47 (m, 3H), 7.44-7.34 (m, 3H), 6.96 (d, J=9.0

Hz, 2H), 5.68 (m, 1H), 5.18-5.00 (m, 2H), 4.39-4.19 (m, 2H), 3.19-3.08 (m, 4H), 2.40 (br s, 4H), 2.30 (s, 3H), 1.68-1.62 (m, 4H), 1.60-1.57 (m, 4H)

MS m/z: 554.1 [M+H]+

Embodiment 40: Compound 40

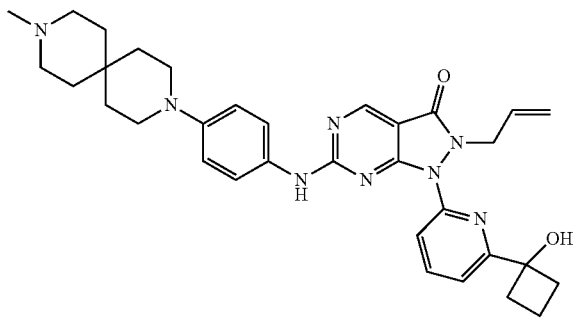 [SMILES: C=CCn1c(=O)c2cnc(Nc3ccc(N4CCC5(CCN(C)CC5)CC4)cc3)nc2n1-c1cccc(C2(O)CCC2)n1]

Synthetic Route:

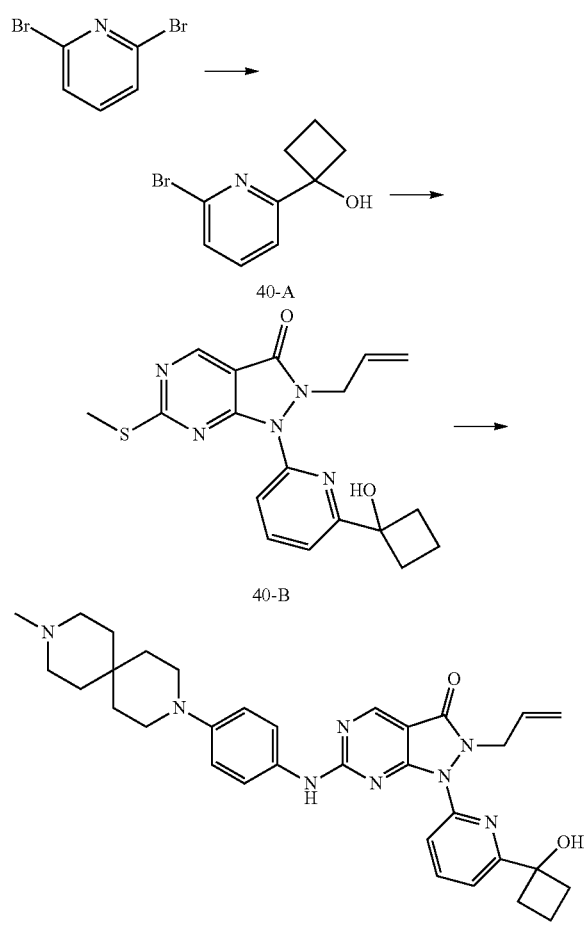

Step 1: Synthesis of Compound 40-A n-Butyllithium (2.5 M, 1.86 mL) was added into 2,6-dibromopyridine (1.00 g, 4.22 mmol) in 30 mL dichloromethane suspension at −60° C. The reaction mixture was stirred for 15 min, cyclobutanone (355.05 mg, 5.06 mmol) was added at one time into the reaction mixture at −60° C. The reaction mixture was stirred at −60° C. for 30 min. The reaction was monitored to be complete by LCMS. The reaction mixture was poured into saturated ammonium chloride, the organic phase was separated and washed by brine 10 mL, dried over anhydrous sodium sulfate, concentrated under reduced pressure to give a dark red oil. The residue was purified by column chromatography (PE/EtOAc=4/1) to give the compound 40-A. The product was confirmed by $^1$H NMR (CDCl$_3$).

$^1$H NMR (400 MHz, CDCl$_3$) δ=7.62-7.57 (m, 1H), 7.53-7.50 (dd, J=0.8, 7.6 Hz, 1H), 7.39 (dd, J=0.8, 7.6 Hz, 1H), 4.30 (br, 1H), 2.55-2.45 (m, 4H), 2.12-2.00 (m, 1H), 1.91-1.78 (m, 1H)

Step 2: Synthesis of Compound 40-B

According to the method for preparing the compound 3-A and 2-bromopyridine was replaced by 40-A, the compound 40-B was obtained. MS m z: 370.1 [M+H]+

Step 3: Synthesis of Compound 23

According to the method for preparing the compound 16, and started with the compound 40-B, crude product of the compound 40 was obtained, the product was purified by preparative separation (neutral condition) to give the compound 23. $^1$H NMR (CDCl$_3$, 400 MHz): δ=8.76 (s, 1H), 7.80-7.86 (m, 1H), 7.70 (d, J=7.8 Hz, 1H), 7.36-7.44 (m, 3H), 6.86 (d, J=9.0 Hz, 2H), 5.64 (ddt, J=16.8, 10.4, 6.2 Hz, 1H), 4.98 (dd, J=10.3, 1.0 Hz, 1H), 4.88 (dd, J=17.1, 1.3 Hz, 1H), 4.66 (br d, J=6.3 Hz, 2H), 4.00 (s, 1H), 3.04-3.12 (m, 4H), 2.46 (br t, J=7.9 Hz, 8H), 2.31 (s, 3H), 1.99-2.06 (m, 1H), 1.77-1.89 (m, 1H), 1.61 ppm (br s, 8H).

MS m/z: 581.1[M+1]+

Embodiment 41: Compound 41

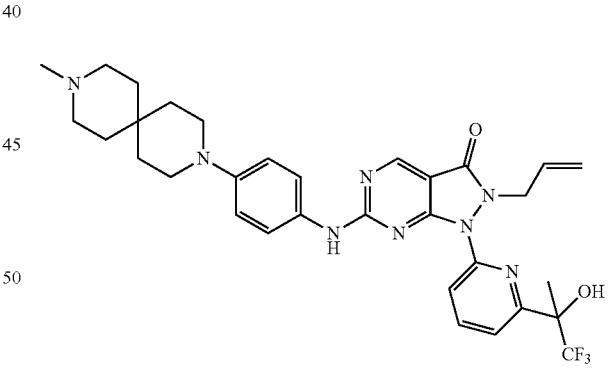

Synthetic Route:

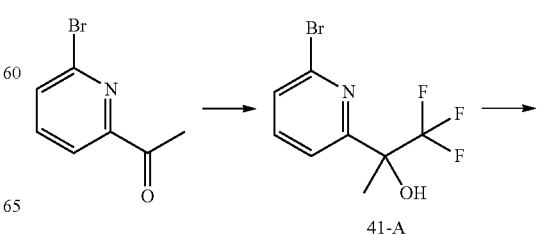

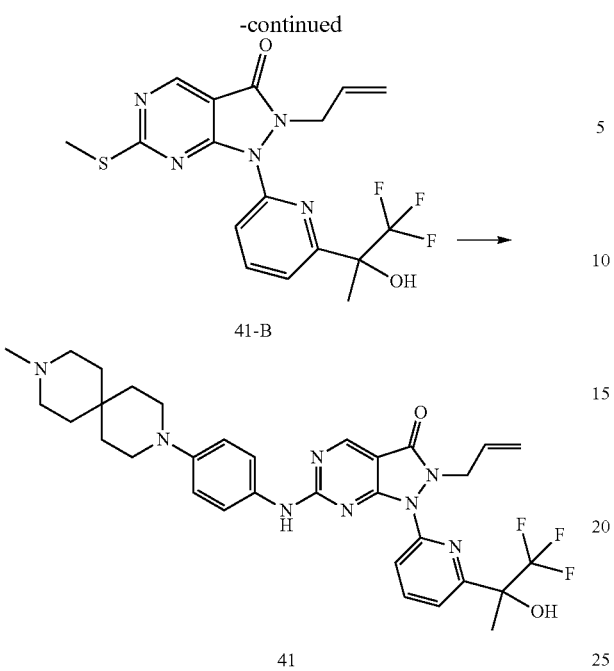

41-B

41

Step 1: Synthesis of Compound 41-A

Compound 2-bromo-6-acetyl pyridine (500.00 mg, 2.50 mmol) was added into sodium acetate (205.04 mg, 2.50 mmol) in dimethyl sulfoxide (3.00 mL) suspension. Trifluoromethyl trimethylsilane (1.42 g, 10.00 mmol) in dimethyl sulfoxide (0.50 mL) solution was added dropwise at 10-25° C., after the completion of the adding, the reaction mixture was reacted at 10-25° C. for 12 hours. Water (4.00 mL) was added to quench the reaction, the reaction flask was cooled down in an ice bath, the inner temperature was 10-25° C. After extraction by EtOAc (9.00 mL×3), the organic phases were combined, the organic phases were washed by saturated sodium bicarbonate (10.00 mL), then washed by saturated brine (10 mL), dried over anhydrous sodium sulfate. The desiccant was filtered off, the filtrate was concentrated under reduced pressure to remove the solvent and give the crude product. The crude product was purified by column chromatography (PE/EtOAc=15/1) to give 41-A. $^1$H NMR (400 MHz, CDCl$_3$) δ1.57 (s, 3H) 5.39 (s, 1H) 7.33 (d, J=7.54 Hz, 1H) 7.40 (d, J=8.04 Hz, 1H) 7.52 (t, J=7.78 Hz, 1H)

MS m/z: 271.8 [M+H]$^+$

Step 2: Synthesis of Compound 41-B

According to the method for preparing the compound 27-A, the 2-bromo-6-fluoropyridine was replaced by 41-A, crude product of the compound 41-B was obtained, the crude product was purified by column chromatography (PE/EtOAc=3/1, 0/1) to give the compound 41-B. $^1$H NMR (400 MHz, CDCl$_3$) δ1.59 (s, 3H) 2.41 (s, 3H) 4.38-4.47 (m, 1H) 4.62-4.79 (m, 2H) 4.86-4.91 (m, 1H) 5.12 (s, 1H) 5.50 (ddt, J=16.68, 10.54, 6.22, 6.22 Hz, 1H) 7.30 (d, J=7.54 Hz, 1H) 7.75-7.79 (m, 1H) 7.81-7.87 (m, 1H) 8.77 (s, 1H)

Step 3: Synthesis of Compound 41

According to the method for preparing the compound 22, and started with the compound 41-B, the compound 41 was obtained. $^1$H NMR (400 MHz, CDCl$_3$) δ1.58-1.67 (m, 8H) 1.70 (s, 3H) 2.35 (s, 3H) 2.51 (br s, 4H) 3.05-3.11 (m, 4H) 4.50 (dd, J=15.56, 6.54 Hz, 1H) 4.71 (dd, J=15.56, 5.52 Hz, 1H) 4.86 (d, J=17.08 Hz, 1H) 4.98 (d, J=10.04 Hz, 1H) 5.56-5.67 (m, 1H) 6.86 (d, J=9.04 Hz, 2H) 7.36 (br d, J=8.54 Hz, 3H) 7.86-7.90 (m, 2H) 8.77 (s, 1H)

MS m/z: 623.1 [M+H]$^+$

Embodiment 42: Compound 42

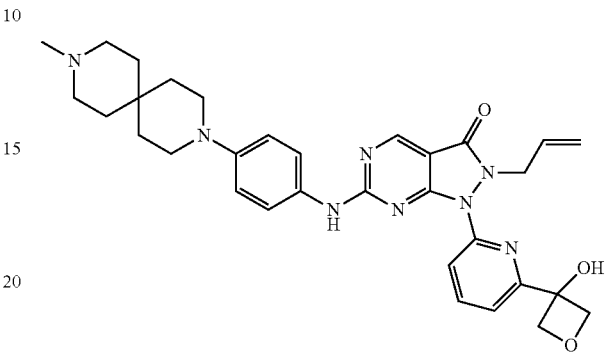

42

Synthetic Route:

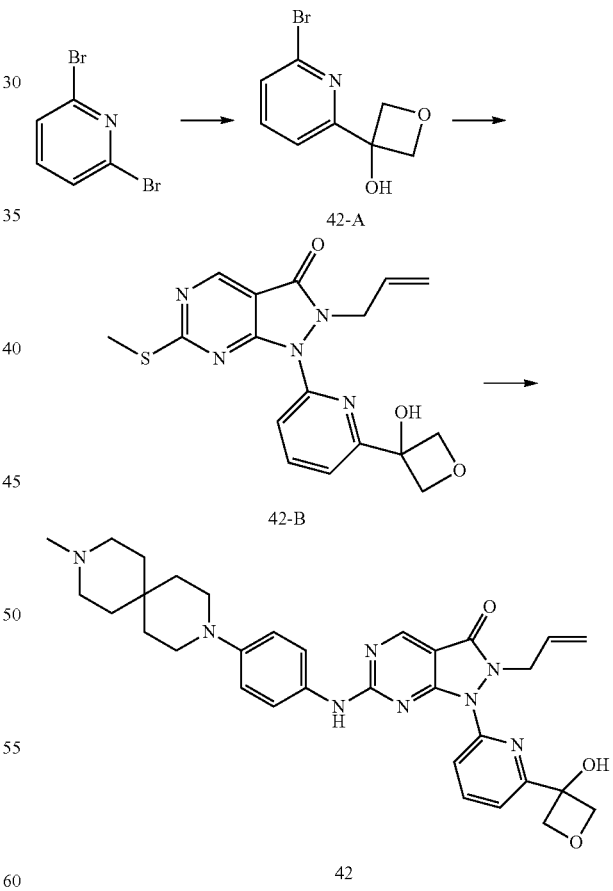

Step 1: Synthesis of Compound 42-A n-Butyllithium (2.5 M, 1.86 mL) was added into 2,6-dibromopyridine (1.00 g, 4.22 mmol) in 30 mL dichloromethane suspension at −60° C. The reaction mixture was stirred for 15 min, then 3-carbonyl oxetane (304.10 mg, 4.22 mmol) was added for one-time into the reaction mixture at −60° C. The reaction mixture was stirred for further 60 min at −60° C. The reaction was monitored to be complete by thin layer chromatography. The reaction mixture was poured into saturated ammonium chloride, the organic phases were separated, and washed by brine 10 mL, dried over anhydrous sodium sulfate, concentrated under reduced pressure to give yellow solid. The residue was purified by column chromatography (PE/EtOAc=2/1) to give the compound 42-A. ¹H NMR (400 MHz, CDCl₃) δ=7.86 (dd, J=0.8, 7.8 Hz, 1H), 7.67 (t, J=7.8 Hz, 1H), 7.44 (d, J=7.8 Hz, 1H), 5.20 (s, 1H), 5.04-4.96 (m, 2H), 4.69-4.59 (m, 2H)

Step 2: Synthesis of Compound 42-B

N,N'-dimethylethylenediamine (43.62 mg, 494.89 μmol) was added into the mixture of I1 (100.00 mg, 449.90 μmol), cuprous iodide (85.68 mg, 449.90 μmol), compound 42-A (103.50 mg, 449.90 μmol) and potassium carbonate (87.05 mg, 629.86 μmol) in 5 mL dioxane, under nitrogen atmosphere, the mixture was heated to 95° C. and stirred for 2 hours. The reaction was monitored to be complete by LCMS. The reaction mixture was cooled down, then 30 mL ammonia was added, and then extracted with EtOAc (10 mL×2), washed by saturated brine, dried over anhydrous magnesium sulfate, concentrated under reduced pressure to give 42-B. MS m/z: 372.1 [M+H]⁺

Step 3: Synthesis of Compound 42 m-Chloroperoxybenzoic acid (110.69 mg, 545.22 μmol, 85%) was added into compound 42-B (150.00 mg, 403.87 μmol) in 20 mL toluene solution at 25-30° C. The mixture was stirred for 30 min at 25-30° C. Diisopropylethylamine (143.54 8 mg, 1.11 mmol) and 12 (104.76 mg, 403.87 μmol) was added into the mixture under 30° C., and the mixture was stirred at 30-32° C. for 15 hours. The reaction was monitored to be complete by LCMS. The reaction mixture was diluted by 40 mL EtOAc, then washed sequentially by saturated sodium sulfite solution 20 mL, saturated sodium bicarbonate 20 mL and brine 20 mL, dried over anhydrous sodium sulfate, concentrated under reduced pressure to give the residue. The residue was separated by preparative HPLC, and then purified by thin layer chromatography (dichloromethane/methanol=10/1) to give the compound 42. ¹H NMR (400 MHz, CDCl₃) δ=8.76 (s, 1H), 8.00-7.93 (m, 1H), 7.80 (dd, J=7.7, 13.7 Hz, 2H), 7.36 (br d, J=8.3 Hz, 3H), 6.86 (d, J=9.0 Hz, 2H), 5.70-5.58 (m, 1H), 5.15 (br s, 1H), 5.04-5.00 (m, 3H), 4.90 (d, J=17.2 Hz, 1H), 4.70 (d, J=7.2 Hz, 2H), 4.57 (d, J=6.0 Hz, 2H), 3.13-3.05 (m, 4H), 2.33 (br s, 4H), 2.23 (s, 3H), 1.64-1.55 (m, 8H)

MS m/z: 583.1 [M+H]⁺

Embodiment 43: Compound 43

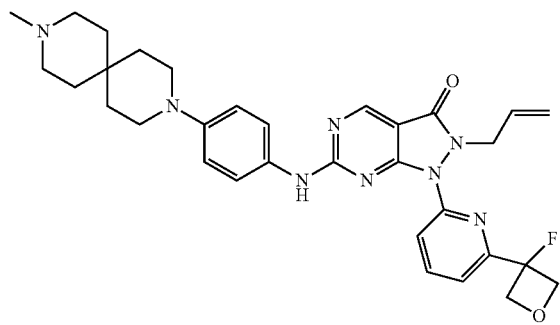 [SMILES: C=CCn1c(=O)c2cnc(Nc3ccc(N4CCC5(CCN(C)CC5)CC4)cc3)nc2n1-c1cccc(C2(F)COC2)n1]

Synthetic Route:

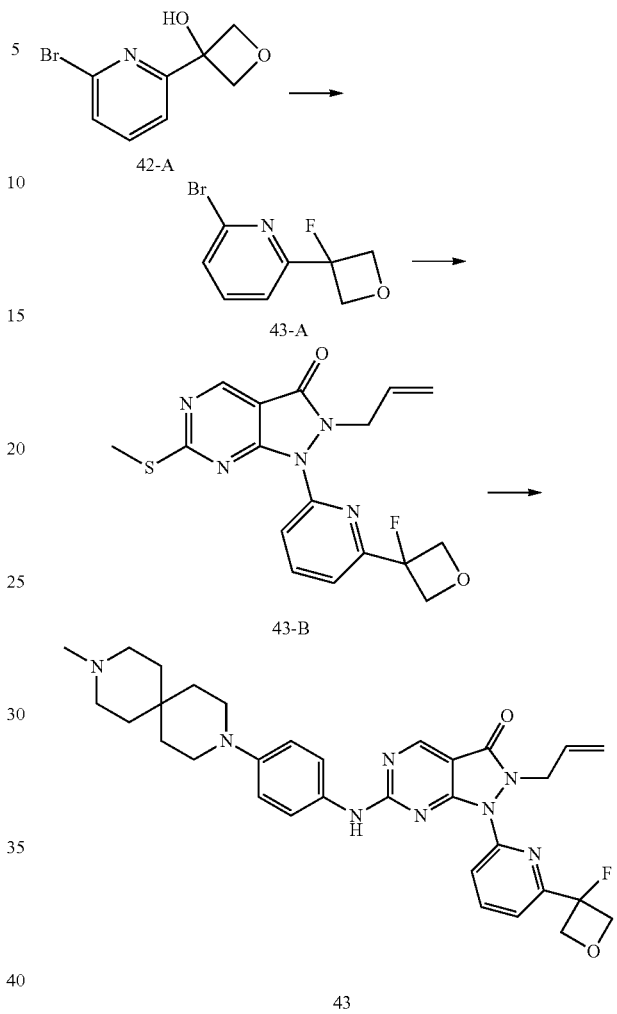

Step 1: Synthesis of Compound 43-A

At −10° C. and under nitrogen atmosphere, diethylaminosulfur trifluoride (70.06 mg, 434.66 μmol) was added dropwise rapidly into the compound 42-A (50.00 mg, 217.33 μmol) in 2 mL dichloromethane solution. Then the mixture was stirred at −10° C. for 30 min under nitrogen atmosphere. The reaction was monitored to be complete by thin layer chromatography. The reaction mixture was quenched by 10 mL saturated sodium bicarbonate, and then extracted by dichloromethane (10 mL×2), the combined organic phases were dried over anhydrous sodium sulfate, then concentrated to give the compound 43-A. The product was used directly in the next step without further purification. MS m/z: 231.8 [M+H]⁺, 233.9 [M+H]⁺

Step 2: Synthesis of Compound 43-B

According to the method for preparing the compound 27-A, and 2-bromo-6-fluoropyridine was replaced by 43-A, the compound 43-B was obtained. MS m/z: 374.1 [M+H]⁺

Step 3: Synthesis of Compound 43

According to the method for preparing the compound 22, and started with the compound 43-B, the compound 43 was obtained. ¹H NMR (400 MHz, CDCl₃) δ ppm 1.60-1.71 (m, 8H) 2.32 (s, 3H) 2.43 (br s, 4H) 3.15-3.20 (m, 4H) 4.90-4.94 (m, 2H) 5.01 (dd, J=14.32, 6.28 Hz, 2H) 5.07 (d, J=7.04 Hz, 2H) 5.11 (d, J=7.54 Hz, 1H) 5.17 (d, J=8.04 Hz, 1H) 5.73 (ddt, J=16.76, 10.36, 6.28, 6.28 Hz, 1H) 6.95 (d, J=9.04 Hz, 2H) 7.40-7.50 (m, 3H) 7.90 (t, J=7.84 Hz, 1H) 8.01 (d, J=8.54 Hz, 1H) 8.85 (s, 1H)

MS m/z: 585.1 [M+H]⁺

Embodiment 44: Compound 44

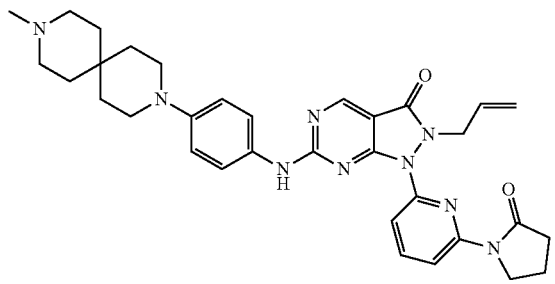 [SMILES: C=CCn1c(=O)c2cnc(Nc3ccc(N4CCC5(CCN(C)CC5)CC4)cc3)nc2n1-c1cccc(N2CCCC2=O)n1]

Synthetic Route:

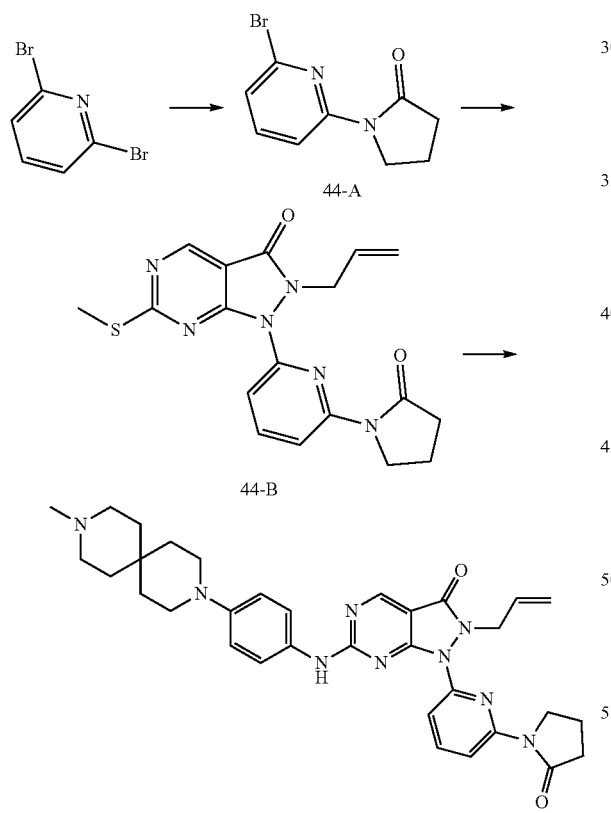

Step 1: Synthesis of Compound 44-A

Potassium carbonate (402.57 mg, 2.91 mmol), cuprous iodide (401.98 mg, 2.11 mmol), N,N'-dimethylethylenediamine (208.38 mg, 2.36 mmol, 254.12 μL), and compound 2-pyrrolidone (250.00 mg, 2.94 mmol, 225.23 μL, 1.39 eq) were added into compound 2,6-dibromopyridine (500.00 mg, 2.11 mmol) in toluene (15.00 mL) solution, the reaction mixture was stirred at 110° C. for 12 hours under nitrogen atmosphere. The reaction was cooled down to r.t., ammonia (30 mL) was added into the reaction mixture, extracted by EtOAc (20 mL×3), the organic phases were combined, and washed by saturated brine (50 mL), dried over anhydrous sodium sulfate, the organic phase was concentrated under reduced pressure to give the crude product, which was purified by column chromatography (PE/EtOAc=5/1, 3/1) to give the compound 44-A. MS m/z: 240.8 [M+H]⁺

Step 2: Synthesis of Compound 44-B

According to the method for preparing the compound 27-A, and the 2-bromo-6-fluoropyridine was replaced by 44-A to give the compound 44-B.

MS m/z: 383.1[M+H]+, 405.1 [M+Na]⁺

Step 3: Synthesis of Compound 44

According to the method for preparing the compound 22, and started with the compound 44-B, the compound 44 was obtained. ¹H NMR (400 MHz, CDCl₃) δ1.51-1.61 (m, 8H) 2.05-2.12 (m, 2H) 2.24 (s, 3H) 2.34 (br s, 4H) 2.62 (t, J=8.04 Hz, 2H) 3.06-3.10 (m, 4H) 4.02 (t, J=7.04 Hz, 2H) 4.67-4.72 (d, J=6.02 Hz, 2H) 4.88 (d, J=17.08 Hz, 1H) 4.97 (d, J=10.04 Hz, 1H) 5.61 (ddt, J=16.88, 10.36, 6.22, 6.22 Hz, 1H) 6.85 (d, J=9.04 Hz, 2H) 7.36 (br d, J=8.54 Hz, 2H) 7.52 (d, J=8.04 Hz, 1H) 7.77 (t, J=8.04 Hz, 1H) 8.26 (d, J=8.04 Hz, 1H) 8.74 (s, 1H)

MS m/z: 594.1 [M+H]⁺

Embodiment 45: Compound 45

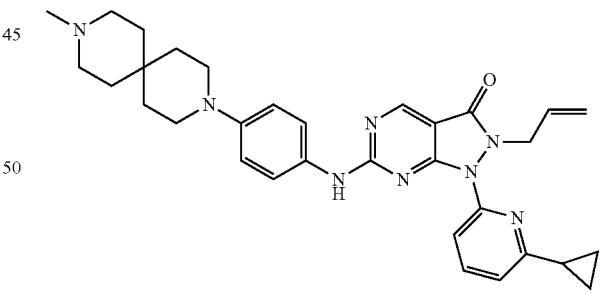

Synthetic Route:

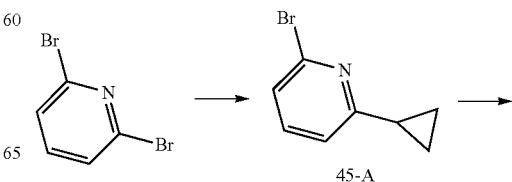

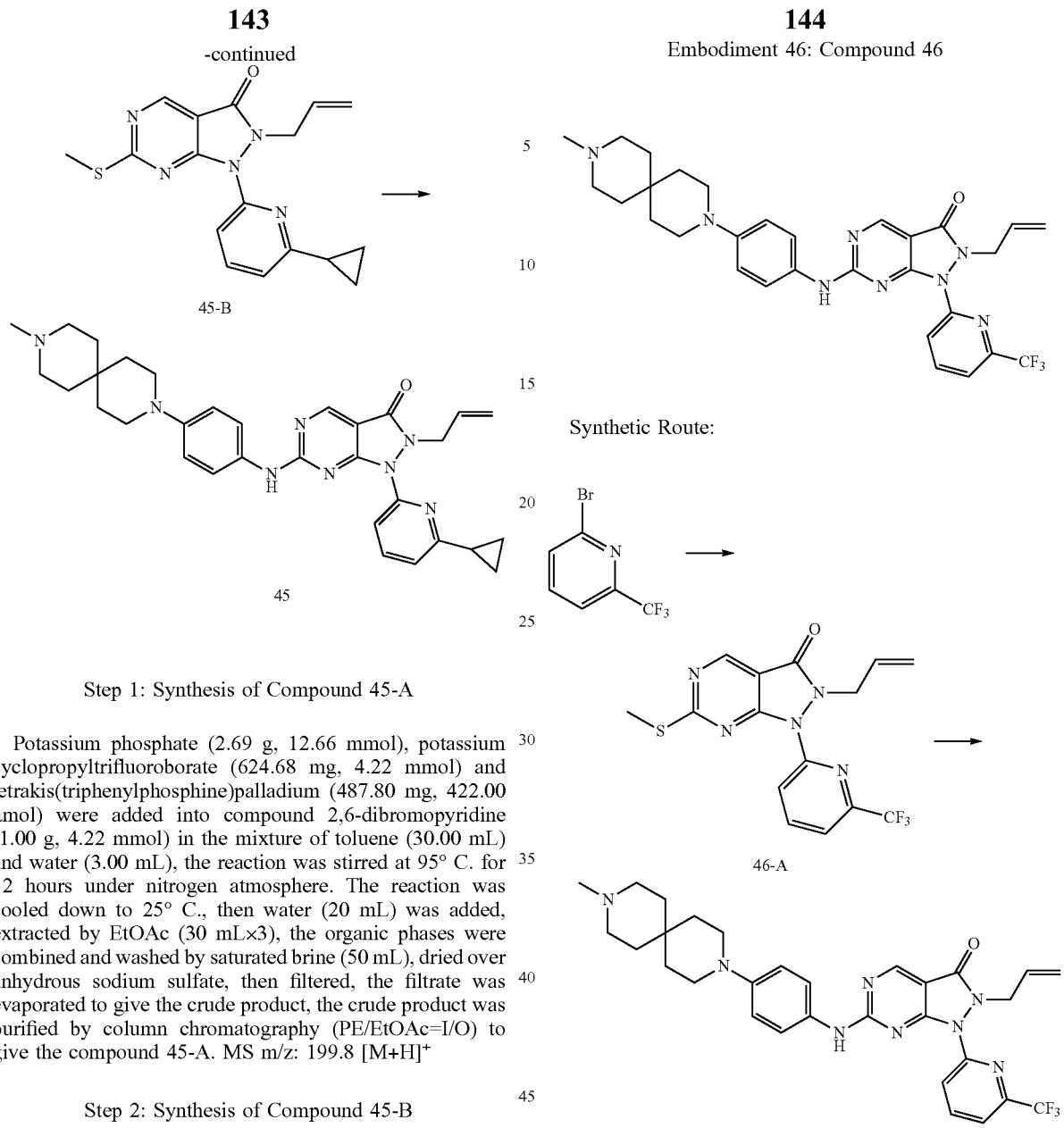

Step 1: Synthesis of Compound 45-A

Potassium phosphate (2.69 g, 12.66 mmol), potassium cyclopropyltrifluoroborate (624.68 mg, 4.22 mmol) and tetrakis(triphenylphosphine)palladium (487.80 mg, 422.00 μmol) were added into compound 2,6-dibromopyridine (1.00 g, 4.22 mmol) in the mixture of toluene (30.00 mL) and water (3.00 mL), the reaction was stirred at 95° C. for 12 hours under nitrogen atmosphere. The reaction was cooled down to 25° C., then water (20 mL) was added, extracted by EtOAc (30 mL×3), the organic phases were combined and washed by saturated brine (50 mL), dried over anhydrous sodium sulfate, then filtered, the filtrate was evaporated to give the crude product, the crude product was purified by column chromatography (PE/EtOAc=1/0) to give the compound 45-A. MS m/z: 199.8 [M+H]$^+$

Step 2: Synthesis of Compound 45-B

According to the method for preparing the compound 27-A, and 2-bromo-6-fluoropyridine was replaced by 45-A, the compound 45-B was obtained. MS m/z: 340.0 [M+H]$^+$

Step 3: Synthesis of Compound 45

According to the method for preparing the compound 22, and started with the compound 45-B, compound 45 was obtained. The method for synthesis of compound 45 was the same as the embodiment 22 used for synthesis of compound 22 except for the starting material, the compound 45 was thus obtained. $^1$H NMR (400 MHz, CDCl$_3$) δ 0.98-1.07 (m, 4H) 1.58-1.76 (m, 8H) 1.99-2.11 (m, 2H) 2.35 (s, 3H) 2.37-2.53 (m, 4H) 3.12-3.16 (m, 2H) 3.45-3.55 (m, 1H) 4.76 (br d, J=6.54 Hz, 2H) 4.91 (d, J=17.08 Hz, 1H) 5.01 (d, J=10.04 Hz, 1H) 5.61-5.74 (m, 1H) 6.85-6.94 (m, 2H) 7.06-7.11 (m, 1H) 7.45 (br d, J=8.54 Hz, 2H) 7.56-7.62 (m, 1H) 7.64-7.72 (m, 1H) 8.81 (s, 1H)

MS m/z: 551.1 [M+H]$^+$

Embodiment 46: Compound 46

Synthetic Route:

Step 1: Synthesis of Compound 46-A

N,N'-dimethylethylenediamine (87.25 mg, 989.79 μmol) was added into the mixture of I1 (200.00 mg, 899.81 μmol), cuprous iodide (171.37 mg, 899.81 μmol), 2-trifluoromethyl-6-bromopyridine (209.45 mg, 926.80 μmol) and potassium carbonate (174.11 mg, 1.26 μmol) in 3 mL dioxane, the mixture was heated to 95° C. and stirred for 1 hour under nitrogen atmosphere. The reaction was monitored to be complete by LCMS. The reaction mixture was cooled down, 30 mL ammonia was added, then extracted by EtOAc (10 mL×2), then washed by saturated brine, dried over anhydrous magnesium sulfate. The filtrate was concentrated under reduced pressure to give the pale brown colloidal product, which was purified by column chromatography (PE/EtOAc=4/1-3/1) to give the compound 46-A. $^1$H NMR (400 MHz, CDCl$_3$) δ=8.89 (s, 1H), 8.20 (d, J=8.5 Hz, 1H), 7.98 (t, J=8.0 Hz, 1H), 7.54 (d, J=7.8 Hz, 1H), 5.64-5.54 (m 1H), 4.94 (d, J=10.4 Hz, 1H), 4.90-4.83 (m, 3H), 2.54 (s, 3H)

Step 2: Synthesis of Compound 46

At 30-40° C., m-chloroperoxybenzoic acid (52.23 mg, 297.46 μmol, 85%) was added into compound 46-A (70.00 mg, 190.55 μmol) in 5 mL toluene solution. The mixture was stirred at 25-30° C. for 30 min. Then diisopropylethylamine (73.88 mg, 571.65 μmol) and 12 (49.43 mg, 190.55 μmol) were added below 30° C., the mixture was stirred at 25-30° C. for 16 hours. The reaction was monitored to be complete by LCMS. The reaction mixture was diluted by 20 mL EtOAc, then washed sequentially by saturated sodium sulfite solution 10 mL, saturated sodium bicarbonate 10 mL and brine 10 mL, dried over anhydrous sodium sulfate, concentrated under reduced pressure to give the residue, which was separated by preparative HPLC to give the compound 46. $^1$H NMR (400 MHz, CDCl$_3$) δ=8.77 (s, 1H), 8.16 (d, J=8.4 Hz, 1H), 7.89 (t, J=7.8 Hz, 1H), 7.48 (d, J=7.6 Hz, 1H), 7.35 (d, J=9.0 Hz, 2H), 6.87 (d, J=9.0 Hz, 2H), 5.63-5.56 (m, 1H), 4.96-4.79 (m, 4H), 3.15-3.06 (m, 4H), 2.35 (br s, 4H), 2.24 (s, 3H), 1.62-1.51 (m, 8H)

MS m/z: 579.0 [M+H]$^+$

Embodiment 47: Compound 47

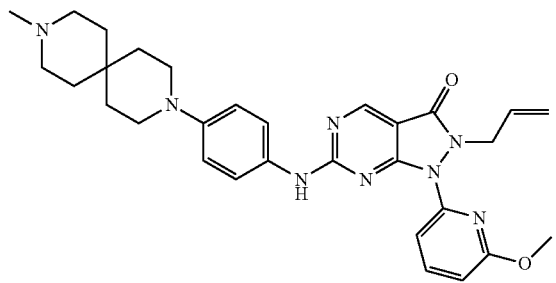

Synthetic Route:

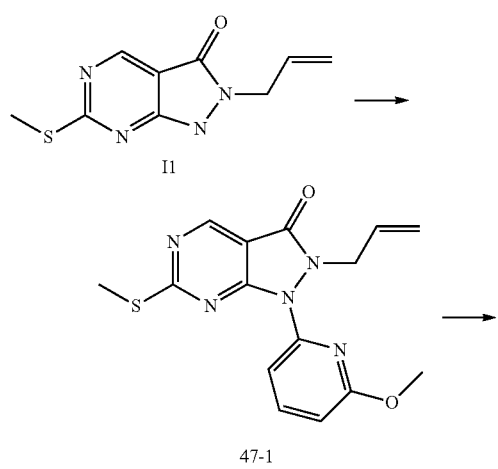

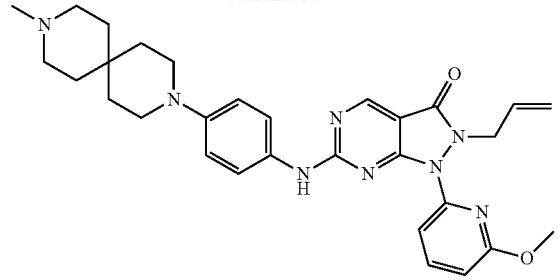

47

Step 1: Synthesis of Compound 47-1

I1 (1.0 g, 4.5 mmol) was added into 1,4-dioxane (10 mL), and 2-bromo-6-methoxylpyridine (1.02 g, 5.4 mmol, 664 μL), potassium carbonate (622 mg, 4.5 mmol), cuprous iodide (857 mg, 4.5 mmol) and N,N'-dimethylethylenediamine (397 mg, 4.5 mmol, 490 μL) were added while stirring, heated to 95° C. under nitrogen atmosphere, then reacted for 12 h. 100 mL ammonia was added into the reacted mixture, then extracted by 100 mL EA, the organic phase was washed by 100 mL brine, dried over anhydrous sodium sulfate, filtered and concentrated, the crude product was crystallized by EtOAc, then purified by silica gel chromatography (PE/EA=10/1 to 2/1), to give the compound 47-1. $^1$H NMR (400 MHz, CDCl$_3$) δ=8.92 (s, 1H), 7.89 (t, J=8.0 Hz, 1H), 7.43 (d, J=7.2 Hz, 1H), 6.82 (d, J=8.0 Hz, 1H), 5.83-5.69 (m, 1H), 5.07 (d, J=10.4 Hz, 1H), 4.96 (br d, J=17.2 Hz, 1H), 4.84 (d, J=6.0 Hz, 2H), 3.93 (s, 3H), 2.56 (s, 3H)

Step 2: Synthesis of Compound 47 m-CPBA (139.71 mg, 688.15 μmol, 85% purity) was added into 47-1 (200 mg, 607 μmol) in 1 mL DCM solution, and was stirred at 25° C. for 30 min. 12 (272.47 mg, 1.05 mmol) and DIPEA (215.8 mg, 1.67 mmol, 291.62 μL) were added at 30° C. and stirred for 12 h. The reacted mixture was partitioned between 10 mL DCM and 10 mL, the organic phase was washed by 10 mL saturated sodium sulfite solution, 10 mL sodium carbonate solution and 10 mL sodium chloride solution, then dried over anhydrous sodium sulfate, filtered and the filtrate was concentrated, the product was purified by preparative HPLC (chromatographic column: waters Xbridge 150×25 mmmm 5 um; mobile phases: [water (0.225% FA)-ACN]; B %: 10%-30%, 12 min).) to give the compound 47. $^1$H NMR (400 MHz, MeOD) δ 8.79 (s, 1H) 7.66-7.80 (m, 1H) 7.38-7.54 (m, 2H) 6.90 (d, J=8.8 Hz, 2H) 6.61-6.70 (m, 2H) 5.64-5.87 (m, 1H) 4.91-5.07 (m, 2H) 4.70-4.82 (m, 2H) 3.92 (s, 3H) 3.12-3.15 (br, 4H) 3.12-3.15 (m, 4H) 2.31-2.52 (m, 4H) 2.28 (s, 3H) 1.54-1.73 (m, 8H)

MS m/z: 541.3 [M+H]$^+$

Embodiment 48: Compound 48

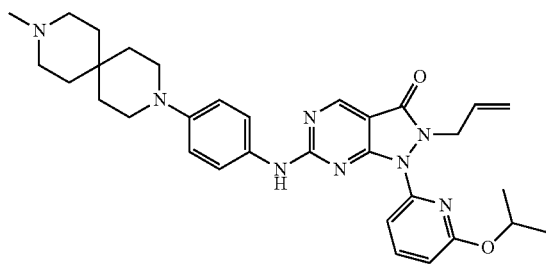 [SMILES: C=CCn1c(=O)c2cnc(Nc3ccc(N4CCC5(CCN(C)CC5)CC4)cc3)nc2n1-c1cccc(OC(C)C)n1]

Synthetic Route:

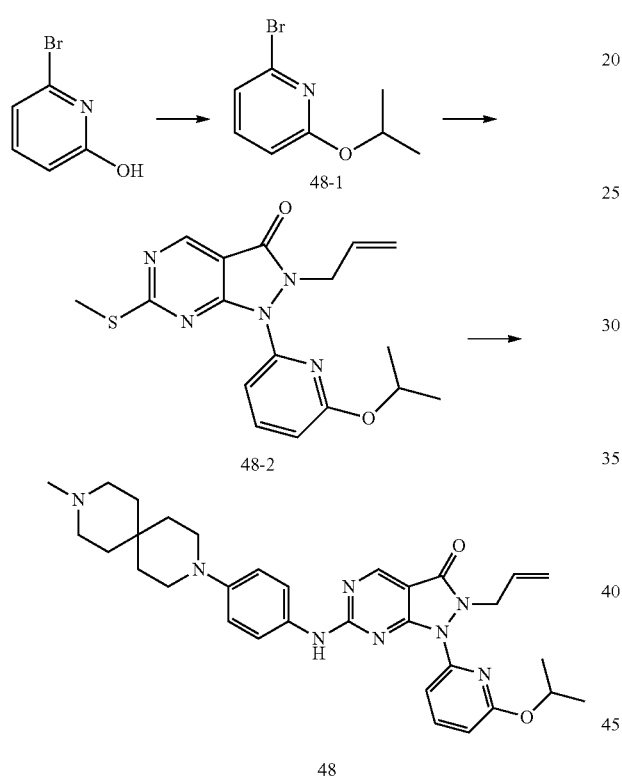

Step 1: Synthesis of Compound 48-1

2-Bromo-6-hydroxypyridine (1.00 g, 5.75 mmol) was dissolved in 10 mL in DMF, potassium carbonate (1.59 g, 11.50 mmol) was added at 0° C., and stirred for 30 min, then iodoisopropane (1.17 g, 6.90 mmol, 689.96 μL) was added dropwise. The reaction mixture was then stirred at 0° C. for 30 min, then warmed to 20° C., then the mixture was stirred for 12 h. The reaction mixture was partitioned between and extracted by 30 mL water and 30 mL, the organic phase was washed by 30 mL brine, then dried, and the filtrate was concentrated to give 48-1. $^1$H NMR (400 MHz, CDCl$_3$) δ7.38 (t, J=7.2 Hz, 1H) 7.00 (d, J=7.2 Hz, 1H) 6.61 (d, J=8.0 Hz, 1H) 5.26-5.432 (m, 1H) 1.35 (dd, J=6.0, 1.6 Hz, 6H)

Step 2: Synthesis of Compound 48-2

I1 (980.00 mg, 4.41 mmol) was added into 1,4-dioxane (10.00 mL), and 2-bromo-6-isopropylpyridine (1.14 g, 5.29 mmol), potassium carbonate (835.02 mg, 6.04 mmol), cuprous iodide (839.70 mg, 4.41 mmol) and N,N'-dimethylethylenediamine (427.62 mg, 4.85 mmol, 527.92 μL) were added while stirring, heated to 95° C. under nitrogen atmosphere, then stirred for 12 h. 100 mL ammonia was added into the reacted mixture, the mixture was extracted by 100 mL EA, the organic phase was washed by 100 mL brine, dried over anhydrous sodium sulfate, filtered and the filtrate was concentrated to give a residue, which was then crystallized in EtOAc, then purified by silica gel chromatography (PE/EA=10/1-2/1) to give 48-2. $^1$H NMR (400 MHz, CDCl$_3$) δ8.90 (s, 1H) 7.71 (t, J=8.0 Hz, 1H) 7.31 (d, J=7.6 Hz, 1H) 6.63 (d, J=8.2 Hz, 1H) 5.54-5.82 (m, 1H) 5.12-5.32 (m, 1H) 4.90-5.24 (m, 2H) 4.78 (d, J=6.4 Hz, 2H) 2.55 (s, 3H) 1.32 (d, J=6.0 Hz, 6H)

Step 3: Synthesis of Compound 48

Compound 48-2 (525.00 mg, 1.47 mmol) and m-CPBA (338.24 mg, 1.67 mmol) were added into 1 mL DCM, and stirred at 25° C. for 1 h. 12 (659.65 mg, 2.54 mmol) and DIPEA (522.45 mg, 4.04 mmol, 706.01 μL) were added into the mixture, and stirred at 30° C. for 12 h. The reacted mixture was partitioned between 10 mL DCM and 10 mL, the organic phase was washed separately with 10 mL saturated sodium sulfite solution, 10 mL sodium carbonate solution and 10 mL sodium chloride solution, dried over anhydrous sodium sulfate, filtered and concentrated, the product was purified by preparative HPLC (chromatographic column: waters Xbridge 150×25 mm 5 μm; mobile phases: [A-HCl/H$_2$O=0.04% v/v; B-ACN]B %: 5%-30%, 12 min]) to give the compound 48. $^1$H NMR (400 MHz, CDCl$_3$) δ8.78 (s, 1H) 7.63-7.73 (m, 1H) 7.43-7.51 (m, 1H) 7.28-7.35 (m, 1H) 6.83-6.99 (m, 2H) 6.52-6.66 (m, 2H) 5.62-5.82 (m, 1H) 5.14-5.30 (m, 1H) 4.90-5.07 (m, 2H) 4.73-4.81 (m, 2H) 3.44 (s, 2H) 3.09-3.12 (m, 4H) 2.34-2.46 (m, 4H) 2.26 (s, 3H) 1.46-1.68 (m, 8H) 1.31 (d, J=6.0 Hz, 6H) MS m/z: 569.3[M+H]$^+$

Embodiment 49: Synthesis of Compound 49

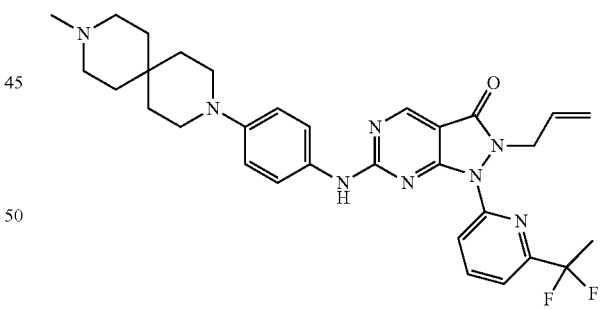

Synthetic Route:

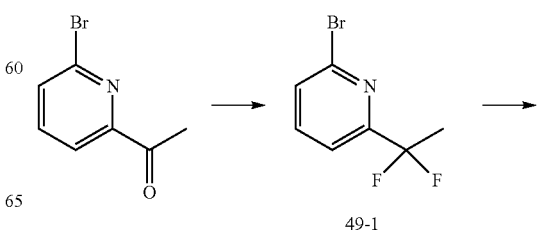

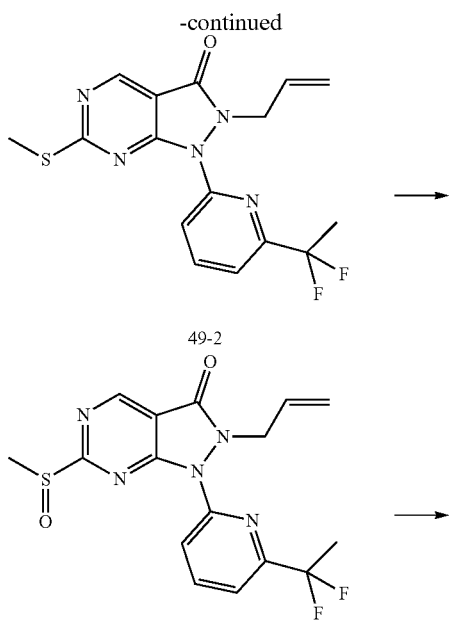

49-2

49-3

49

Step 1: Synthesis of Compound 49-1

2-bromo-6-acetonylpyridine (2 g, 10.10 mmol) was added into 20 mL DCM solution, then diethylaminosulfur trifluoride (4.85 g, 30.30 mmol) was added to the mixture at 0° C., then stirred for 5 min, and the temperature was raised to 35° C., stirred for 2 hours until the reaction was complete. The reaction mixture was slowly poured into 50 mL ice water, extracted by 50 mL EA, the organic phase was washed by 50 mL saturated brine, dried over excess anhydrous sodium sulfate, then filtered, evaporated, mixed, then purified by chromatography (EA/PE=1/15) to give 49-1. MS m/z: 361.1 [M+H]$^+$

Step 2: Synthesis of Compound 49-2

49-1 (1.40 g, 6.31 mmol) and I1 (1.40 g, 6.31 mmol) were added into 1,4-dioxane solution, then N,N'-dimethylethylenediamine (733.25 mg, 6.31 mmol, 904.13 µL), potassium carbonate (1.13 g, 8.20 mmol) and cuprous iodide (1.20 g, 6.31 mmol) were added sequentially under nitrogen atmosphere, the temperature was raised to 95° C. and stirred at reflux for 12 hours until the reaction was complete. After cooled down to 25° C., the reaction was concentrated at 45° C. 50 mL water was added to quench the reaction, then extracted by 50 mL EA, the organic phase was washed by 50 mL saturated brine, dried over anhydrous sodium sulfate, then filtered, evaporated, mixed, purified by chromatography (EA/PE=1/10-1/4) to give 49-2. $^1$H NMR (400 MHz, CDCl$_3$) δ8.93 (s, 1H), 8.04-7.95 (m, 2H), 7.57 (d, J=7.4 Hz, 1H), 7.24 (s, 1H), 5.67-5.60 (m, 1H), 4.99 (d, J=10.0 Hz, 1H), 4.91-4.87 (m, 2H), 2.58 (s, 3H), 2.04-1.95 (m, 3H)

Step 3: Synthesis of Compound 49-3

49-2 (300.00 mg, 0.82 mmol) was added into DCM solution, then m-CPBA (203.52 mg, 1.00 mmol, 85% purity) was added, then stirred at 25° C. for 2 hours until the reaction was complete. The mixture was concentrated under reduced pressure at 45° C., and the filtrate was slowly added into 20 mL saturated sodium sulfite solution to quench the reaction, then extracted by 20 mL DCM, the organic phase was washed by 20 mL saturated brine, dried over anhydrous sodium sulfate, then filtered, evaporated to dry to give the crude product 49-3, which was used directly in the next step. MS m/z: 380.1[M+H]$^+$

Step 4: Synthesis of Compound 49

Under nitrogen atmosphere, 49-3 (300 mg, 0.79 mmol) and 12 (205.12 mg, 0.79 mmol) was added into DCM solution, then DIPEA (306.59 mg, 2.37 mmol, 0.40 mL) was added, and stirred at 30° C. for 12 hours. The solvent therein was evaporated, then purified by preparative HPLC ((chromatographic column: waters Xbridge 150×25 mm 5 µm; mobile phases: [water (0.225% FA)-ACN]; B (ACN) %: 10%-35%, 12 min).)) to give 49. $^1$H NMR (400 MHz, CDCl$_3$) δ 8.83 (s, 1H), 8.03 (d, J=8.4 Hz, 1H), 7.95-7.91 (m, 1H), 7.53 (d, J=7.6 Hz, 1H), 7.44 (br d, J=8.6 Hz, 2H), 6.92 (d, J=9.2 Hz, 2H), 5.67-5.63 (m, 1H), 4.94 (d, J=19.6 Hz, 1H), 4.84 (s, 3H) 3.17-3.14 (m, 4H), 2.49 (br s, 4H), 2.36 (s, 3H), 1.68-1.67 (m, 3H), 1.66-1.62 (m, 8H) MS m/z: 575.3 [M+H]$^+$

Embodiment 50: Compound 50

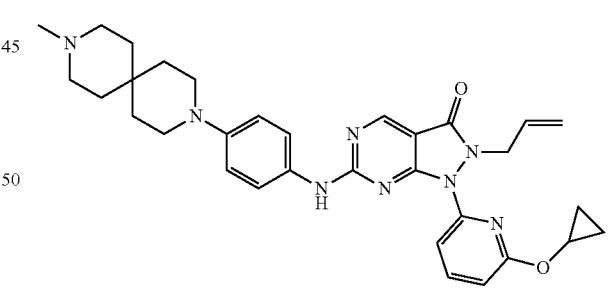

Synthetic Route:

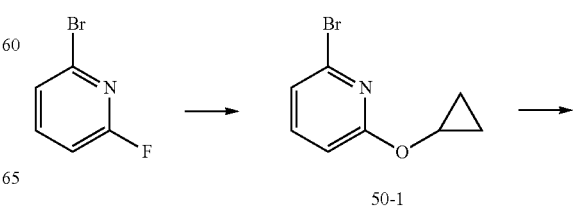

50-1

151

-continued

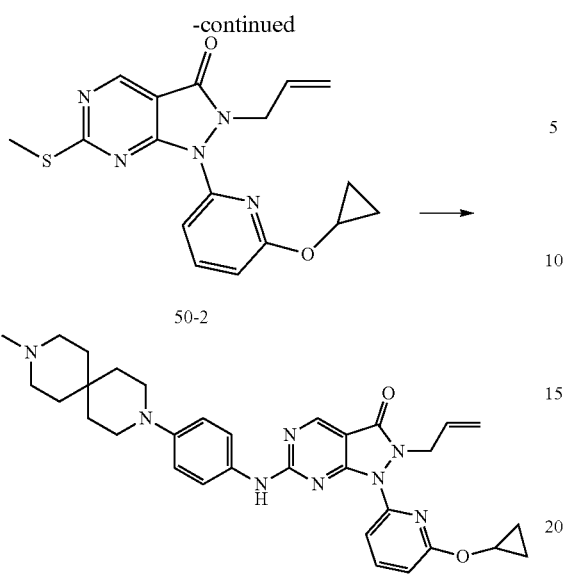

50-2

50

Step 1: Synthesis of Compound 50-1

2-Bromo-6-fluoropyridine (3.00 g, 17.05 mmol) and cyclopropanol (1.09 g, 18.76 mmol) were dissolved in 30 mL THF, potassium tert-butoxide (2.47 g, 22.01 mmol) was added at 0° C., then stirred at 0° C. for 12 h. 50 mL water was added into, then extracted by 100 mL EA, the organic phase was washed by 100 mL brine, dried over anhydrous sodium sulfate, and the filtrate was concentrated to give 50-1. MS m/z: 216.0 [M+H]+

Step 2: Synthesis of Compound 50-2

I1 (2.00 g, 9.00 mmol) was added into 1,4-dioxane (30.00 mL), and 50-1 (2.12 g, 9.90 mmol), potassium carbonate (1.70 g, 12.33 mmol), cuprous iodide (1.71 g, 9.00 mmol) and N,N'-dimethylethylenediamine (872.50 mg, 9.90 mmol, 1.08 mL) were added while stirring, the temperature was raised to 95° C. and stirred for 12 h under nitrogen atmosphere. 100 mL ammonia was added to the mixture, then extracted by 100 mL EA, the organic phase was washed by 100 mL brine, dried over anhydrous sodium sulfate, the filtrate was concentrated, crystallized in EtOAc to give 50-2. MS m/z: 356.1 [M+H]+

Step 3: Synthesis of Compound 50

Compound 50-2 (500.00 mg, 1.41 mmol) and m-CPBA (324.43 mg, 1.60 mmol) were added into 5 mL DCM, then reacted at 25° C. for 1 h. 12 (632.73 mg, 2.44 mmol) and DIPEA (501.13 mg, 3.88 mmol, 677.20 μL) were added and stirred at 30° C. for 12 h. The reacted mixture was partitioned between 10 mL DCM and 10 mL, the organic phase was washed separately by 10 mL saturated sodium sulfite solution, 10 mL sodium carbonate solution and 10 mL sodium chloride solution, dried over anhydrous sulfuric acid, the filtrate was concentrated. The residue was purified by preparative HPLC (chromatographic column: waters Xbridge 150×25 mm 5 μm; mobile phases: [water (0.225% FA)-ACN]; B %: 10%-30%, 12 min) to give 50. ¹H NMR (400 MHz, CDCl₃)
8.80 (s, 1H), 7.71 (t, J=8.0 Hz, 1H), 7.47-7.50 (m, 2H), 6.91 (d, J=8.8 Hz, 2H), 6.65 (d, J=8.4 Hz, 1H), 5.70-5.61 (m,

152

1H), 5.02-4.98 (m, 2H), 4.88 (d, J=6.4 Hz, 2H), 4.17-4.22 (m, 1H) 3.11-3.14 (m, 4H), 2.38 (br, 4H), 2.28 (s, 3H), 1.59-1.65 (m, 8H), 0.78 (d, J=6.4 Hz, 4H), MS m/z: 569.3 [M+H]+

Embodiment 51: Compound 51

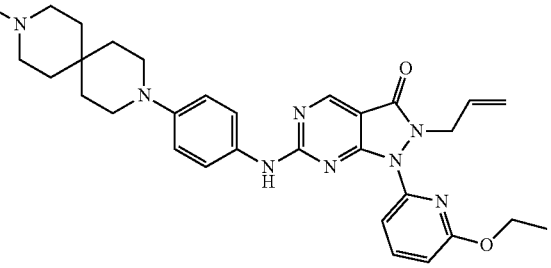

Synthetic Route:

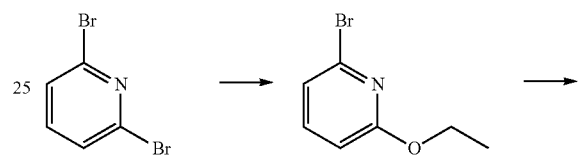

51-1

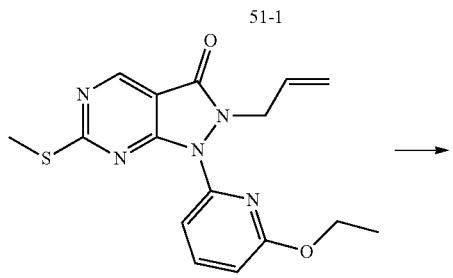

51-2

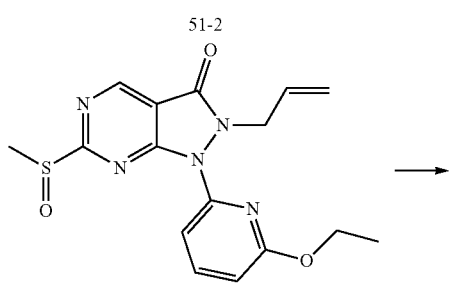

51-3

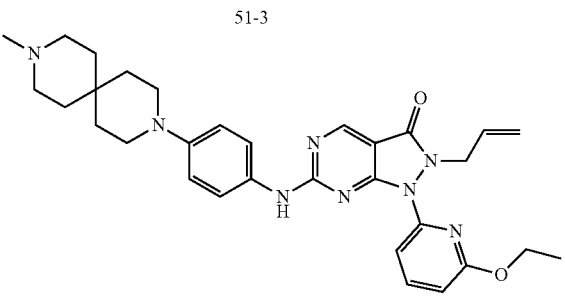

51

Step 1: Synthesis of Compound 51-1

Anhydrous ethanol (2.92 g, 63.33 mmol, 3.70 mL) was added into THF (20.00 mL) solution, then sodium hydride (1.52 g, 63.33 mmol) was added to the mixture and stirred for 5 min, then 2,6-dibromopyridine (5.00 g, 21.11 mmol) was added, the mixture was stirred at 25° C. for 2 hours until the reaction was complete. The reaction mixture was slowly poured into 50 mL ice water, then extracted by 50 mL EA, the organic phase was washed by 50 mL saturated brine, dried over anhydrous sodium sulfate, then filtered, evaporated, mixed and purified by chromatography (EA/PE=1/20-1/10) to give 51-1. $^1$H NMR (400 MHz, CDCl$_3$) δ7.37-7.33 (m, 1H), 6.98 (d, J=7.2 Hz, 1H), 6.61 (d, J=8.0 Hz, 1H), 4.33-4.28 (m, 2H), 1.35-1.33 (m, 3H)

Step 2: Synthesis of Compound 51-2

Compound 51-1 (2.00 g, 9.90 mmol) and Intermediate 11 (2.20 g, 9.90 mmol) were added into 1,4-dioxane solution, then N,N'-diethylethylenediamine (1.27 g, 10.89 mmol), potassium carbonate (1.37 g, 9.90 mmol) and cuprous iodide (1.89 g, 9.90 mmol) were added sequentially under nitrogen atmosphere, the temperature was raised to 95° C. and the reaction was stirred at reflux for 12 hours until it was complete. Then the mixture was cooled down to r.t. and concentrated, quenched by 50 mL water, then extracted by 50 mL EA, the organic phase was washed by 50 mL saturated brine, dried over anhydrous sodium sulfate, then filtered, evaporated and purified by chromatography (EA/PE=1/10-1/4) to give 51-2. $^1$H NMR (400 MHz, CDCl$_3$) δ 8.90 (s, 1H), 7.75-7.71 (m, 1H), 7.35 (d, J=8.0 Hz, 1H), 6.67 (d, J=8.2 Hz, 1H), 5.71-5.64 (m, 1H), 5.04 (dd, J=10.0 Hz, 1H), 5.05-4.80 (m, 1H), 4.81 (d, J=6.4 Hz, 1H), 4.34-4.29 (m, 2H), 2.55 (s, 3H), 1.56 (d, J=2.4 Hz, 1H), 1.42-1.38 (m, 3H)

Step 3: Synthesis of Compound 51-3

Compound 51-2 (300.00 mg, 0.87 mmol) was added into DCM solution, m-CPBA (215.37 mg, 1.06 mmol, 85% purity) was added into the reaction mixture, then stirred at 25° C. for 2 hours, until the reaction was complete. The reaction mixture was concentrated, then slowly added into 20 mL saturated sodium sulfite solution to quench the reaction, then extracted by 20 mL DCM, the organic phase was washed by 20 mL saturated brine, dried over anhydrous sodium sulfate, then filtered and evaporated to give the crude product 51-3 which was used directly in the next step.

Step 4: Synthesis of Compound 51

Crude product 51-3 and Intermediate 12 (216.52 mg, 0.83 mmol) was added into DCM solution, then DIPEA (323.64 mg, 2.50 mmol, 0.44 mL) was added, under N$_2$ atmosphere, the mixture was stirred at 30° C. for 12 hours until the reaction was complete. The solvent was evaporated, then purified by preparative HPLC (chromatographic column: waters Xbridge 150×25 mm 5 μm; mobile phases: [water (0.225% FA)-ACN]; B (acetonitrile) %: 10%-20%, 12 min) to give 51. $^1$H NMR (400 MHz, CDCl$_3$) δ 8.76 (br s, 1H), 7.71-7.67 (m, 1H), 7.47 (br d, J=8.0 Hz, 2H), 7.34 (br d, J=7.6 Hz, 1H), 6.87 (br d, J=8.4 Hz, 2H), 6.64 (br d, J=8.2 Hz, 1H), 5.71-5.63 (m, 1H), 5.03-4.92 (m, 2H), 4.75 (br d, J=5.6 Hz, 2H), 4.32 (q, J=7.2 Hz, 2H), 3.11-2.88 (m, 8H), 2.71 (s, 3H), 1.84 (br s, 4H), 1.70 (br s, 4H), 1.38-1.36 (m, 3H) MS m/z: 555.3[M+H]$^+$

Embodiment 52: Compound 52

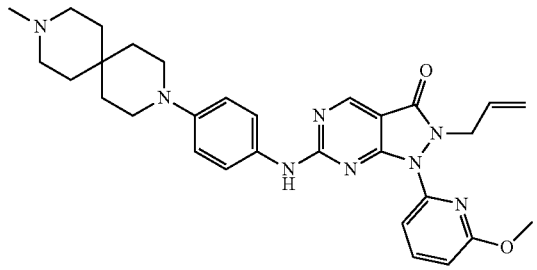

Synthetic Route:

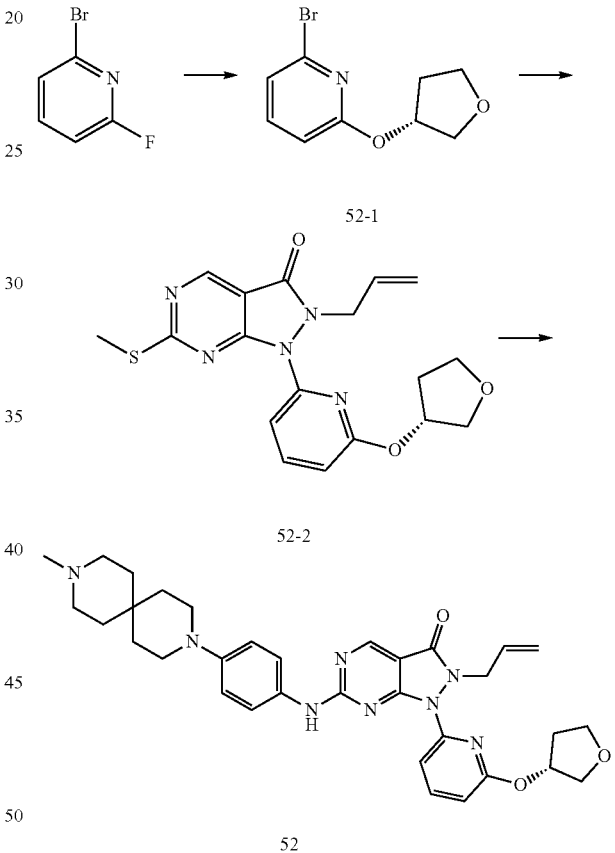

Step 1: Synthesis of Compound 52-1

2-Bromo-6-fluoro-pyridine (2 g, 11.36 mmol), (R)-3-hydroxytetrahydrofuran (1.10 g, 12.50 mmol, 1.00 mL) and THF (20 mL) were added into a pre-dried 100 mL three neck flask, then t-BuOK (1.65 g, 14.65 mmol) was added at 0° C., replaced with nitrogen for 3 times, the reaction was kept for 0.5 hours at 25° C. under nitrogen atmosphere. 20 mL Water was added, extracted by 30 mL×3 EA, the organic phase was dried over anhydrous sodium sulfate, filtered and evaporated to give 52-1. $^1$H NMR (400 MHz, CDCl$_3$) δ=7.50-7.34 (m, 1H), 7.06 (d, J=7.4 Hz, 1H), 6.69 (d, J=8.2 Hz, 1H), 5.57 (tdd, J=2.0, 4.4, 6.4 Hz, 1H), 4.05-3.83 (m, 4H), 2.35-2.19 (m, 1H), 2.19-2.04 (m, 1H)

Step 2: Synthesis of Compound 52-2

Compound I1 (1 g, 4.50 mmol) and 1,4-dioxane (20 mL) were added into a pre-dried 100 mL three neck flask, followed by adding compound 52-1 (1.21 g, 4.95 mmol), cuprous iodide (856.85 mg, 4.50 mmol), potassium carbonate (851.89 mg, 6.16 mmol), and N,N'-dimethylethylenediamine (436.26 mg, 4.95 mmol, 540.60 µL), replaced with nitrogen for 3 times, the reaction was kept for 16 hr at 95° C. under nitrogen atmosphere. 30 mL ammonia was added, then extracted by 30 mL×3 EA, the organic phase was dried over anhydrous sodium sulfate, filtered and evaporated. The crude product was purified by chromatography (SiO$_2$, 100-200 mesh, PE/EtOAc=10/1-1/1) to give the 52-2. $^1$H NMR (400 MHz, CDCl$_3$) δ=8.93 (s, 1H), 7.78 (t, J=8.0 Hz, 1H), 7.39 (d, J=7.7 Hz, 1H), 6.73 (d, J=8.2 Hz, 1H), 5.69 (tdd, J=6.2, 10.4, 16.9 Hz, 1H), 5.51 (dt, J=2.3, 4.3 Hz, 1H), 5.08 (d, J=10.2 Hz, 1H), 4.98 (dd, J=1.0, 17.1 Hz, 1H), 4.77 (t, J=6.5 Hz, 2H), 4.05-3.98 (m, 2H), 3.95-3.86 (m, 2H), 2.57 (s, 3H), 2.32-2.20 (m, 1H), 2.17-2.05 (m, 1H)

Step 3: Synthesis of Compound 52

Compound 52-2 (0.2 g, 518.89 µmol) and DCM (2 mL) were added into a pre-dried 40 mL flask, followed by adding m-CPBA (136.95 mg, 674.55 µmol, 85% purity), replaced with nitrogen for 3 times, and the reaction was kept at 25° C. for 1 hr under nitrogen atmosphere. DCM (1 mL), DIEA (193.17 mg, 1.49 mmol, 260.34 µL) and 12 (135.69 mg, 523.12 µmol) were added, and replaced with nitrogen, the reaction was kept at 25° C. for 16 hr under nitrogen atmosphere. 5 mL saturated sodium sulfite solution was added, then extracted with 10 mL×2 DCM, dried over anhydrous sodium sulfate, the organic phase was filtered and evaporated to dry. The residue was purified by prep-HPLC (chromatographic column: Agela Durashell C18 150×25 mm 5 µm; mobile phases: [water (10 mM NH$_4$HCO$_3$)-ACN]; B %: 35%-55%, 10.5 min), freeze-dried to give 52. $^1$H NMR (400 MHz, CDCl$_3$) δ=8.82 (s, 1H), 7.75 (t, J=7.9 Hz, 1H), 7.43 (br dd, J=7.8, 19.1 Hz, 3H), 6.92 (d, J=8.9 Hz, 2H), 6.69 (d, J=8.2 Hz, 1H), 5.76-5.64 (m, 1H), 5.54 (br s, 1H), 5.06 (d, J=9.8 Hz, 1H), 4.98 (d, J=16.8 Hz, 1H), 4.88-4.65 (m, 4H), 4.06-3.87 (m, 4H), 3.18-3.11 (m, 4H), 2.41 (br s, 3H), 2.31 (s, 3H), 2.29-2.22 (m, 1H), 2.17-2.09 (m, 1H), 1.63-1.58 (m, 8H) MS m/z: 597.4$^+$ Embodiment 53: Compound 53

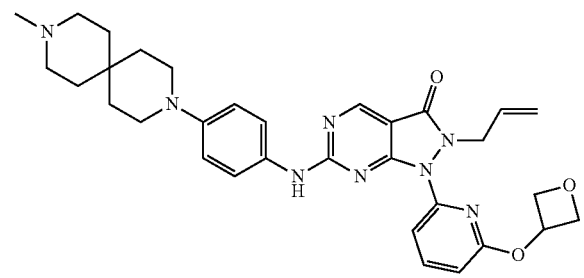 [SMILES: C=CCn1c(=O)c2cnc(Nc3ccc(N4CCC5(CCN(C)CC5)CC4)cc3)nc2n1-c1cccc(OC2COC2)n1]

Synthetic Route:

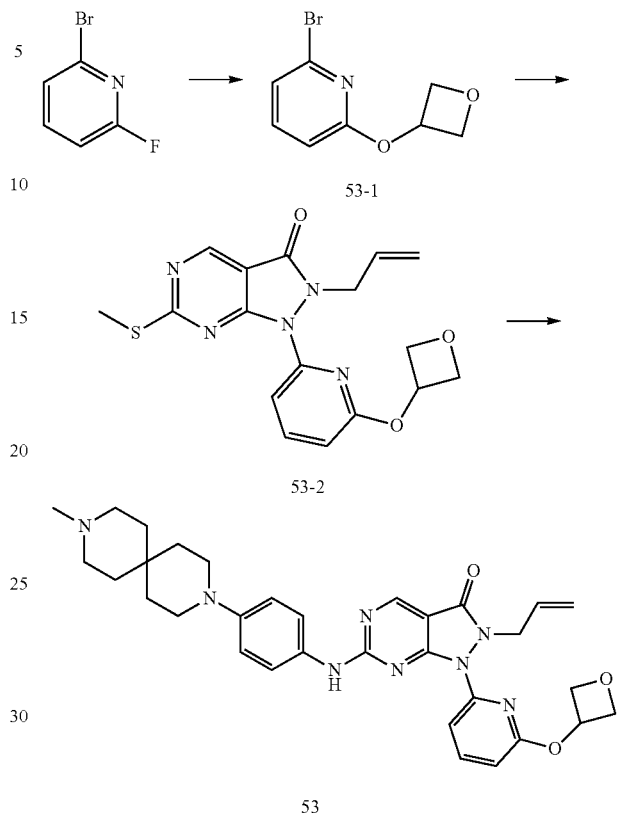

Step 1: Synthesis of Compound 53-1

2-Bromo-6-fluoropyridine (2 g, 11.36 mmol) and 3-hydroxyoxetane (926.05 mg, 12.50 mmol) were dissolved in anhydrous THF (10 mL), potassium tert-butoxide (1.65 g, 14.66 mmol) was added at 0° C., and stirred at 0° C. for 2 h. The reaction mixture was added into water (20 mL), then extracted with EA (2×20 mL), the organic phase was washed by saturated brine (30 mL), dried over anhydrous sodium sulfate, and the filtrate was concentrated to give 53-1. $^1$H NMR (400 MHz, CDCl$_3$) δ ppm 7.40-7.40 (m, 1H) 7.36-7.65 (m, 1H) 7.11 (d, J=7.6 Hz, 1H) 5.60-5.71 (m, 1H) 4.73-5.01 (m, 2H) 4.60-4.79 (m, 2H) MS m/z: 230.06 [M+H]$^+$ Step 2: Synthesis of Compound 53-2

I1 (805.11 mg, 3.62 mmol) and 53-1 (1 g, 4.35 mmol) were added into 1,4-dioxane (20.00 mL), followed by cuprous iodide (689.86 mg, 3.62 mmol), potassium carbonate (685.85 mg, 4.96 mmol) and N,N'-methylethylenediamine (351.24 mg, 3.98 mmol, 428.86 µL), the reaction mixture was heated to 95° C. under nitrogen atmosphere, then reacted for 12 h. After adding ammonia (100 L), the reacted mixture was then extracted by EA (2×50 L), the organic phase was washed by saturated brine (50 mL), dried over anhydrous sodium sulfate, the filtrate was concentrated to give the crude product, which was purified by silica gel column chromatography (silica gel mesh: 100-200 mesh; PE/EA=20/1-0/1) to give 53-2. MS m/z: 371.41 [M+H]$^+$

157

Step 3: Synthesis of Compound 53

53-2 (200 mg, 538.48 µmol) was added into anhydrous DCM (6 mL), followed by m-CPBA (159.14 mg, 783.85 µmol, 85% purity), the mixture was stirred at 25° C. for 1.5 hours. Then DIPEA (173.47 mg, 1.34 mmol, 233.79 µL), 12 (167.12 mg, 644.27 µmol) were added, the reaction mixture was stirred at 35° C. for 16 hours. The reaction mixture was evaporated to dry, then saturated sodium sulfite solution (10 mL) was added, and extracted by DCM (3×10 mL), the organic phase was dried over anhydrous sodium sulfate, then filtered, concentrated under reduced pressure to give a residue, which was purified by prep-HPLC (chromatographic column: Agela Durashell C18 150×25 mm 5 µm; mobile phases/[water (10 mM $NH_4HCO_3$)-ACN]; B (acetonitrile) %: 28%-58%, 10.5 min) and thin layer chromatography silica gel plate (DCM/MeOH=10/1) to give the 53. $^1$H NMR (400 MHz, $CDCl_3$) δ ppm 8.80 (s, 1H) 7.76 (br t, J=8.4 Hz, 1H) 7.37-7.47 (m, 3H) 6.91 (br d, J=8.0 Hz, 2H) 6.72 (br d, J=8.0 Hz, 1H) 5.48-5.78 (m, 2H) 4.90-5.04 (m, 1H) 4.90-5.07 (m, 3H) 4.73 (br t, J=6.4 Hz, 2H) 4.64 (br d, J=6.8 Hz, 2H) 3.13 (br d, J=4.85 Hz, 4H) 2.45 (br s, 4H) 2.32 (s, 3H) 1.62-1.65 (m, 8H) MS m/z: 582.69 [M+H]$^+$

Embodiment 54: Compound 54

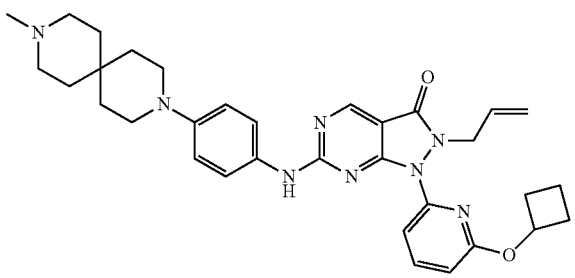 [SMILES: C=CCn1c(=O)c2cnc(Nc3ccc(N4CCC5(CCN(C)CC5)CC4)cc3)nc2n1-c1cccc(OC2CCC2)n1]

Synthetic Route:

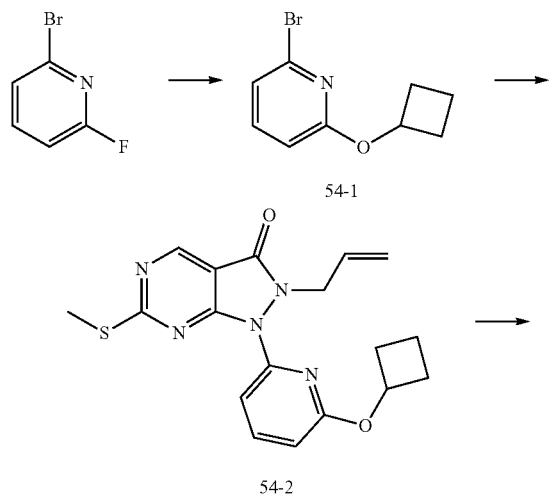

158

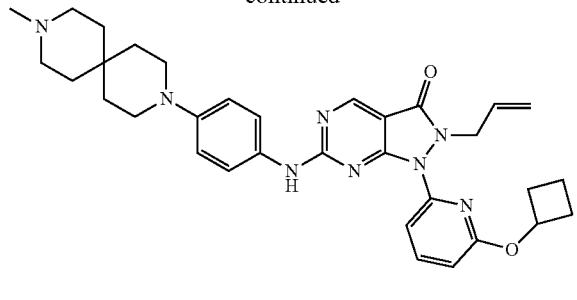

54

Step 1: Synthesis of Compound 54-1

2-Bromo-6-fluoropyridine (2 g, 11.36 mmol) and cyclobutanol (819.12 mg, 11.36 mmol) were dissolved in anhydrous THF (10 mL), potassium tert-butoxide (1.65 g, 14.65 mmol) was added at 0° C. and then stirred at 0° C. for 2 h. Water (20 mL) was added into the reaction mixture, and extracted by EA (2×20 mL), the organic phase was washed by saturated brine (30 mL), dried over anhydrous sodium sulfate, the filtrate was concentrated to give 54-1. $^1$H NMR (400 MHz, $CDCl_3$) δ=7.46-7.30 (m, 1H), 7.01 (d, J=7.5 Hz, 1H), 6.60 (d, J=8.2 Hz, 1H), 5.14 (quin, J=7.5 Hz, 1H), 2.49-2.38 (m, 2H), 2.17-2.02 (m, 2H), 1.72-1.47 (m, 2H) MS m z: 228.09 [M+H]$^+$

Step 2: Synthesis of Compound 54-2

I1 (812.07 mg, 3.65 mmol, 1 eq) and 54-1 (1 g, 4.38 mmol) were added into 1,4-dioxane (20.00 mL), followed by cuprous iodide (695.83 mg, 3.65 mmol), potassium carbonate (691.80 mg, 5.01 mmol) and N,N'-dimethylethylenediamine (354.27 mg, 4.02 mmol, 432.57 µL), the temperature was raised to 95° C. under nitrogen atmosphere, then the reaction was kept for 12 h. Ammonia (100 mL) was added into the reacted mixture, then extracted by EA (2×50 mL), the organic phase was washed by saturated brine (50 mL), dried over anhydrous sodium sulfate, the filtrate was concentrated to give the crude product, which was purified by silica gel column chromatography (silica gel mesh: 100-200 mesh; PE/EA=20/1-10/1) to give 54-2. $^1$H NMR (400 MHz, $CDCl_3$) δ=8.85 (s, 1H), 7.67 (t, J=7.9 Hz, 1H), 7.29 (d, J=7.7 Hz, 1H), 6.59 (d, J=8.2 Hz, 1H), 5.73-5.48 (m, 1H), 5.19-4.93 (m, 2H), 4.88 (br d, J=17.2 Hz, 1H), 4.75 (d, J=6.2 Hz, 2H), 2.50 (s, 3H), 2.40-2.23 (m, 2H), 2.07-2.14 (m, 2H), 1.58-1.82 (m, 2H) MS m z: 369.44 [M+H]$^+$

Step 3: Synthesis of Compound 54-3

54-2 (200 mg, 541.36 µmol) was added into anhydrous DCM (5 mL), followed by m-CPBA (159.99 mg, 788.04 µmol, 85% purity), the reaction mixture was stirred at 25° C. for 1.5 hours. DIPEA (174.36 mg, 1.35 mmol, 234.99 µL) and I2 (153.98 mg, 593.61 µmol) were added, the reaction mixture was stirred at 35° C. for 16 hours. Saturated sodium sulfite solution (10 mL) was added, then extracted by DCM (3×10 mL), the organic phase was dried over anhydrous sodium sulfate, then filtered, concentrated under reduced pressure to give a residue, which was purified by prep-HPLC (chromatographic column: Agela Durashell C18 150×25 mm 5 µm; mobile phases: [water (10 mM $NH_4HCO_3$)-ACN]; B (acetonitrile) %: 46%-66%, 10.5 min) to give the 54. ¹H NMR (400 MHz, CDCl₃) δ=8.83 (s, 1H), 7.74 (t, J=7.9 Hz, 1H), 7.48 (br d, J=8.3 Hz, 2H), 7.40 (br d, J=7.8 Hz, 1H), 6.94 (d, J=9.0 Hz, 2H), 6.64 (d, J=8.2 Hz, 1H), 5.75-5.66 (m, 1H), 4.95-5.16 (m, 3H), 4.79 (br d, J=5.8 Hz, 2H), 3.18-3.13 (m, 4H), 2.52-2.41 (m, 6H), 2.33 (s, 3H), 2.18 (ddd, J=2.7, 7.6, 9.8 Hz, 2H), 1.92-1.82 (m, 1H), 1.76-1.63 (m, 11H) MS m/z: 580.72 [M+H]⁺

Embodiment 55: Compound 55

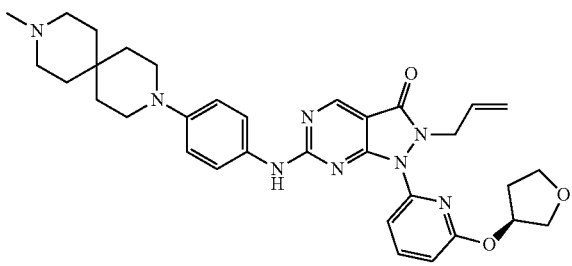 [SMILES: C=CCn1c(=O)c2cnc(Nc3ccc(N4CCC5(CCN(C)CC5)CC4)cc3)nc2n1-c1cccc(O[C@H]2CCOC2)n1]

Synthetic Route:

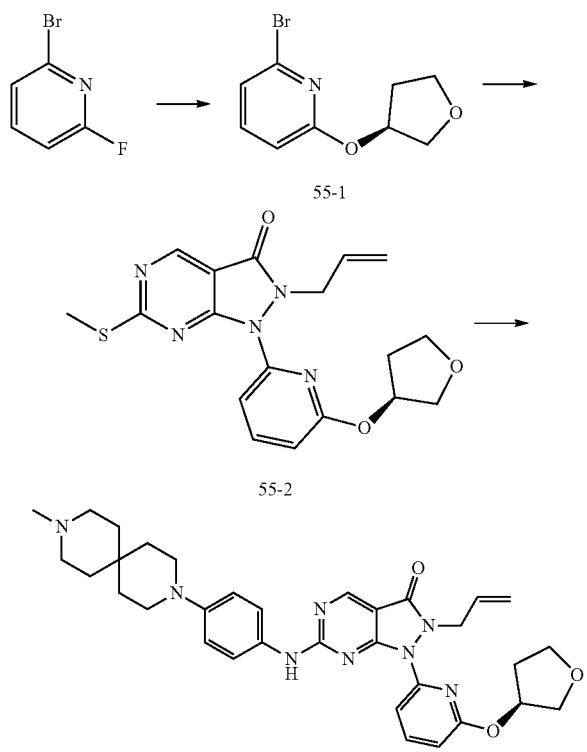

Step 1: Synthesis of Compound 55-1

2-Bromo-6-fluoropyridine (9.99 g, 56.75 mmol) and S-3-hydroxytetrahydrofuran (5 g, 56.75 mmol) were dissolved in THF (100 mL), potassium tert-butoxide (8.28 g, 73.78 mmol) was added at 0° C., then reacted at 25° C. for 12 h. The reaction mixture was extracted by 50 mL water and 100 mL EA, the organic phase was washed by 100 mL brine, dried over anhydrous sodium sulfate, filtered and concentrated to give 55-1, which was used directly in the next step.

Step 2: Synthesis of Compound 55-2

55-1 (576.54 mg, 2.36 mmol), I1 (500 mg, 2.25 mmol), cuprous iodide (428.43 mg, 2.25 mmol), potassium carbonate (432.17 mg, 3.13 mmol) and N,N'-methylethylenediamine (218.13 mg, 2.47 mmol, 266.33 µL, 1.10 eq) was added into 1,4-dioxane (15 mL), replaced with nitrogen 3 times and, the mixture was stirred at 95° C. for 13 hr under nitrogen atmosphere. 10 mL ammonia was added to quench the reaction, then extracted with 30 mL DCM, the organic phase was washed by 20 mL saturated brine, dried over anhydrous sodium sulfate, then filtered and evaporated to dry to give 55-2, which was used directly in the next step. MS m/z: 386.3 [M+H]⁺

Step 3: Synthesis of Compound 55

55-2 (200 mg, 518.89 µmol) was dissolved in DCM (2 mL), followed by adding m-CPBA (144.32 mg, 710.88 µmol, 85% purity), the mixture was stirred at 25° C. for 1 h. DIPEA (167.66 mg, 1.30 mmol, 225.95 µL) and I2 (134.59 mg, 518.88 µmol) were added, then reacted at 25° C. for 12 h. Saturated sodium sulfite solution 5 mL was added into the reaction mixture, then extracted by DCM 10 mL, the organic phase was dried over anhydrous sodium sulfate, then filtered and evaporated to dry to give the crude product. The crude product was purified by prep-HPLC (chromatographic column: waters Xbridge 150×25 mm 5 µm; mobile phases: [A-HCl/H₂O=0.04% v/v; B-ACN] B %: 1%-25%, 12 min]) and adjusted pH=7 with basic resin, then filtered and concentrated to give 55.

¹H NMR (400 MHz, CDCl₃) δ=8.80 (s, 1H), 7.73 (t, J=8.0 Hz, 1H), 7.38-7.44 (m, 3H), 6.90 (d, J=8.8 Hz, 2H), 6.67 (d, J=8.0 Hz, 1H), 5.74-5.62 (m, 1H), 5.50-5.52 (m, 1H), 5.07-4.93 (m, 2H), 4.71 (br t, J=6.1 Hz, 2H), 4.05-3.84 (m, 4H), 3.17-3.08 (m, 4H), 2.38 (br s, 4H), 2.28 (s, 3H), 2.27-2.20 (m, 1H), 2.15-2.06 (m, 1H), 1.68-1.58 (m, 10H), MS m/z: 597.3 [M+H]⁺

Embodiment 56: Compound 56

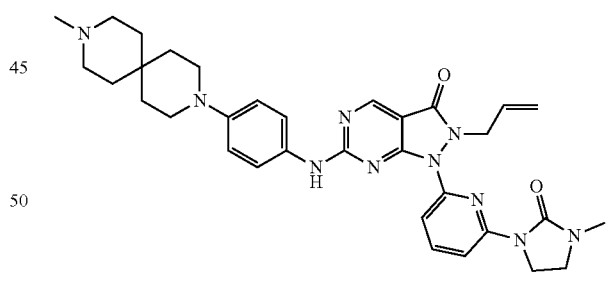

Synthetic Route:

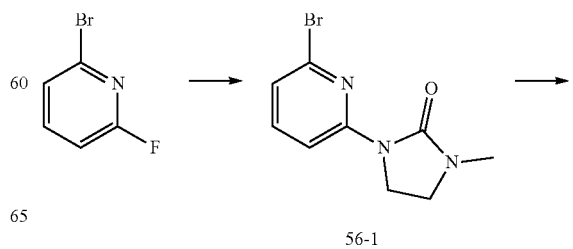

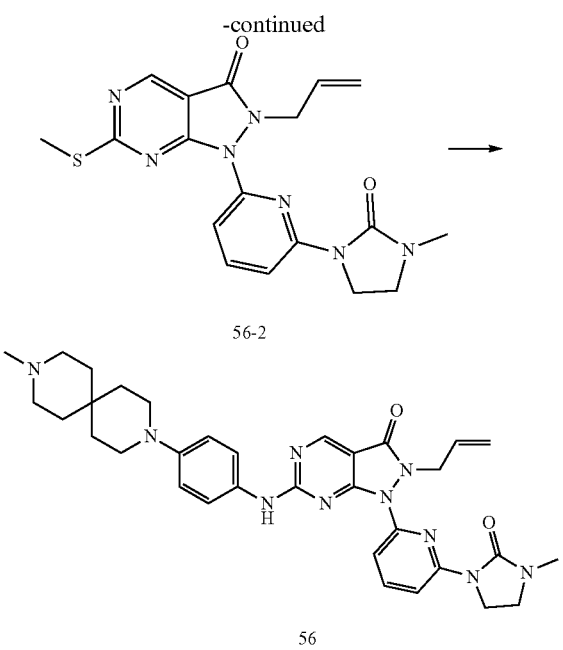

56-2

56

Step 1: Synthesis of Compound 56-1

Sodium hydrogen (909.07 mg, 22.73 mmol, 60% purity) was dissolved in anhydrous THF (5 mL), the reaction was placed in an ice bath, replaced with nitrogen for 3 times, 2-bromo-6-fluoropyridine (2 g, 11.36 mmol), and 1-methylimidazolidinone (2.28 g, 22.73 mmol) were added at 0° C., the mixture was stirred at 70° C. for 16 hours. Water (20 mL) was added to quench the reaction, then extracted with EA (3×20 mL), the organic phase was washed by saturated brine (20 mL), dried over anhydrous sodium sulfate, the filtrate was concentrated to give the crude product, the crude product was purified by column to give the 56-1. $^1$H NMR (400 MHz, CDCl$_3$) δ=8.23 (d, J=8.5 Hz, 1H), 7.43 (t, J=7.7 Hz, 1H), 7.05 (d, J=7.5 Hz, 1H), 4.10-3.93 (m, 2H), 3.53-3.40 (m, 2H), 2.95-2.85 (m, 3H), MS m/z: 256.10 [M+H]$^+$

Step 2: Synthesis of Compound 56-2

I1 (867.89 mg, 3.90 mmol), 56-1 (1 g, 3.90 mmol), cuprous iodide (743.66 mg, 3.90 mmol), potassium carbonate (755.54 mg, 5.47 mmol) and N,N'-dimethylethylenediamine (378.62 mg, 4.30 mmol, 469.17 μL) were added into 1,4-dioxane (20.00 mL), the temperature was raised to 95° C. under nitrogen atmosphere, then reacted for 16 h. Ammonia (50 mL) was added into the reacted mixture, extracted by EA (3×50 mL), the organic phase was washed by saturated brine (50 mL), dried over anhydrous sodium sulfate, the filtrate was concentrated to give the crude product, the residue was separated by an automatic column machine (PE/EA=10/1-5/1) to give the 56-2. $^1$H NMR (400 MHz, CDCl$_3$) δ ppm 8.94 (s, 1H), 8.29 (d, J=8.4 Hz, 1H) 7.83 (t, J=8.41 Hz, 1H) 7.43 (d, J=7.6 Hz, 1H) 5.68-5.75 (m, 1H), 4.95-5.09 (m, 2H), 4.82 (d, J=6.0 Hz, 2H) 4.03 (t, J=8.4 Hz, 2H) 3.53 (t, J=8.4 Hz, 2H) 2.96 (s, 3H) 2.59 (s, 3H) MS m/z: 397.45 [M+H]$^+$

Step 3: Synthesis of Compound 56

56-2 (200 mg, 503.20 μmol) was added into anhydrous DCM (10 mL), followed by adding m-CPBA (148.71 mg, 689.39 μmol, 85% purity), the reaction mixture was stirred at 25° C. for 1.5 hours. DIPEA (162.55 mg, 1.26 mmol, 219.06 μL) and 12 (156.59 mg, 603.70 μmol) were added, the reaction mixture was stirred at 35° C. for 16 hours. Saturated sodium sulfite solution (10 mL) was added to quench the reaction, then extracted by DCM (3×10 mL), the organic phase was dried over anhydrous sodium sulfate, then filtered, concentrated under reduced pressure to give a residue, the residue was purified by prep-HPLC (chromatographic column/Xtimate C18 150×25 mm×5 μm; mobile phases/[water (10 mM NH$_4$HCO$_3$)-ACN]; B (acetonitrile) %: 30%-50%, 10.5 min) to give 56. $^1$H NMR (400 MHz, CDCl$_3$) δ=8.79 (s, 1H), 8.20 (d, J=8.4 Hz, 1H), 7.77 (t, J=8.0 Hz, 1H), 7.47-7.30 (m, 3H), 6.91-6.89 (d, J=8.8 Hz, 2H), 5.73-5.61 (m, 1H), 4.94-5.04 (m, J=17.2 Hz, 2H), 4.73 (br d, J=6.2 Hz, 2H), 4.01 (t, J=7.6 Hz, 2H) 3.48 (t, J=7.6 Hz, 2H) 3.14-3.10 (m, 4H), 2.92 (s, 3H), 2.41 (br s, 4H), 2.30 (s, 3H), 1.66-1.61 (m, 8H) MS m/z: 608.73 [M+H]$^+$

Embodiment 57: Compound 57

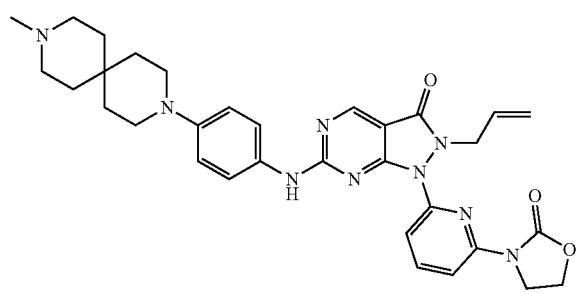 [SMILES: C=CCn1c(=O)c2cnc(Nc3ccc(N4CCC5(CCN(C)CC5)CC4)cc3)nc2n1-c1cccc(N2CCOC2=O)n1]

Synthetic Route:

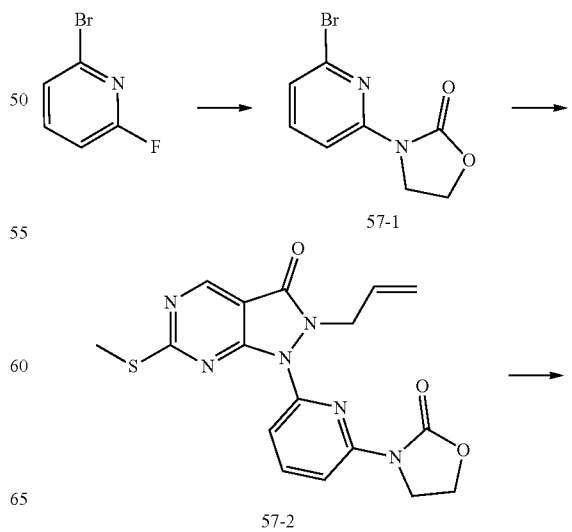

57-1

57-2

-continued

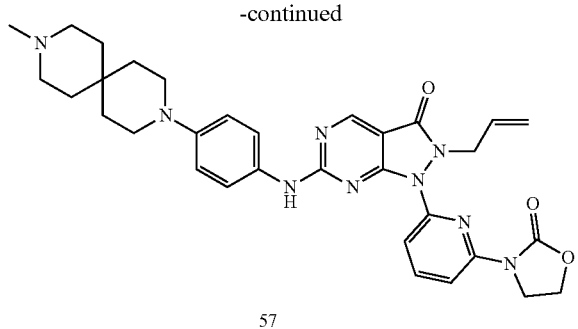

57

Step 1: Synthesis of Compound 57-1

2-Bromo-6-fluoropyridine (2 g, 11.36 mmol), potassium carbonate (3.14 g, 22.73 mmol) and oxazolidinone (1.98 g, 22.73 mmol) was placed in DMF (5 mL), and stirred at 90° C. for 16 hours. Water (10 mL) was added into the reaction mixture, then extracted by EA (10 mL), washed by water (2×5 mL), the organic phase was washed by brine (5 mL), dried over anhydrous sodium sulfate, the filtrate was concentrated to give the crude product, the crude product was purified by an automatic column machine COMBI-FLASH (PE/EA=50/1-2/1) to give 57-1. MS m/z: 243.06 [M+H]$^+$

Step 2: Synthesis of Compound 57-2

I1 (182.89 mg, 822.85 μmol) and 57-1 (200 mg, 822.85 μmol) were added into 1,4-dioxane (5.00 mL), followed by adding cuprous iodide (156.71 mg, 822.85 μmol), potassium carbonate (159.22 mg, 1.15 mmol) and N,N'-dimethylethylenediamine (79.79 mg, 905.14 μmol, 98.87 μL), the temperature was raised to 95° C. under nitrogen atmosphere, then reacted for 16 h. Ammonia (20 mL) was added into the reacted mixture, then extracted by EA (3×10 mL), the organic phase was washed by saturated brine (20 mL), dried over anhydrous sodium sulfate, the filtrate was concentrated to give the crude product, which was separated by an automatic column machine COMBI-FLASH (PE/EA=10/1-1/1) to give 57-2. MS m/z: 384.41 [M+H]$^+$

Step 3: Synthesis of Compound 57

57-2 (195 mg, 507.27 μmol) was added into anhydrous DCM (10 mL), followed by adding m-CPBA (149.91 mg, 738.39 μmol, purity is 85%), the reaction mixture was stirred at 25° C. for 1.5 hours. DIPEA (163.80 mg, 1.27 mmol, 220.76 μL), 12 (157.81 mg, 608.37 μmol) was then added, the reaction mixture was stirred at 35° C. for 16 hours. Saturated sodium sulfite solution (10 mL) was added into the reaction mixture, then extracted by DCM (3×10 mL), the organic phase was dried over anhydrous sodium sulfate, then filtered, concentrated under reduced pressure to give a residue, which was purified by prep-HPLC (chromatographic column: Xtimate C18 150×25 mm×5 μm; mobile phases: [water (10 mM $NH_4HCO_3$)-ACN]; B (acetonitrile) %: 25%-55%, 10.5 min). then thin layer chromatography silica gel plate (DCM/MeOH=10/1) to give the 57. $^1$H NMR (400 MHz, $CDCl_3$) δ=8.79 (s, 1H), 8.12 (d, J=7.9 Hz, 1H), 7.84 (t, J=8.1 Hz, 1H), 7.55 (d, J=7.9 Hz, 1H), 7.40 (br d, J=8.8 Hz, 2H), 6.89 (d, J=9.0 Hz, 2H), 5.66 (tdd, J=6.3, 10.3, 16.9 Hz, 1H), 5.03 (dd, J=1.0, 10.2 Hz, 1H), 4.94 (dd, J=1.1, 17.1 Hz, 1H), 4.69 (br d, J=6.3 Hz, 2H), 4.49 (t, J=8.1 Hz, 2H), 4.23 (t, J=8.0 Hz, 2H), 3.17-3.08 (m, 4H), 2.39 (br s, 4H), 2.29 (s, 3H), 1.64-1.56 (m, 8H) MS m/z: 595.69 [M+H]$^+$

Embodiment 58: Compound 58

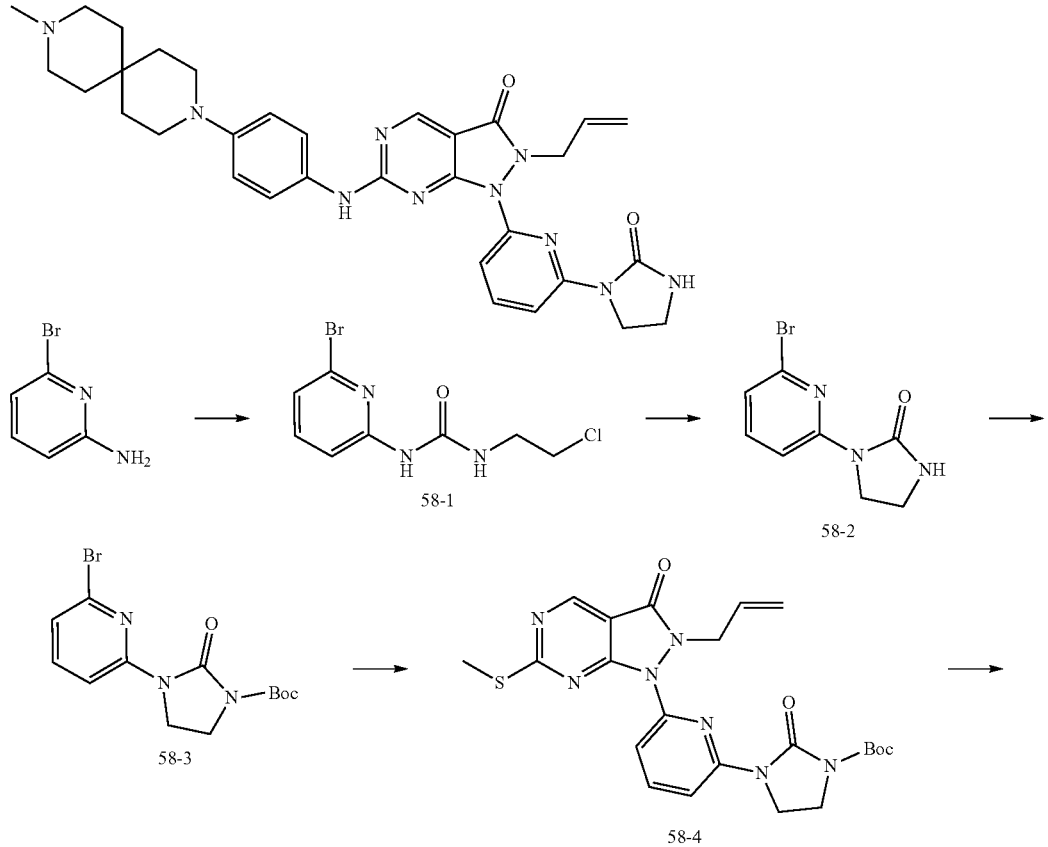

-continued

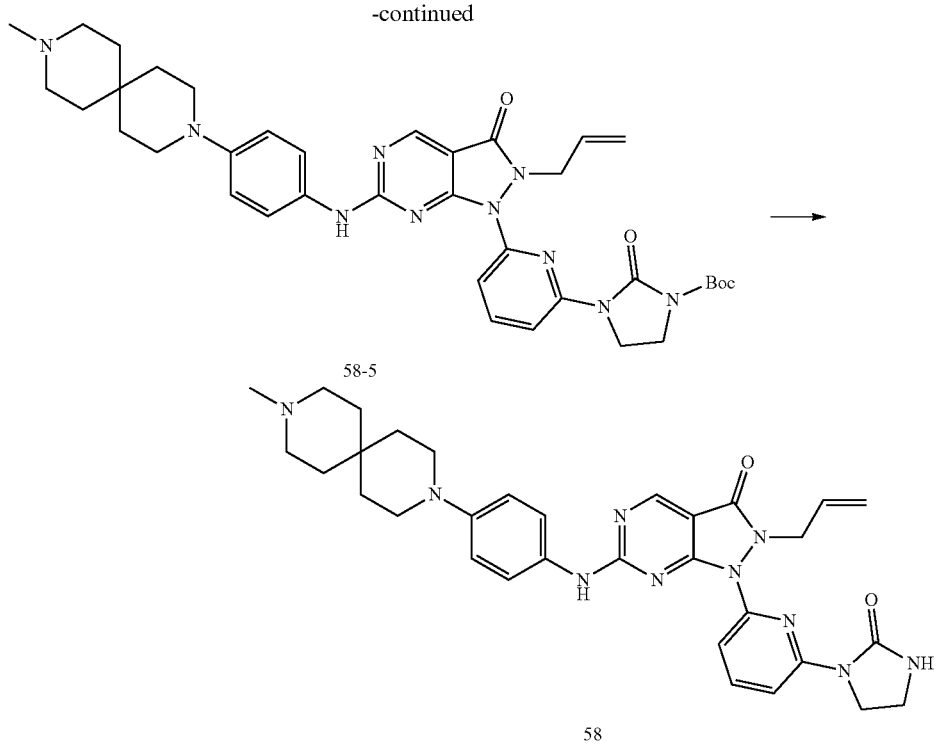

Step 1: Synthesis of Compound 58-1

6-Bromopyridin-2-amine (2 g, 11.56 mmol) was dissolved in anhydrous THF (5 mL), the reaction was placed in an ice bath, and replaced with nitrogen for 3 times, 1-chloro-2-isocyanato-ethane (1.83 g, 17.34 mmol, 1.48 mL) was added at 0° C., the reaction system was stirred at 25° C. for 16 hours. Water (10 mL) was added into the reaction mixture, then extracted with EA (3×10 mL), the organic phase was washed by saturated brine (2×10 mL), dried over anhydrous sodium sulfate, the filtrate was concentrated to give the crude product, 20 mL PE was added into the crude product and stirred for 1 hour, then filtered, the filter cake was washed by PE (2×20 mL) and collected, evaporated under increased pressure to give a white solid compound (1.34 g, 4.81 mmol, yield 41.62%). MS m/z: 278.53 [M+H]$^+$

Step 2: Synthesis of Compound 58-2

Sodium hydride (384.84 mg, 9.62 mmol, 60% purity) was added into anhydrous THF (20 mL), the reaction system was placed in an ice bath, replaced with nitrogen for 3 times, 58-1 (1.34 g, 4.81 mmol,) was added at 0° C., the mixture was stirred to react at 25° C. for 15 min, then placed in an oil bath at 70° C. and stirred to react for 2 hours, water (10 mL) was added into the reaction mixture, and extracted by EA (2×20 mL), the organic phase was washed by saturated brine (10 mL), dried over anhydrous sodium sulfate, the filtrate was concentrated to give 58-2. MS m/z: 242.07 [M+H]$^+$

Step 3: Synthesis of Compound 58-3

58-2 (1.1 g, 4.54 mmol), di-tert-butyl dicarbonate (991.75 mg, 4.54 mmol, 1.04 mL) and triethylamine (1.38 g, 13.63 mmol, 1.90 mL) were dissolved in anhydrous THF (5 mL), and replaced with nitrogen for 3 times, then DMAP (55.52 mg, 454.41 μmol) was added, the reaction system was stirred to react at 60° C. 10 hours. The reaction mixture was concentrated under reduced pressure and evaporated to dry, saturated brine 10 mL was added, then extracted by EA 20 mL, the organic phase was washed by saturated brine 10 mL, dried over anhydrous sodium sulfate, then filtered and evaporated under reduced pressure to give the crude product. The crude product was purified by an automatic column machine COMBI-FLASH (PE/EA=20/1-5/1) to give 58-3. MS m/z: 342.19 [M+H]+

Step 4: Synthesis of Compound 58-4

I1 (194.86 mg, 876.71 μmol), 58-3 (300 mg, 876.71 μmol), cuprous iodide (166.97 mg, 876.71 μmolq), potassium carbonate (169.64 mg, 1.23 mmol) and N,N'-dimethylethylenediamine (85.01 mg, 964.38 μmol, 105.34 μL) were added into 1,4-dioxane (5 mL), the temperature was raised to 95° C. under nitrogen atmosphere, the reaction was kept for 16 h. Ammonia (10 mL) was added into the reacted mixture, then extracted by EA (3×10 mL), the organic phase was washed by saturated brine (10 mL), dried over anhydrous sodium sulfate, the filtrate was concentrated to give the crude product, which was separated and purified by an automatic column machine COMBI-FLASH (PE/EA=10/1-5/1) to give the 58-4. MS m/z: 483.54 [M+H]$^+$

Step 5: Synthesis of Compound 58-5

58-4 (330 mg, 682.46 μmol) was added into anhydrous DCM (10 mL), followed by adding m-CPBA (161.35 mg, 794.74 μmol, 85% purity), the reaction mixture was stirred at 25° C. for 1.5 hours. DIPEA (219.91 mg, 1.70 mmol, 296.37 μL) and 12 (211.86 mg, 816.75 μmol) were added, the reaction mixture was stirred at 35° C. for 16 hours.

Saturated sodium sulfite solution (10 mL) was added into the reaction mixture, then extracted by DCM (3×10 mL), the organic phase was dried over anhydrous sodium sulfate, then filtered and concentrated under reduced pressure to give the crude product 58-5. MS m/z: 694.82 [M+H]+

Step 6: Synthesis of Compound 58

DCM (12 mL) and trifluoroacetate (3 mL) were added into 58-5 (529 mg, crude product), then replaced with nitrogen for 3 times, the reaction system was stirred to react at 25° C. for 2 hours. The reaction system was directly concentrated under reduced pressure and evaporated to give a residue, the residue was purified by prep-HPLC (separated chromatographic column/Nano-micro Kromasil C18 100× 30 mm 5 μm; mobile phases/[water (0.1% TFA)-ACN]; B (acetonitrile) %/5%-25%, 10 min), then by thin layer chromatography silica gel plate (DCM/MeOH=10/1) to give the 58. ¹H NMR (400 MHz, CDCl₃) δ=8.83 (s, 1H), 8.22 (d, J=8.3 Hz, 1H), 7.81 (t, J=8.0 Hz, 1H), 7.55-7.30 (m, 3H), 6.93 (d, J=9.0 Hz, 2H), 5.76-5.66 (m, 1H), 4.98-5.07 (m, 2H), 4.84 (s, 1H), 4.77 (br d, J=6.0 Hz, 2H), 4.18 (t, J=8.0 Hz, 2H), 3.61 (t, J=8.0 Hz, 2H), 3.20-3.13 (m, 4H), 2.65 (br s, 4H), 2.47 (s, 3H), 1.71 (br s, 8H) MS m/z: 594.71 [M+H]+

Embodiment 59: Compound 59

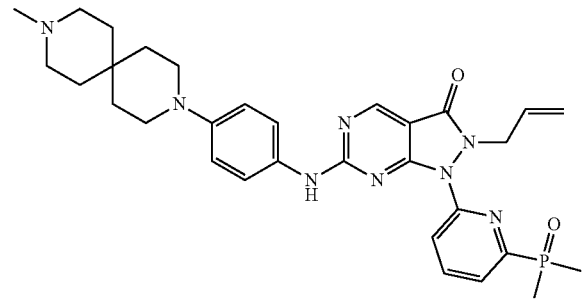

Synthetic Route:

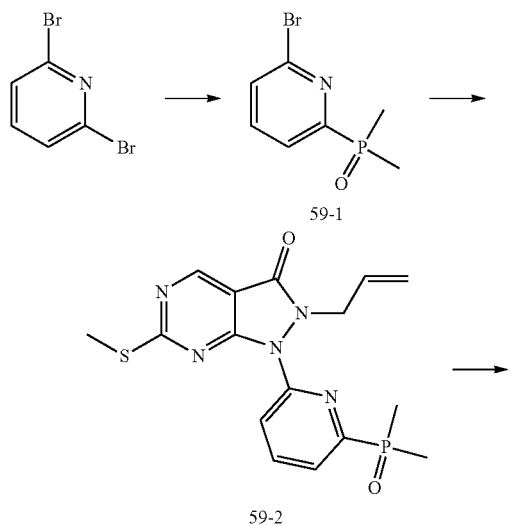

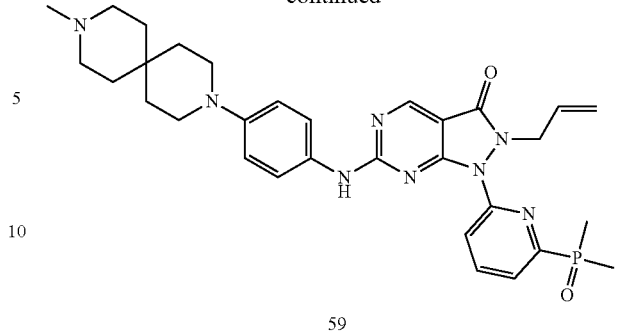

59

Step 1: Synthesis of Compound 59-1

In a pre-dried 100 mL thumb flask, 2,6-dibromopyridine (1 g, 4.22 mmol, 255.10 μL), dimethylphosphine oxide (329.47 mg, 4.22 mmol), Pd (PPh₃)₄ (211.88 mg, 183.36 μmol), acetonitrile (10 mL) and TEA (1.54 g, 15.22 mmol, 2.12 mL) were added. The reaction mixture was replaced by nitrogen for 3 times, then placed in an oil bath at 90° C. and stirred for 13 hours. The reaction mixture was concentrated. The residue was purified by a silica gel column (100-200 mesh silica gel, DCM:MeOH=I/0-5/1) to give the crude product 59-1. ¹H NMR (400 MHz, CDCl₃): 8.10-8.07 (m, 1H), 7.73-7.68 (m, 1H), 7.59-7.57 (m, 1H), 1.80-1.76 (d, J=13.6 Hz, 6H) MS m/z: 234.1 [M+H]+

Step 2: Synthesis of Compound 59-2

In a pre-dried thumb flask, 59-1 (0.8 g, 3.42 mmol), I1 (690.72 mg, 3.11 mmol), cuprous iodide (591.84 mg, 3.11 mmol), potassium carbonate (588.42 mg, 4.26 mmol) N,N'-dimethylethylenediamine (301.33 mg, 3.42 mmol, 367.92 μL) and 1,4-dioxane (20 mL) were added in sequence, the reaction mixture was replaced by nitrogen for 3 times, then heated and stirred in an oil bath at 95° C. for 13 hours. For another batch, 59-1 (200.85 mg, 858.21 μmol), I1 (190.75 mg, 858.21 μmol), cuprous iodide (163.45 mg, 858.21 μmol), potassium carbonate (162.50 mg, 1.18 mmol), N,N'-dimethylethylenediamine (83.22 mg, 944.04 μmol, 101.61 μL) and 1,4-dioxane (5 mL) were added sequentially in a pre-dried thumb flask, the reaction mixture was replaced by nitrogen for 3 times, then heated and stirred in an oil bath at 95° C. for 13 hours. Half of the reaction mixture and previous batch of the reaction mixture were combined and directly evaporated. The residue was purified by a silica gel column (100-200 mesh silica gel, PE:EA=5/1-0/1) to give 0.7 g pale brown oily product. 0.5 g of the oily product was added into 20 mL water, then extracted by 60 mL DCM for 3 times, the organic phase was dried, then filtered and evaporated to dry. The residue was purified by a silica gel column (100-200 mesh silica gel, PE:EA=5/1-0/1) to give 59-2. ¹H NMR (400 MHz, CDCl₃): 8.97 (s, 1H), 8.09-8.06 (m, 1H), 7.70-7.43 (m, 2H), 5.71-5.64 (m, 1H), 5.07-5.05 (d, J=10.4 Hz, 1H), 4.93-4.88 (m, 1H), 4.81-4.79 (d, J=6.4 Hz, 2H), 2.61 (s, 3H), 1.81-1.75 (m, 6H)

Step 3: Synthesis of Compound 59

(50 mg, 133.20 μmol) was dissolved in dichloromethane (2 mL), then m-CPBA (41.99 mg, 206.82 μmol, 85% purity) was added and stirred at 25° C. for 1 h. 12 (34.55 mg, 133.19 μmol) and DIPEA (47.34 mg, 366.27 μmol, 63.80 μL) were added and stirred at 35° C. for 2 h. The reacted mixture was partitioned between dichloromethane (10 mL) and water (10 mL), the organic phase was washed separately by Na₂SO₃ solution 10 mL, Na₂CO₃ solution 10 mL and NaCl solution 10 mL, dried over anhydrous sodium sulfate, then filtered, the filtrate was concentrated to give a residue. The residue was purified by prep-HPLC (chromatographic column: waters Xbridge Prep OBD C18 150×30 mm 5 μm; mobile phases: [A-HCl/H₂O=0.04% v/v; B-ACN] B %: 1%-25%, 12 min]) to give the 59.

¹H NMR (400 MHz, CDCl₃) δ ppm 8.85 (s, 1H) 8.00-8.17 (m, 3H) 7.44 (d, J=7.6 Hz, 2H) 6.96 (d, J=7.2 Hz, 2H) 5.66-5.83 (m, 1H) 4.88-5.12 (m, 2H) 4.76 (d, J=6.0 Hz, 2H) 3.18 (br, 4H) 2.42 (br, 4H) 2.32 (s, 3H) 1.80 (dd, J=2.0, 13.8 Hz, 6H), 1.61-1.63 (m, 8H) MS m/z: 587.4 [M+H]⁺

Embodiment 60: Compound 60

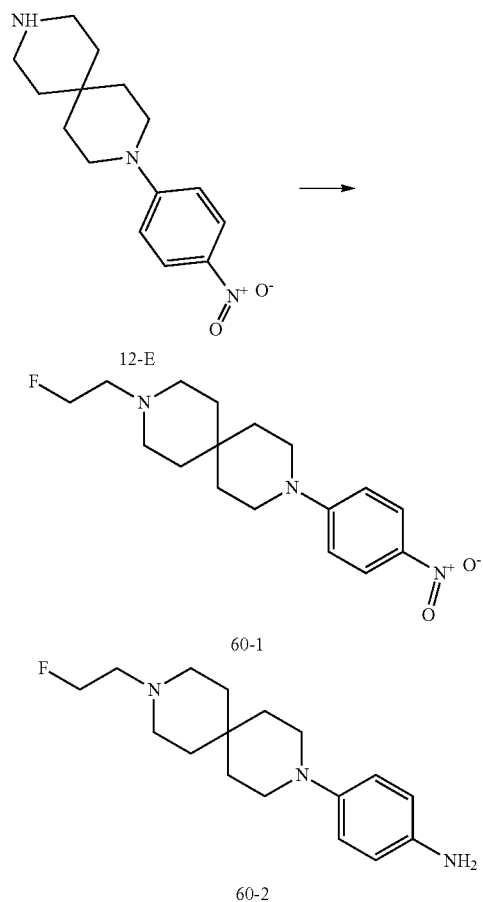

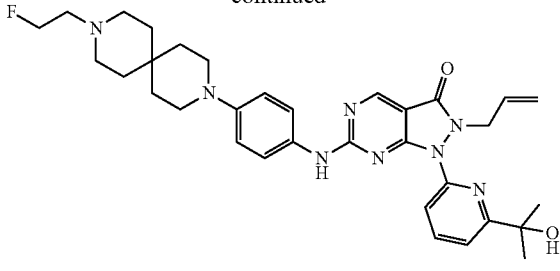

Step 1: Synthesis of Compound 60-1

Cesium carbonate (295.82 mg, 907.94 μmol) and 1-bromo-2-fluoroethane (92.22 mg, 726.34 μmol) were added into the compound 12-E (100.00 mg, 363.17 μmol) in DMF solution (4.00 mL), the reaction was stirred at 80° C. for 1 hour, 10 mL water was added into the reaction mixture, the aqueous phase was washed by EA (15 mL×3), the organic phases were combined and washed by saturated brine (20 mL), dried over anhydrous sodium sulfate, filtered and concentrated to give a crude product, the crude product was purified by column chromatography (dichloromethane/methanol=10/1) to give the 60-1. MS m/z: 322.1 [M+H]⁺

Step 2: Synthesis of Compound 60-2

Ammonium chloride (183.08 mg, 3.42 mmol) and zinc (179.04 mg, 2.74 mmol) were added into the compound 60-1 (110.00 mg, 342.26 μmol) in ethanol (20.00 mL) and water (2.5.00 mL), the reaction was stirred at 70° C. for 1 hour, the reaction mixture was filtered, the filtrate was concentrated to give a crude product 60-2. MS m/z: 292.1 [M+H]⁺

Step 3: Synthesis of Compound 60

Compound 60 was obtained by using the same methods as preparing the compound 22 in embodiment 22, except for the corresponding starting material.

¹H NMR (400 MHz, CDCl₃) δ ppm 1.60 (s, 6H) 1.63-1.70 (m, 8H) 2.55 (br t, J=5.14 Hz, 4H) 2.71 (t, J=5.02 Hz, 1H) 2.78 (t, J=4.88 Hz, 1H) 3.14-3.19 (m, 4H) 4.00 (br s, 1H) 4.55 (t, J=4.8 Hz, 1H) 4.67 (t, J=4.8 Hz, 1H) 4.76 (d, J=6.4 Hz, 2H) 4.89-5.03 (m, 1H) 5.06 (d, J=10.0 Hz, 1H) 5.72 (ddt, J=16.82, 10.42, 6.22, 6.22 Hz, 1H) 6.95 (d, J=9.02 Hz, 2H) 7.35 (d, J=7.52 Hz, 1H) 7.47 (br d, J=8.52 Hz, 2H) 7.78 (d, J=8.02 Hz, 1H) 7.88 (t, J=7.92 Hz, 1H) 8.85 (s, 1H). MS m/z: 601.1 [M+H]⁺

Embodiment 61: Compound 61

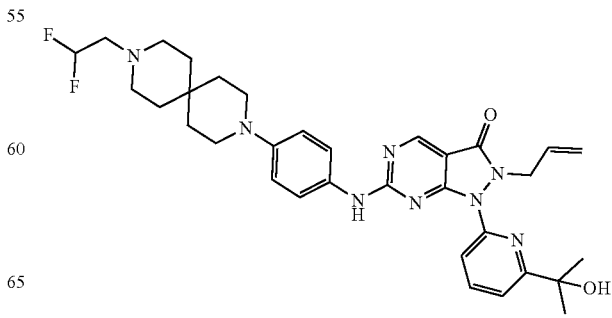

Synthetic Route:

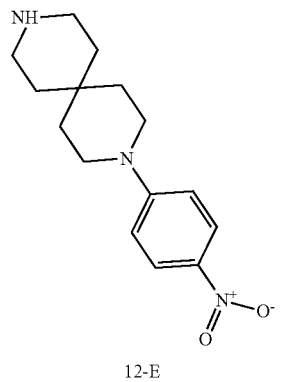
12-E

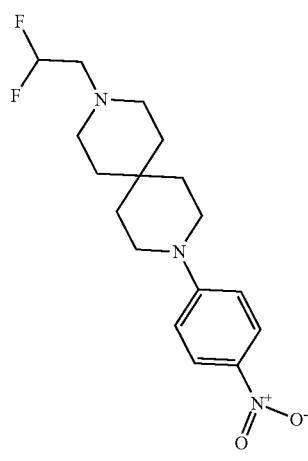
61-1

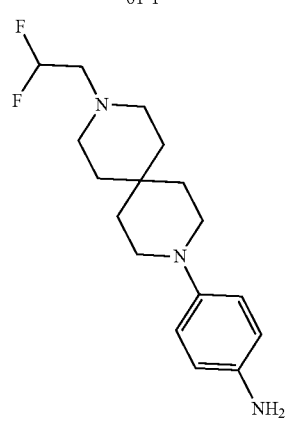
61-2

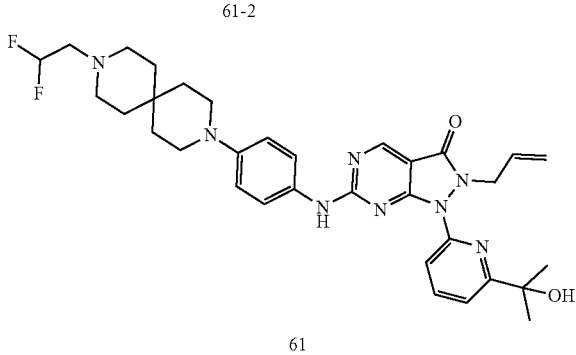
61

Step 1: Synthesis of Compound 61-A

Cesium carbonate (295.82 mg, 907.94 µmol) and 2-bromo-1,1-difluoroethane (52.64 mg, 363.17 µmol) were added into the compound 12-E (100.00 mg, 363.17 µmol) in DMF solution (4.00 mL), the reaction was stirred at 80° C. for 1 hour, the reaction was stirred at 85° C. for further 12 hours. Then 10 mL water was added into the reaction mixture, the aqueous phase was washed by EA (15 mL×3), the organic phases were combined and washed by saturated brine (20 mL), dried over anhydrous sodium sulfate, filtered and concentrated to give a crude product, the crude product was separated by column chromatography (PE/EA=1/1) to give the compound 61-1. MS m/z: 340.1 [M+H]$^+$ Step 2: Synthesis of Compound 61-2

Ammonium chloride (295.82 mg, 907.94 µmol) and zinc (52.41 mg, 801.44 µmol) were added into the compound 61-1 (34.00 mg, 100.18 µmol) in ethanol (10.00 mL) and water (1.00 mL), the reaction was stirred at 70° C. for 1 hour, the reaction mixture was filtered and the filtrate was concentrated to give a crude product 61-2. MS m z: 310.1 [M+H]$^+$ Step 3: Synthesis of Compound 61

Compound 61 was obtained by using the same methods as preparing the compound 22 in embodiment 22, except for the corresponding starting material.

$^1$H NMR (400 MHz, CDCl$_3$) δ ppm 1.52 (s, 6H) 1.52-1.63 (m, 8H) 2.48-2.52 (m, 4H) 2.69 (td, J=15.06, 4.52 Hz, 2H) 3.06-3.09 (m, 4H) 3.89 (br s, 1H) 4.67 (d, J=6.02 Hz, 2H) 4.87 (dd, J=17.08, 1.00 Hz, 1H) 4.97 (dd, J=10.04, 1.00 Hz, 1H) 5.58-5.70 (m, 1H) 5.80-5.99 (m, 1H) 6.86 (d, J=9.02 Hz, 2H) 7.27 (d, J=7.52 Hz, 1H) 7.38 (br d, J=8.52 Hz, 2H) 7.69 (d, J=8.02 Hz, 1H) 7.76-7.81 (m, 1H) 8.75 (s, 1H). MS m/z: 619.1 [M+H]$^+$ Embodiment 62: Compound 62

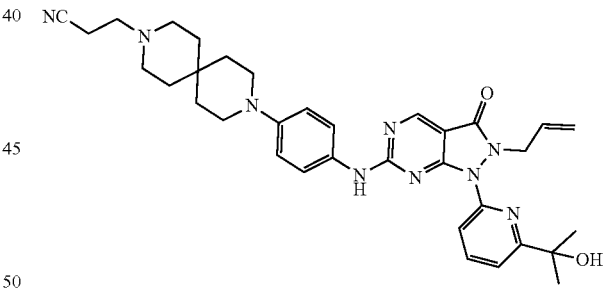

Synthetic Route:

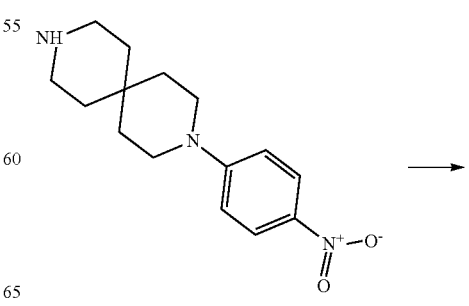
12-E

-continued

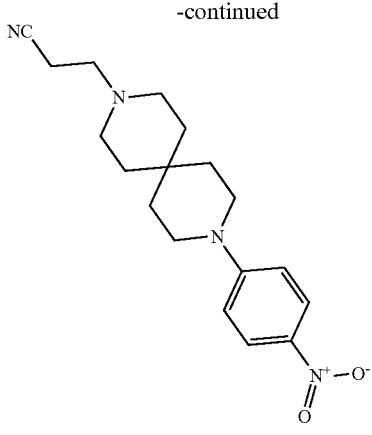

62-1

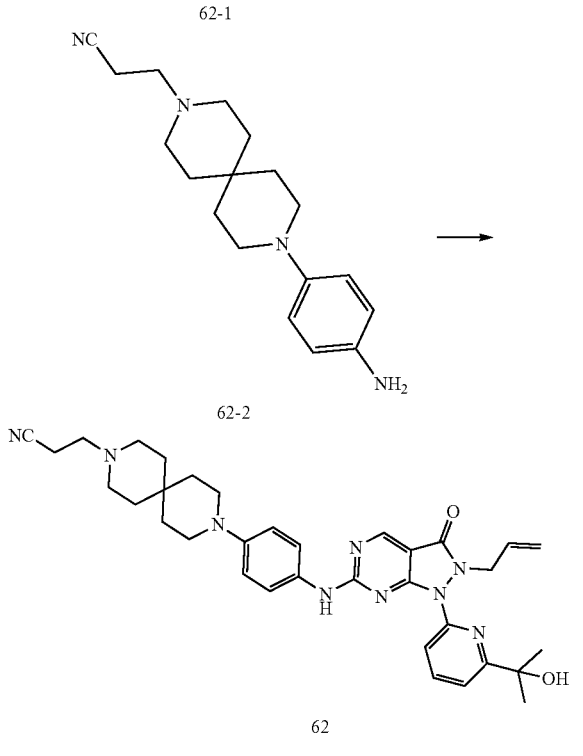

Step 1: Synthesis of Compound 62-1

The compound 62-A was obtained by using the same methods as preparing the compound 60-1 in embodiment 60, except for the corresponding starting material. MS m/z: 329.1 [M+H]⁺

Step 2: Synthesis of Compound 62-2

Wet palladium carbon (28.74 mg, 24.36 μmol, 10% purity) was added in the compound 62-1 (80.00 mg, 243.60 μmol) in THF solution (10.00 mL), the reaction was stirred at 20° C. for 12 hours under hydrogen (15 psi) atmosphere, the reaction mixture was filtered and the filtrate was concentrated to give a crude product 62-2. MS m/z: 299.2 [M+H]⁺

Step 3: Synthesis of Compound 62

The compound 62 was obtained by using the same methods as preparing the compound 22 in embodiment 22, except for the corresponding starting material. ¹H NMR (400 MHz, CDCl₃) δ ppm 1.52 (s, 6H) 1.56-1.60 (m, 8H) 2.41-2.45 (m, 4H) 2.45-2.50 (m, 2H) 2.63-2.68 (m, 2H) 3.05-3.09 (m, 4H) 3.89 (br s, 1H) 4.67 (br d, J=6.02 Hz, 2H) 4.87 (d, J=17.82 Hz, 1H) 4.97 (d, J=10.54 Hz, 1H) 5.56-5.71 (m, 1H) 6.86 (d, J=8.78 Hz, 2H) 7.27 (d, J=7.52 Hz, 1H) 7.38 (br d, J=8.02 Hz, 2H) 7.69 (d, J=8.02 Hz, 1H) 7.76-7.82 (m, 1H) 8.76 (s, 1H). MS m/z: 608.1 [M+H]⁺

Embodiment 63: Compound 63

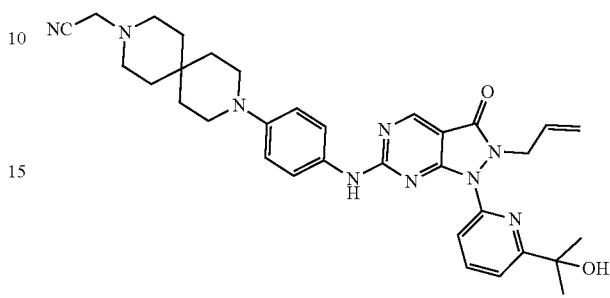

Synthetic Route:

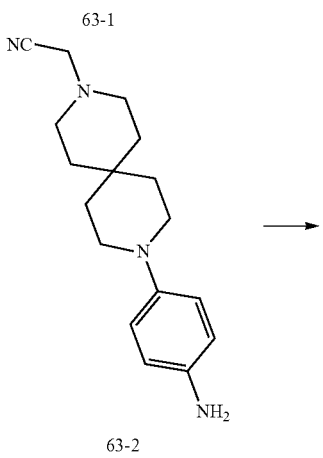

-continued

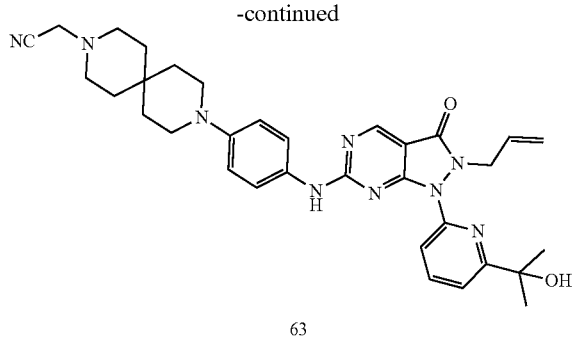

63

Synthetic Route:

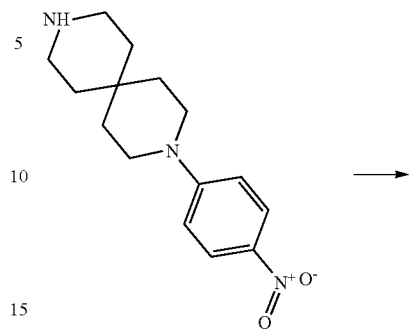

Step 1: Synthesis of Compound 63-1

The compound 63-1 was obtained by using the same methods as preparing the compound 60-1 in embodiment 60, except for the corresponding starting material. MS m/z: 315.1 [M+H]⁺

Step 2: Synthesis of Compound 63-2

The compound 63-2 was obtained by using the same methods as preparing the compound 62-2 in embodiment 62, except for the corresponding starting material. MS m/z: 285.1 [M+H]⁺

Step 3: Synthesis of Compound 63

The compound 63 was obtained by using the same methods as preparing the compound 22 in embodiment 22, except for the corresponding starting material. $^1$H NMR (400 MHz, CDCl$_3$) δ ppm 1.51 (s, 6H) 1.54-1.57 (m, 4H) 1.58-1.63 (m, 4H) 2.49-2.55 (m, 4H) 3.04-3.11 (m, 4H) 3.48 (s, 2H) 3.87 (s, 1H) 4.66 (d, J=6.02 Hz, 2H) 4.86 (d, J=17.08 Hz, 1H) 4.96 (d, J=10.04 Hz, 1H) 5.57-5.68 (m, 1H) 6.85 (d, J=9.02 Hz, 2H) 7.24-7.28 (m, 1H) 7.38 (br d, J=8.52 Hz, 2H) 7.68 (d, J=8.02 Hz, 1H) 7.76-7.81 (m, 1H) 8.75 (s, 1H). MS m/z: 594.1 [M+H]⁺

Embodiment 64: Compound 64

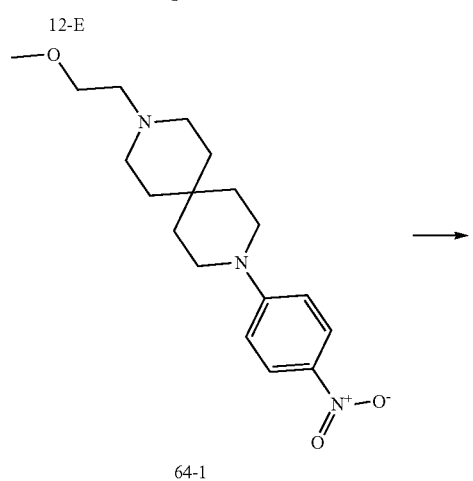

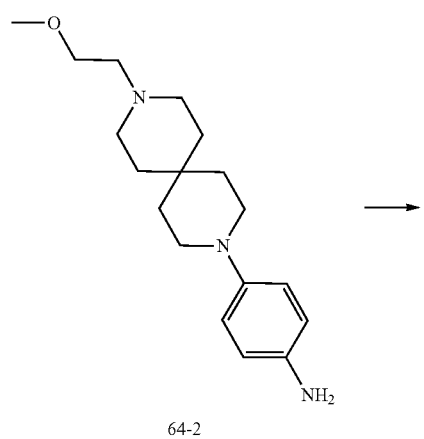

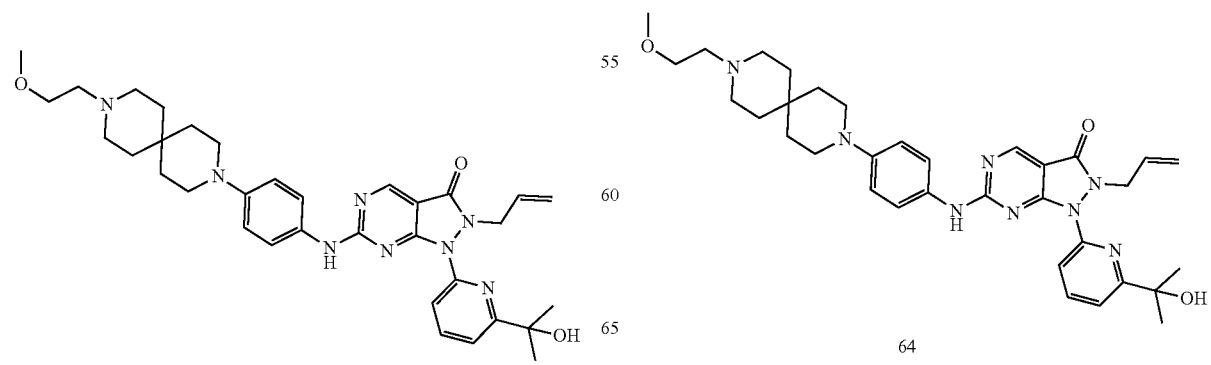

64

Step 1: Synthesis of Compound 64-1

The compound 64-1 was obtained by using the same methods as preparing the compound 60-1 in embodiment 60, except for the corresponding starting material. MS m/z: 334.2[M+H]+

Step 2: Synthesis of Compound 64-1

The compound 64-1 was obtained by using the same methods as preparing the compound 61-1 in embodiment 61, except for the corresponding starting material. MS m/z: 304.1 [M+H]+

Step 3: Synthesis of Compound 64

The compound 64 was obtained by using the same methods as preparing the compound 22 in embodiment 22, except for the corresponding starting material. $^1$H NMR (400 MHz, CDCl$_3$) δ ppm 1.52 (s, 6H) 1.52-1.62 (m, 8H) 2.41 (br s, 4H) 2.53 (t, J=5.78 Hz, 2H) 3.05-3.10 (m, 4H) 3.29 (s, 3H) 3.46 (t, J=5.66 Hz, 2H) 3.92 (br s, 1H) 4.67 (br d, J=6.02 Hz, 2H) 4.87 (dd, J=17.08, 1.00 Hz, 1H) 4.97 (d, J=10.04 Hz, 1H) 5.63 (ddt, J=16.86, 10.38, 6.22, 6.22 Hz, 1H) 6.86 (d, J=9.04 Hz, 2H) 7.27 (d, J=7.54 Hz, 1H) 7.38 (br d, J=8.54 Hz, 2H) 7.69 (d, J=8.04 Hz, 1H) 7.76-7.82 (m, 1H) 8.75 (s, 1H). MS m/z: 613.1[M+H]+

Embodiment 65: Compound 65

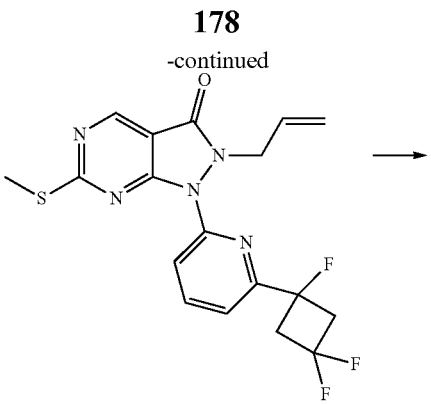

Synthetic Route:

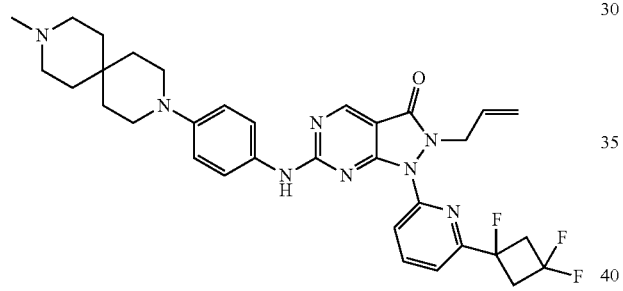

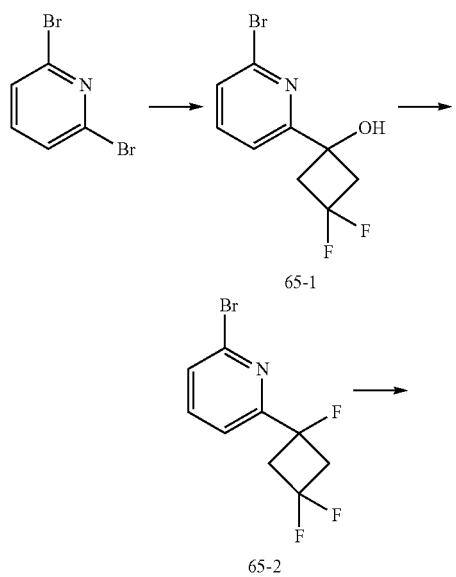

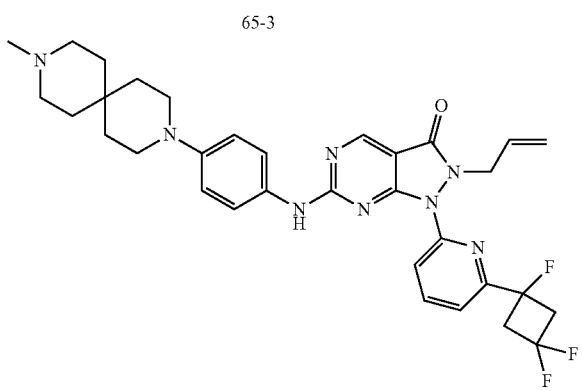

Step 1: Synthesis of Compound 65-1 n-Butyllithium (2.5 M, 371.48 μL) was added into 2,6-dibromopyridine (200 mg, 844.27 μmol) in 6 mL DCM suspension at −60° C. The reaction mixture was stirred for 15 min, 3,3-difluorocyclobutanone (134.71 mg, 1.27 mmol) was added into the reaction mixture by one time at −60° C. The reaction mixture was stirred at −60° C. for further 60 min. The reaction mixture was poured into saturated ammonium chloride, the organic phase was separated, washed by brine 10 mL, dried over anhydrous sodium sulfate, concentrated under reduced pressure, separated and purified by silica gel column chromatography (PE/EA=5/1) to give the compound 65-1. $^1$H NMR (400 MHz, CDCl$_3$) δ ppm 7.57 (t, J=8.0 Hz, 1H) 7.48 (d, J=7.6 Hz, 1H) 7.39 (d, J=8.0 Hz, 1H) 4.48 (s, 1H) 2.98-3.08 (m, 4H)

Step 2: Synthesis of Compound 65-2

At −10° C. and under nitrogen atmosphere, DAST (351.39 mg, 2.18 mmol) was added rapidly dropwise into 65-1 (250.00 mg, 1.09 mmol) in DCM (10.00 mL) solution. Then the mixture was stirred at −10° C. for 60 min under nitrogen atmosphere. The reaction was quenched by saturated sodium bicarbonate solution 10 mL, then extracted by DCM (20 mL×2), the combined organic phases were dried over anhydrous sodium sulfate, then filtered and concentrated to give 65-2 crude product, which was used directly in the next step. $^1$H NMR (400 MHz, CDCl$_3$) δ ppm 7.53 (t, J=8.0 Hz, 1H) 7.39-7.43 (m, 2H) 5.05-5.13 (m, 2H) 4.87-4.95 (m, 2H)

Step 3: Synthesis of Compound 65-3

N,N'-dimethylethylenediamine (18.76 mg, 212.81 μmol) was added into I1 (43.00 mg, 193.46 μmol), cuprous iodide (36.84 mg, 193.46 μmol), 65-2 (51.47 mg, 193.46 μmol) and potassium carbonate (37.43 mg, 270.84 μmol) in dioxane (3.00 mL) solution, the mixture was stirred at 95° C. for 2 hours under nitrogen atmosphere. 10 mL ammonia was added into the mixture and extracted with EA (15 mL×2), the combined organic phases were washed by saturated brine, dried over anhydrous magnesium sulfate, then filtered and concentrated to give the crude product 65-3 (yellow oily product, 60.00 mg), which was used directly in the next step. MS m/z: 408.0 [M+H]$^+$ Step 4: Synthesis of Compound 65 m-CPBA (70.64 mg, 347.93 μmol, 85%) were added into 65-3 (105.00 mg, 257.73 μmol) in toluene (5.00 mL) solution at 20-25° C., the mixture was stirred at 20-25° C. for 60 min, then DIEA (91.60 mg, 708.75 μmol) and 12 (66.85 mg, 257.73 μmol) were added below 30° C., the mixture was stirred at 20-25° C. for 16 hours. Then the mixture was diluted by 40 mL EA, and washed sequentially by 20 mL saturated sodium sulfite solution, saturated sodium carbonate 20 mL and brine 20 mL, dried over anhydrous sodium sulfate, concentrated under reduced pressure to give a crude product. The crude product was purified by high performance liquid phase (alkaline condition) and thin layer chromatography (DCM/MeOH=10/1) to give the compound 65. $^1$H NMR (400 MHz, CDCl$_3$) δ ppm 8.76 (s, 1H) 7.88 (d, J=8.0 Hz, 1H) 7.82 (t, J=8.0 Hz, 1H) 7.36-7.40 (m, 3H) 6.86 (d, J=8.8 Hz, 2H) 5.56-5.66 (m, 1H) 4.83-4.97 (m, 2H), 4.74 (d, J=6.4 Hz, 2H) 3.31-3.39 (m, 2H) 3.07-3.17 (m, 6H) 2.45 (br, 4H) 2.30 (s, 3H) 1.59-1.52 (m, 8H) MS m/z/619.0 [M+H]$^+$ Embodiment 66: Compound 66

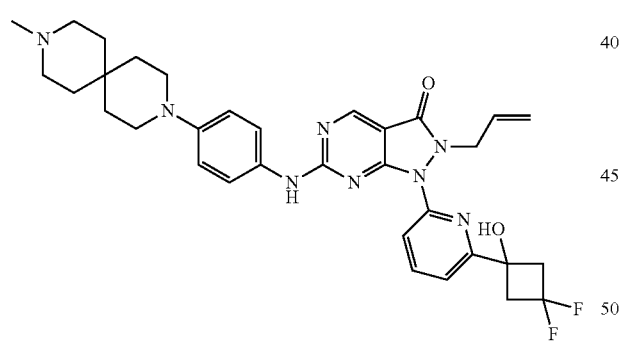

Synthetic Route:

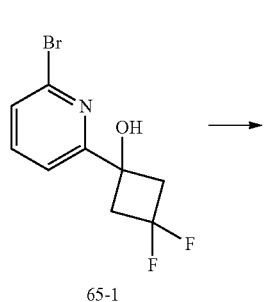

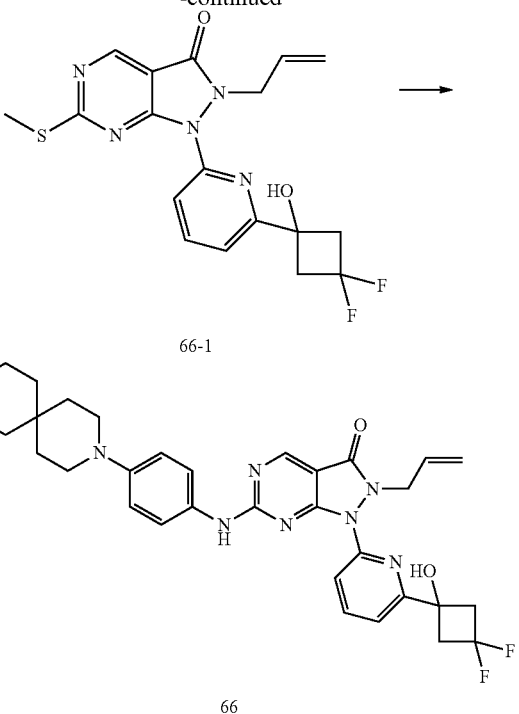

Step 1: Synthesis of Compound 66-1

The compound 66-1 was obtained by using the same methods as preparing the compound 46-A in embodiment 46, except for the corresponding starting material. MS m/z: 406.0 [M+H]$^+$ Step 2: Synthesis of Compound 66

The compound 66 was obtained by using the same methods as preparing the compound 22 in embodiment 22, except for the corresponding starting material.

$^1$H NMR (400 MHz, CDCl$_3$) δ ppm 1.58-1.70 (m, 8H) 2.32 (s, 3H) 2.42 (br s, 4H) 3.09-3.23 (m, 8H) 4.72 (br d, J=6.52 Hz, 2H) 4.98 (dd, J=17.06, 1.00 Hz, 1H) 5.06-5.10 (m, 1H) 5.73 (ddt, J=16.82, 10.42, 6.22, 6.22 Hz, 1H) 6.94 (d, J=9.02 Hz, 2H) 7.44 (br d, J=8.52 Hz, 2H) 7.54 (d, J=7.54 Hz, 1H) 7.86 (d, J=8.04 Hz, 1H) 7.92-7.97 (m, 1H) 8.83 (s, 1H). MS m/z: 617.1[M+H]$^+$ Embodiment 67: Synthesis of Compound 67

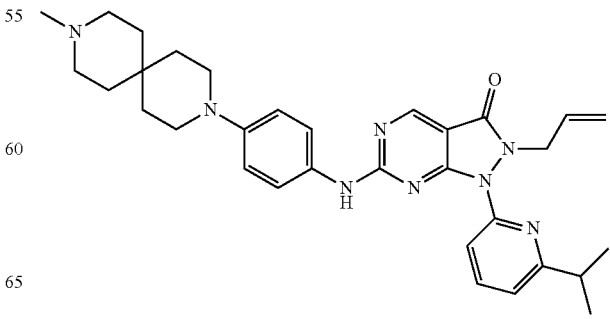

Synthetic Route:

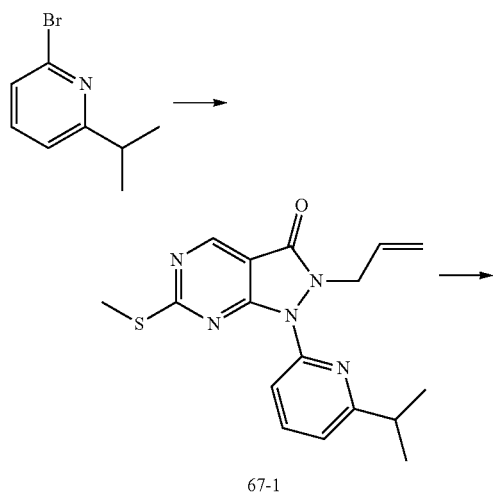

67-1

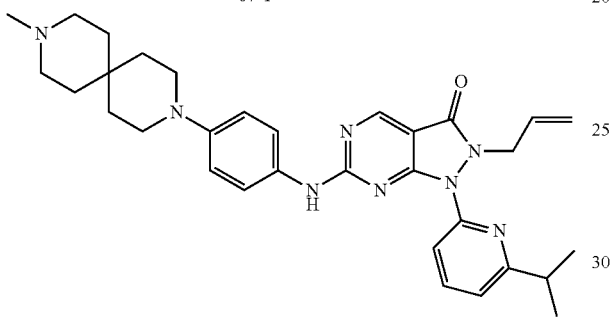

67

Step 1: Synthesis of Compound 67-1

The compound 67-1 was obtained by using the same methods as preparing the compound 46-A in embodiment 46, except for the corresponding starting material. MS m/z: 342.1 [M+H]$^+$ Step 2: Synthesis of Compound 67

The compound 67 was obtained by using the same methods as preparing the compound 22 in embodiment 22, except for the corresponding starting material. $^1$H NMR (400 MHz, CDCl$_3$) δ ppm 1.24 (s, 3H) 1.26 (s, 3H) 1.50-1.61 (m, 8H) 2.23 (s, 3H) 2.33 (br s, 4H) 2.96-3.04 (m, 1H) 3.04-3.11 (m, 4H) 4.78-4.85 (m, 3H) 4.92 (d, J=10.04 Hz, 1H) 5.61 (ddt, J=16.76, 10.36, 6.54, 6.54 Hz, 1H) 6.85 (d, J=9.04 Hz, 2H) 7.00 (d, J=7.02 Hz, 1H) 7.39 (br d, J=8.52 Hz, 2H) 7.60-7.69 (m, 2H) 8.74 (s, 1H). MS m/z: 553.1[M+H]$^+$ Embodiment 68: Synthesis of Compound 68

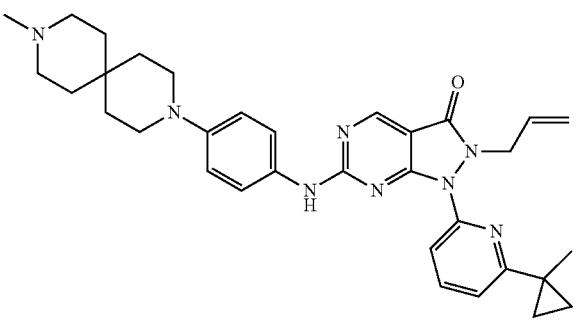 [SMILES: C=CCn1c(=O)c2cnc(Nc3ccc(N4CCC5(CCN(C)CC5)CC4)cc3)nc2n1-c1cccc(C2(C)CC2)n1]

Synthetic Route:

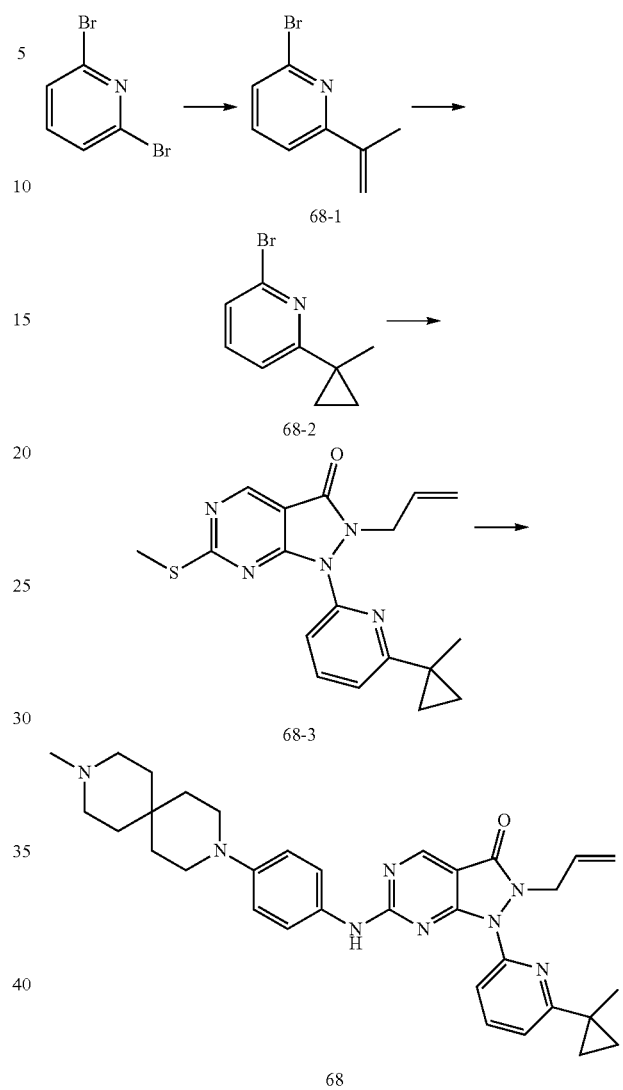

Step 1: Synthesis of Compound 68-1

Potassium isopropenyltrifluoroborate (1.12 g, 7.60 mmol) were added into 2,6-dibromopyridine (1.50 g, 6.33 mmol) in ethanol (20 mL) solution in a sealed tube. After nitrogen bubbling for 10 min, Pd (dppf)Cl$_2$·CH$_2$Cl$_2$ (258.47 mg, 316.50 μmol) and triethylamine (640.53 mg, 6.33 mmol, 877.44 μL) were added into the mixture. The sealed tube was heated to 85° C., then stirred for 4.5 hours. After cooling cooled down to r.t., the mixture was concentrated to dryness, then water 50 mL and EA 30 mL were added, partitioned, the aqueous phase was extracted by EA (20 mL×2), the combined organic phases were dried over anhydrous sodium sulfate, filtered and concentrated. The crude product was purified by column machine (PE/EA=100/0-30/1) to give the compound 68-1. $^1$H NMR (400 MHz, CDCl$_3$) δ ppm 7.28-7.44 (m, 3H) 5.86 (s, 1H) 5.22-5.25 (m, 1H) 2.10 (s, 3H)

Step 2: Synthesis of Compound 68-2

Potassium tert-butoxide (679.85 mg, 6.06 mmol) was added into trimethyl iodine sulfoxide (1.33 g, 6.06 mmol) in DMSO (9.2 mL) and THF (6.00 mL) solution at 15-20° C. by one time. The mixture was stirred for 30 min, then 68-1 (800.00 mg, 4.04 mmol) in THF solution (9.20 mL) solution was added at the same temperature. The mixture was stirred for more than 120 min at 15-20° C., then stirred for 1 hour at 60° C. The reaction was quenched by 10 mL water, then diluted by 50 mL EA. The organic phase was washed by water (20 mL×3) and brine (20 mL), dried over anhydrous sodium sulfate, filtered and concentrated to give a crude product. The crude product was purified by thin layer chromatography (PE/EA=50/1) to give the crude product compound 68-2. MS m/z: 211.8 [M+H]+

Step 3: Synthesis of Compound 68-3

N,N'-dimethyllethylenediamine (40.85 mg, 463.40 μmol) was added into I1 (103.00 mg, 463.40 μmol), cuprous iodide (88.25 mg, 463.40 μmol), 68-2 (184.74 mg, 463.40 μmol) and potassium carbonate (64.05 mg, 463.40 μmol) in dioxane (4.00 mL) solution, the mixture was stirred at 95° C. for 2 hours under nitrogen atmosphere. 10 mL ammonia was added and the mixture was extracted by EA (15 mL×2), the combined organic phases were washed by saturated brine, dried over anhydrous sodium sulfate, then filtered and concentrated to give a red oily product. The product was purified by thin layer chromatography (PE/EA=3/1) to give 68-3. MS m/z: 354.1 [M+H]+

Step 4: Synthesis of Compound 68 m-CPBA (15.51 mg, 76.40 μmol, 85%) was added into 68-3 (20.00 mg, 56.59 μmol) in toluene (5.00 mL) solution at 20-25° C., the mixture was stirred at 20-25° C. for 60 min, then DIEA (20.11 mg, 155.62 μmol) and 12 (14.68 mg, 56.59 μmol) were added below 30° C., the mixture was stirred at 20-25° C. for 16 hours. The mixture was diluted by 40 mL EA, then washed sequentially by 20 mL saturated sodium sulfite solution, saturated sodium carbonate 20 mL and brine 20 mL, dried over anhydrous sodium sulfate, concentrated under reduced pressure to give a crude product. The crude product was purified by preparative thin layer chromatography (DCM/MeOH=10/1) twice to give the compound 68. $^1$H NMR (400 MHz, CDCl$_3$) δ ppm 8.74 (s, 1H), 7.66 (t, J=8.0 Hz, 1H) 7.54 (d, J=8.0 Hz, 1H) 7.39 (d, J=8.0 Hz, 2H) 7.12 (d, J=8.0 Hz, 1H) 6.84 (d, J=8.8 Hz, 2H) 5.56-5.64 (m, 1H) 4.81-4.95 (m, 2H), 4.71 (d, J=6.0 Hz, 2H) 3.08-3.09 (m, 4H) 2.59 (br, 4H) 2.40 (s, 3H) 1.62-1.68 (m, 8H) 1.42 (s, 3H) 0.77-0.81 (m, 4H) MS m/z/565.1 [M+H]+

Embodiment 69: Compound 69

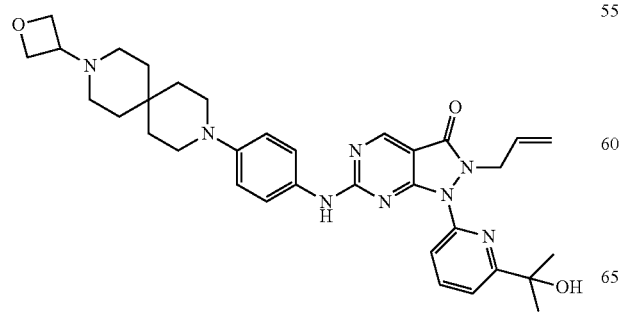

Synthetic Route:

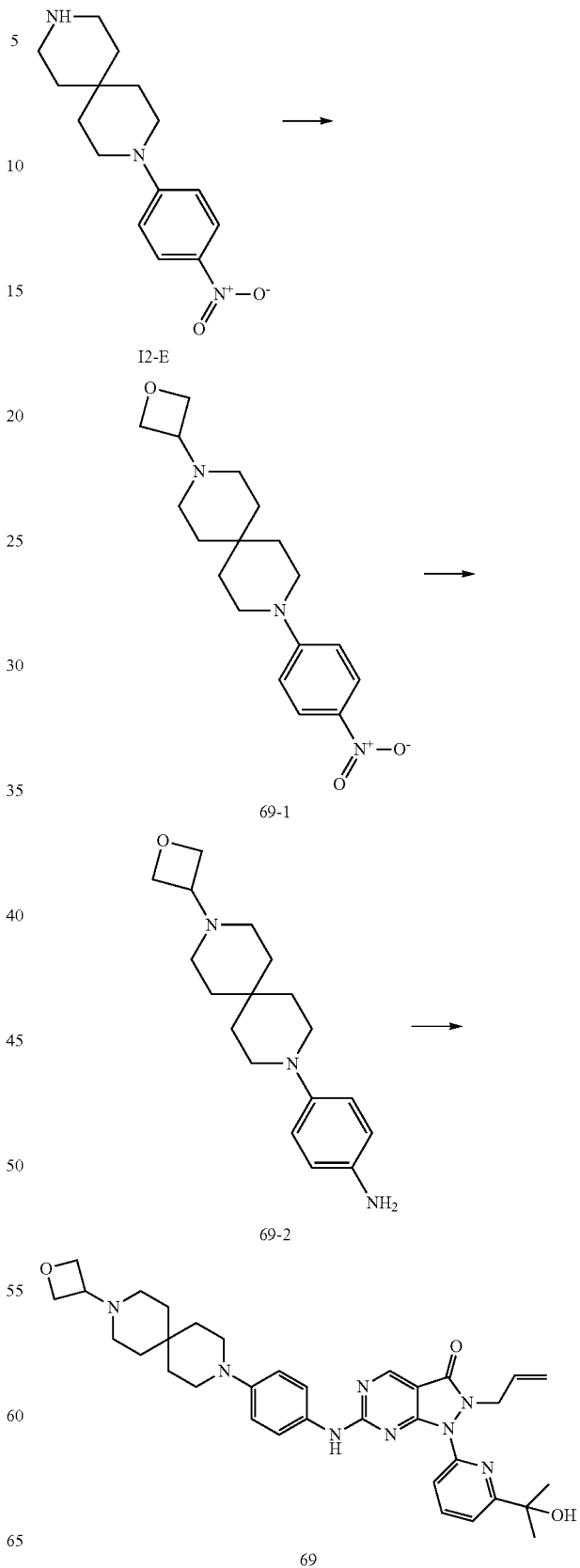

Step 1: Synthesis of Compound 69-1

3-Oxacyclobutanone (23.55 mg, 326.85 μmol) was added into the compound 12-E (60.00 mg, 217.90 μmol) in DCM (4.00 mL) solution, the reaction mixture was stirred at 20° C. for 30 min, then sodium triacetylborohydride (92.36 mg, 435.80 μmol) was added, the reaction mixture was stirred at 25° C. for 30 min. The reaction mixture adjusted to pH=5-6 by adding hydrochloric acid, then adjusted to pH=9-10 by adding sodium hydroxide solution, and then extracted by DCM (10 mL×3), the organic phases were combined and washed by saturated brine (15 mL×1), dried over anhydrous sodium sulfate, then filtered, the filtrate was evaporated to dry to give the crude product 69-1. MS m/z: 332.2 [M+H]$^+$

Step 2: Synthesis of Compound 69-2

The compound 69-2 was obtained by using the same methods as preparing the compound 61-2 in embodiment 61, except for the corresponding starting material. MS m/z: 302.1 [M+H]$^+$

Step 3: Synthesis of Compound 69

The compound 69 was obtained by using the same methods as preparing the compound 22 in embodiment 22, except for the corresponding starting material. $^1$H NMR (400 MHz, CDCl$_3$) δ ppm 1.52 (s, 6H) 1.53-1.62 (m, 8H) 2.22 (br s, 4H) 3.03-3.12 (m, 4H) 3.42 (quin, J=6.54 Hz, 1H) 3.91 (br s, 1H) 4.54-4.62 (m, 4H) 4.67 (br d, J=6.02 Hz, 2H) 4.83-4.94 (m, 1H) 4.97 (d, J=10.54 Hz, 1H) 5.63 (ddt, J=16.82, 10.42, 6.22, 6.22 Hz, 1H) 6.86 (d, J=8.54 Hz, 2H) 7.27 (d, J=7.54 Hz, 1H) 7.38 (br d, J=8.04 Hz, 2H) 7.67-7.71 (m, 1H) 7.76-7.81 (m, 1H) 8.75 (s, 1H). MS m/z: 611.1 [M+H]$^+$

Embodiment 70: Compound 70

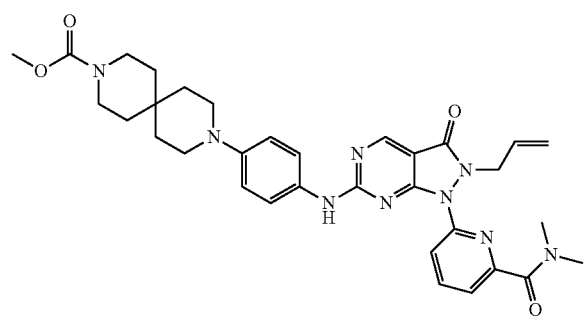

Synthetic Route

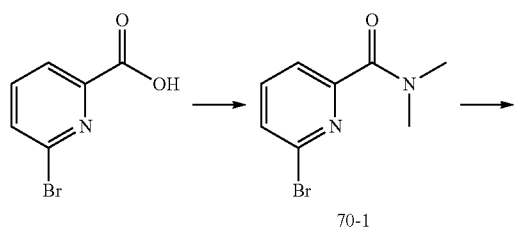

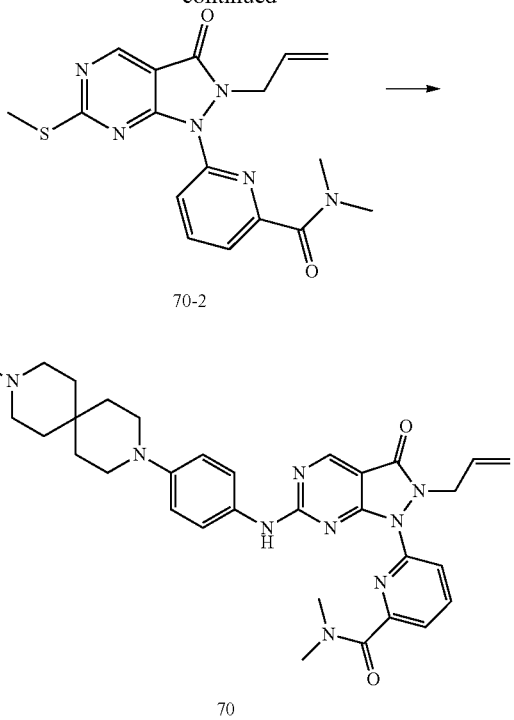

Step 1: Synthesis of Compound 70-1

At 0-5° C., oxalyl chloride (629.57 mg, 4.96 mmol, 434.19 μL) was added into 6-bromo-2-pyridinecarboxylic acid (500.00 mg, 2.48 mmol) in DCM (10.00 mL) solution, followed by adding DMF (181.26 mg, 2.48 mmol, 190.80 μL). The mixture was stirred at 0-5° C. for 0.5 hours, and then stirred at 25-35° C. for 1.5 hours, then concentrated under reduced pressure to give the yellow solid. Dimethylamine solution (2 M, 3.25 mmol, 11.38 mL) was slowly added into said yellow solid in THF solution (3.00 mL) at 0° C., the reaction mixture was stirred at 25° C. for 3 hours. The reaction mixture was concentrated up to dryness, then diluted by water 20 mL, the aqueous phase was extracted by DCM (10 mL×3), the organic phase was washed by 20 mL saturated brine, dried over anhydrous sodium sulfate, filtered and the filtrate was concentrated up to dryness to give the crude product 70-1. MS m/z: 230.9 [M+H]$^+$

Step 2: Synthesis of Compound 70-2

Cuprous iodide (362.41 mg, 1.90 mmol), N,N-dimethylethylenediamine (187.87 mg, 2.13 mmol, 229.11 μL) and potassium carbonate (362.94 mg, 2.63 mmol) were added separately into the compound 11 (422.96 mg, 1.90 mmol) and 70-1 (450.00 mg, 1.96 mmol) in dioxane (5 mL) solution. The reaction mixture was stirred at 95° C. for 1 hour under nitrogen atmosphere then concentrated, 20 mL ammonia was added after concentration, then extracted by EA 150 mL (50 mL×3) and washed by saturated brine 30 mL, dried over anhydrous sodium sulfate, then filtered to give the crude compound. The crude product was purified by silica gel chromatography (PE/EA=1/1-0/1) to give the 70-2. MS m/z: 371.0 [M+H]$^+$

Step 3: Synthesis of Compound 70 m-CPBA (67.29 mg, 331.44 μmol, 85% purity) was added into the compound 70-2 (111.10 mg. 299.93 μmol) in toluene (8.00 mL) solution at 35-40° C., and stirred at 25-30° C. for 0.5 hours, then the compound 13 (91.00 mg, 299.93 μmol) and DIPEA (91.00 mg, 299.93 μmol, 157.15 μL) were added into the mixture, and stirred for further 16 hours. The reaction mixture was diluted by DCM 45 mL, washed by saturated sodium bicarbonate 15 mL, dried over sodium sulfate, then filtered and concentrated to give the crude compound, the crude compound was purified by preparative HPLC (chromatographic column: Xtimate C18 150×25 mm×5 μm; mobile phases: [water (0.05% ammonia hydroxide v/v)-ACN]; B (acetonitrile) %: 30%-60%, 10 min) to give the 70. $^1$H NMR (400 MHz, CDCl$_3$) δ=8.76 (s, 1H), 7.92-7.83 (m, 2H), 7.48 (d, J=8.1 Hz, 1H), 7.37 (d, J=9.2 Hz, 2H), 6.87 (d, J=9.2 Hz, 2H), 5.63-5.56 (m, 1H), 4.98-4.85 (m, 2H), 4.69 (d, J=6.4 Hz, 2H), 3.63 (s, 3H), 3.40 (br, 4H), 3.13-3.07 (m, 7H), 3.02 (s, 3H), 1.65-1.59 (m, 4H), 1.44 (br, 4H). MS m/z/626.1 [M+H]$^+$ Embodiment 71: Synthesis of Compound 71

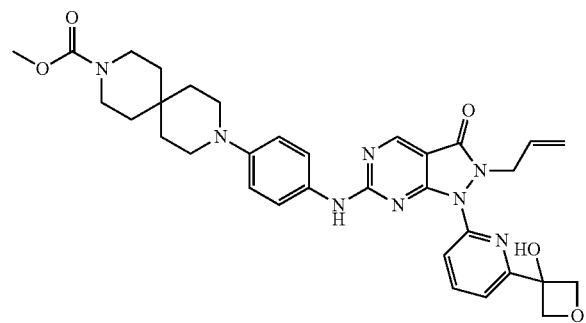 [SMILES: C=CCn1c(=O)c2cnc(Nc3ccc(N4CCC5(CCN(C(=O)OC)CC5)CC4)cc3)nc2n1-c1cccc(C2(O)COC2)n1]

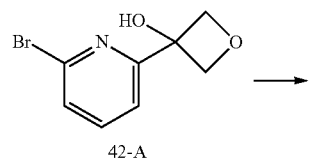

42-A

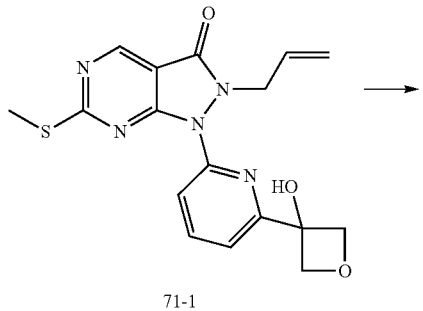

71-1

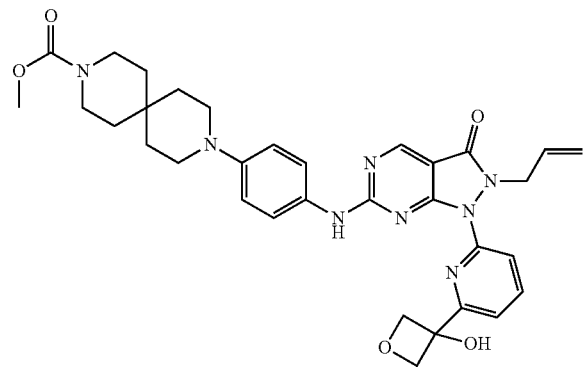

71

Step 1: Synthesis of Compound 71-1

Cuprous iodide (413.91 mg, 2.17 mmol), N,N'-dimethylethylenediamine (214.57 mg, 2.43 mmol, 261.67 μL) and potassium carbonate (414.52 mg, 3.00 mmol) were added separately into the compound 11 (483.07 mg, 2.17 mmol) and 42-A (500.00 mg, 2.17 mmol) in dioxane (5 mL) solution. The reaction mixture was stirred at 95° C. for 1 hour under nitrogen atmosphere, then concentrated and 20 mL ammonia was added, extracted by EA 150 mL (50 mL×3) and washed by saturated brine 30 mL, dried over anhydrous sodium sulfate, then filtered to give the crude compound. The crude product was purified by column chromatography (PE/EA=1/1) to give the 71-1. MS m/z: 372.0 [M+H]$^+$ Step 2: Synthesis of Compound 71 m-CPBA (71.06 mg, 350.01 μmol, 85% purity) was added into the compound 71-1 (100.00 mg, 269.24 μmol) in toluene (6.00 mL) solution at 35-40° C., then the mixture was stirred at 25-30° C. for 0.5 hours and then the compound 13 (81.69 mg, 269.24 μmol) and DIPEA (104.39 mg, 807.72 μmol, 141.07 μL) were added, then stirred for further 16 hours. The reaction mixture was diluted by DCM 45 mL, washed by saturated sodium bicarbonate 15 mL, dried over sodium sulfate, then filtered and concentrated to give the crude compound, the crude compound was purified by preparative HPLC (column: YMC-Actus Triart C18 150×30 mm 5 μm; mobile phases: [water (0.05% HCl)-ACN]; B (acetonitrile) %: 25%-55%, 9 min) to give the 71. $^1$H NMR (400 MHz, CDCl$_3$) δ=8.83 (s, 1H), 8.07-8.00 (m, 1H), 7.88 (dd, J=7.8, 13.6 Hz, 2H), 7.45 (br d, J=8.5 Hz, 2H), 6.94 (d, J=9.0 Hz, 2H), 5.72 (tdd, J=6.0, 10.4, 16.8 Hz, 1H), 5.26 (s, 1H), 5.13-5.06 (m, 3H), 4.97 (d, J=17.1 Hz, 1H), 4.78 (d, J=7.0 Hz, 2H), 4.65 (br d, J=6.0 Hz, 2H), 3.71 (s, 3H), 3.49 (br d, J=6.0 Hz, 4H), 3.23-3.13 (m, 4H), 1.72-1.68 (m, 4H), 1.52 (br s, 4H). MS m/z: 627.1 [M+H]$^+$ Embodiment 72: Compound 72

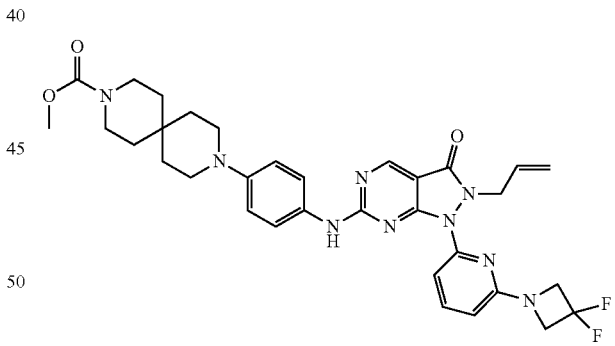

Synthetic Route:

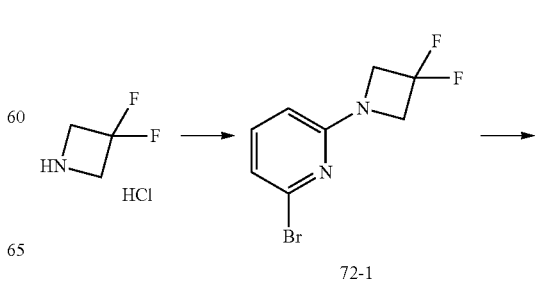

72-1

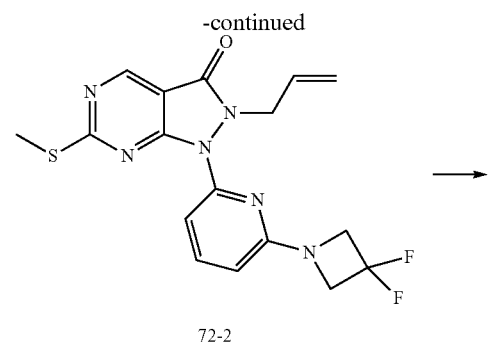

72-2

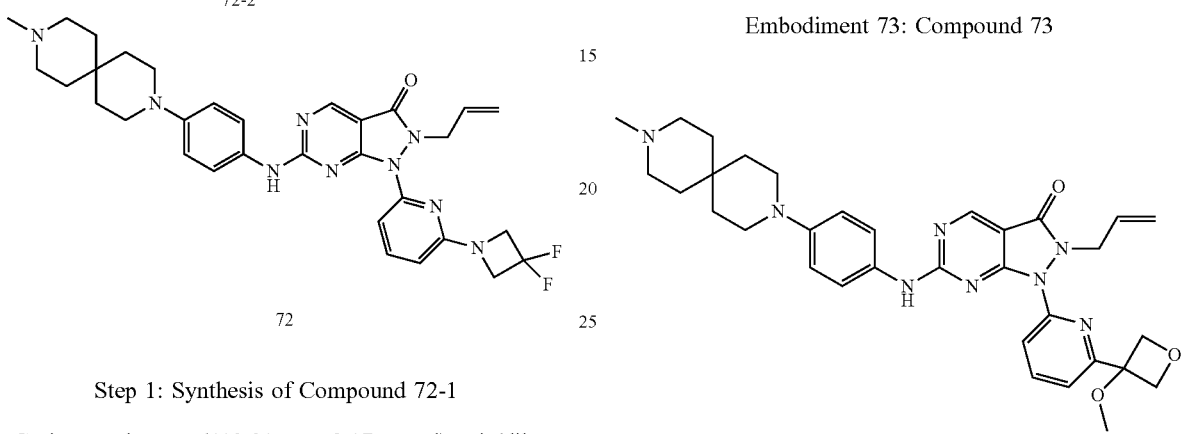

72

Step 1: Synthesis of Compound 72-1

Cesium carbonate (413.91 mg, 2.17 mmol), tris(dibenzylideneacetone)dipalladium (21.21 mg, 23.16 μmol) and 4,5-bisdiphenylphosphino-9,9-dimethyloxazepine (26.80 mg, 46.32 μmol) were added separately into the compound 3,3-difluoroazetidine hydrochloride (30.00 mg, 231.59 μmol) and 2,6-dibromopyridine (54.86 mg, 231.59 μmol) in dioxane solution (1 mL), the reaction mixture was stirred at 90° C. for 16 hours under nitrogen atmosphere, then concentrated and added 10 mL water, extracted by DCM 30 mL (10 mL×3) and washed by saturated brine 20 mL, dried over anhydrous sodium sulfate, filtered and concentrated under reduced pressure to give the crude product. The crude product was purified by thin layer chromatography (PE/EA=10/1) to give the 72-1. MS m/z: 250.9[M+H]$^+$

Step 2: Synthesis of Compound 72-2

Cuprous iodide (42.82 mg, 224.85 μmol), N,N'-dimethyllethylenediamine (22.20 mg, 251.83 μmol, 27.07 μL) and potassium carbonate (42.88 mg, 310.29 μmol) were added separately into the compound I1 (49.98 mg, 224.85 μmol) and 72-1 (56.00 mg, 224.85 μmol) in dioxane (3 mL) solution, the reaction mixture was stirred at 95° C. for 1 hour under nitrogen atmosphere, then concentrated and added 20 mL ammonia, extracted by EA 150 mL (50 mL×3) and washed by saturated brine 30 mL, dried over anhydrous sodium sulfate, then filtered to give the crude compound. The crude product was purified by silica gel column chromatography (PE/EA=3/1) 72-1. MS m/z: 391.0 [M+H]$^+$

Step 3: Synthesis of Compound 72 m-CPBA (22.51 mg, 110.88 μmol, 85% purity) was added into the compound 72-2 (33.30 mg, 85.29 μmol) in toluene (3.00 mL) solution at 35-40° C., the mixture was stirred at 25-30° C. for 0.5 hours and then the compound 12 (22.12 mg, 85.29 μmol) and DIPEA (33.07 mg, 255.87 μmol, 44.69 μL) were added, then stirred for further 16 hours. The reaction mixture was diluted by EA 45 mL, then washed by saturated sodium bicarbonate 15 mL, dried over sodium sulfate, then filtered and concentrated to give the crude compound. The other batch employed the same method and used 12 7.7 mg to give a batch of crude product. The two batches of crude product was combined and purified by preparative HPLC (chromatographic column: YMC-Actus Triart C18 150×30 mm 5 μm; mobile phases: [water (0.05% HCl)-ACN]; B (acetonitrile) %: 15%-45%, 9 min) to give the 72. $^1$H NMR (400 MHz, METHANOL-d$_4$) δ=8.67 (s, 1H), 7.68 (t, J=8.0 Hz, 1H), 7.45 (d, J=8.4 Hz, 2H), 7.11 (d, J=8.0 Hz, 1H), 6.67-6.84 (m, 2H), 6.39 (d, J=8.8 Hz, 1H), 5.66-5.60 (m, 1H), 4.97 (d, J=10 Hz, 1H), 4.88 (d, J=15.6 Hz, 1H), 4.62 (d, J=6.0 Hz, 2H), 4.30 (t, J=12 Hz, 4H), 3.02-2.99 (m, 4H), 2.41 (br, 4H), 2.23 (s, 3H), 1.57-1.49 (m, 8H) MS m/z: 602.0[M+H]$^+$

Embodiment 73: Compound 73

Synthetic Route

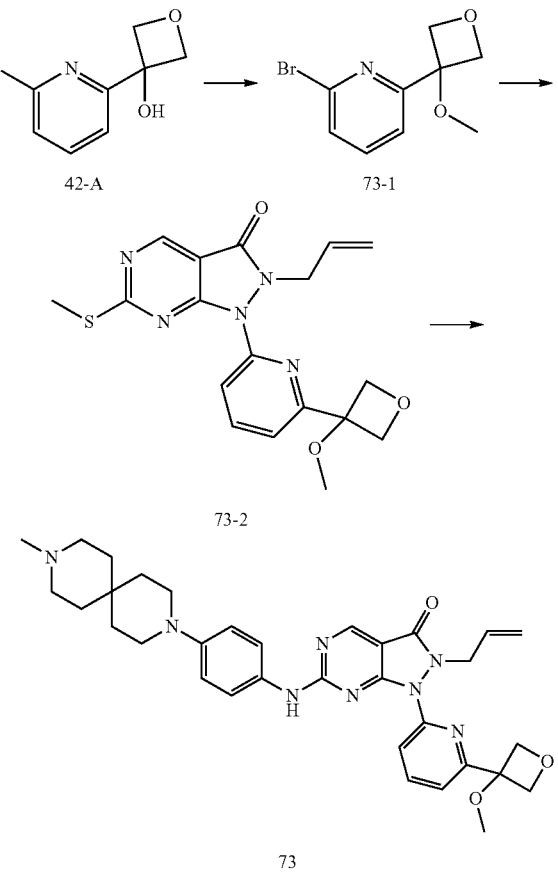

Step 1: Synthesis of Compound 73-1

Sodium hydride (3.48 g, 86.93 mmol, 60% purity) was added into the compound 42-A (5 g, 21.73 mmol) in THF solution (3 mL) at 0° C., and then methyl iodide (10.6 g, 74.68 mmol, 4.65 mL) was added, the reaction mixture was stirred at 10° C. for 16 hours. Saturated ammonium chloride solution (30 mL) was added into the reaction mixture and the mixture was extracted with EA (20 mL×2), then washed by saturated brine 20 mL, dried over sodium sulfate, then filtered and concentrated to give 73-1. $^1$H NMR (400 MHz, CDCl$_3$) δ=7.43 (d, J=8.0 Hz, 1H), 7.29 (d, J=8.0 Hz, 1H), 7.23 (d, J=6.4 Hz, 1H), 4.88 (d, J=7.6 Hz, 2H), 4.69 (d, J=6.0 Hz, 2H), 3.08 (s, 3H)

Step 2: Synthesis of Compound 73-2

Cuprous iodide (4.11 g, 21.60 mmol), N,N'-dimethylethylenediamine (2.13 g, 24.19 mmol, 2.60 mL) and potassium carbonate (4.12 g, 29.80 mmol) were added separately into the compound I1 (4.8 g, 21.60 mmol) and 73-1 (5.27 g, 21.60 mmol) in dioxane (80 mL) solution, the reaction mixture was stirred at 95° C. for 1 hour under nitrogen atmosphere. Then the mixture was cooled down, 40 mL ammonia was added and extracted by EA (50 mL×3), then washed by saturated brine 50 mL, dried over anhydrous sodium sulfate, then filtered to give the crude compound. The crude product was purified by column chromatography (PE/EA=3/1-1/1) to give the 73-2. MS m/z: 386.0 [M+H]$^+$

Step 3: Synthesis of Compound 73 m-CPBA (2.40 g, 11.82 mmol, 85% purity) was added into the compound 73-2 (3.4 g, 8.82 mmol) in toluene (40 mL) solution at 35-40° C., the mixture was stirred at 20° C. for 1 hour and then the compound DIPEA (3.42 g, 26.46 mmol, 4.61 mL) and I2 (2.40 g, 9.26 mmol) were added, then stirred at 20° C. for further 12 hours. 30 mL water was added, the mixture was extracted by EtOAc (40 mL×3), the organic phases were combined and washed sequentially by saturated sodium bicarbonate 40 mL, saturated brine 30 mL, dried over sodium sulfate, then filtered and concentrated to give the crude compound. The crude compound was purified by preparative HPLC (chromatographic column: Phenomenex luna C18 250×50 mm×10 µm; mobile phases: [water (0.1% TFA)-ACN]; B (acetonitrile) %: 5%-30%, 23 min) to give the 73. $^1$H NMR (400 MHz, CDCl$_3$) δ ppm 1.69 (br dd, J=11.54, 6.02 Hz, 8H) 2.38 (s, 3H) 2.50 (br s, 4H) 3.13-3.22 (m, 4H) 3.28 (s, 3H) 4.91-4.97 (m, 5H) 5.01-5.06 (m, 3H) 5.66-5.76 (m, 1H) 6.96 (d, J=9.04 Hz, 2H) 7.35-7.39 (m, 1H) 7.48 (br d, J=9.04 Hz, 2H) 7.88-7.98 (m, 2H) 8.86 (s, 1H). MS m/z: 597.1 [M+H]$^+$

Embodiment 74: Synthesis of Compound 74, 75

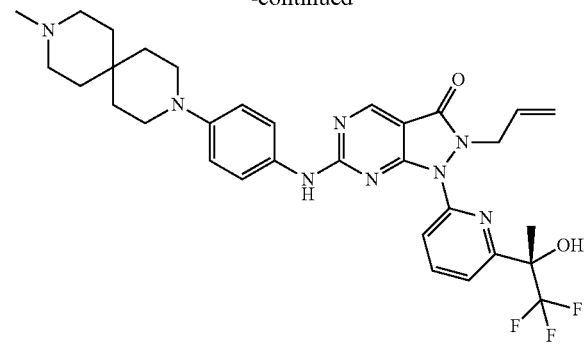

Synthetic Route:

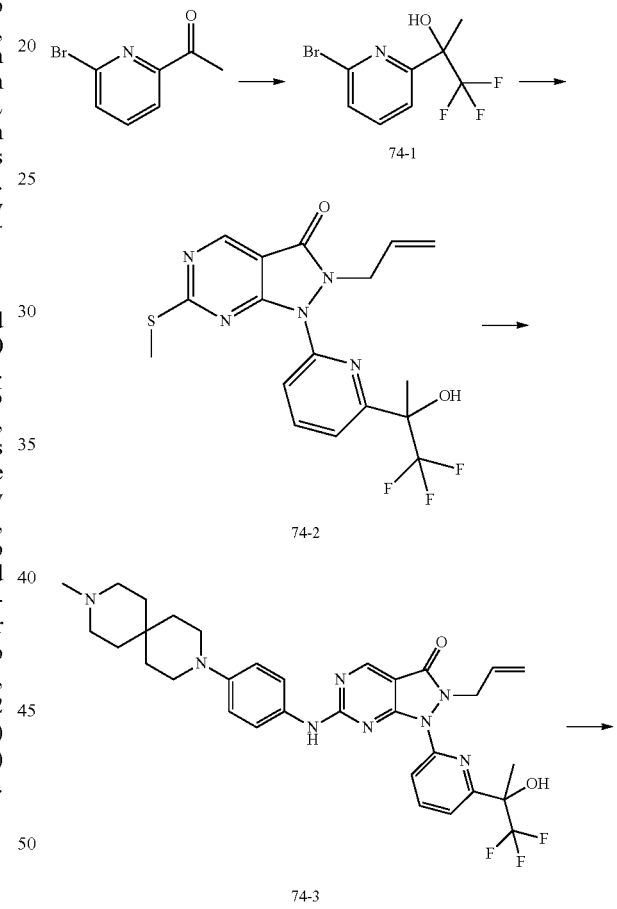

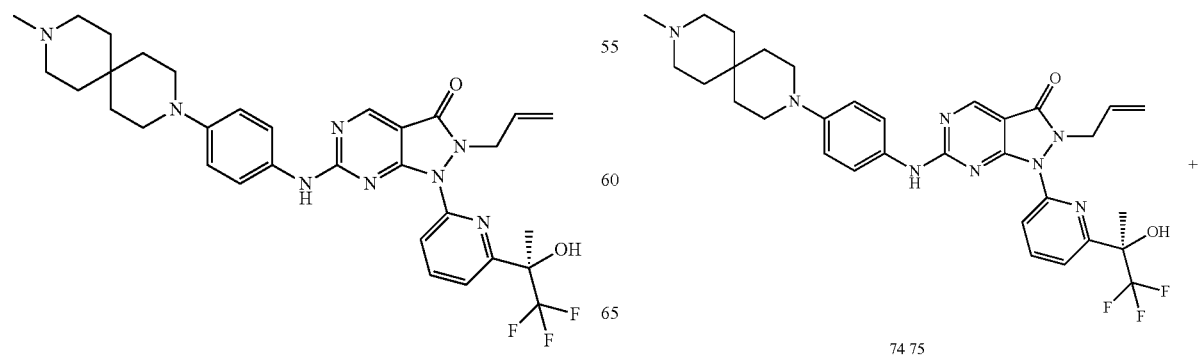

-continued

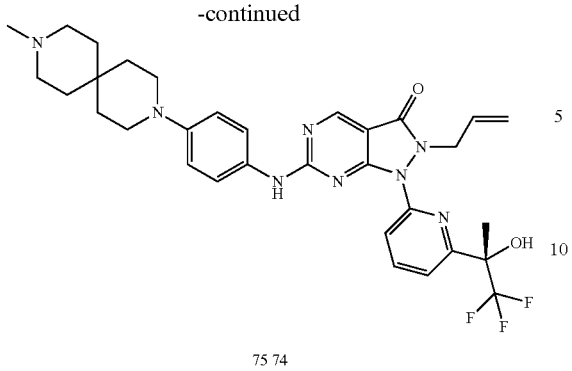

75 74

Step 2: Synthesis of Compound 74-1

2-Bromo-6-acetyl pyridine (2 g, 10.00 mmol) was added into the white suspension of the compound sodium acetate (820.21 mg, 10.00 mmol) in dimethyl sulfoxide (12 mL), then 2 mL dimethyl sulfoxide was added, trifluoromethyl trimethylsilane (5.69 g, 39.99 mmol) was slowly added dropwise into the reaction mixture at 10-20° C., the reaction mixture was stirred at 20° C. for 12 hours. The reaction mixture was placed in an ice bath, the inner temperature was kept between 10-25° C., 16 mL water was added into the reaction mixture to quench the reaction, the aqueous phase was extracted by EA (36 mL×3), the organic phases were combined and washed by saturated sodium bicarbonate 40 mL, and the organic phase was then washed by saturated brine 40 mL, dried over anhydrous sodium sulfate, then filtered, the filtrate was evaporated to give the crude product, which was purified by silica gel column chromatography (PE/EA=15/1) to give 74-1.

MS m/z: 269.9[M+H]$^+$

Step 2: Synthesis of Compound 74-2

The compound 74-2 was obtained by using the same methods as preparing the compound 46-A in embodiment 46, except for the corresponding starting material. MS m/z: 412.0 [M+H]$^+$

Step 3: Synthesis of Compound 74-3

The compound 74-3 was obtained by using the same methods as preparing the compound 22 in embodiment 22, except for the corresponding starting material.

$^1$H NMR (400 MHz, CDCl$_3$) δ ppm 1.52-1.61 (m, 8H) 1.70 (s, 3H) 2.23 (s, 3H) 2.34 (br s, 4H) 3.05-3.12 (m, 4H) 4.50 (dd, J=15.56, 7.04 Hz, 1H) 4.71 (dd, J=15.56, 6.02 Hz, 1H) 4.86 (d, J=18.06 Hz, 1H) 4.98 (d, J=9.54 Hz, 1H) 5.62 (ddt, J=16.76, 10.48, 6.22, 6.22 Hz, 1H) 6.87 (d, J=9.04 Hz, 2H) 7.32-7.42 (m, 3H) 7.88 (d, J=3.52 Hz, 2H) 8.76 (s, 1H). MS m/z: 623.1[M+H]$^+$

Step 4: Synthesis of Compound 74, 75

Compound 74-3 was separated by SFC (chiral column: CHIRALCELR OJ-H (Particle Size: 5 μm Dimensions: 30 mm Ø×250 mm) DAICEL CHEMICAL INDUSTRIES, LTD. mobile phases: A: CO$_2$, B: EtOH (0.10% NH$_3$H$_2$O), A:B=65:35, flow rate: 50 mL/min) to give 74 (7.00 min). $^1$H NMR (400 MHz, CDCl$_3$) δ ppm 1.52 (br t, J=5.52 Hz, 4H) 1.58-1.61 (m, 4H) 1.70 (s, 3H) 2.23 (s, 3H) 2.33 (br s, 4H) 3.07-3.11 (m, 4H) 4.50 (dd, J=15.81, 6.78 Hz, 1H) 4.71 (dd, J=15.81, 5.77 Hz, 1H) 4.86 (dd, J=17.07, 1.00 Hz, 1H) 4.98 (d, J=9.54 Hz, 1H) 5.39 (br s, 1H) 5.56-5.67 (m, 1H) 6.87 (d, J=9.03 Hz, 2H) 7.36 (br d, J=7.53 Hz, 3H) 7.87-7.91 (m, 2H) 8.76 (s, 1H). MS m/z: 623.1 [M+H]$^+$ and 75 (5.55 min).

$^1$H NMR (400 MHz, CDCl$_3$) δ ppm 1.52 (br t, J=5.52 Hz, 4H) 1.57-1.61 (m, 4H) 1.70 (s, 3H) 2.23 (s, 3H) 2.33 (br s, 4H) 3.04-3.13 (m, 4H) 4.50 (dd, J=15.81, 6.78 Hz, 1H) 4.71 (dd, J=15.56, 5.52 Hz, 1H) 4.86 (dd, J=17.07, 1.00 Hz, 1H) 4.98 (d, J=9.54 Hz, 1H) 5.38 (br s, 1H) 5.56-5.67 (m, 1H) 6.87 (d, J=9.03 Hz, 2H) 7.33-7.39 (m, 3H) 7.89 (d, J=3.51 Hz, 2H) 8.77 (s, 1H). MS m/z: 623.1[M+H]$^+$

Embodiment 75: Synthesis of Compound 76

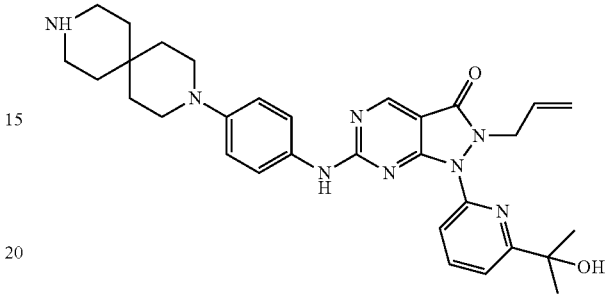

Synthetic Route:

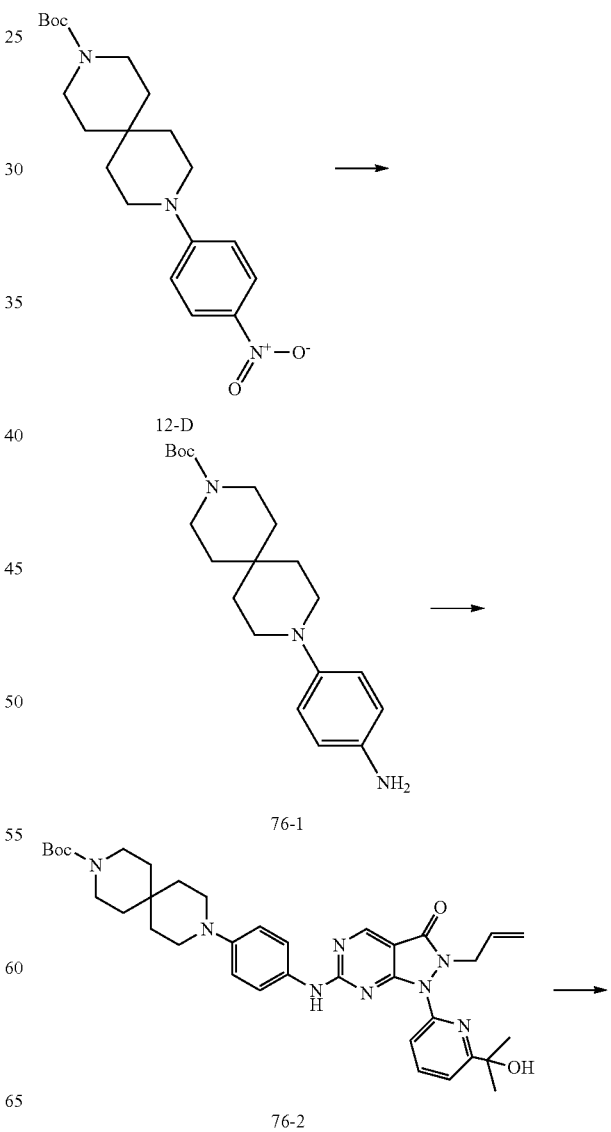

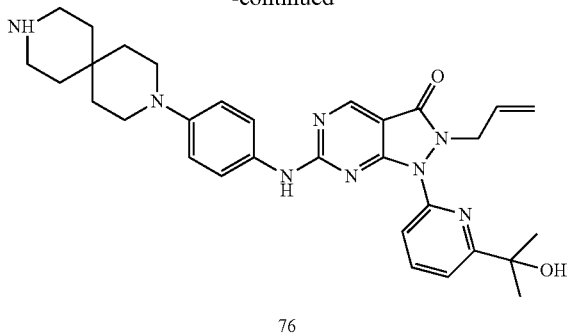

76

Step 1: Synthesis of Compound 76-1

The compound 76-1 was obtained by using the same methods as preparing the compound 37-B in embodiment 37, except for the corresponding starting material I2-D. MS m/z: 346.1 [M+H]$^+$ Step 2: Synthesis of Compound 76-2

The compound 76-2 was obtained by using the same methods as preparing the compound 22 in embodiment 22, except for the corresponding starting material. MS m/z: 655.3 [M+H]$^+$ Step 3: Synthesis of Compound 76

The compound 76 was obtained by using the same methods as preparing the compound 2 in embodiment 2, except for the corresponding starting material. $^1$H NMR (400 MHz, CDCl$_3$) δ ppm 1.43-1.58 (m, 4H) 1.61 (s, 6H) 1.69-1.72 (m, 4H) 2.88 (br s, 4H) 3.16-3.20 (m, 4H) 4.76 (br d, J=6.02 Hz, 2H) 4.96 (d, J=17.06 Hz, 1H) 5.06 (d, J=10.04 Hz, 1H) 5.72 (ddt, J=16.94, 10.54, 6.08, 6.08 Hz, 1H) 6.95 (d, J=9.04 Hz, 2H) 7.36 (d, J=7.54 Hz, 1H) 7.47 (br d, J=8.54 Hz, 2H) 7.78 (d, J=8.04 Hz, 1H) 7.85-7.90 (m, 1H) 8.85 (s, 1H). MS m/z: 555.1[M+H]$^+$ Embodiment 76: Synthesis of Compound 77

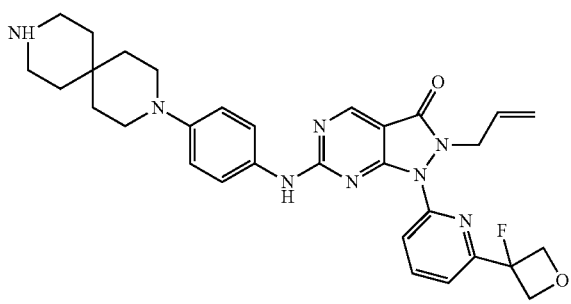 [SMILES: C=CCn1c(=O)c2cnc(Nc3ccc(N4CCC5(CCNCC5)CC4)cc3)nc2n1-c1cccc(C2(F)COC2)n1]

Synthetic Route:

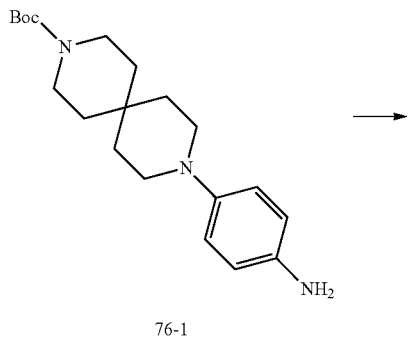

76-1

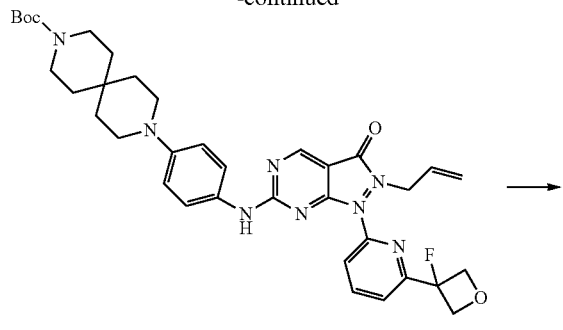

77-1

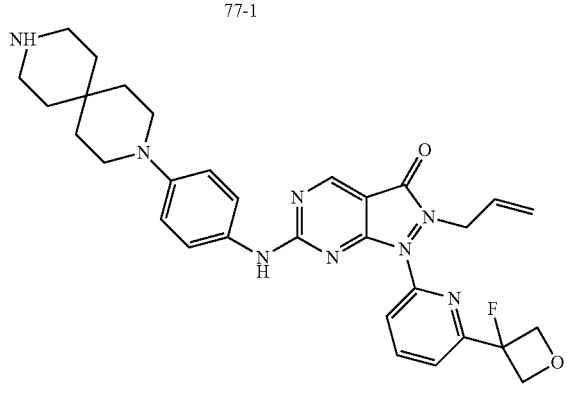

77

Step 1: Synthesis of Compound 77-A

The compound 77-1 was obtained by using the same methods as preparing the compound 22 in embodiment 22, except for the corresponding starting material. MS m/z: 671.3 [M+H]$^+$ Step 2: Synthesis of Compound 77

The compound 77 was obtained by using the same methods as preparing the compound 2 in embodiment 2, except for the corresponding starting material. $^1$H NMR (400 MHz, CDCl$_3$) δ ppm 1.54 (br s, 4H) 1.68-1.75 (m, 4H) 2.89 (br s, 4H) 3.15-3.25 (m, 4H) 4.90-4.95 (m, 2H) 4.96-5.15 (m, 5H) 5.17 (d, J=7.54 Hz, 1H) 5.73 (ddt, J=16.82, 10.42, 6.22, 6.22 Hz, 1H) 6.96 (d, J=8.54 Hz, 2H) 7.38-7.51 (m, 3H) 7.87-7.95 (m, 1H) 8.01 (d, J=8.04 Hz, 1H) 8.86 (s, 1H). MS m/z: 571.1[M+H]$^+$ Embodiment 77: Synthesis of Compound 78

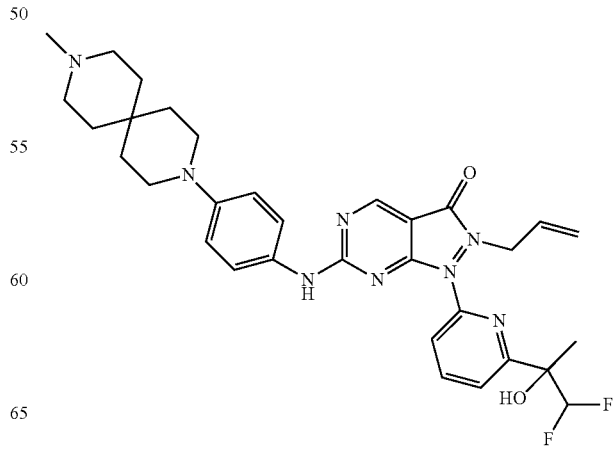

Synthetic Route:

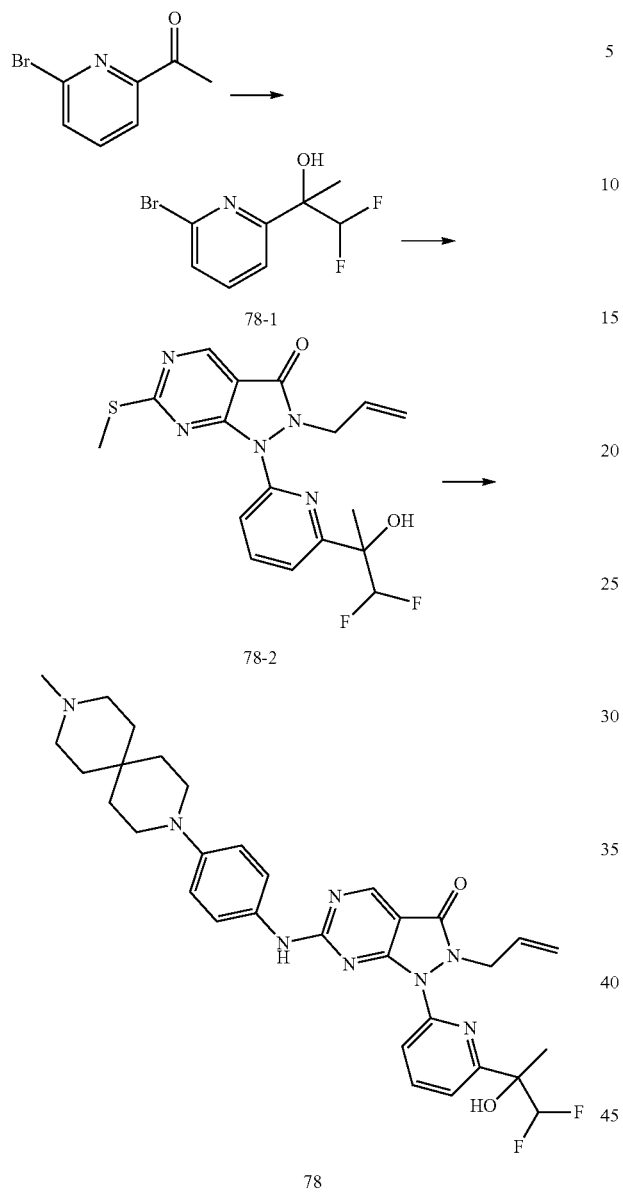

Step 1: Synthesis of Compound 78-A

Difluorobromomethyl trimethylsilane (761.50 mg, 3.75 mmol), triphenylphosphine (786.73 mg, 3.00 mmol) and 1,3-dimethyl-tetrahydro-2-pyrimidinone (640.75 mg, 5.00 mmol) was added sequentially into 2-bromo-6-acetyl pyridine (500 mg, 2.50 mmol) in acetonitrile (7 mL) solution. The reaction was stirred at 20° C. for 2 hours under nitrogen atmosphere. Potassium hydroxide (3 M, 2.5 mL) solution was added into the reaction mixture, the reaction was stirred at 20° C. for 1.5 hours under nitrogen atmosphere. 2.5 mL 2 mol/L diluted HCl solution was added into the reaction mixture, then stirred for 10 min, saturated sodium bicarbonate solution was added into the reaction mixture, adjusted to pH=7-8, the aqueous phase was extracted by EA (11 mL×3), the organic phases were combined and washed by saturated brine (15 mL), dried over anhydrous sodium sulfate, then filtered, the filtrate was evaporated to give the crude product. The crude product was separated by column chromatography (PE/EA=5/1, 3/1) to give 78-1. $^1$H NMR (400 MHz, CDCl$_3$) δ ppm 1.62-1.66 (m, 3H) 4.83 (s, 1H) 5.64-5.95 (m, 1H) 7.50 (dd, J=12.80, 7.78 Hz, 2H) 7.63-7.68 (m, 1H). MS m/z: 253.8 [M+H]$^+$ Step 2: Synthesis of Compound 78-2

The compound 78-2 was obtained by using the same methods as preparing the compound 46-A in embodiment 46, except for the corresponding starting material.

$^1$H NMR (400 MHz, CDCl$_3$) δ ppm 1.68 (s, 3H) 2.61 (s, 3H) 4.66-4.74 (m, 2H) 4.80-4.88 (m, 1H) 4.95 (dd, J=17.08, 1.00 Hz, 1H) 5.08 (d, J=9.54 Hz, 1H) 5.64-6.01 (m, 2H) 7.49 (d, J=7.54 Hz, 1H) 7.91 (d, J=7.54 Hz, 1H) 7.98-8.03 (m, 1H) 8.97 (s, 1H). MS m/z: 394.4 [M+H]$^+$ Step 3: Synthesis of Compound 78

The compound 78 was obtained by using the same methods as preparing the compound 22 in embodiment 22, except for the corresponding starting material.

$^1$H NMR (400 MHz, CDCl$_3$) δ ppm 1.62 (br s, 3H) 1.68 (br s, 8H) 2.33 (s, 3H) 2.43 (br s, 4H) 3.15-3.20 (m, 4H) 4.61-4.69 (m, 1H) 4.73-4.81 (m, 1H) 4.96 (br d, J=17.08 Hz, 1H) 5.07 (d, J=10.28 Hz, 1H) 5.65-6.00 (m, 2H) 6.96 (d, J=9.04 Hz, 2H) 7.41-7.49 (m, 3H) 7.87-7.99 (m, 2H) 8.85 (s, 1H). MS m/z: 605.2 [M+H]$^+$ Embodiment 78: Compound 79

Synthetic Route:

199
-continued

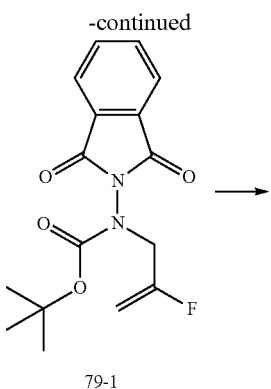

79-1

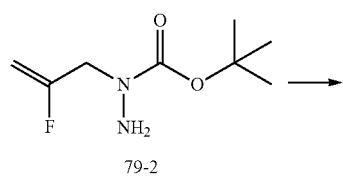

79-2

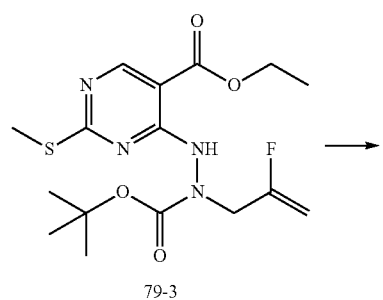

79-3

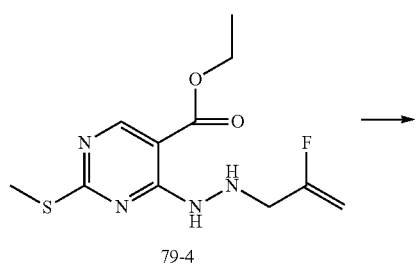

79-4

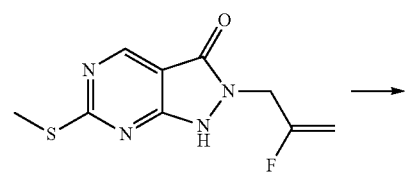

79-5

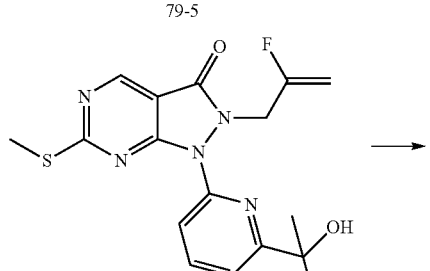

79-6

200
-continued

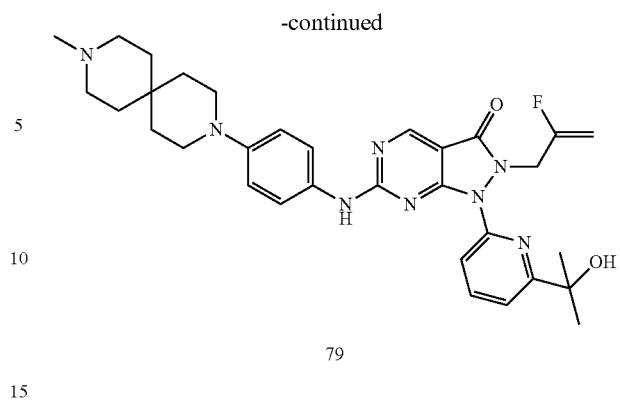

79

Step 1: Synthesis of Compound 79-1

The compound 79-1 was obtained by using the same methods as preparing the compound 22-B in embodiment 22, except for the corresponding starting material. MS m/z: 278.9[M−41]$^+$ Step 2: Synthesis of Compound 79-2

The compound 79-2 was obtained by using the same methods as preparing the compound 22-C in embodiment 22, except for the corresponding starting material. $^1$H NMR (400 MHz, CDCl$_3$) δ ppm 1.41 (s, 9H) 3.97-4.07 (m, 4H) 4.26-4.41 (m, 1H) 4.63 (dd, J=16.56, 3.02 Hz, 1H).

Step 3: Synthesis of Compound 79-3

The compound 79-3 was obtained by using the same methods as preparing the compound 22-D in embodiment 22, except for the corresponding starting material. $^1$H NMR (400 MHz, CDCl$_3$) δ ppm 1.31-1.44 (m, 9H) 1.52 (br s, 3H) 2.52 (s, 3H) 4.19-4.64 (m, 6H) 4.75 (dd, J=16.06, 3.01 Hz, 1H) 8.75 (s, 1H). MS m/z: 387.4 [M+H]$^+$ Step 4: Synthesis of Compound 79-4

The compound 79-4 was obtained by using the same methods as preparing the compound 22-E in embodiment 22, except for the corresponding starting material. MS m/z: 287.3 [M+H]$^+$ Step 5: Synthesis of Compound 79-5

The compound 79-5 was obtained by using the same methods as preparing the compound 22-F in embodiment 22, except for the corresponding starting material. MS m/z: 240.9 [M+H]$^+$ Step 6: Synthesis of Compound 79-6

The compound 79-6 was obtained by using the same methods as preparing the compound 22-G in embodiment 22, except for the corresponding starting material. $^1$H NMR (400 MHz, CDCl$_3$) δ ppm 1.59 (s, 6H) 2.59 (s, 3H) 4.09-4.24 (m, 1H) 4.56 (dd, J=15.82, 3.26 Hz, 1H) 4.96 (d, J=15.56 Hz, 2H) 7.42-7.46 (m, 1H) 7.83-7.87 (m, 1H) 7.90-7.95 (m, 1H) 8.94 (s, 1H). MS m/z: 376.0[M+H]$^+$ Step 7: Synthesis of Compound 79

The compound 79 was obtained by using the same methods as preparing the compound 22 in embodiment 22, except for the corresponding starting material. ¹H NMR (400 MHz, CDCl₃) δ ppm 1.61 (s, 6H) 1.62-1.71 (m, 8H) 2.27-2.39 (m, 3H) 2.43 (br s, 4H) 3.14-3.22 (m, 4H) 3.80 (br s, 1H) 4.11-4.25 (m, 1H) 4.57 (dd, J=16.06, 3.52 Hz, 1H) 4.91 (d, J=15.56 Hz, 2H) 6.96 (d, J=9.04 Hz, 2H) 7.34-7.39 (m, 1H) 7.47 (br d, J=8.04 Hz, 2H) 7.85-7.90 (m, 2H) 8.86 (br s, 1H). MS m/z: 587.1 [M+H]⁺

Embodiment 79: Compound 80

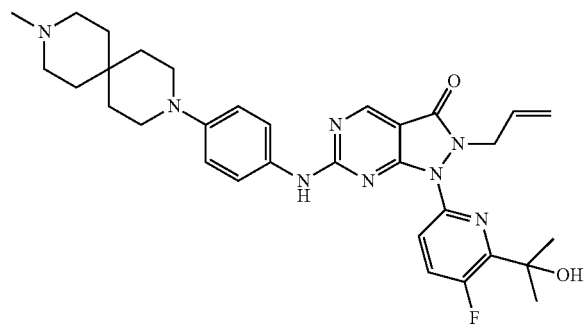 [SMILES: C=CCn1c(=O)c2cnc(Nc3ccc(N4CCC5(CCN(C)CC5)CC4)cc3)nc2n1-c1ccc(F)c(C(C)(C)O)n1]

Synthetic Route:

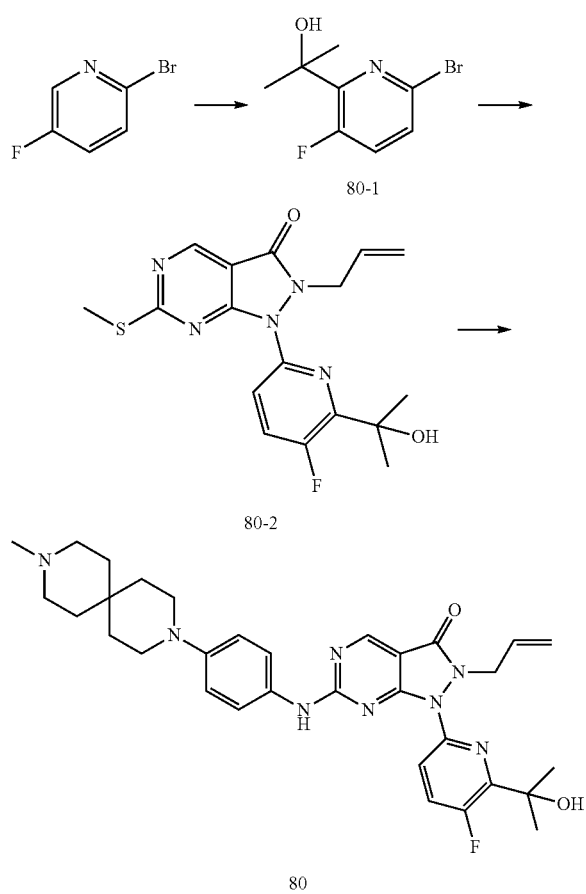

Step 1: Synthesis of Compound 80-1

At −70~−60° C. and under nitrogen atmosphere, n-butyllithium (2.5 M, 5.68 mL) was slowly added dropwise into 2-bromo-5-fluoropyridine (2.5 g, 14.21 mmol) in ether (20 mL) solution, after completion of the addition, the reaction mixture was stirred at 70~−60° C. for 0.5 hours, then dry acetone (907.55 mg, 15.63 mmol) was added dropwise into the reaction mixture, the reaction mixture was stirred at 70~−60° C. for 1 hour. At 0° C., saturated ammonium chloride (20 mL) solution was added into the reaction mixture to quench the reaction, then the mixture was extracted by EA (20 mL×3), the organic phases were combined and washed by saturated brine (20 mL), dried over anhydrous sodium sulfate, then filtered, the filtrate was evaporated to give the crude product, which was purified by silica gel column chromatography (PE/EA=10/1) to give a red compound 80-1. ¹H NMR (400 MHz, CDCl₃) δ ppm 1.51 (d, J=2.02 Hz, 6H) 7.21-7.27 (m, 1H) 7.35 (dd, J=8.54, 3.02 Hz, 1H). MS m/z: 215.9 [M+H]⁺

Step 2: Synthesis of Compound 80-2

The compound 80-2 was obtained by using the same methods as preparing the compound 22-G in embodiment 22, except for the corresponding starting materials. ¹H NMR (400 MHz, CDCl₃) δ ppm 1.55 (d, J=1.00 Hz, 6H) 2.51 (s, 3H) 4.47 (s, 1H) 4.66 (d, J=6.02 Hz, 2H) 4.87 (dd, J=17.08, 1.00 Hz, 1H) 4.98-5.03 (m, 1H) 5.62 (ddt, J=16.94, 10.42, 6.16, 6.16 Hz, 1H) 7.57 (t, J=9.04 Hz, 1H) 7.71 (dd, J=8.54, 3.01 Hz, 1H) 8.86-8.89 (m, 1H). MS m/z: 376.0 [M+H]⁺

Step 3: Synthesis of Compound 80

The compound 80 was obtained by using the same methods as preparing the compound 22 in embodiment 22, except for the corresponding starting materials. ¹H NMR (400 MHz, CDCl₃) δ ppm 1.59-1.63 (m, 4H) 1.64 (d, J=1.26 Hz, 6H) 1.66-1.70 (m, 4H) 2.32 (s, 3H) 2.42 (br s, 4H) 3.13-3.22 (m, 4H) 4.65-4.70 (m, 2H) 4.71 (br s, 1H) 4.96 (dd, J=17.08, 1.00 Hz, 1H) 5.07 (d, J=10.28 Hz, 1H) 5.71 (ddt, J=16.82, 10.42, 6.22, 6.22 Hz, 1H) 6.95 (d, J=9.04 Hz, 2H) 7.44 (br d, J=9.04 Hz, 2H) 7.60 (t, J=9.16 Hz, 1H) 7.79 (dd, J=8.66, 2.89 Hz, 1H) 8.84 (s, 1H). MS m/z: 587.1 [M+H]⁺

Experiment 1: In Vitro Enzymatic Inhibitory Activity of the Compound of the Present Invention The compounds of the present invention for experimental use were all self-prepared, and their chemical names and structural formulas are shown in the preparation embodiments of the respective compounds. The experimental tests were carried out in Reaction Biology Corporation, USA, and the experimental results were provided by the company.

Experimental Reagents:

Basic reaction buffer: 20 mM hydroxyethylpiperazine ethanesulfuric acid (pH 7.5), 10 mM magnesium chloride, 1 mM EGTA, 0.02% Brij35, 0.02 mg/mL bovine serum albumin, 0.1 mM Na₃VO₄, 2 mM DTT, 1% DMSO Enzyme: Wee-1 concentration is 150 nM Matrix: MBP concentration is 20 μM Compound Treatment:

The tested compound was formulated into a 5 mM solution with 100% DMSO, and a 10 points 3-fold gradient dilution was performed with DMSO through an automated pipetting station epMotion 5070.

Experiment Procedure:

1. Fresh matrix configuration reaction buffer was prepared;
2. The Wee-1 was added into the matrix solution and shaked gently;

3. DMSO solution of the compound were added into the kinase reaction mixture using an acoustic technique (Echo 550; nanoliter range) and incubated for 20 minutes at room temperature;
4. $^{33}$P-ATP (specific activity, 10 μCi/μL) was added into the reaction mixture to stimulate the reaction;
5. Incubated for 2 hours at room temperature;
6. Kinase activity was detected by filter-binding method.

TABLE 1

In vitro enzymatic activity determination results of the compound of the present invention ($IC_{50}$)

| Compound No. | Wee1 ($IC_{50}$ nM) |
|---|---|
| 1 | 67.4 |
| 2 | 43.6 |
| 3 | 24.6 |
| 4 | 250.9 |
| 5 | 90.4 |
| 6 | 101.9 |
| 7 | 82.5 |
| 8 | 51.9 |
| 9 | 108.6 |
| 11 | 48.1 |
| 12 | 25.3 |
| 13 | 42.0 |
| 14 | 47.8 |
| 15 | 31.5 |
| 16 | 52.8 |
| 17 | 42.5 |
| 18 | 131.4 |
| 19 | 83.2 |
| 22 | 238.6 |
| 23 | 79.6 |
| 24 | 48.8 |
| 25 | 20.4 |
| 26 | 14.1 |
| 27 | 24.9 |
| 28 | 13.2 |
| 29 | 13.4 |
| 30 | 58.8 |
| 31 | 15.0 |
| 32 | 64.6 |
| 34 | 120.2 |
| 35 | 240.7 |
| 36 | 57.1 |
| 37 | 328.1 |
| 38 | 20.7 |
| 39 | 620.4 |
| 40 | 30.7 |
| 41 | 13.1 |
| 42 | 17.4 |
| 43 | 12.1 |
| 44 | 12.6 |
| 45 | 7.4 |
| 46 | 44.6 |
| 47 | 3.0 |
| 48 | 6.3 |
| 49 | 3.1 |
| 50 | 2.5 |
| 51 | 2.8 |
| 52 | 71 |
| 53 | 63 |
| 54 | 57 |
| 55 | 90 |
| 56 | 74 |
| 57 | 47 |
| 58 | 73 |
| 59 | 22.6 |
| 60 | 14.8 |
| 61 | 15.7 |
| 62 | 36.1 |
| 63 | 8.3 |
| 64 | 9.9 |
| 65 | 41.6 |
| 66 | 15.0 |
| 67 | 12.8 |
| 68 | 30.4 |
| 69 | 5.7 |
| 70 | 20.3 |
| 71 | 15.7 |
| 72 | 8.2 |
| 73 | 5.3 |
| 74 | 13.0 |
| 75 | 17 |
| 76 | 13 |
| 77 | 9 |
| 78 | 32 |
| 79 | 43 |
| 80 | 49 |

Experimental Conclusion:
According to Table 1, the compounds of the present invention have a good inhibitory effect on Wee1 kinase.

Experiment 2: Pharmacokinetic Evaluation of the Compound

Experimental objective: pharmacokinetics evaluation of the compound in BALB/c nude mice.
Experimental Material:
BALB/c mice (female)
Experimental Procedure:
The rodent pharmacological characteristics of the compound after intravenous administration and oral administration were tested by a standard protocol, the candidate compound in the experiment was formulated into a clear solution, and the mice were administered by a single intravenous injection and oral administration. The intravenous and oral vehicles are a certain proportion of aqueous hydroxypropyl 3-cyclodextrin or physiological saline solution. Whole blood samples within 24 hours were collected, centrifuged at 3000 g for 15 minutes, and the supernatant was separated to obtain plasma samples, 4 times volume containing internal standard of acetonitrile solution was added to precipitate protein, centrifuged to remove the supernatant and equal volume of water was added and again centrifuged to remove the supernatant, the plasma concentration was quantitatively analyzed by LC-MS/MS analysis, and the pharmacokinetic parameters such as peak concentration, peak time, clearance rate, half-life, area under the curve of the drug, and bioavailability were calculated.
Experimental Results:

TABLE 2 pharmacokinetic test results

| Tested compound prepared by embodiments | Clearance rate (mL/min/kg) | Half-life $T_{1/2}$ (h) | Concentration integral AUC (nM · hr) | bioavailability F (%) |
|---|---|---|---|---|
| AZD1775 | 85.7 | 0.25 | 1200 | 31.0 |
| Embodiment 15 | 57.1 | 1.7 | 1729 | 35.3 |
| Embodiment 29 | 51 | 1.49 | 2151 | 32.4 |
| Embodiment 43 | 23 | 1.81 | 5593 | 45.1 |

Conclusion: the compounds of the present invention can significantly improve the pharmacokinetics indexes in mice, reduce the clearance rate of the compound in vivo, increase the half-life time, and significantly increase the concentration integral.

Experiment 3: In Vivo Drug PD Research (1) In vivo PD study of the compound used on tumors of human colon cancer LoVo cells subcutaneously xenografted to BALB/c nude mice model Experimental method: the experimental animals used were BALB/c nude mice (provided by Shanghai Xipuer-Beikai Experimental animal CO., Ltd), 6-8 weeks old, weighting 18-22 g.

Human colon cancer LoVo cells, monolayer-cultured in vitro, culturing condition was Ham's F-12 medium supplemented with 10% fetal bovine serum, 100 U/mL penicillin, 100 μg/mL streptomycin and 2 mM glutamine, 37° C., 5% $CO_2$. Conventional digestion treatment passage was done with trypsin-EDTA twice a week. When the cell saturation reached 80%-90%, the cells were collected, counted, and inoculated. 0.1 mL (10×106) of LoVo cells were subcutaneously inoculated into the right back of each nude mouse, and group administration was started when the average tumor volume reached 213 mm³. The administration mode was oral administration, 40 mg/kg twice a day for three consecutive weeks.

After the last administration of the experiment, a portion of plasma, tumor, intestine, brain, lung, liver and pancreas was collected from the number 1-2 animals after 0.5 h of administration, and quick-froze for PK detection; a portion of plasma, tumor, intestine, brain, lung, liver and pancreas was collected from the number 3-4 animals after 2 h of administration, and quick-froze for PK detection; a portion of plasma, tumor, intestine, brain, lung, liver and pancreas was collected from the number 5-6 animals after 8 h of administration, and quick-froze for PK detection. The tumor, intestine, brain, lung, liver and pancreas were weighted separately and added 9 times volumes of homogenate MeOH/15 mM PBS (1:2, v:v) for homogenization. 20 μL sample was added into 300 μL of the stop buffer including internal standard for protein precipitation, and shaked to mix well. The mixture was centrifuged at 13,000 rpm for 10 minutes at 20-25° C., and 3 μL of the supernatant was taken for LCMS analysis.

The final experimental results was shown in Table 3:

TABLE 3 distribution result for the mice tissues

| Body part | Parameter | AZD1775 | Embodiment 30 |
|---|---|---|---|
| plasma | Cmax (nM) | 3070 | 4270 |
|  | Tmax (h) | 0.5 | 2 |
|  | $AUC_{0\text{-}last}$ (nM · h) | 6970 | 14183 |
| Brain | Cmax (nM) | ND | 959 |
|  | Tmax (h) | ND | 0.5 |
|  | $AUC_{0\text{-}last}$ (nM · h) | ND | 2124 |
| Colon | Cmax (nM) | 238000 | 134950 |
|  | Tmax (h) | 0.5 | 0.5 |
|  | $AUC_{0\text{-}last}$ (nM · h) | 225458 | 401622 |
| liver | Cmax (nM) | 38100 | 67700 |
|  | Tmax (h) | 0.5 | 2 |
|  | $AUC_{0\text{-}last}$ (nM · h) | 117325 | 256862 |
| lung | Cmax (nM) | 17240 | 14600 |
|  | Tmax (h) | 0.5 | 2 |
|  | $AUC_{0\text{-}last}$ (nM · h) | 36531 | 74704 |
| pancreas | Cmax (nM) | 35650 | 49300 |
|  | Tmax (h) | 0.5 | 2 |
|  | $AUC_{0\text{-}last}$ (nM · h) | 55530 | 253458 |
| turner | Cmax (nM) | 3855 | 5425 |
|  | Tmax (h) | 2 | 8 |
|  | $AUC_{0\text{-}last}$ (nM · h) | 15291 | 37263 |

Conclusion: The compound of the present invention may significantly enhance its exposed quantity in mice tissues.

Biological Activity Experiment 4: Inhibition Experiment for hERG Potassium Channel Experimental objective: effect detection on the tested compounds on hERG potassium channel with automatic patch clamp method.

Experimental Procedure

1. Preparation of the Compounds

On the day of the experiment, a 20 mM compound mother solution was serially diluted 3 times with 100% DMSO, i.e., 10 μL of a 20 mM compound mother solution was added to 20 μL of DMSO, and intermediate concentrations of 6 consecutively diluted DMSO compounds were sequentially obtained. Then 10 μL of the intermediate concentration of the compound was added to 4990 μL of the extracellular solution, and the final concentration to be tested was obtained by 500-fold dilution, with a highest test concentration of 40 μM, where the concentrations were respectively 40, 13.3, 4.4, 1.48, 0.49, and 0.16 μM. Positive control compound cisapride preparation: 150 μM cisapride mother liquor was serially diluted 3 times with 100% DMSO, i.e., 10 μL of 150 μM cisapride mother liquor was added to 20 μL of DMSO, and 5 intermediate concentrations of cisapride serially diluted with DMSO were sequentially obtained. Then 10 μL of cisapride intermediate concentration was added to 4990 μL of extracellular fluid, the final concentration to be tested was obtained by a 500-fold dilution, with a highest test concentration of 300 nM, where the 5 concentrations was 300, 100, 33.3, 11.1 and 3.70 nM, respectively. The DMSO content in the final test concentration did not exceed 0.2%, and this concentration of DMSO had no effect on the hERG potassium channel.

2. Electrophysiological Recording Process

CHO (Chinese Hamster Ovary) cells that stably expressed hERG potassium channels were recorded for hERG potassium channel currents using whole cell patch clamp technique at room temperature. A glass microelectrode with the tip resistance of about 2-5 MΩ is connected to an Axopatch 200B (Molecular Devices) patch clamp amplifier. The clamping voltage and data recording were controlled and recorded by the pClamp 10 software via computer control with a sampling frequency of 10 kHz and a filtering frequency of 2 kHz. After obtaining the whole cell recording, the cells were clamped at −80 mV, and the step voltage of the induced hERG potassium current (I hERG) was given a 2 s depolarization voltage from −80 mV to +20 mV, and then repolarized to −50 mV for 1 s, and finally returned to −80 mV. This voltage stimulation was given every 10 s, and the administration process was started after confirmation of the stabilization of the hERG potassium current (1 minute). Compound concentrations were administered continuously starting from a low test concentration and each test concentration was given for 1 minute. Each concentration was tested with at least 3 cells (n≥3).

3. Data Processing

Data analysis and processing were performed by pClamp 10, Patch Master, GraphPad Prism 5 and Excel. Inhibition degrees of different compound concentrations on the hERG potassium current (tail current peaks of hERG induced at −50 mV) was calculated by the formula: Fractional block %=[1−(I/Io)]×100%, wherein, Fractional block represents for the inhibition percentage of the potassium current, I and Io represent for the hERG potassium current amplitude before and after dosing. $IC_{50}$ of the compound was fitting calculated by the formula I/Io=1/{1+([C]/IC50)^n}, wherein, Io and I represents for hERG potassium current amplitudes before and after dosing respectively. [C] was the concentration of the compound, n was Hill index.

4. Solution

Extracellular fluid formula (mM): 140 NaCl, 5 KCl, 1 $CaCl_2$, 1.25 $MgCl_2$, 10 HEPES and 10 Glucoses, pH was adjusted to 7.4 by NaOH. Intracellular fluid formula (mM): 140 KCl, 1 $MgCl_2$, 1 $CaCl_2$, 10 EGTA and 10 HEPES, the pH was adjusted to 7.2 by KOH.

Abbreviation

HEPES: 4-(2-hydroxyethyl)piperazin-1-ethanesulfonic acid, N-(2-hydroxyethyl)piperazin-N'-(2-ethanesulfonic acid)

EGTA: ethylene glycol bis(2-aminoethyl ether) tetraacetic acid

5. Quality Control the experimental data in the report satisfied the quality control standard:

Whole cell sealing impedance >1 GΩ

Series resistance compensation would be more than 80% if the resistance was greater than 10 MΩ hERG tail current amplitude >400 pA attenuation <2% per min current stability: 6 recorded tail current peaks and averages would not exceed 2%

Pharmacological indicators: multi-concentration cisapride inhibition effect on hERG channel was used as positive control 6. Experimental Result hERG $IC_{50}$ values of the compounds of the embodiments was shown in Table 4.

TABLE 4 hERG $IC_{50}$ value result for the compound of the embodiments

| Tested sample | hERG $IC_{50}$ (nM) | Test times |
|---|---|---|
| AZD1775 | 11.82 | N = 4 |
| Embodiment 17 | >30 | N = 2 |
| Embodiment 29 | 29.03 | N = 2 |

Conclusion: the compound of the present invention may significantly decrease activity of hERG thus improve safety.

Experiment 5: Thermodynamic Solubility Determination

Method:

1. Preparation, Shaking and Filtration of the Sample

No less than 2 mg sample powder was weighted in a Whatman miniuniprep vial. If the experiment required to test the thermodynamic solubility of the sample in multiple buffer solutions, then separate vial was required for each test.

450 μL buffer (pH=7.4) was added into each of the Whatman miniuniprep vial. After addition of the buffer, the Whatman filter cap of the miniuniprep is mounted and pressed until it was above the liquid level to allow the filter to contact with the buffer solution during shaking. The solubility sample was vortexed for 2 minutes. And the solution phenomenon was recorded. Then the vial was shaked at room temperature (about 22 to 25° C.) for 24 hours at a speed of 550 rpm. And the Whatman Miniunipreps filter cap was pressed to bottom to obtain the filtrate of the solubility solution of the sample. All sample vials should conduct filtration for the insoluble matter before and after and osmotic phenomenon. The buffer was diluted 50 times to obtain a sample dilution.

2 Analysis and Detection

Three UV standard solutions were injected from low to high concentrations into HPLC, and then dilution and supernatant of the test compounds were injected. The sample was injected and tested twice. Integration was conducted to the UV peaks. The standard curve was established and the thermodynamic solubility of the sample was calculated.

TABLE 5

| Compound | Solubility (μM) pH 6.5 | Solubility (μM) pH 7.4 |
|---|---|---|
| AZD1775 | 434.16 | 68.77 |
| Embodiment 29 | 1467.99 | 1046.27 |

As shown in Table 5, comparing to the AZD1775, the embodiment 29 of the present invention shows excellent solubility in water (under pH=6.5 and pH=7.4). Therefore, it's obvious that the compound of the present invention is easier to be dissolved in water.

What is claimed is:

1. The compound represented by formula (I) or a pharmaceutically acceptable salt thereof,

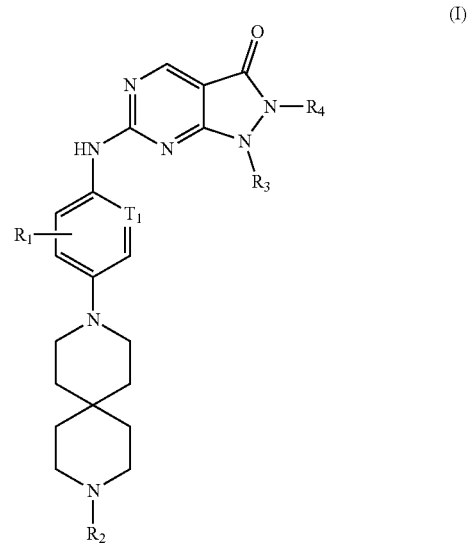

wherein, $T_1$ is N or CH;

$R_1$ is selected from H, halogen, OH, $NH_2$, or selected from the group consisting of $C_{1-3}$ alkyl and $C_{1-3}$ heteroalkyl, each of which is optionally substituted by 1, 2 or 3 R;

R₂ is H, or selected from the group consisting of C₁₋₃ alkyl, C₁₋₃ heteroalkyl and 3-6 membered heterocycloalkyl, each of which is optionally substituted by 1, 2 or 3 R;

R₃ is selected from the group consisting of C₃₋₅ alkenyl and

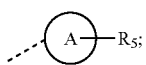

ring A is selected from the group consisting of phenyl and 5-6 membered heteroaryl, each of which is optionally substituted by 1, 2 or 3 R;

R₅ is selected from halogen, OH, NH₂, —C(=O)NH₂, or selected from the group consisting of C₁₋₆ alkyl, C₁₋₆ heteroalkyl, C₃₋₆ cycloalkyl, 3-6 membered heterocycloalkyl, C₃₋₆ cycloalkyl-O—, 3-6 membered heterocycloalkyl-O— and

each of which is optionally substituted by 1, 2 or 3 R;

R₄ is selected from the group consisting of C₁₋₆ alkyl, C₃₋₅ alkenyl, phenyl, and —C₁₋₃ alkyl -phenyl, each of which is optionally substituted by 1, 2 or 3 R;

R is selected from F, Cl, Br, I, OH, NH₂, NH(CH₃), N(CH₃)₂, Me, Et, CH₂F, CHF₂, CF₃,

the "hetero" in C₁₋₃ heteroalkyl, C₁₋₆ heteroalkyl, 5-6 membered heteroaryl, 3-6 membered heterocycloalkyl is selected from the group consisting of —O—, —S—, —C(=O)—, —C(=O)NH—, —C(=O)O—, —NH— and N;

In any one of the cases above, the number of the heteroatoms or the heteroatom groups is independently selected from 1, 2 or 3.

2. The compound or the pharmaceutically acceptable salt as defined in claim 1, wherein, R₁ is selected from H, F, Cl, Br, I, OH, NH₂, or selected from the group consisting of C₁₋₃ alkyl and C₁₋₃ alkoxyl, each of which is optionally substituted by 1, 2 or 3 R.

3. The compound or the pharmaceutically acceptable salt as defined in claim 2, wherein R₁ is selected from the group consisting of H, F, Cl, Br, I, OH, NH₂, Me and

4. The compound or the pharmaceutically acceptable salt as defined in claim 1, wherein, R₂ is H, or selected from the group consisting of C₁₋₃ alkyl, —C(=O)—C₁₋₃ alkyl, —C(=O)O—C₁₋₃ alkyl and oxetanyl, each of which is optionally substituted by 1, 2 or 3 R.

5. The compound or the pharmaceutically acceptable salt as defined in claim 4, wherein, R₂ is selected from the group consisting of H, Me,

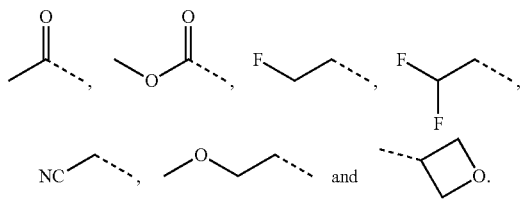

6. The compound or the pharmaceutically acceptable salt as defined in claim 1, wherein, ring A is selected from the group consisting of phenyl, pyridinyl, pyrimidyl, thienyl, thiazolyl, and isothiazolyl, each of which is optionally substituted by 1, 2 or 3 R.

7. The compound or the pharmaceutically acceptable salt as defined in claim 6, wherein, ring A is selected from the group consisting of

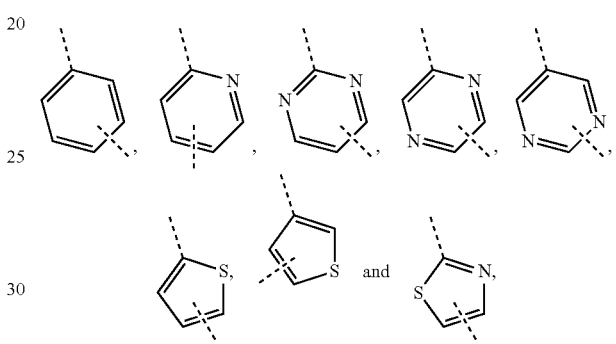

each of which is optionally substituted by 1, 2 or 3 R.

8. The compound or the pharmaceutically acceptable salt as defined in claim 7, wherein, ring A is selected from the group consisting of

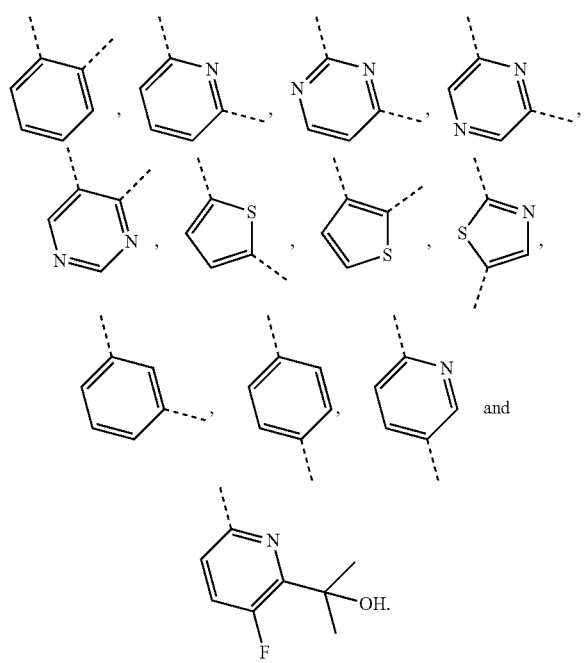

9. The compound or the pharmaceutically acceptable salt as defined in claim 1, wherein, R₅ is selected from F, Cl, Br, I, OH, NH$_2$, —C(=O)NH$_2$, or selected from the group consisting of C$_{1-3}$ alkyl, C$_{1-3}$ alkoxyl, —C(=O)NH—C$_{1-3}$ alkyl, C$_{3-6}$ cycloalkyl, oxetanyl, 2-pyrrolidinonyl, cyclopropyl-O—, cyclobutyl-O—, oxacyclobutyl-O—, oxacyclopentyl-O—, azocyclobutyl, 2-oxazolidinonyl, 2-imidazolidinonyl and

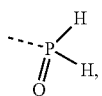

each of which is optionally substituted by 1, 2 or 3 R.

10. The compound or the pharmaceutically acceptable salt as defined in claim 9, wherein, R$_5$ is selected from F, Cl, Br, I, OH, NH$_2$, —C(=O)NH$_2$, or selected from the group consisting of Me, Et,

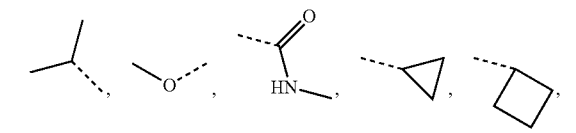
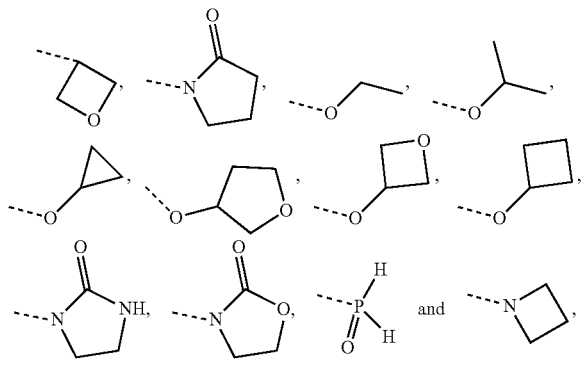

each of which is optionally substituted by 1, 2 or 3 R.

11. The compound or the pharmaceutically acceptable salt as defined in claim 10, wherein, R$_5$ is selected from the group consisting of F, Cl, Br, I, OH, NH$_2$, —C(=O)NH$_2$, Me,

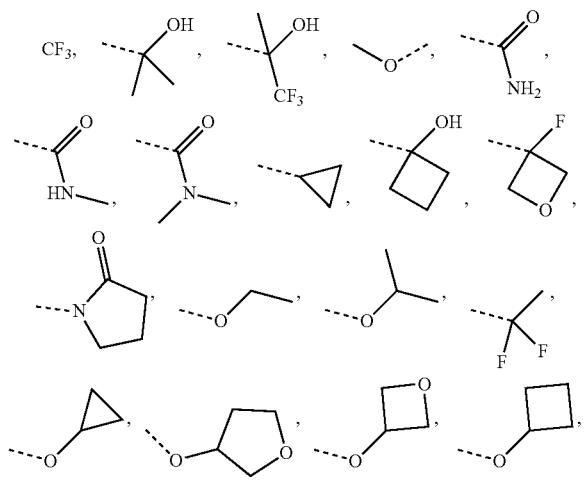
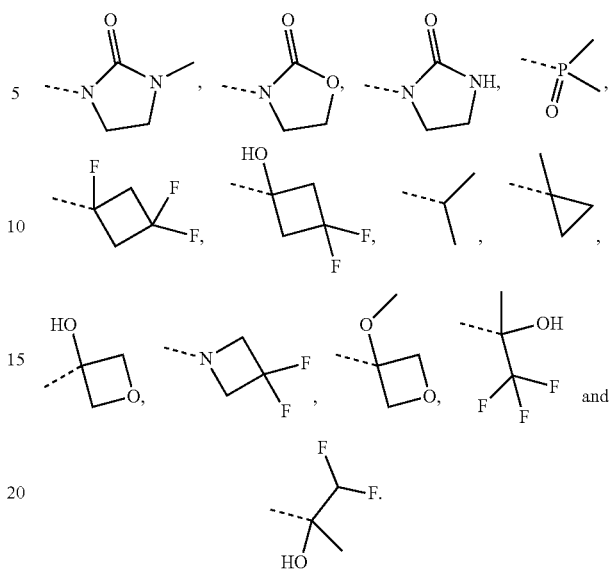

12. The compound or the pharmaceutically acceptable salt as defined in claim 8, wherein, said

is selected from the group consisting of

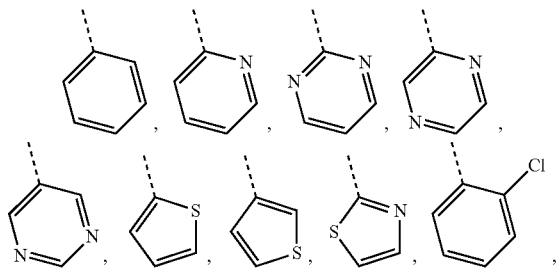
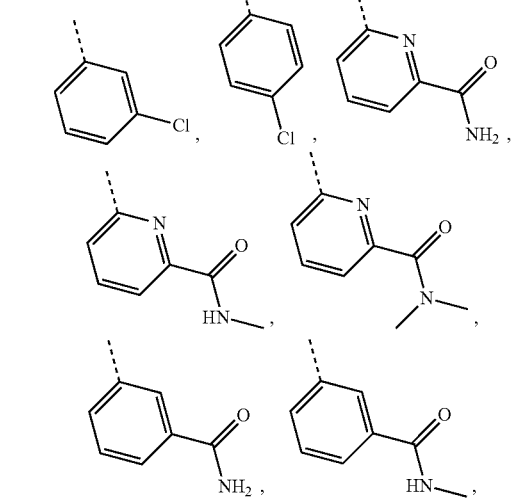

213
-continued
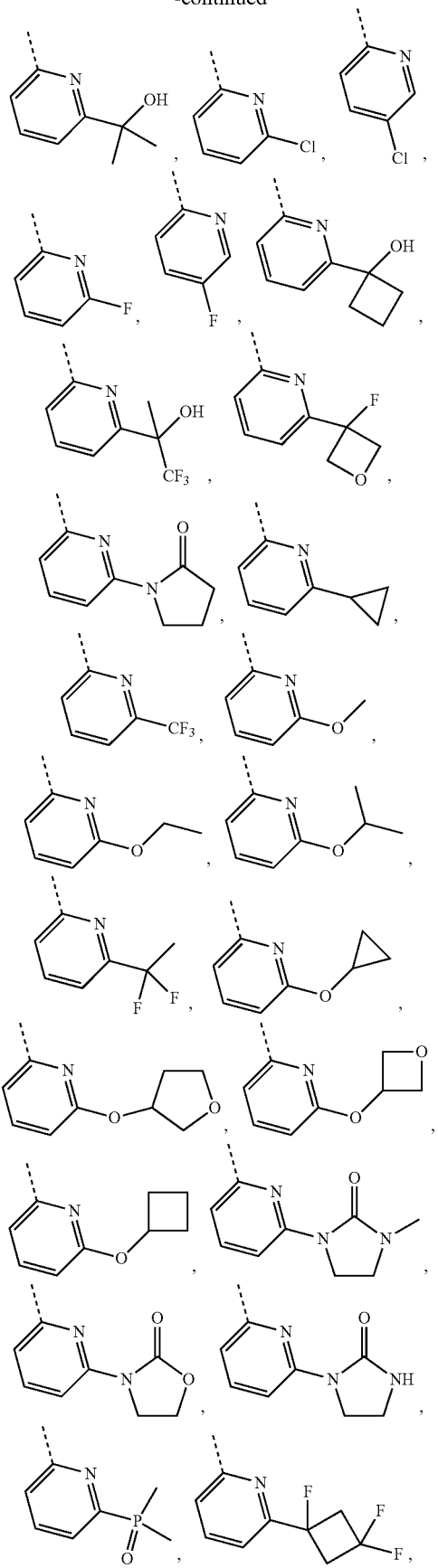
214
-continued
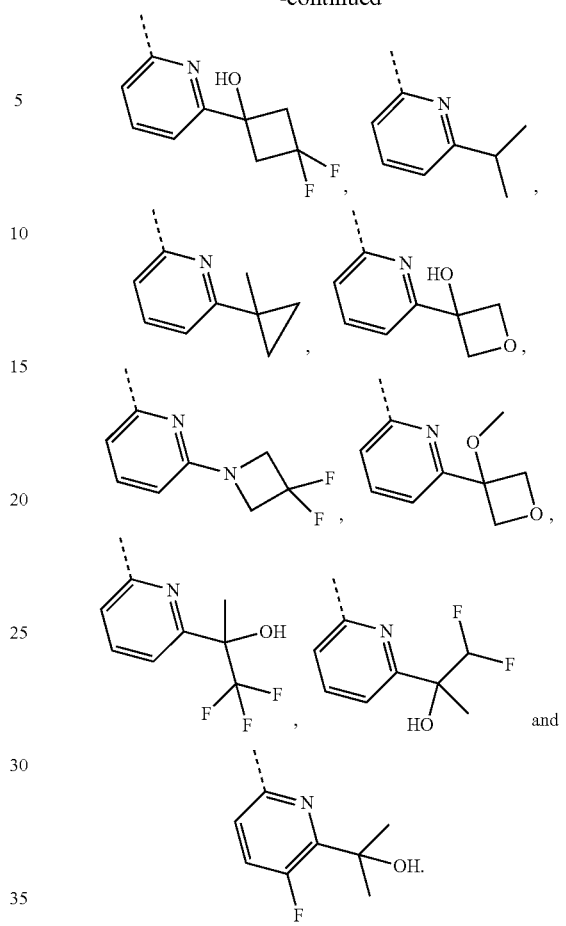
13. The compound or the pharmaceutically acceptable salt as defined in claim 12, wherein, R₃ is selected from the group consisting of
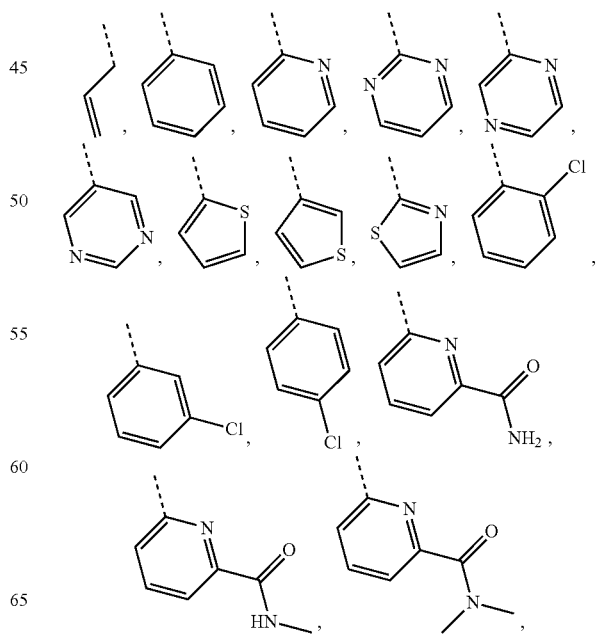

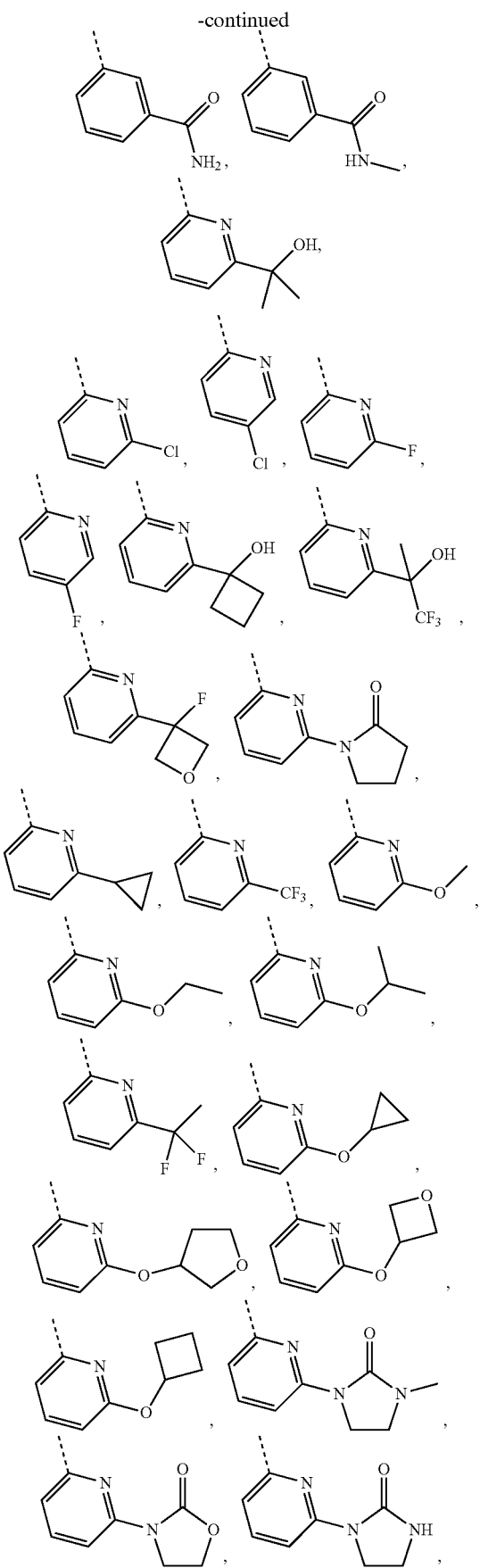
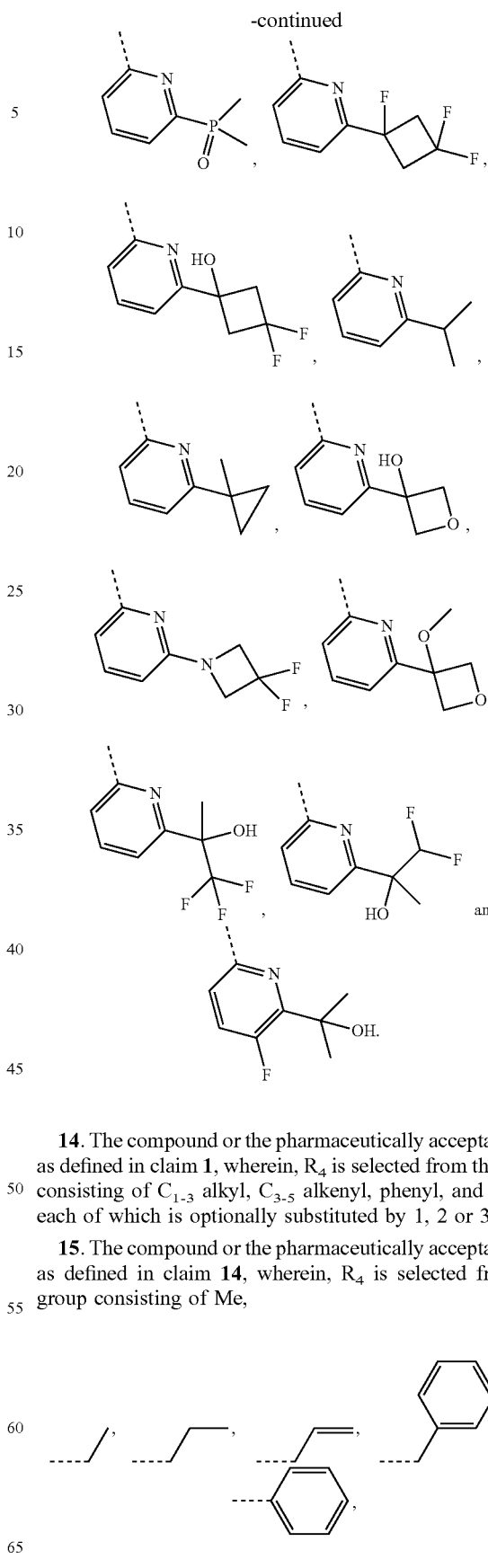

14. The compound or the pharmaceutically acceptable salt as defined in claim 1, wherein, $R_4$ is selected from the group consisting of $C_{1-3}$ alkyl, $C_{3-5}$ alkenyl, phenyl, and benzyl, each of which is optionally substituted by 1, 2 or 3 R.

15. The compound or the pharmaceutically acceptable salt as defined in claim 14, wherein, $R_4$ is selected from the group consisting of Me, each of which is optionally substituted by 1, 2 or 3 R.

16. The compound or the pharmaceutically acceptable salt as defined in claim 1, wherein, the moiety

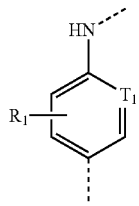

is selected from the group consisting of

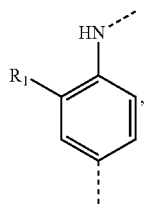 , 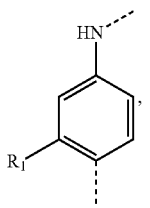 , 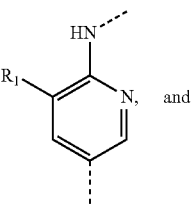 and

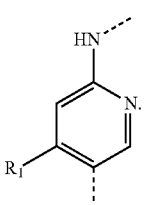

17. The compound or the pharmaceutically acceptable salt defined in claim 1 is selected from:

wherein,

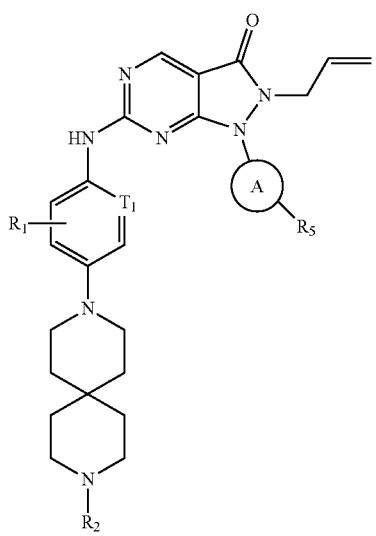

(I-1)

$R_1$, $R_2$, $R_5$, $T_1$ and ring A are as defined in claim 1.

18. The compound or the pharmaceutically acceptable salt as defined in claim 17 is selected from the group consisting of

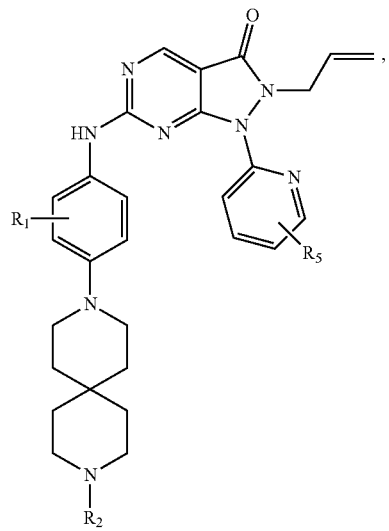

(2-1)

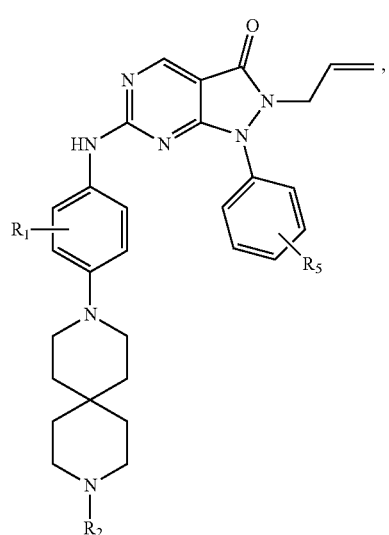

(2-2)

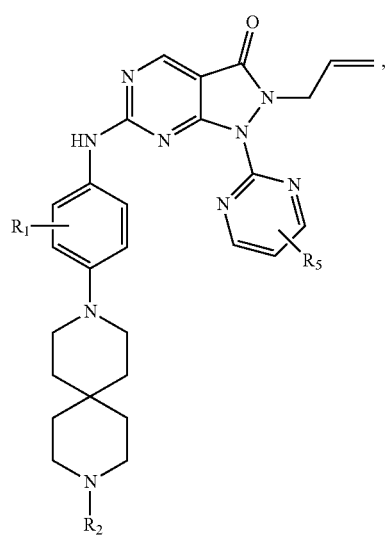

(2-3)

(2-4)
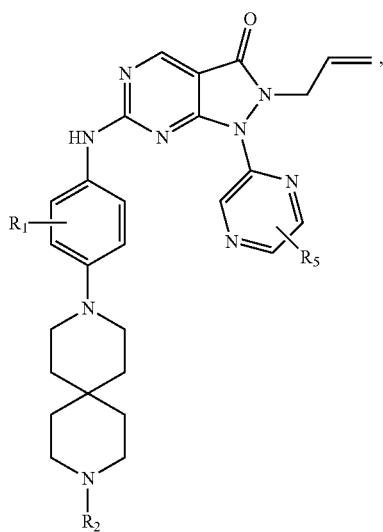
(2-5)
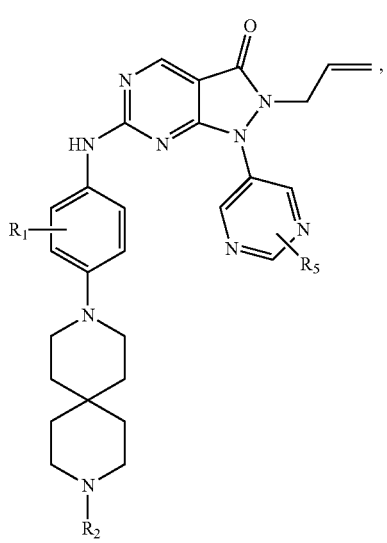
(2-6)
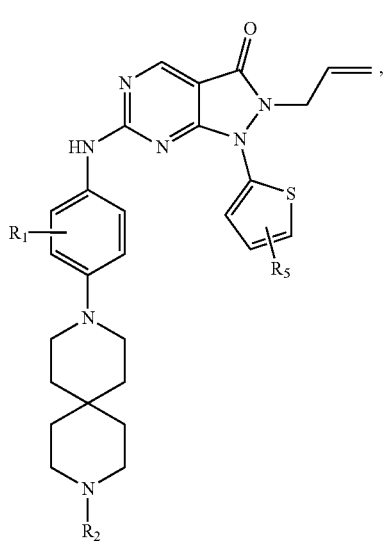
(2-7)
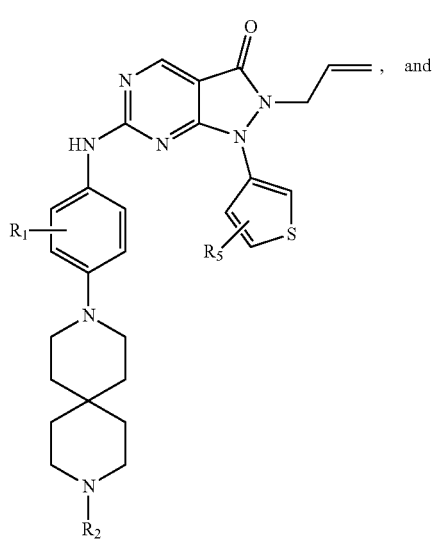
(2-8)
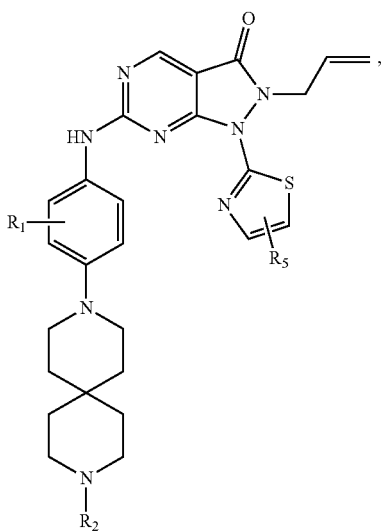
wherein, $R_1$, $R_2$, $R_5$ are as defined in claim 17.
19. The compound or the pharmaceutically acceptable salt thereof shown as below is selected from the group consisting of
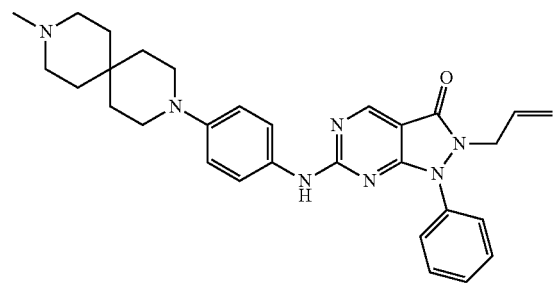

221
-continued
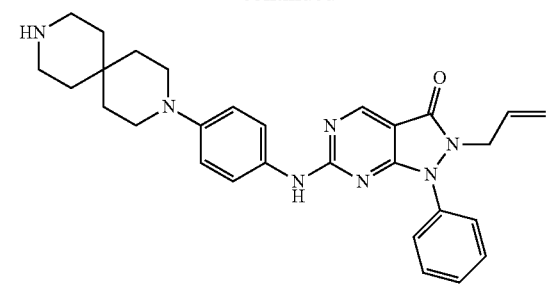
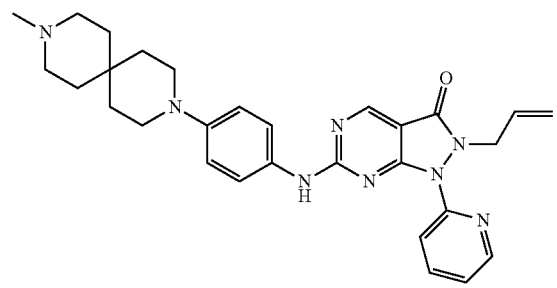
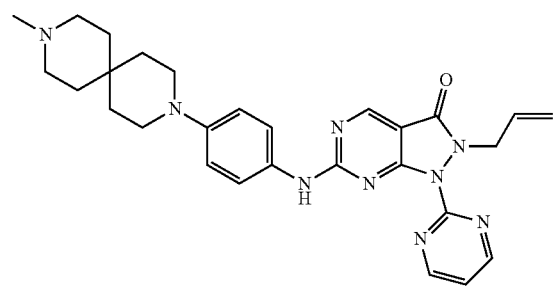
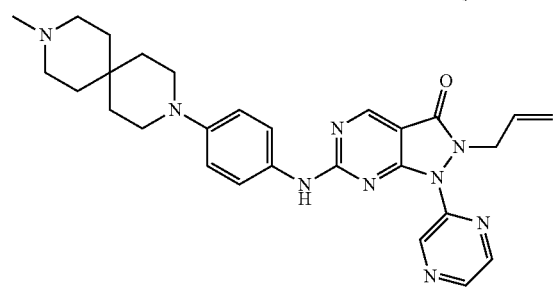
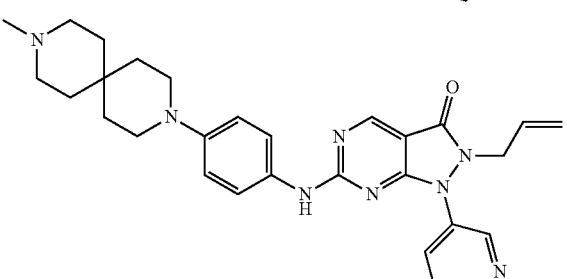
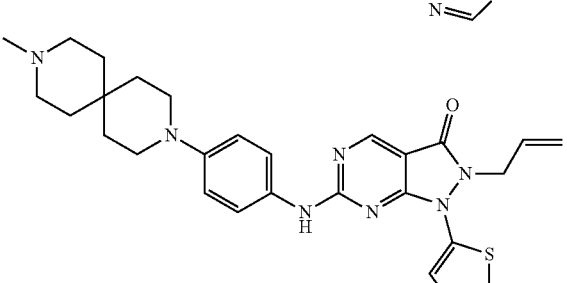
222
-continued
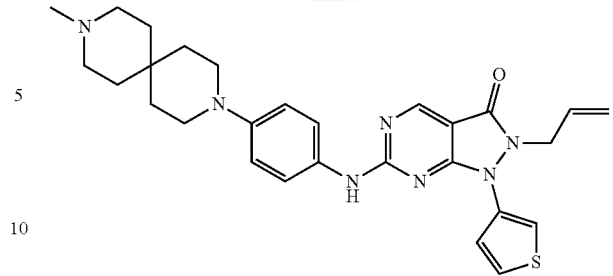
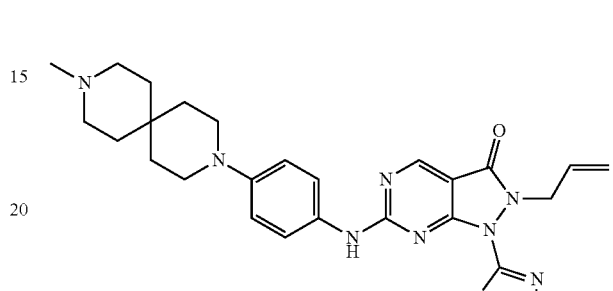
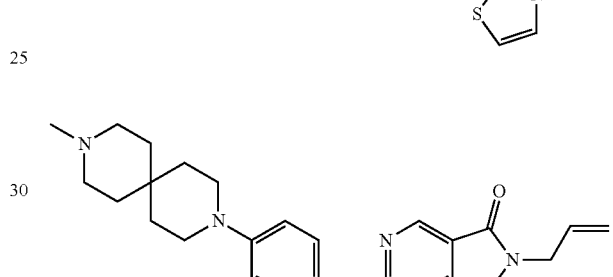
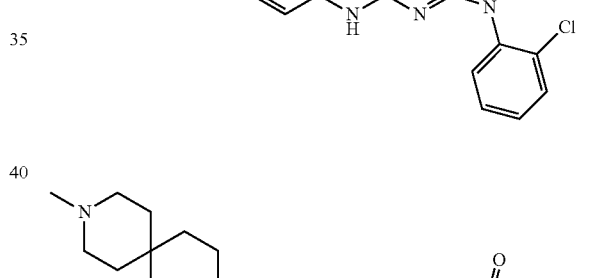
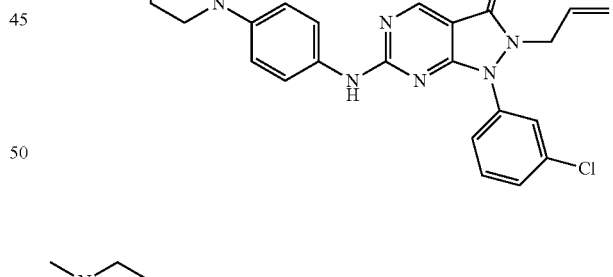
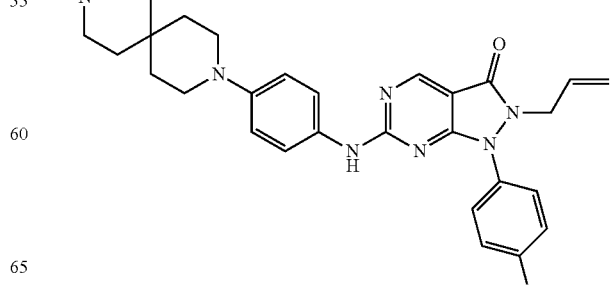

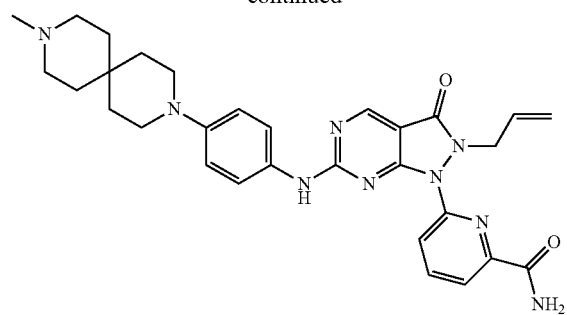
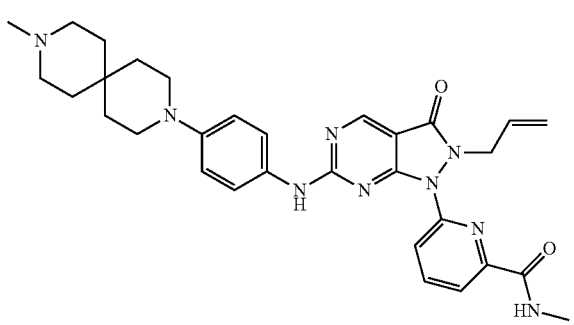
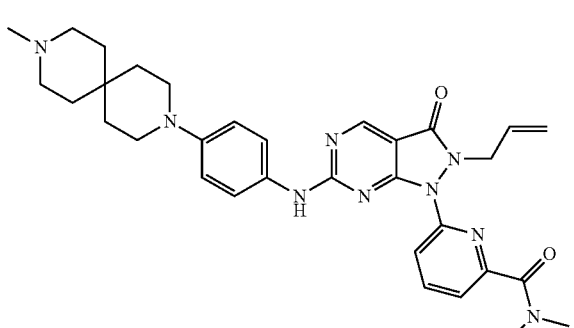
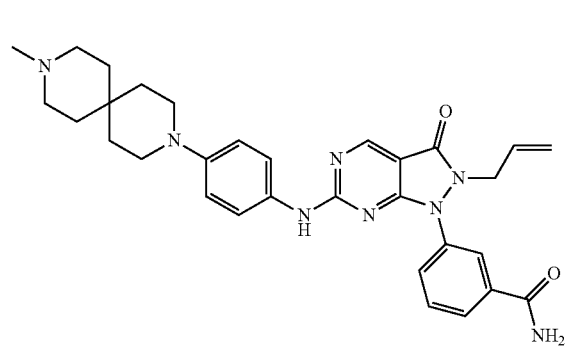
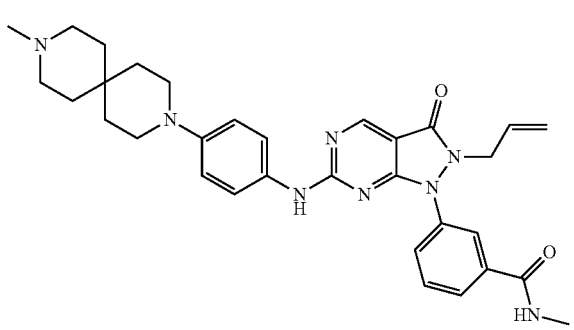
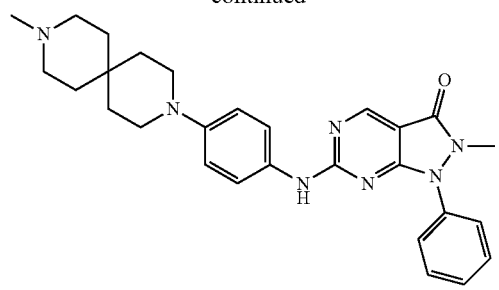
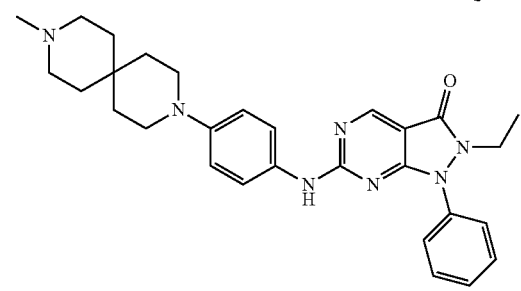
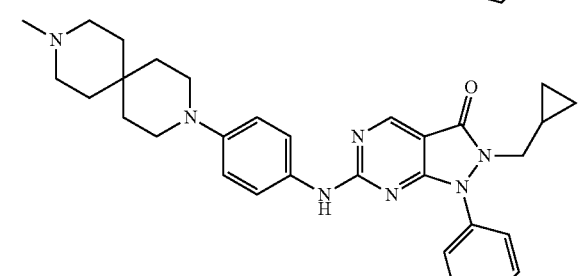
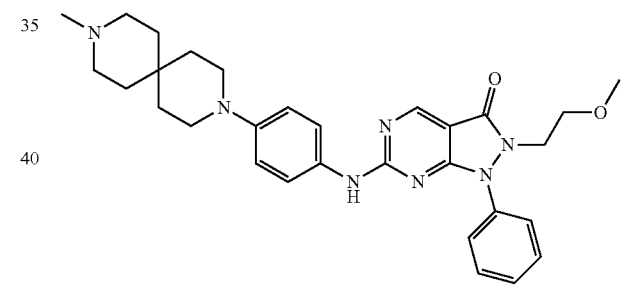
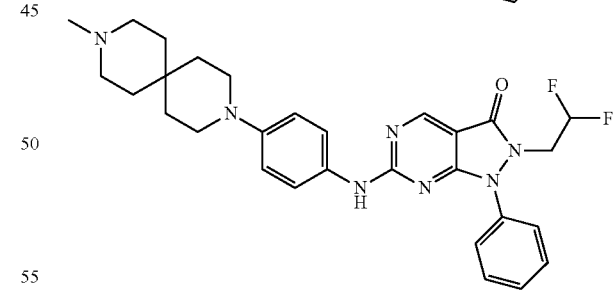
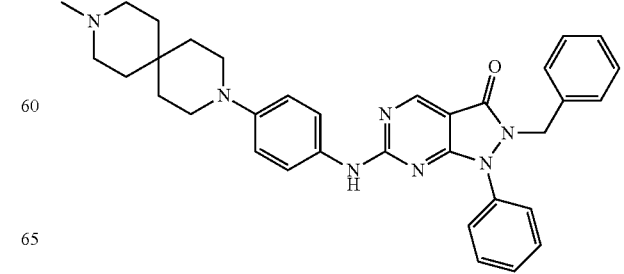

225
-continued
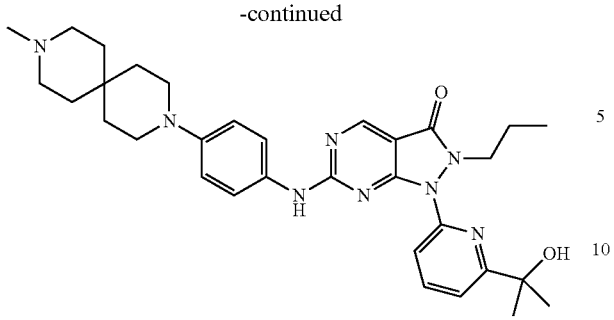
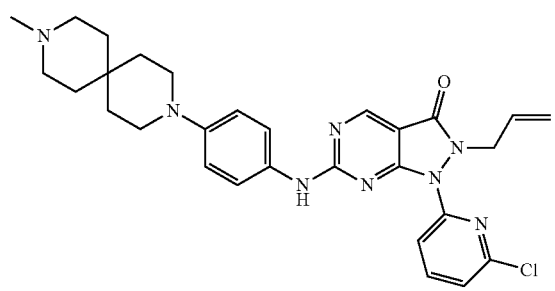
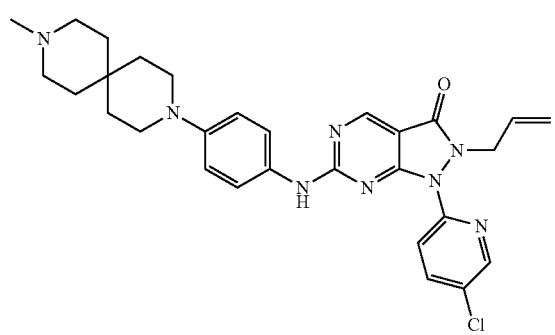
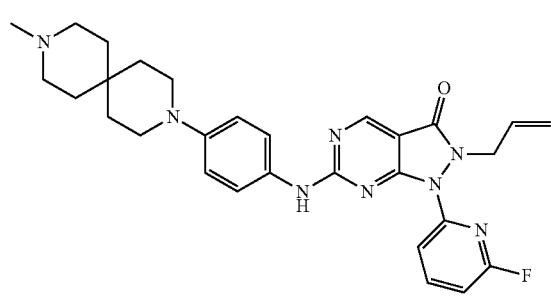
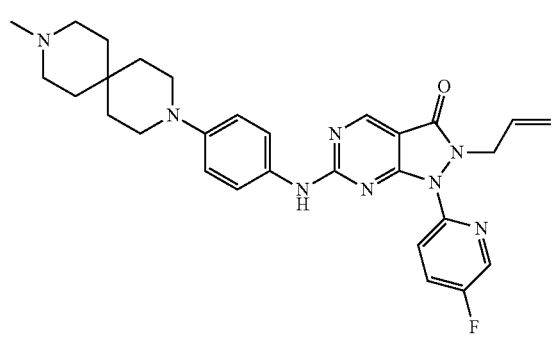
226
-continued
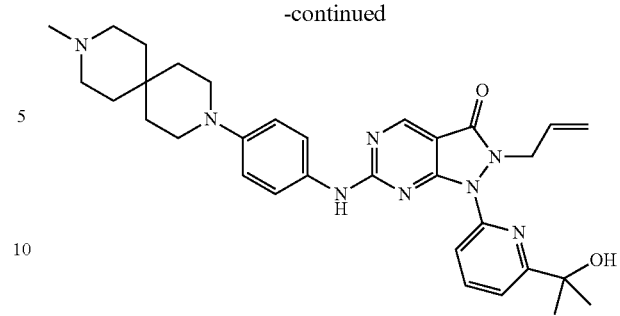
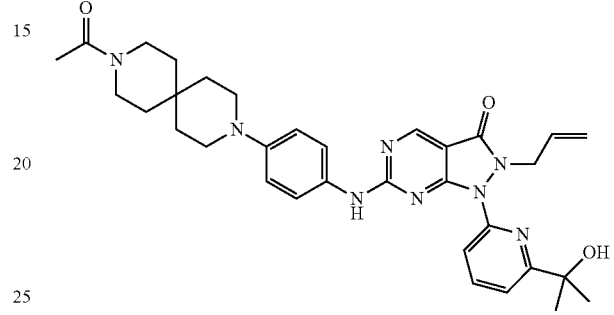
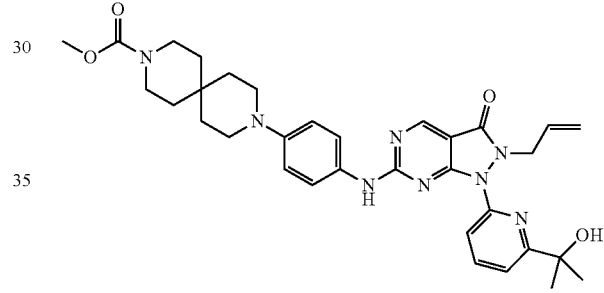
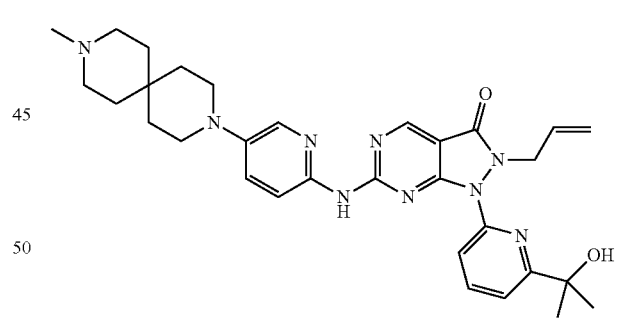
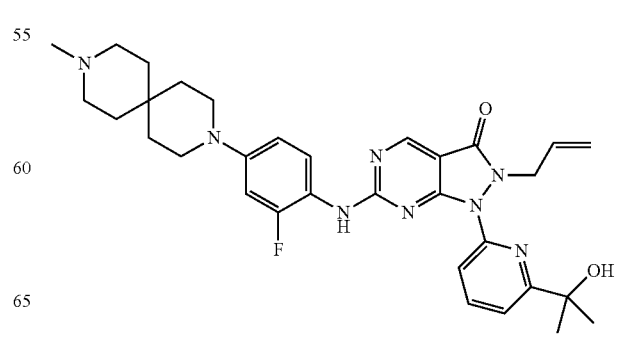

227
-continued
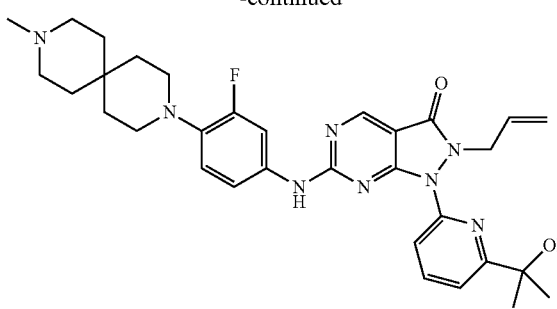
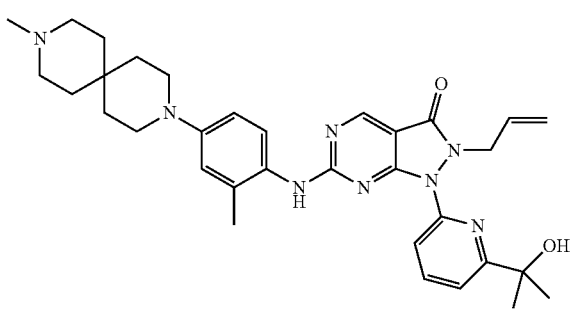
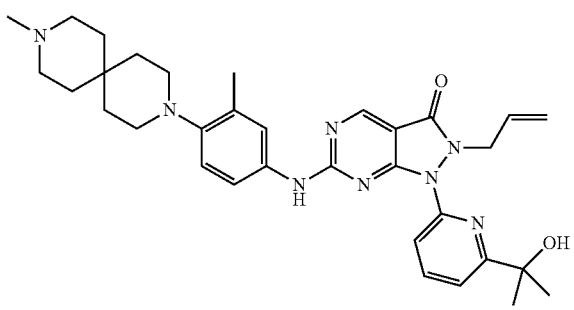
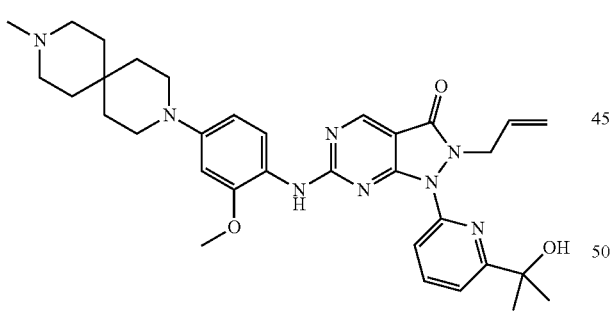
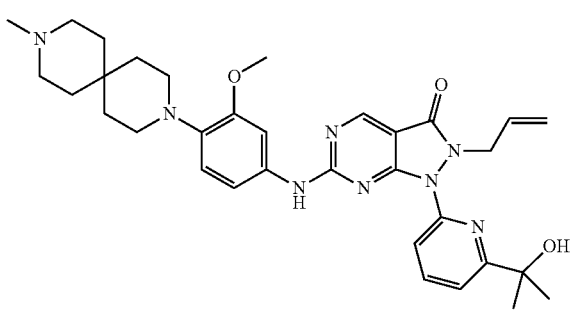
228
-continued
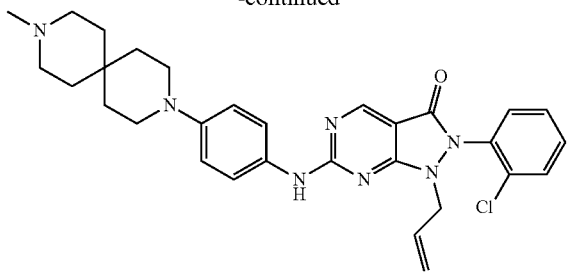
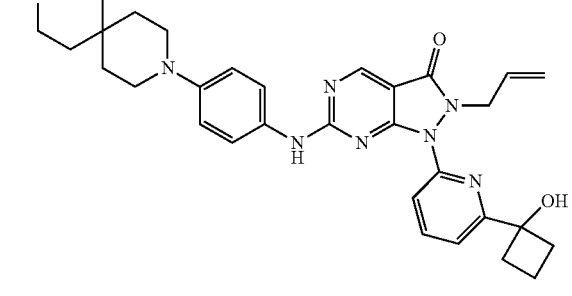
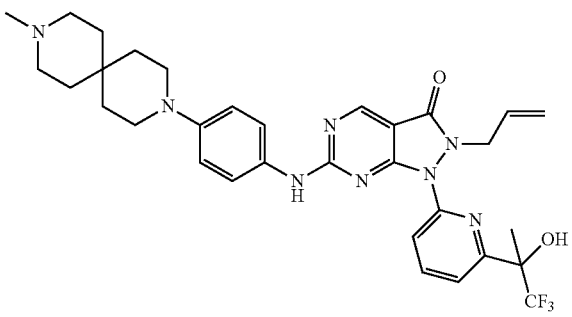
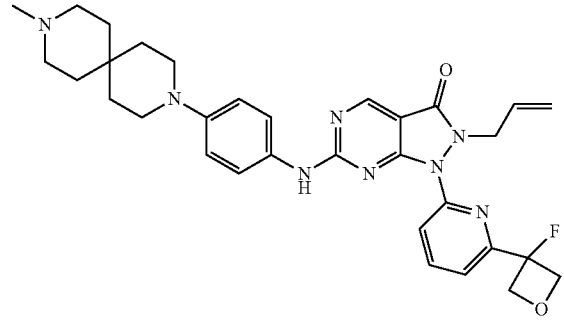

229
-continued
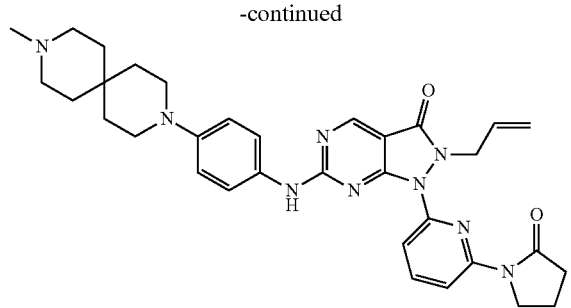
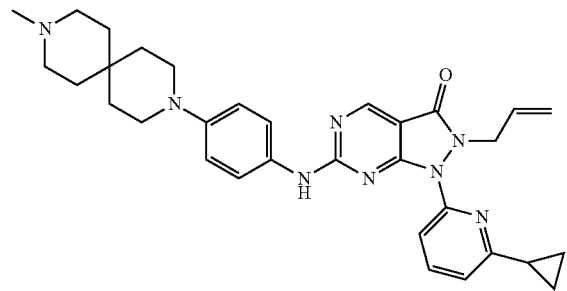
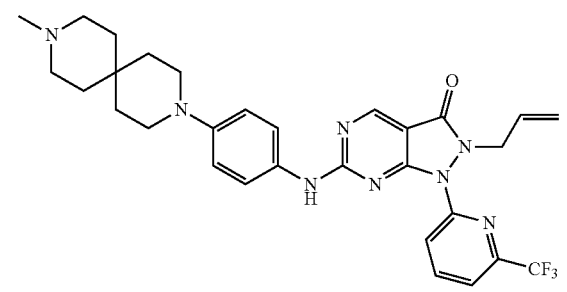
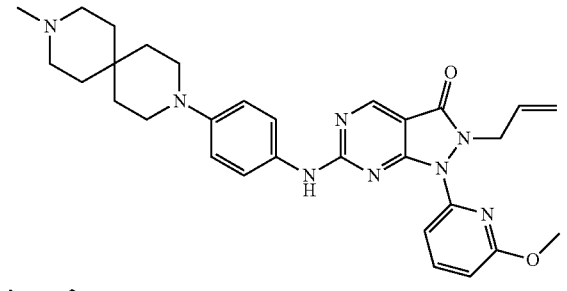
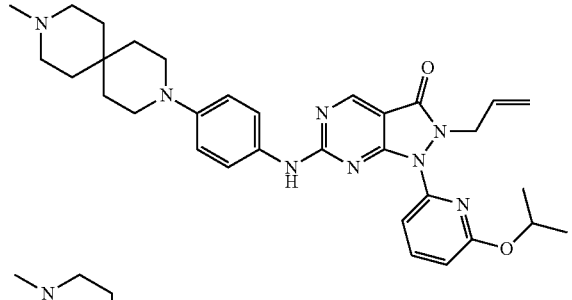
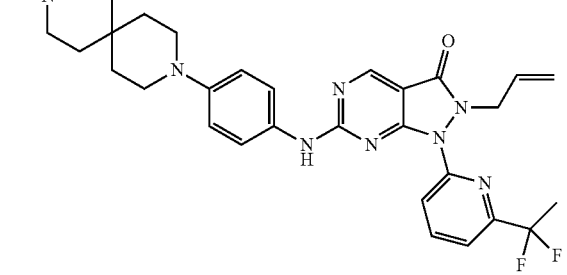
230
-continued
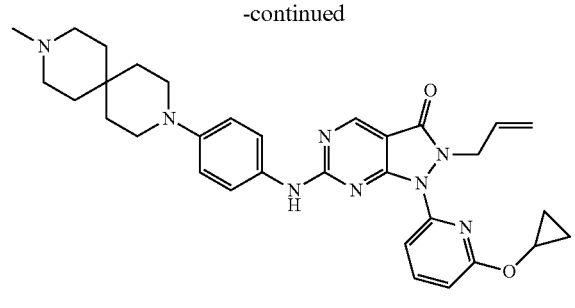
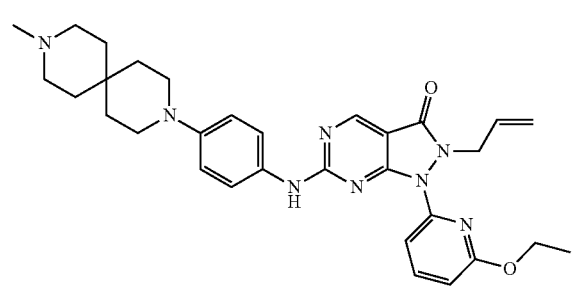
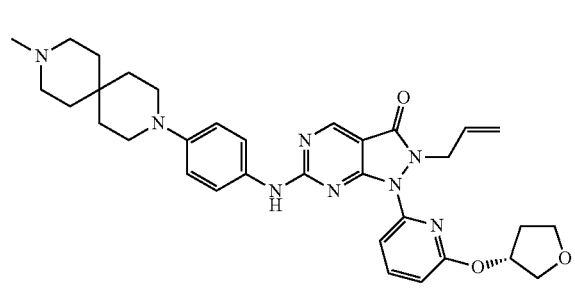
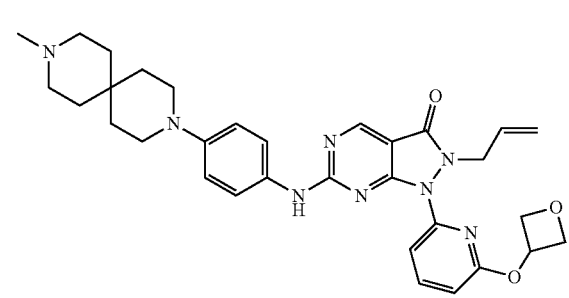
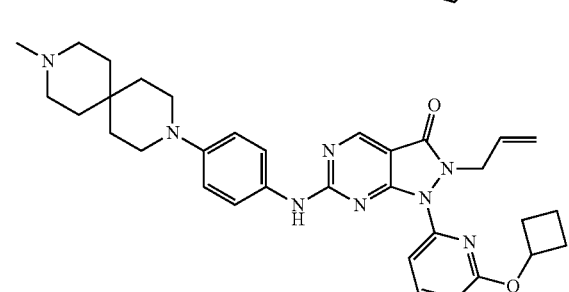
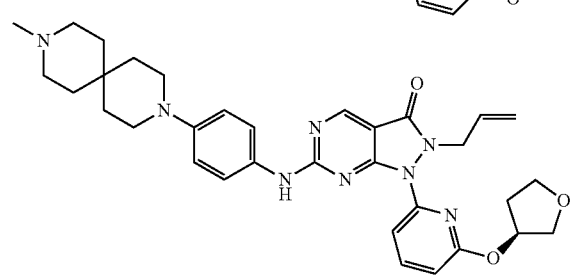

231
-continued
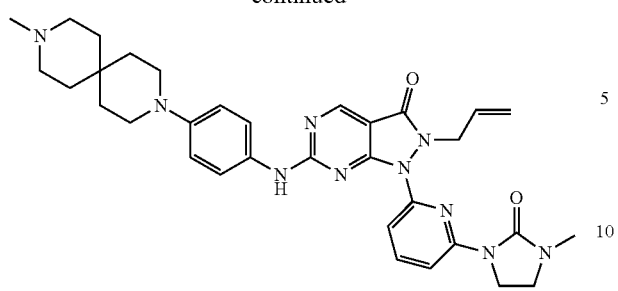
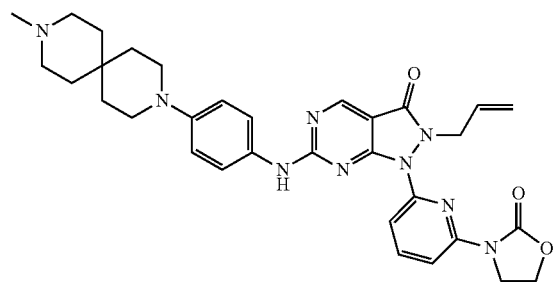
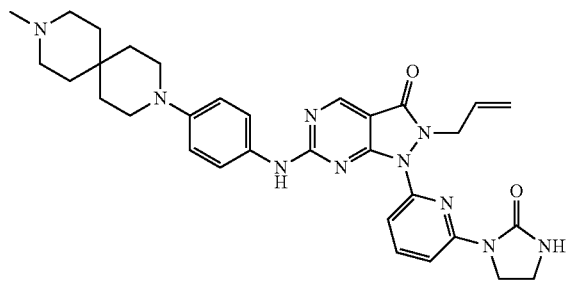
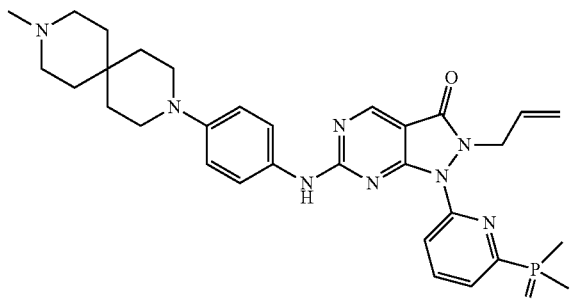
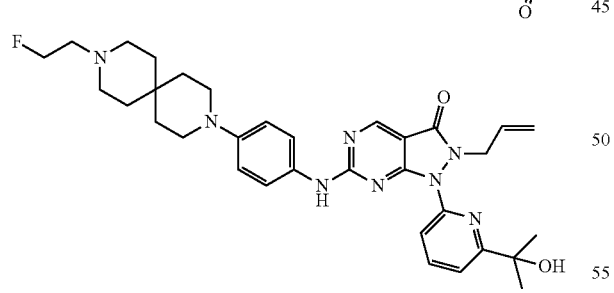
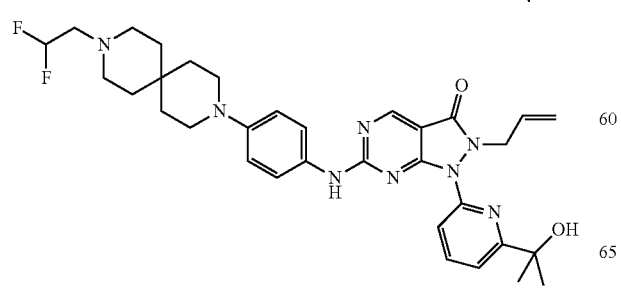
232
-continued
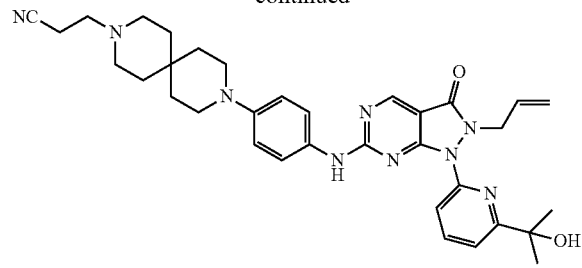
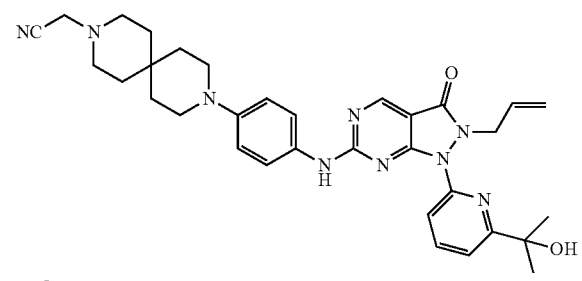
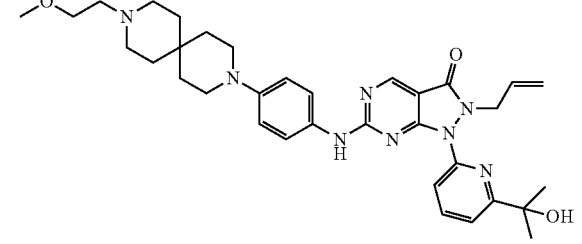
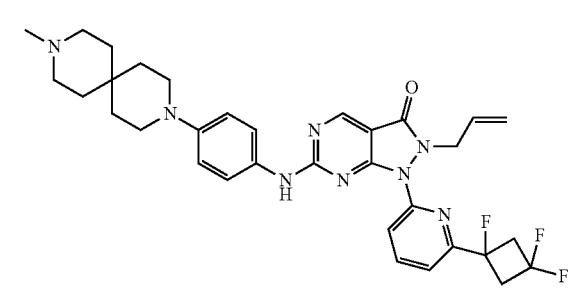
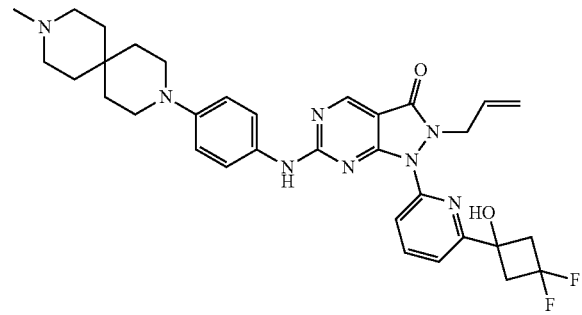
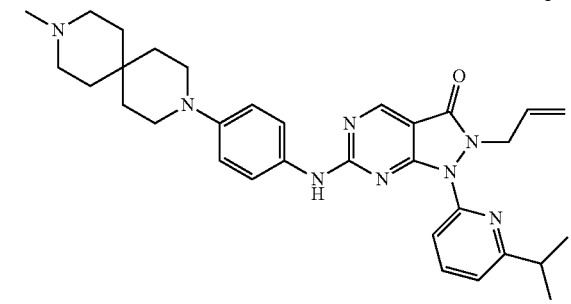

233
-continued
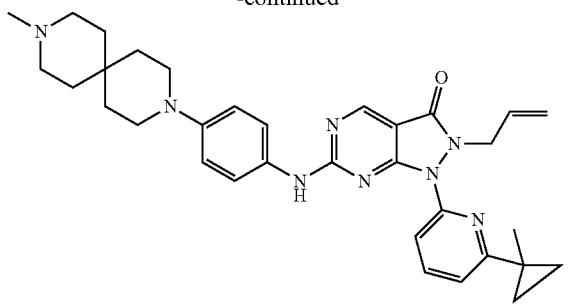
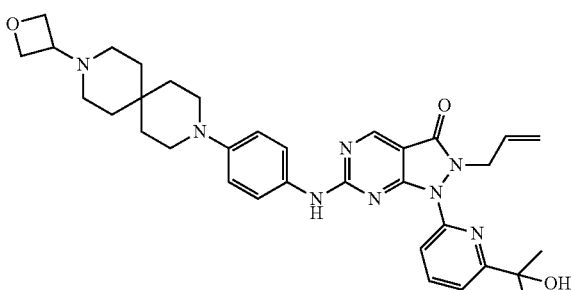
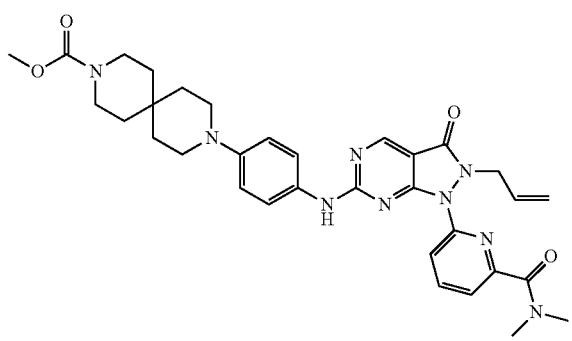
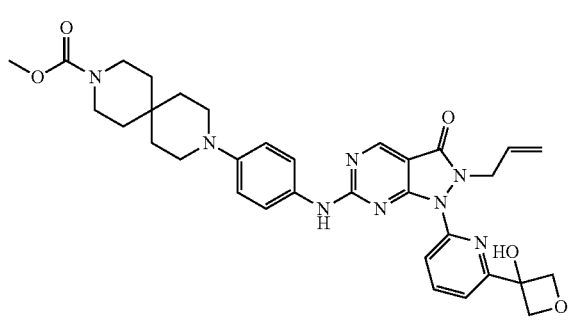
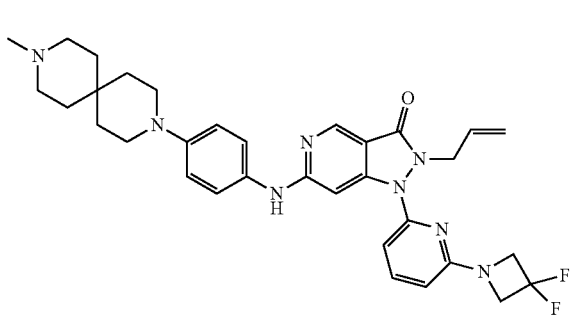
234
-continued
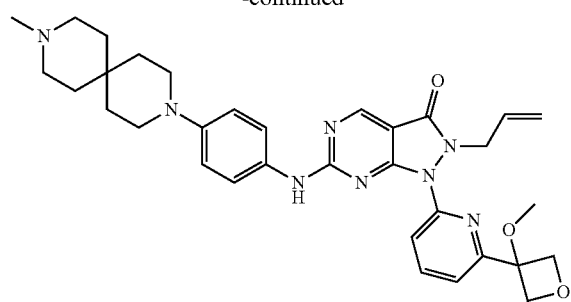
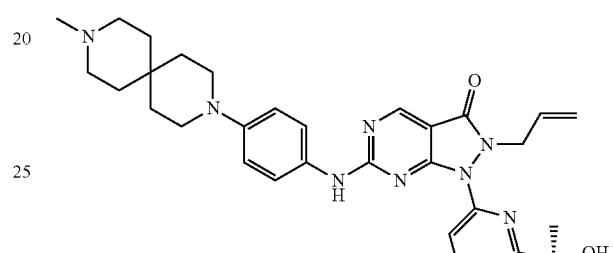
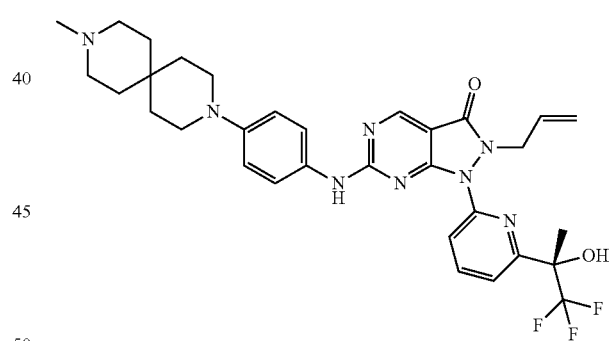
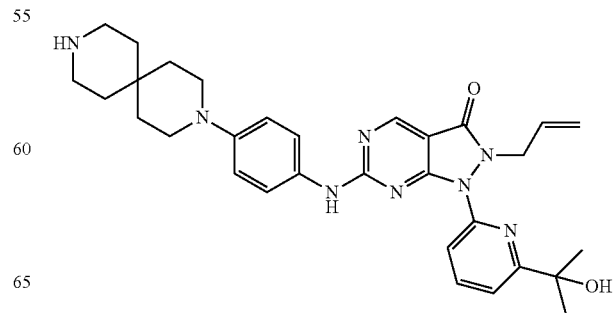

235
-continued
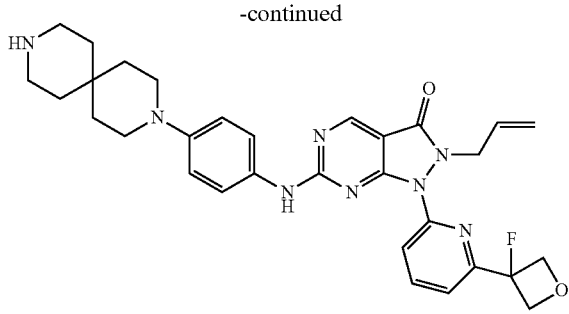
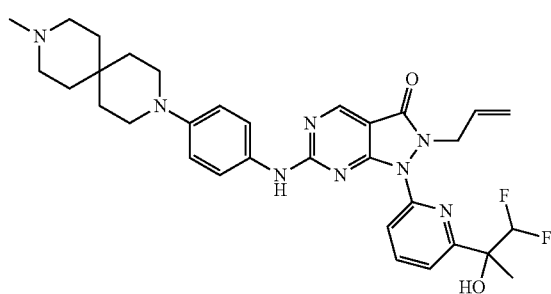
236
-continued
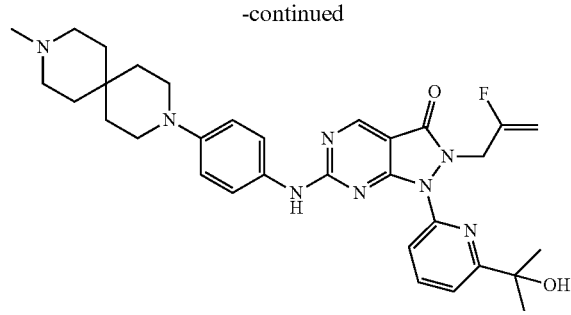
and
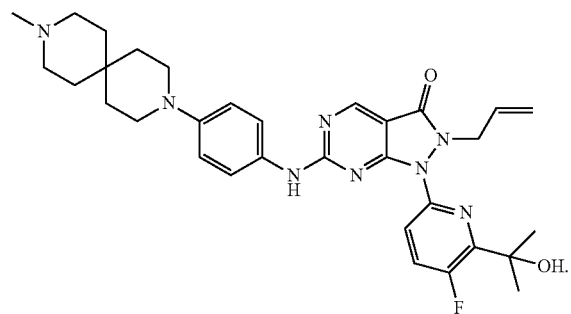
* * * * *